US008372605B2

(12) United States Patent
Nadeau et al.

(10) Patent No.: US 8,372,605 B2
(45) Date of Patent: Feb. 12, 2013

(54) IMMUNO-AMPLIFICATION

(75) Inventors: James Nadeau, Ellicott City, MD (US); Tobin J. Hellyer, Westminster, MD (US); Dolores M. Berger, Baltimore, MD (US); William Nussbaumer, Baltimore, MD (US); Robert Rosenstein, Ellicott City, MD (US); Andrew Kuhn, Baltimore, MD (US); Sha-Sha Wang, Wellesley, MA (US); Keith Edward Thornton, Owings Mill, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/072,314

(22) Filed: Mar. 25, 2011

(65) Prior Publication Data
US 2011/0244457 A1 Oct. 6, 2011

Related U.S. Application Data

(62) Division of application No. 10/826,654, filed on Apr. 19, 2004, now Pat. No. 7,932,060.

(60) Provisional application No. 60/463,712, filed on Apr. 18, 2003.

(51) Int. Cl.
*C12P 19/34* (2006.01)
*C12Q 1/68* (2006.01)
*G01N 33/53* (2006.01)
*C07H 21/04* (2006.01)
*C07K 16/00* (2006.01)

(52) U.S. Cl. ...... 435/91.2; 435/6.1; 435/6.11; 435/6.12; 435/7.1; 435/91.1; 536/24.3; 536/24.33; 530/387.1

(58) Field of Classification Search ............. 435/6, 6.11, 435/6.12, 91.1, 91.2, 7.1, 91.51; 436/94, 436/501; 536/23.1, 24.3, 24.33, 25.3; 530/387.1
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |

(Continued)

FOREIGN PATENT DOCUMENTS

| EP | 0544212 A1 | 6/1993 |
| EP | 0832431 A1 | 4/1998 |

(Continued)

OTHER PUBLICATIONS

Figure 13 from US Patent No. 6,815,164 B2 with the examiners handwritings. Printed on Sep. 17, 2007.*

(Continued)

*Primary Examiner* — Frank W Lu
(74) *Attorney, Agent, or Firm* — Lerner, David, Littenberg, Krumholz & Mentlik, LLP

(57) ABSTRACT

A high-sensitivity, low-background immuno-amplification assay is provided, which offers a streamlined workflow suitable for high-throughput assays of clinically relevant samples, such as blood and other bodily fluids. The assay comprises the use of two proximity members that each comprise an analyte-specific binding component conjugated to an oligonucleotide. Binding an analyte brings the oligonucleotide moieties of the proximity members in sufficiently close contact that the oligonucleotides form an amplicon. The presence of the analyte then is detected through amplification of the amplicon and detection of the amplified nucleic acids. The sensitivity of the assay of the present invention is improved by preventing spurious or non-specific amplicon formation by proximity members that are not complexed with an analyte.

17 Claims, 84 Drawing Sheets

Amplicon formation from hybridized probes of opposite sequence orientation

U.S. PATENT DOCUMENTS

| | | | |
|---|---|---|---|
| 4,839,293 | A | 6/1989 | Cantor et al. |
| 4,965,188 | A | 10/1990 | Mullis et al. |
| 5,109,124 | A | 4/1992 | Ramachandran et al. |
| 5,130,238 | A | 7/1992 | Malek et al. |
| 5,270,184 | A | 12/1993 | Walker et al. |
| 5,328,985 | A | 7/1994 | Sano et al. |
| 5,391,723 | A | 2/1995 | Priest |
| 5,424,413 | A | 6/1995 | Hogan et al. |
| 5,427,930 | A | 6/1995 | Birkenmeyer et al. |
| 5,451,503 | A * | 9/1995 | Hogan et al. ............. 435/6.1 |
| 5,462,854 | A | 10/1995 | Coassin et al. |
| 5,635,602 | A | 6/1997 | Cantor et al. |
| 5,648,211 | A | 7/1997 | Fraiser et al. |
| 5,665,539 | A | 9/1997 | Sano et al. |
| 5,744,311 | A | 4/1998 | Fraiser et al. |
| 5,840,487 | A | 11/1998 | Nadeau et al. |
| 5,846,726 | A | 12/1998 | Nadeau et al. |
| 5,849,478 | A | 12/1998 | Cashman |
| 5,849,878 | A | 12/1998 | Cantor et al. |
| 5,863,736 | A | 1/1999 | Haaland |
| 5,876,924 | A | 3/1999 | Zhang et al. |
| 5,902,724 | A | 5/1999 | Lane et al. |
| 5,919,630 | A | 7/1999 | Nadeau et al. |
| 5,922,553 | A | 7/1999 | Eberwine et al. |
| 5,928,869 | A | 7/1999 | Nadeau et al. |
| 5,935,791 | A | 8/1999 | Nadeau et al. |
| 5,985,548 | A | 11/1999 | Collier et al. |
| 6,066,458 | A | 5/2000 | Haaland et al. |
| 6,083,689 | A | 7/2000 | Martinelli et al. |
| 6,245,513 | B1 | 6/2001 | Lane et al. |
| 6,255,060 | B1 | 7/2001 | Eberwine et al. |
| 6,316,200 | B1 | 11/2001 | Nadeau et al. |
| 6,335,166 | B1 * | 1/2002 | Ammann et al. ............ 435/6.11 |
| 6,379,888 | B1 | 4/2002 | Nadeau et al. |
| 6,489,116 | B2 | 12/2002 | Wagner |
| 6,511,809 | B2 | 1/2003 | Baez et al. |
| 6,815,164 | B2 * | 11/2004 | Kurn ............................. 435/6.1 |
| 2002/0013223 | A1 | 1/2002 | Eijsbouts et al. |
| 2002/0028450 | A1 | 3/2002 | Greene et al. |
| 2002/0051974 | A1 | 5/2002 | Dodge et al. |
| 2002/0051986 | A1 | 5/2002 | Baez et al. |
| 2002/0064779 | A1 | 5/2002 | Landegren et al. |
| 2002/0094534 | A1 | 7/2002 | Greene et al. |
| 2002/0132260 | A1 | 9/2002 | Erlander et al. |

FOREIGN PATENT DOCUMENTS

| | | |
|---|---|---|
| EP | 1249500 A1 | 10/2002 |
| JP | 03-167474 A | 7/1991 |
| JP | 2002-510465 T | 4/2002 |
| WO | 9115599 A1 | 10/1991 |
| WO | 9426932 A1 | 11/1994 |
| WO | 9700446 A1 | 1/1997 |
| WO | 9937806 A2 | 7/1999 |
| WO | 9963109 A1 | 12/1999 |
| WO | 0075663 A1 | 12/2000 |
| WO | 0131056 A2 | 5/2001 |
| WO | 0184146 A2 | 11/2001 |
| WO | 0208757 A1 | 1/2002 |
| WO | 200442030 A2 | 5/2004 |

OTHER PUBLICATIONS

Walker et al.. "Isothermal In Vitro Amplification of DNA by a Restriction Enzyme/DNA Polymerase System," PNAS, 1992, vol. 89. pp. 392-396.

Walker et al.. "Strand Displacement Amplification—An Isothermal, In Vitro DNA Amplification Technique," Nucleic Acids Research. 1992, vol. 20, No. 7. pp. 1691-1696.

Guatelli et al.. "Isothermal. In Vitro Amplification of Nucleic Acids by a Multienzyme Reaction Modeled After Retroviral Replication," PNAS, 1990. vol. 87, pp. 1874-1878; correction p. 7797.

L1zardi et al., "Exponential Amplification of Recombinant-RNA Hybridization Probes," BiolTechnoloav, 1988, vol. 6, pp. 1197-1202.

Hirose et al., New Method to Measure Telomerase Activity by Transcription-Mediated Amplification and Hybridization Protection Assay, Clinical Chemistry, 1998, vol. 44, No. 12, pp. 2446-2452.

Kwoh et al., "Transcription-Based Amplification System and Detection of Amplified Human Immunodeficiency Virus Type 1 with a Bead-Based Sandwich Hybridization Format," PNAS, 1989, vol. 86 pp. 1173-1177.

Sambrook et al., Molecular Cloning: A Laboratory Manual, 3m ed., 2001, Cold Spring Harbor Press, Chapter 10, pp. 10.11-10.52.

Nadeau et al., Real-time, Sequence-Specific Detection of Nucleic Acids during Strand Displacement Amplification, Analytical Biochemistry, 1999, vol. 276, pp. 177-187.

M. Zuker, "Mfold Web Server for Nucleic Acid Folding and Hybridization Prediction," Nucleic Acids Research, 2003, vol. 31, No. 13, pp. 3406-3415.

Barletta, J.M. et al., 'Lowering the Detection Limits of HIV-1 Viral Load Using Real-Time Immuno-PCR for HIV-I p24 Antigen,' Am. J. Clin. Pathol., 20-27(2004).

Niemeyer, C.M. et al., Combination of DNA-directed immobilization and immuno-PCR: very sensitive antigen detection by means of self-assembled DNA-protein conjugates: Nucleic Acids Research, 31 (16): 1-7(2003).

Niemeyer, C.M. et al., DNA-Directed Immobilization: Efficient, Reversible, and Site-Selective Surface Binding of Proteins by Means of Covalent DNA-Streptavidin Conjugates: Analytical Biochemistry, 268; 54-63(1999).

Retro-Tek, 'HIV-1 p24 Antigen ELISA,' ZeptoMetrix Corporation, Catalog No. 0801111, 1-7, Dec. 2001.

Scouten, W.H. and Konecny, P., 'Reversible Immobilization of Antibodies on Magnetic Beads,' Analytical Biochemistry, 205; 313-18(1992).

Fredriksson, S. et al., Protein detection using proximity-dependent DNA ligation assays: Nature Biotech. 20: 473-77 (May 2002).

Suzuki, A. et al., Double Determinant Immune-Polymerase Chain Reaction: A SenSitive Method for Detecting Circulating Antigens in Human Sera: Jpn. J. Cancer Res.86.: 885-89 (Sep. 1995).

Zhang, H.T. et al., Protein quantification from complex protein mixtures using a proteomics methodology with single-cell resolution: Proc. Natl Acad. Sci. USA. 98(10): 5497-5502 (May 8, 2001).

Schiavo, S. et al., Pushing the Limits of Detection with Immune-PCR: PharmaGenomics 36-45 (Jan. 2004).

Niemeyer, C.M. et al., Tech Note: High Sensitivity Detection of Antigens using Immune-PCR: NUNC Brand Products 5(35), at http:/twww.medos.com.aulmedialprodimages/NUN2-48909_appnote.pdf (last accessed Jun. 2004).

Niemeyer, C.M. et al., Combination of DNA-directed immobilization and immuno-PCR: very sensitive antigen detection by means of self-assembled DNA-protein conjugates: Nucleic Acids Res. 31(16): 1-7 (2003).

Antson, D.O. et al., PCR-generated padlock probes detect single nucleotide variation in genomic DNA, Nuc/eicAcids Res. 28(12): 1-6 (2000).

Jarvius, J. et al., 'Oligonucleotide Ligation Assay,' Methods Mol. Bioi. ill: 215-29 (2003).

Ren, J. et al., 'Detection of Circulating CEA Molecules in Human Sera and Leukopheresis of Peripheral Blood Stem Cells with E. coli Expressed Bispecific CEAScFv-Streptavidin Fusion Protein-Based Immune-PCR Technique' Annals N.Y. Acad. Sci. 945: 116-18 (Sep. 2001).

Case, M. et al., The universality of Immune-PCR for ultrasensitive antigen detection, Biochem. Soc'y Trans. 25(2): 374 (May 1997).

Office Action from Japanese Application No. 2006-513098, dated Jun. 25, 2010.

* cited by examiner

Mixing of antigens and oligonucleotide-conjugated antibodies

Hybridization of adjacent oligonucleotide probes

Polymerase extension and restriction enzyme nicking

Extension, displacement and linear amplification

Hybridization, polymerase extension, nicking and exponential amplification

Mixing of antigens and oligonucleotide-conjugated antibodies

Hybridization of adjacent oligonucleotide probes

Extend oligonucleotide probes with polymerase

Denature probe-extension duplex and
bind SDA primers (SP1, SP2) and bumpers (SB1, SB2)

Amplicon formation from hybridized probes of opposite sequence orientation

Hybridization of splint oligonucleotide

Ligation of adjacent oligonucleotide probes

DNA polymerase extension and displacement

Use of two hybridized probes to ligate a third probe

Use of two hybridized probes in opposite sequence orientation to ligate a third probe Single-tether oligonucleotide Single-tether oligonucleotide: extension and displacement

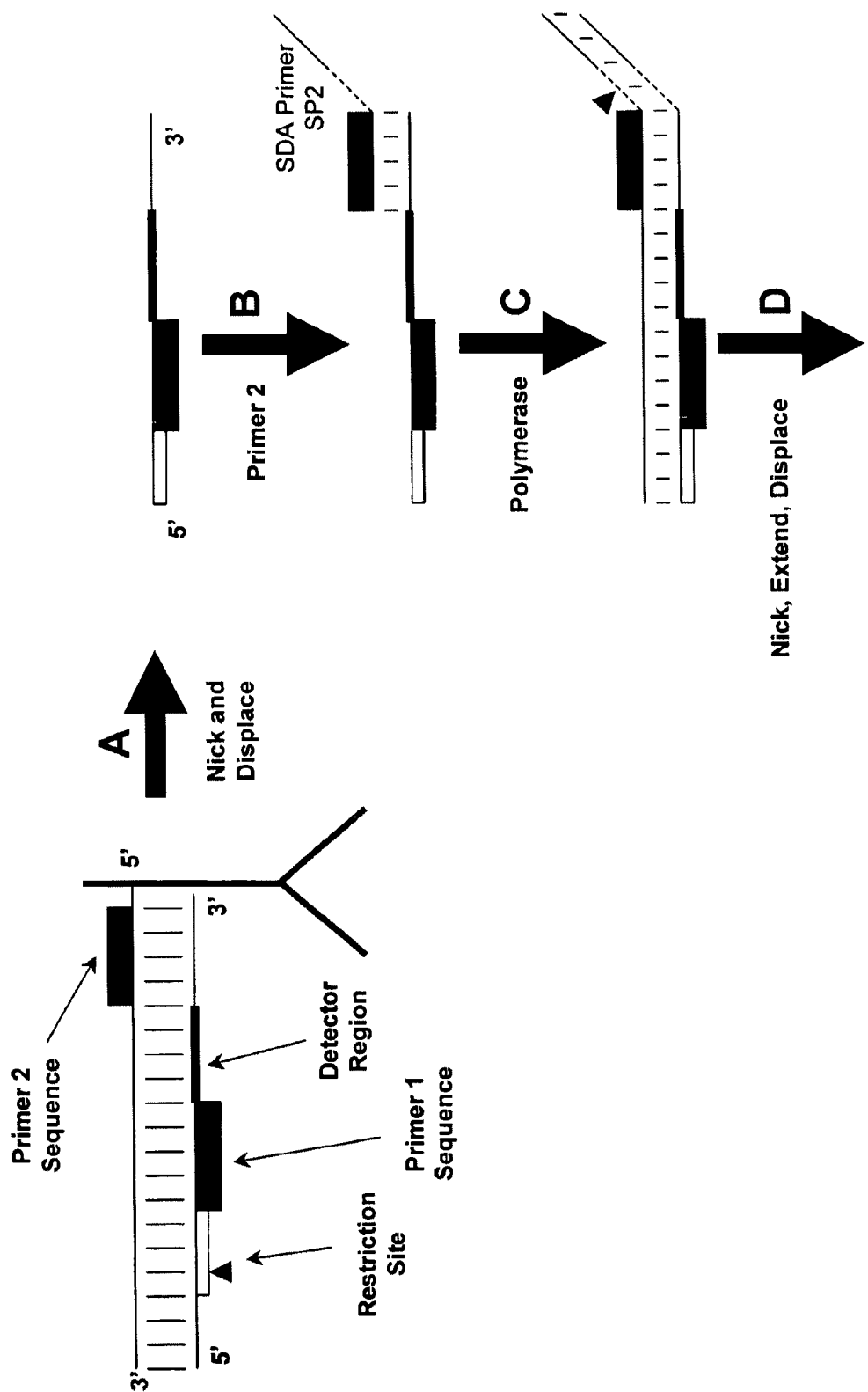

Nicking, extension, displacement and capture (cont.)

Splint probes (3'/3' configuration)

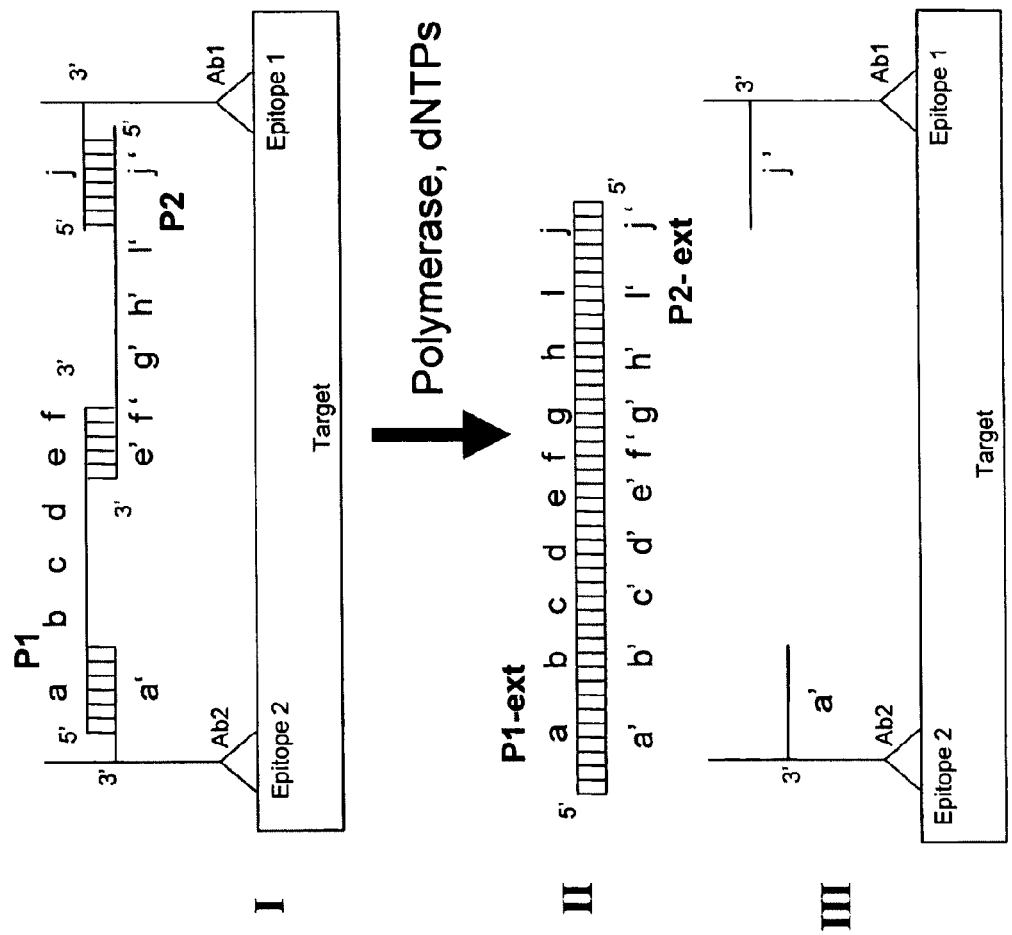

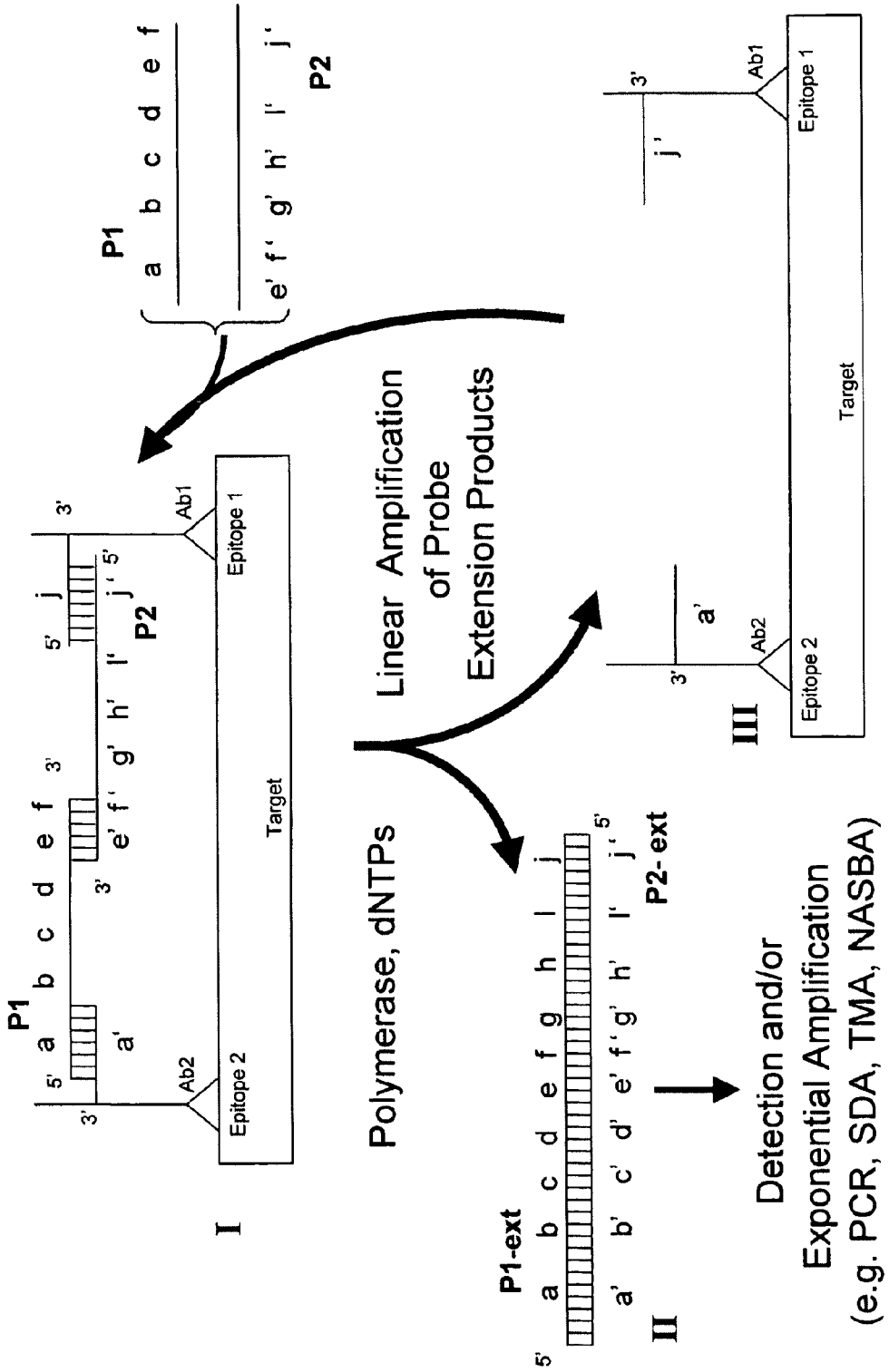

Splint probes (5'/3' configuration)

Splint probes (5'/5' configuration)

Splint probes (3'/3' configuration)

Splint probes (3'/3' configuration)

Extension / displacement of splint probes (cont.)

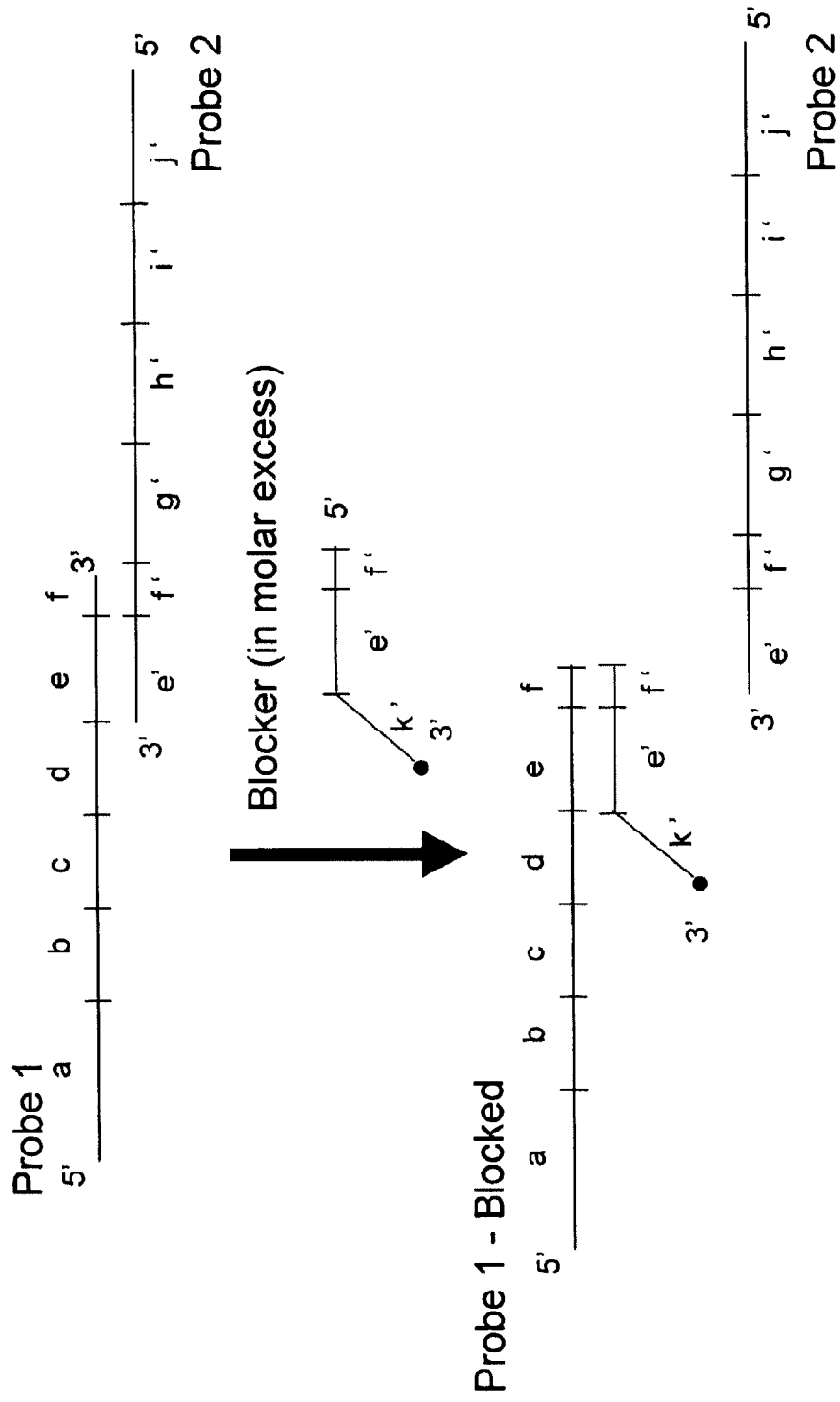

Recessed, competitive blocker oligonucleotide

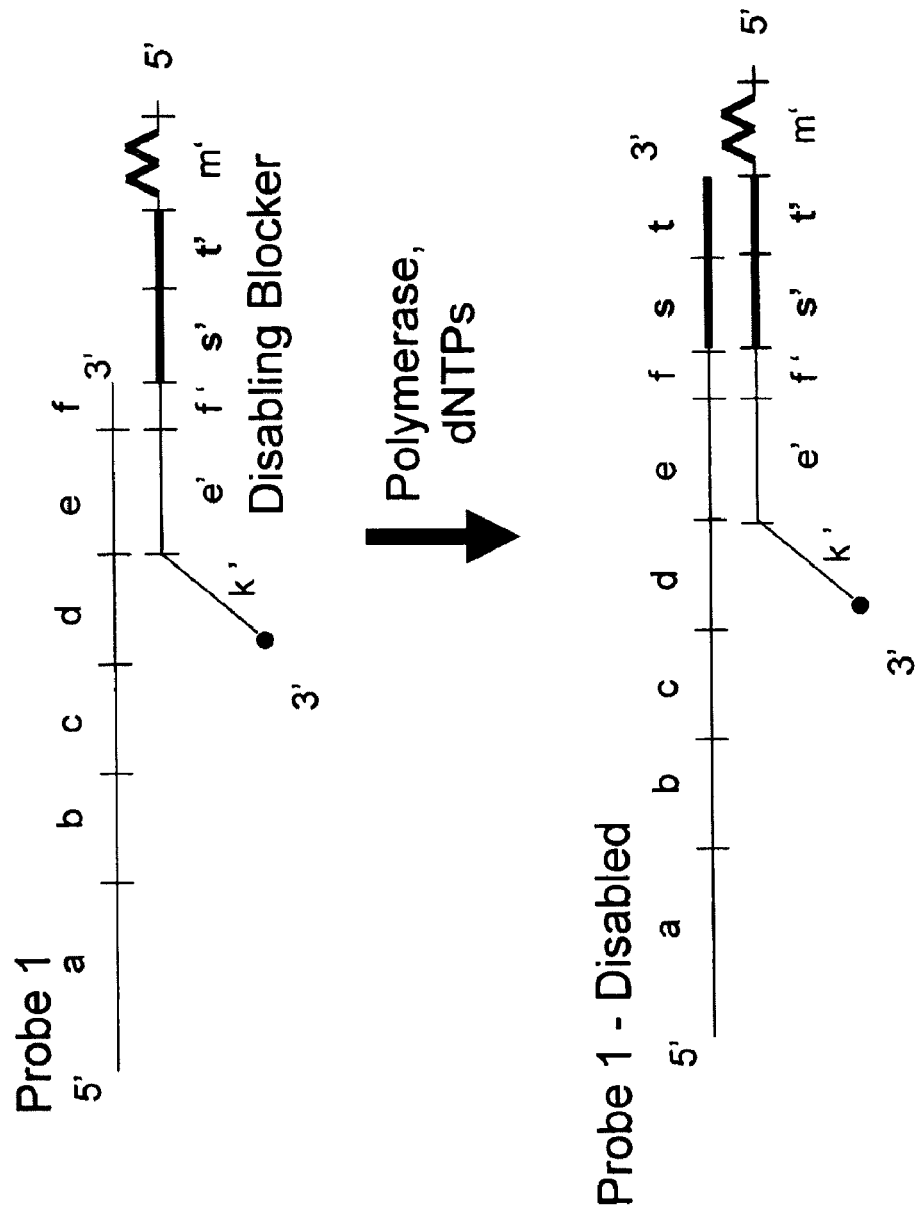

Displaceable blocker oligonucleotide

Self-displacing blocker oligonucleotide

Use of 3' probe tail to stabilize probe-blocker duplex

Competitive blocker oligonucleotide in binary immuno-SDA

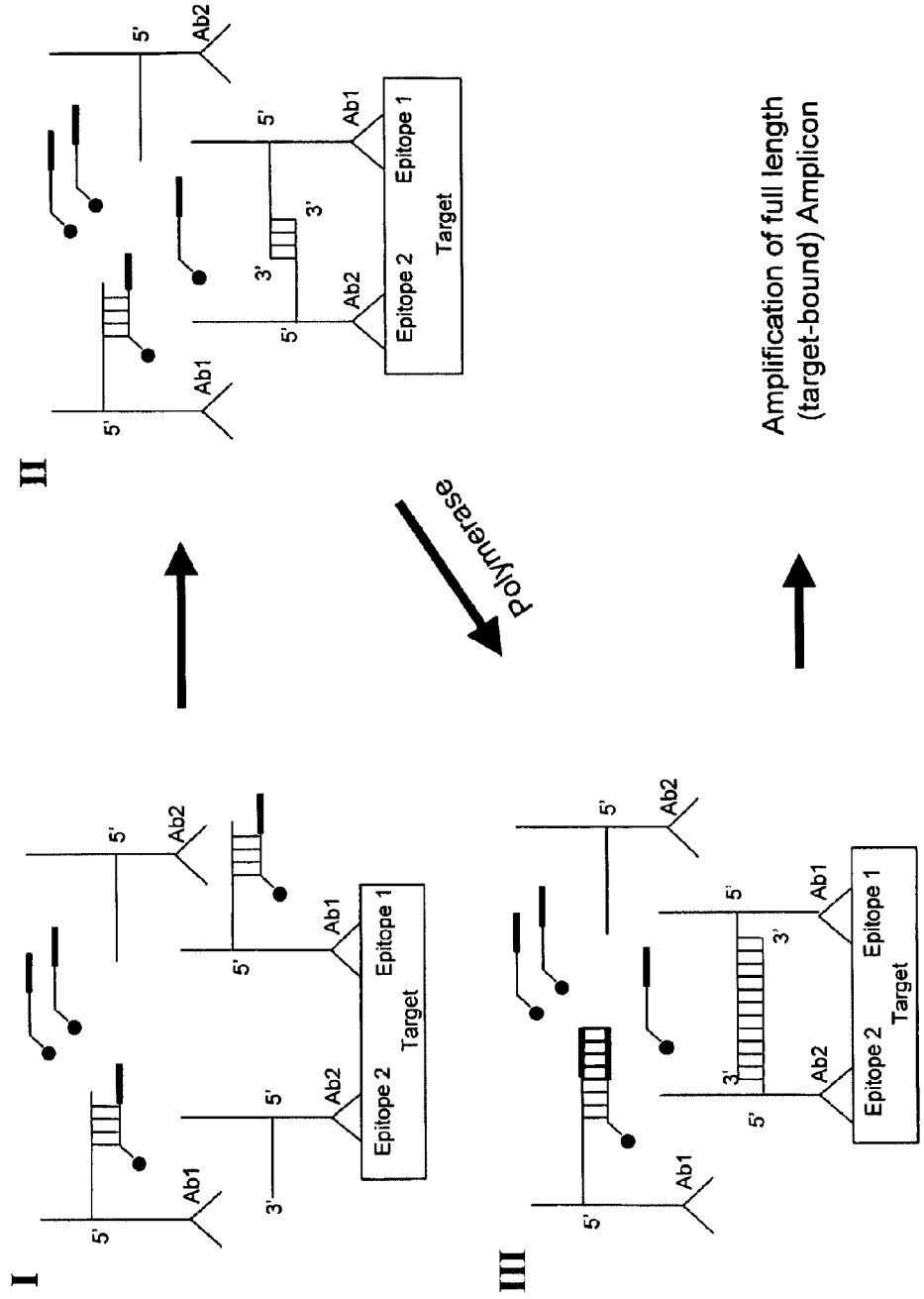

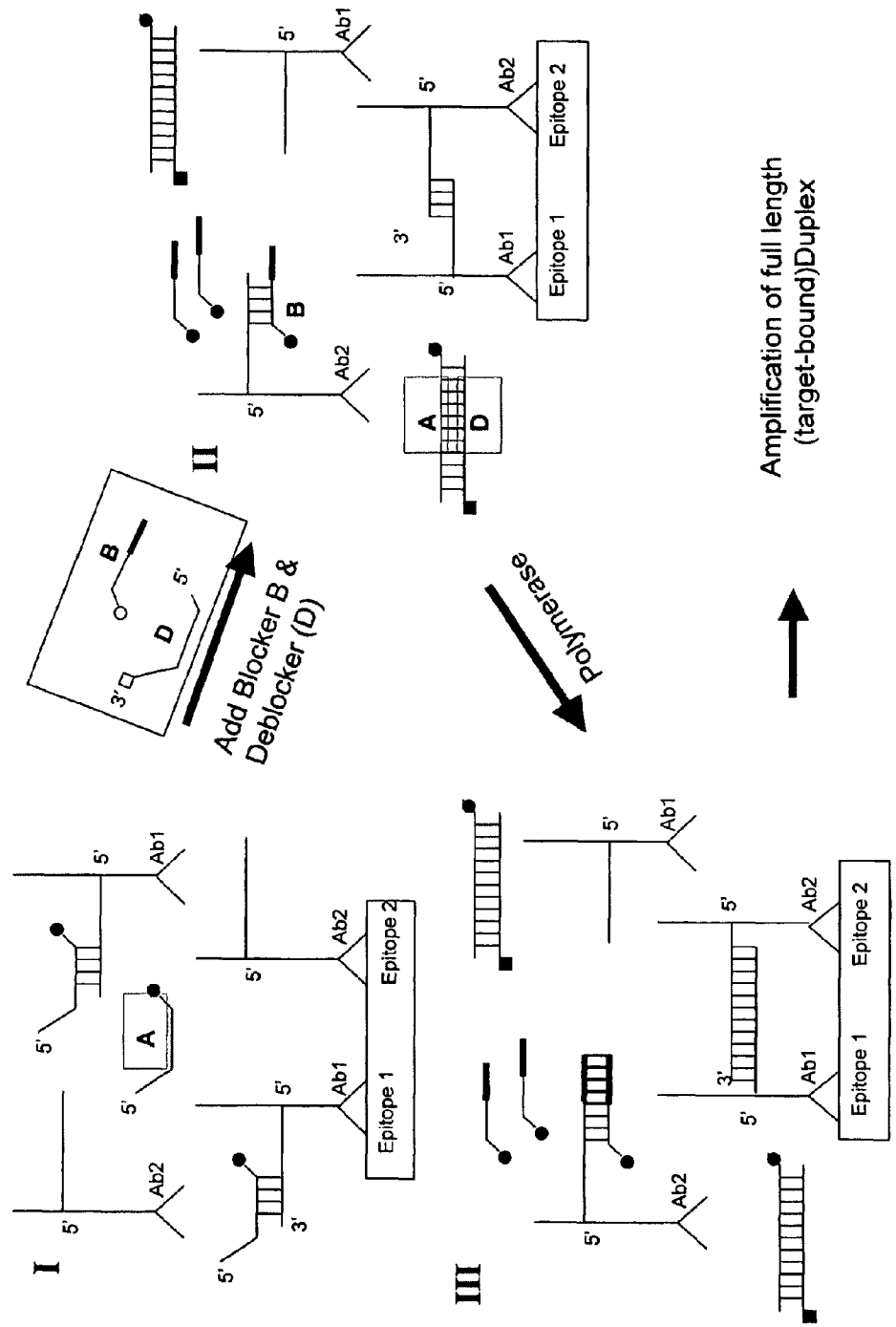

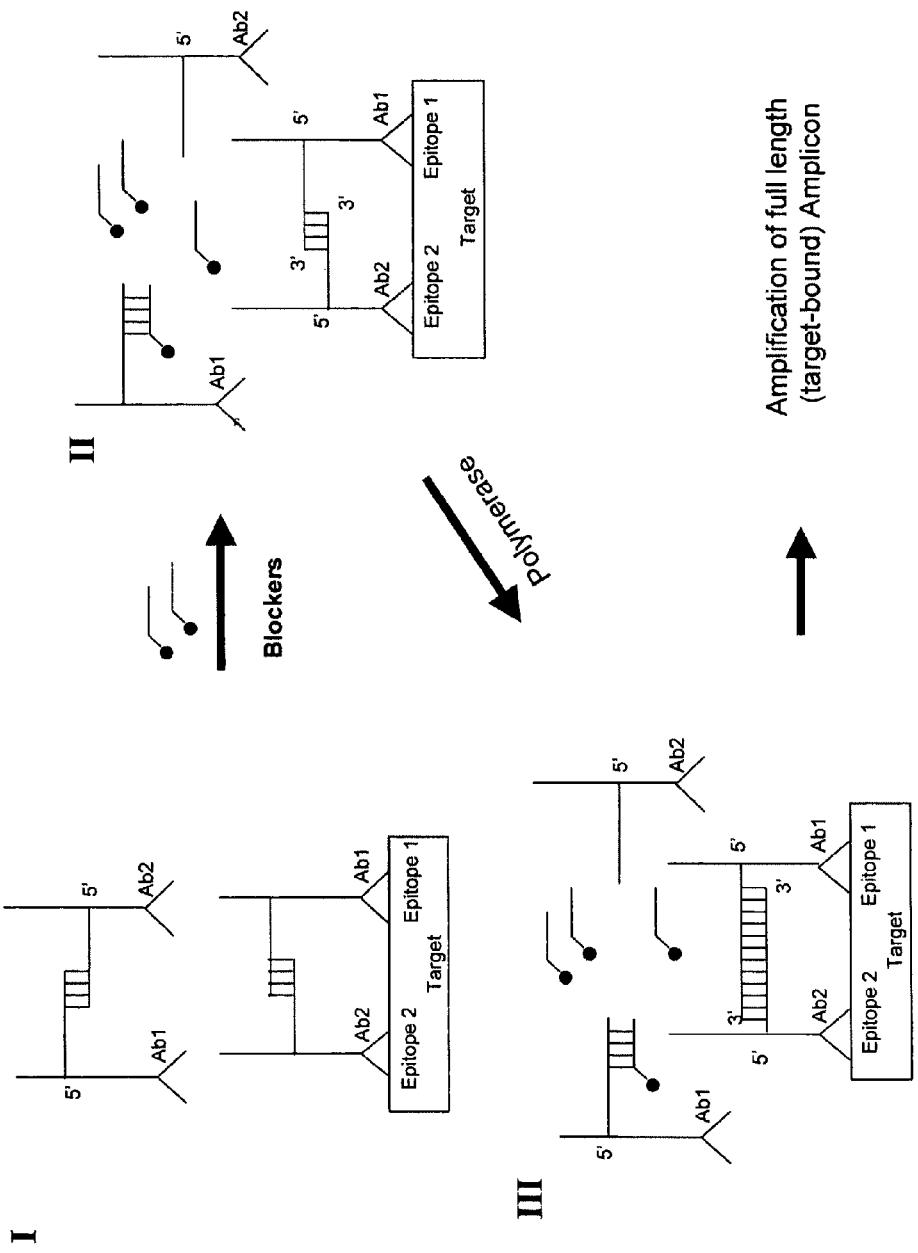

Splint oligonucleotide hybridization

Extension and displacement

RNA polymerase activity, hybridization and extension

RNase H activity, hybridization and extension

Restriction endonuclease-mediated release

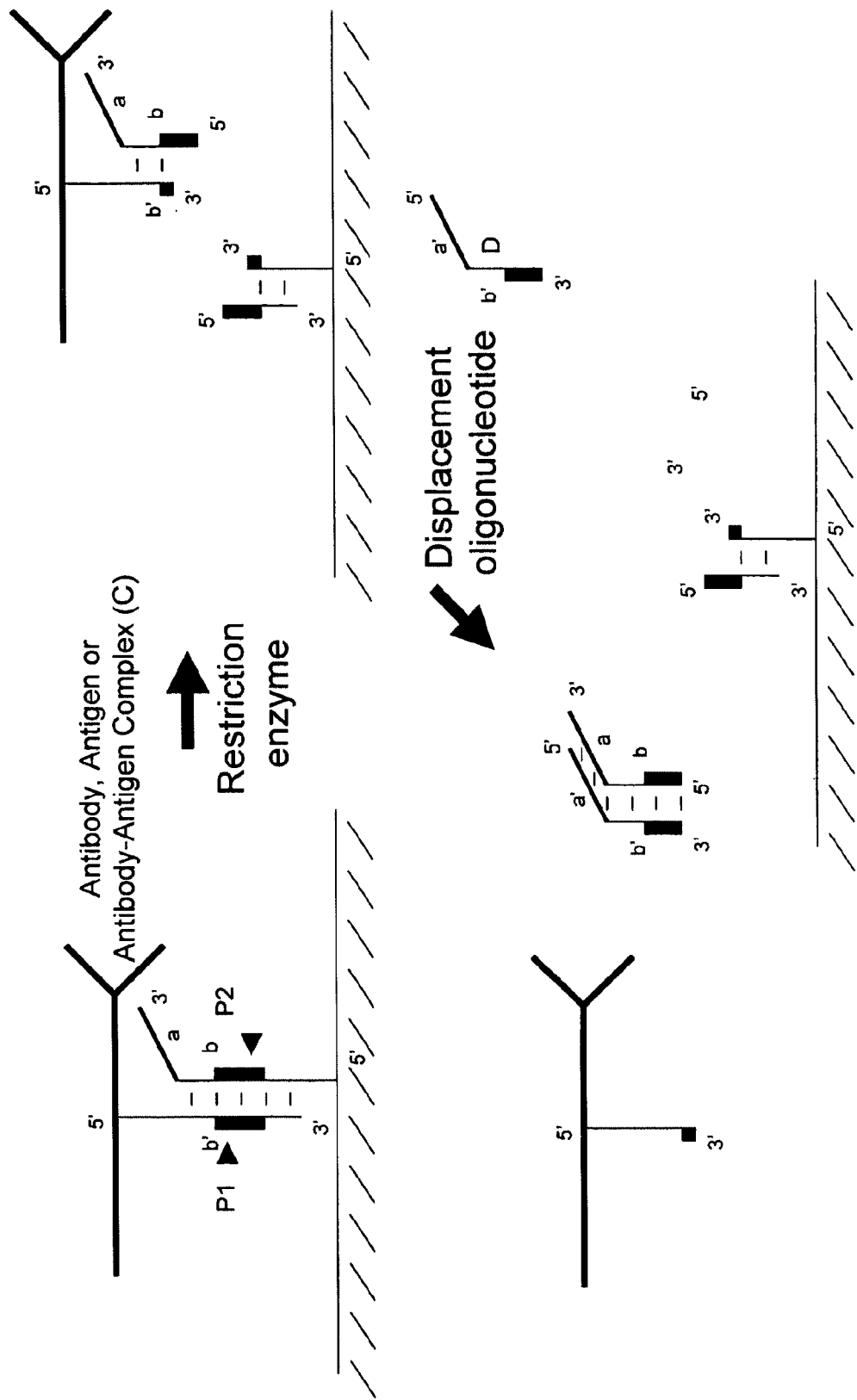

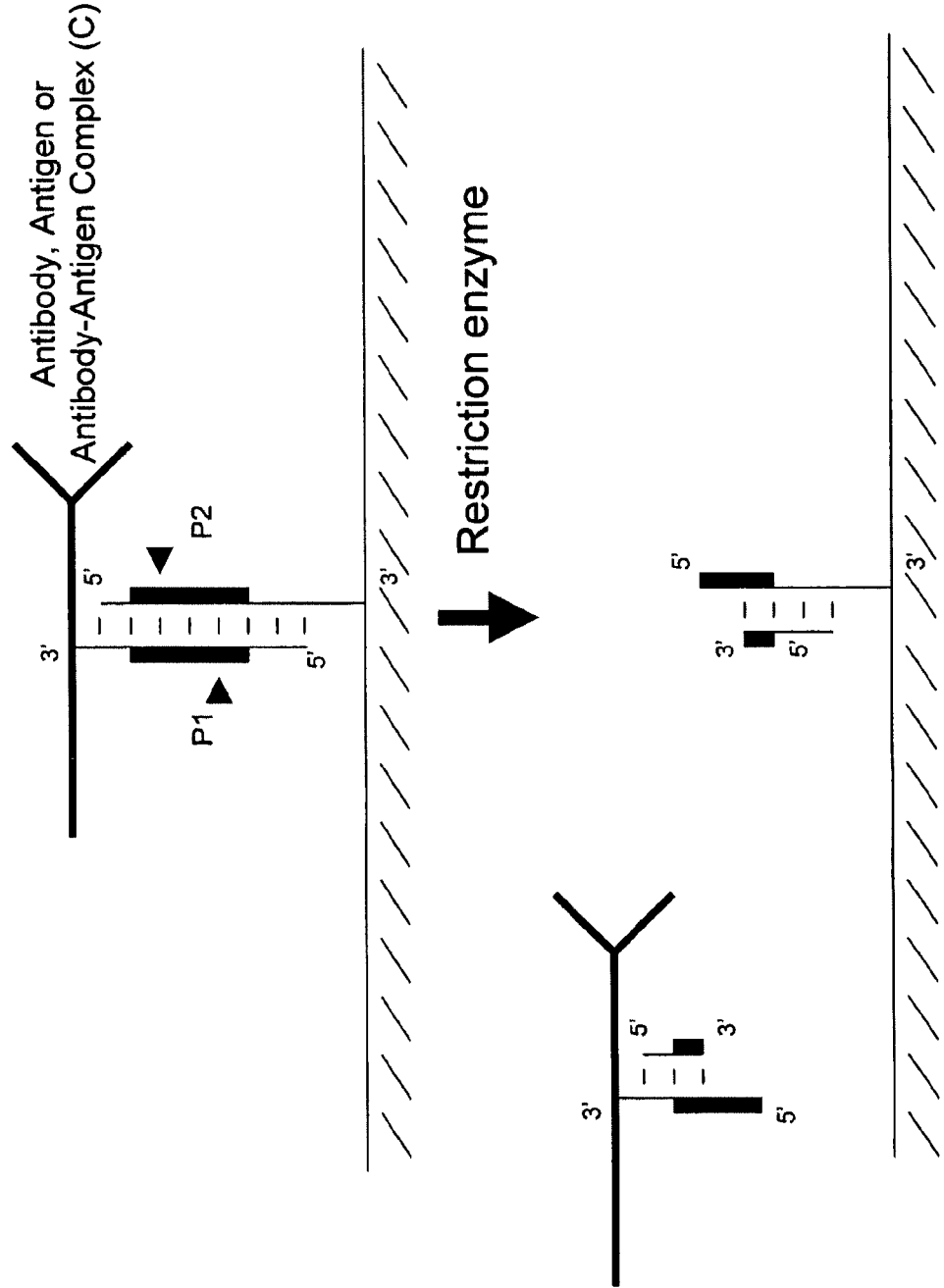

Polymerase and restriction endonuclease-mediated release

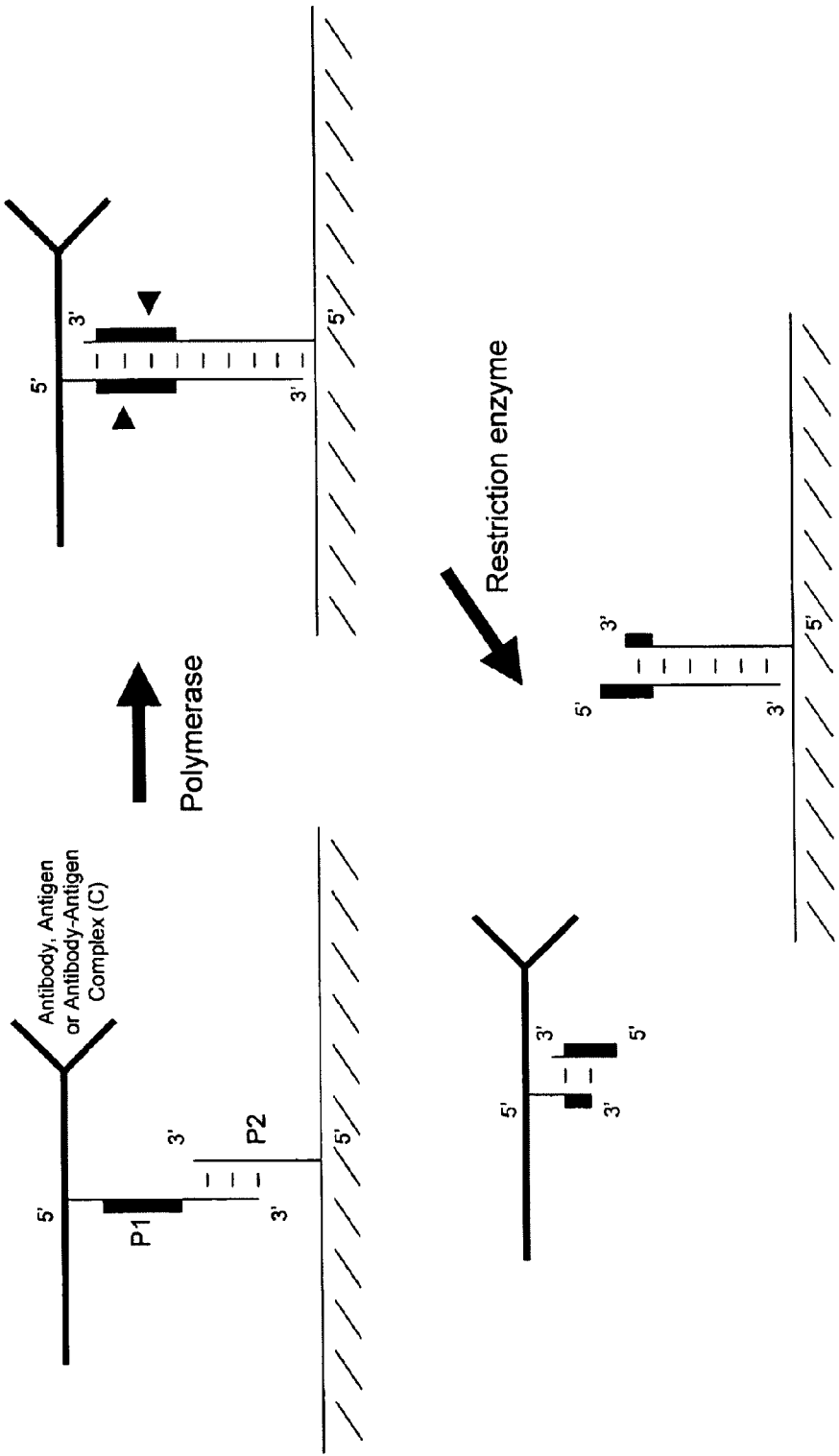

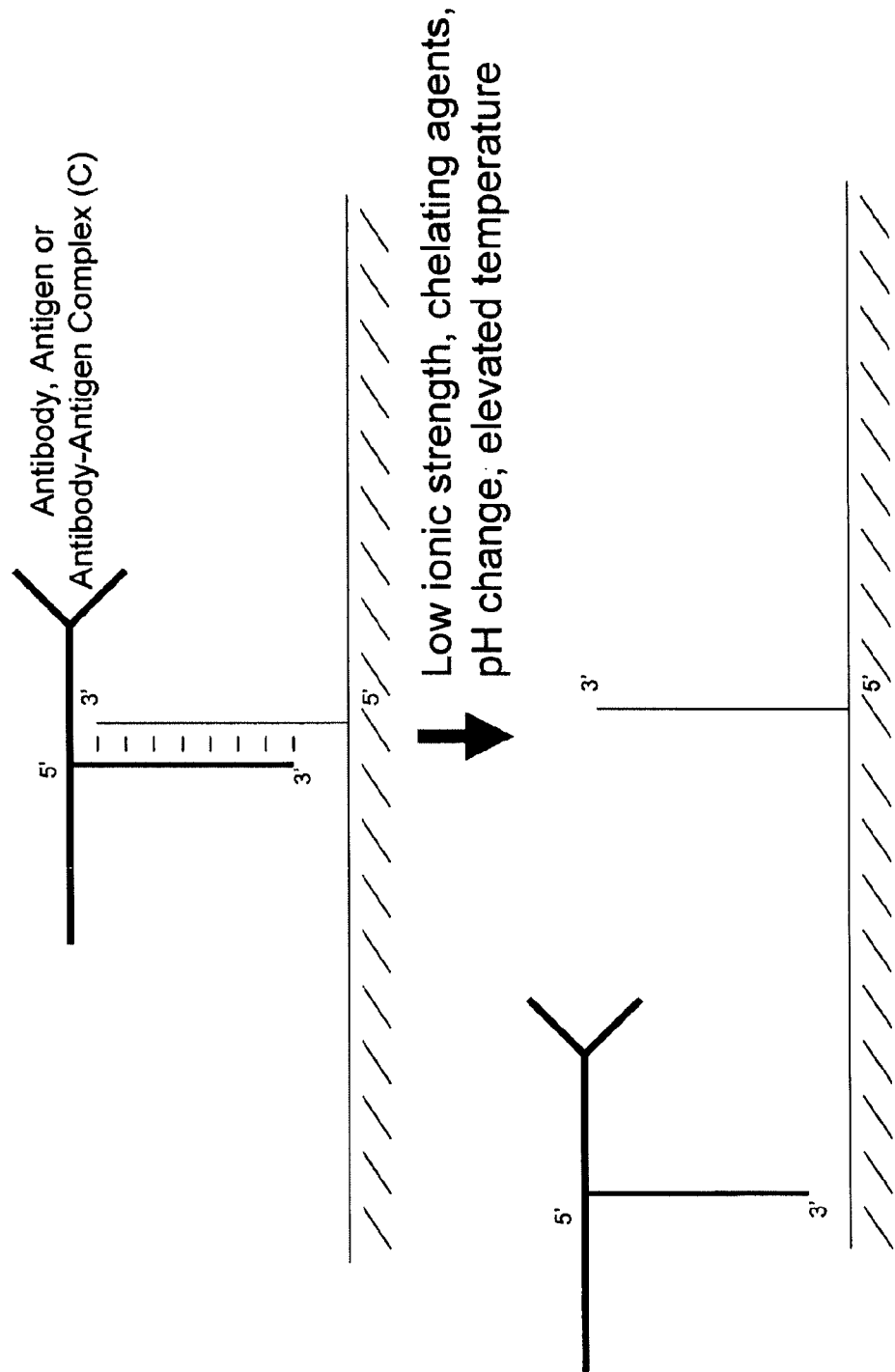

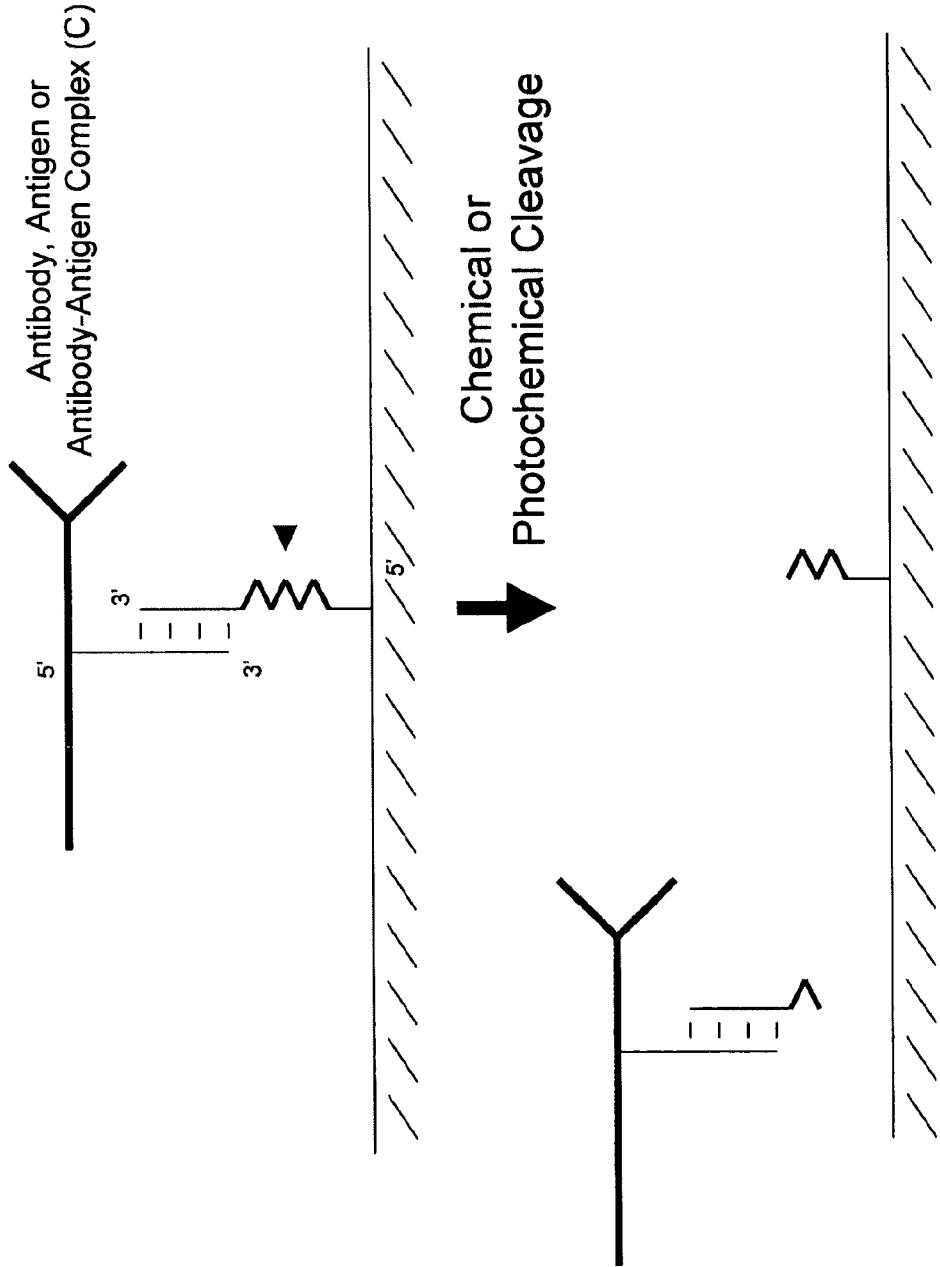

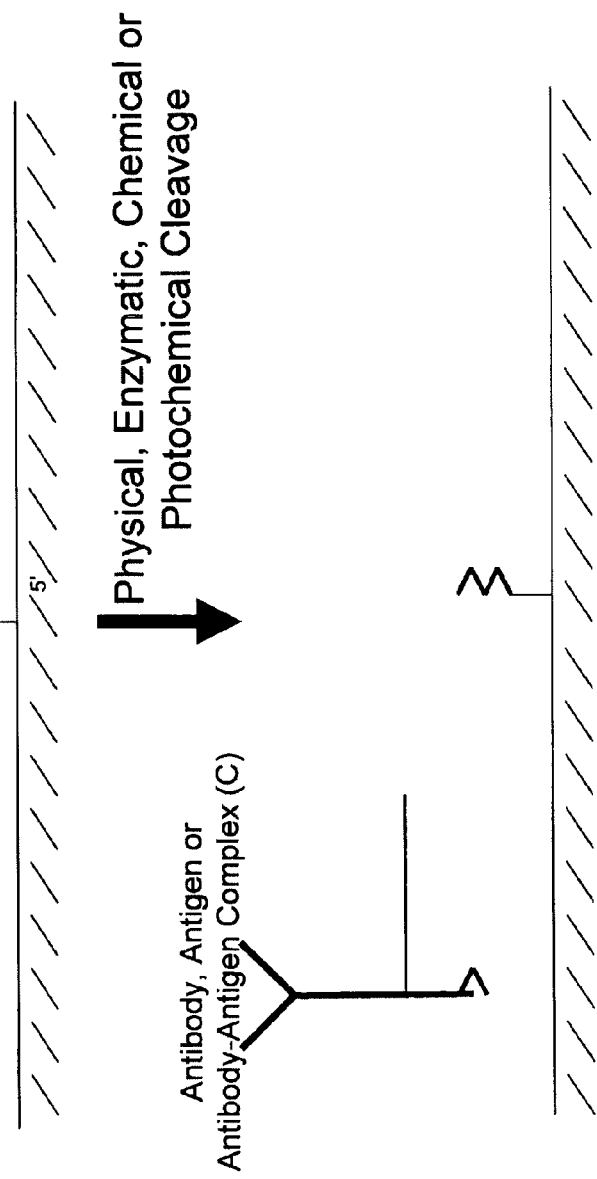

Oligonucleotide displacement

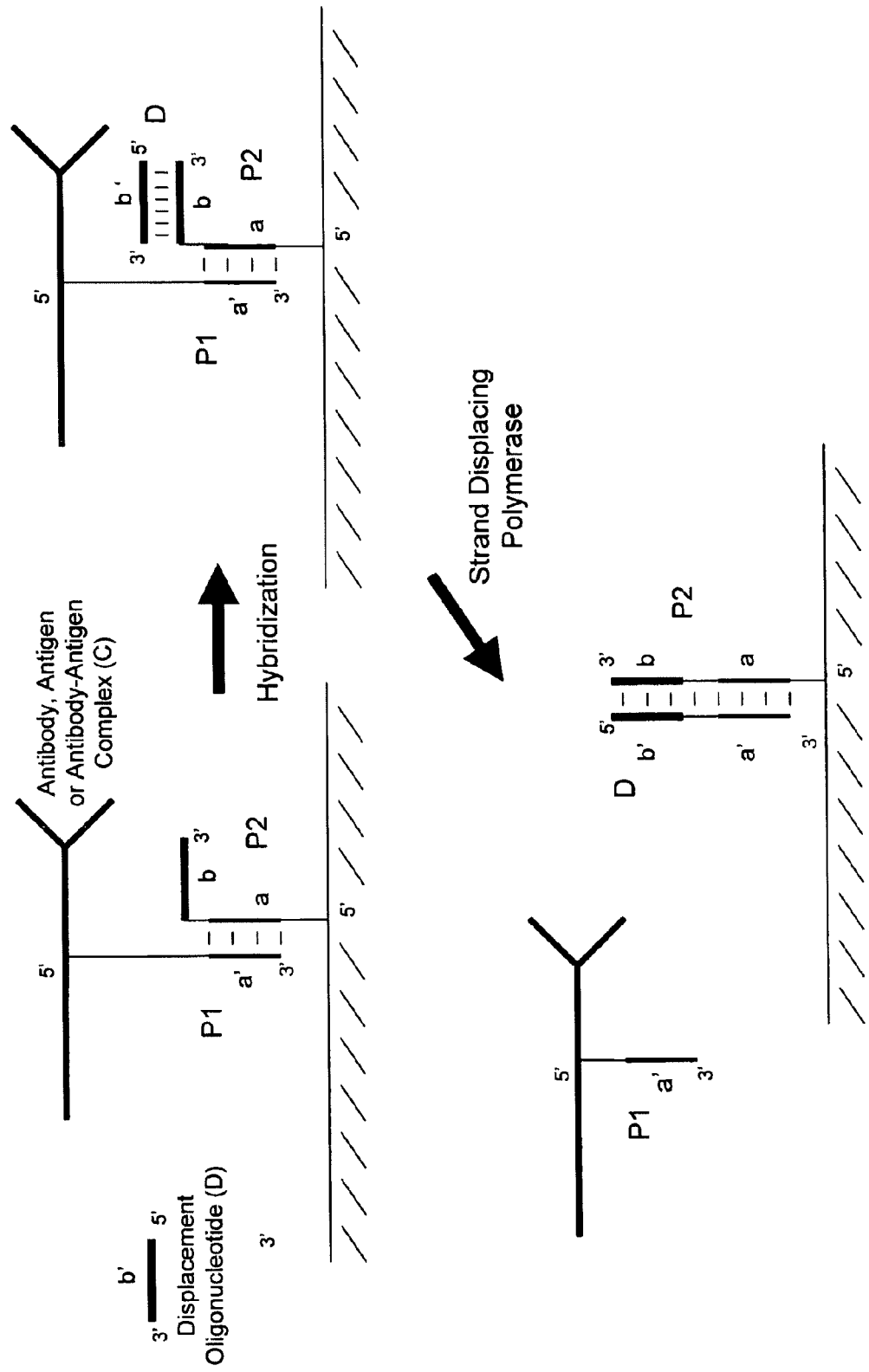

Oligonucleotide extension

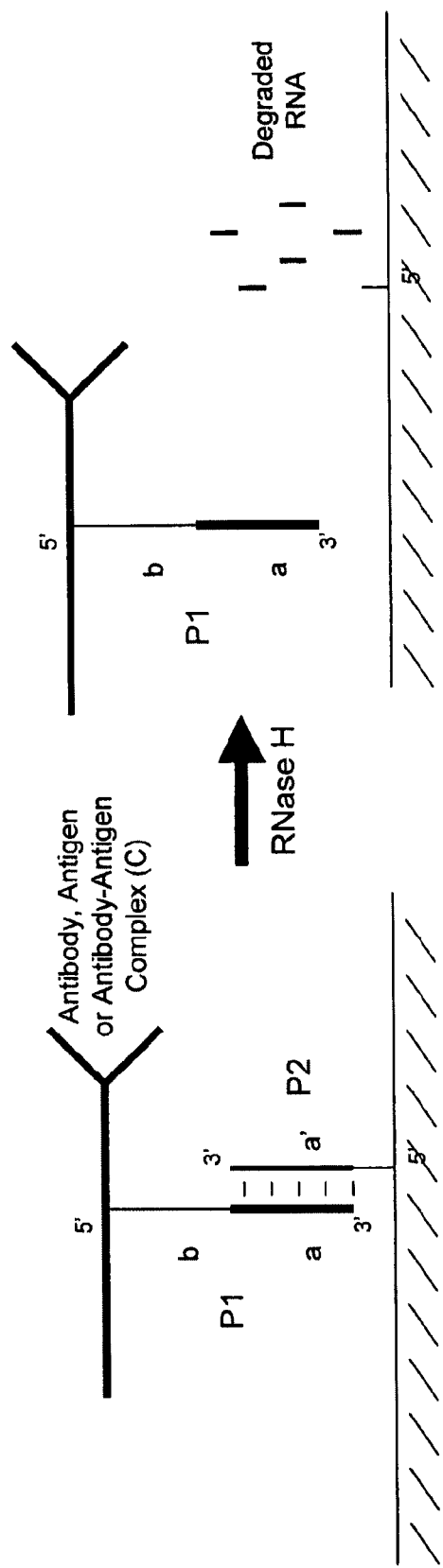

RNase H release

Self-priming capture / displacement oligonucleotide

Restriction enzyme-mediated release and formation of amplifiable target

Immobilization of antibody-probe conjugate by hybridization of a probe oligonucleotide to a capture oligonucleotide Binding of target ligand to antibody-probe conjugate immobilized by a capture oligonucleotide

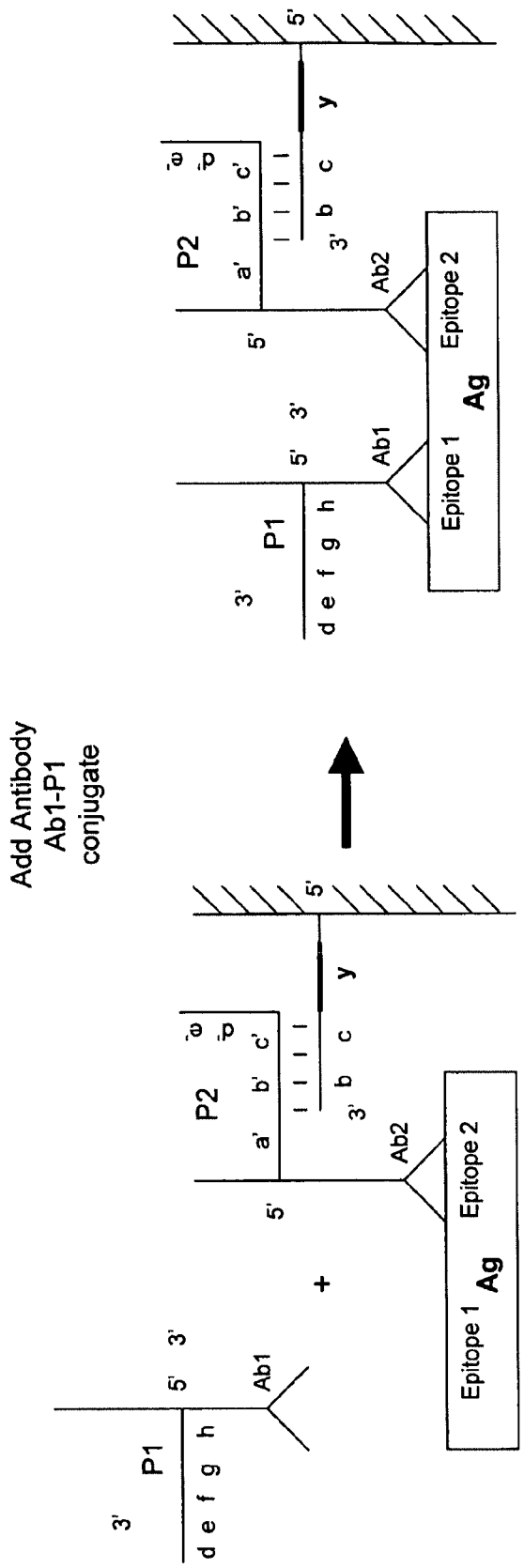

Formation of target-independent complex involving probe-probe (P1-P2) interactions

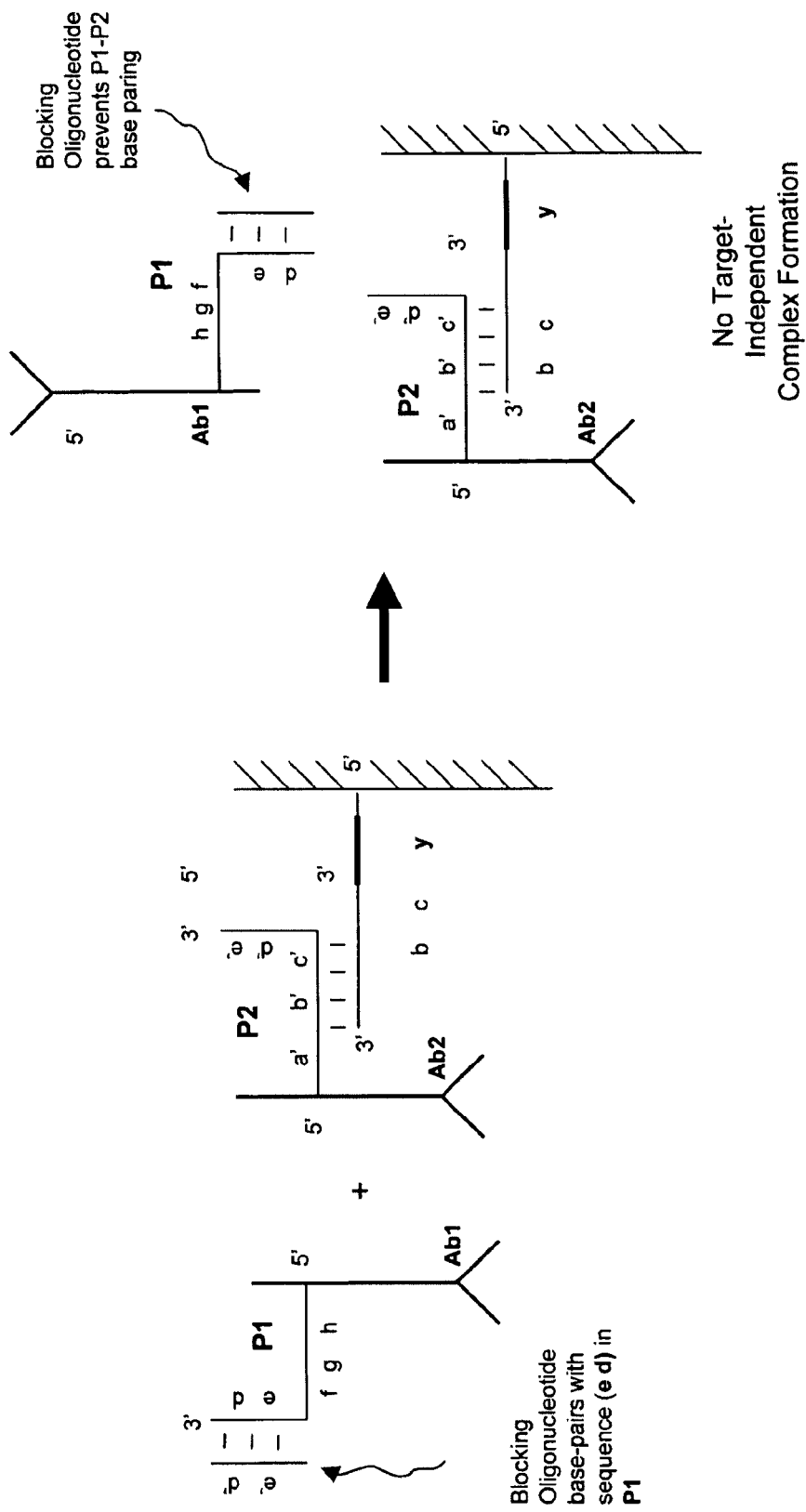

Use of blocking oligonucleotide to suppress P1-P2 interactions and prevent target-independent complex formation Use of blocking oligonucleotide to suppress P1-P2 interactions and prevent target-independent complex formation

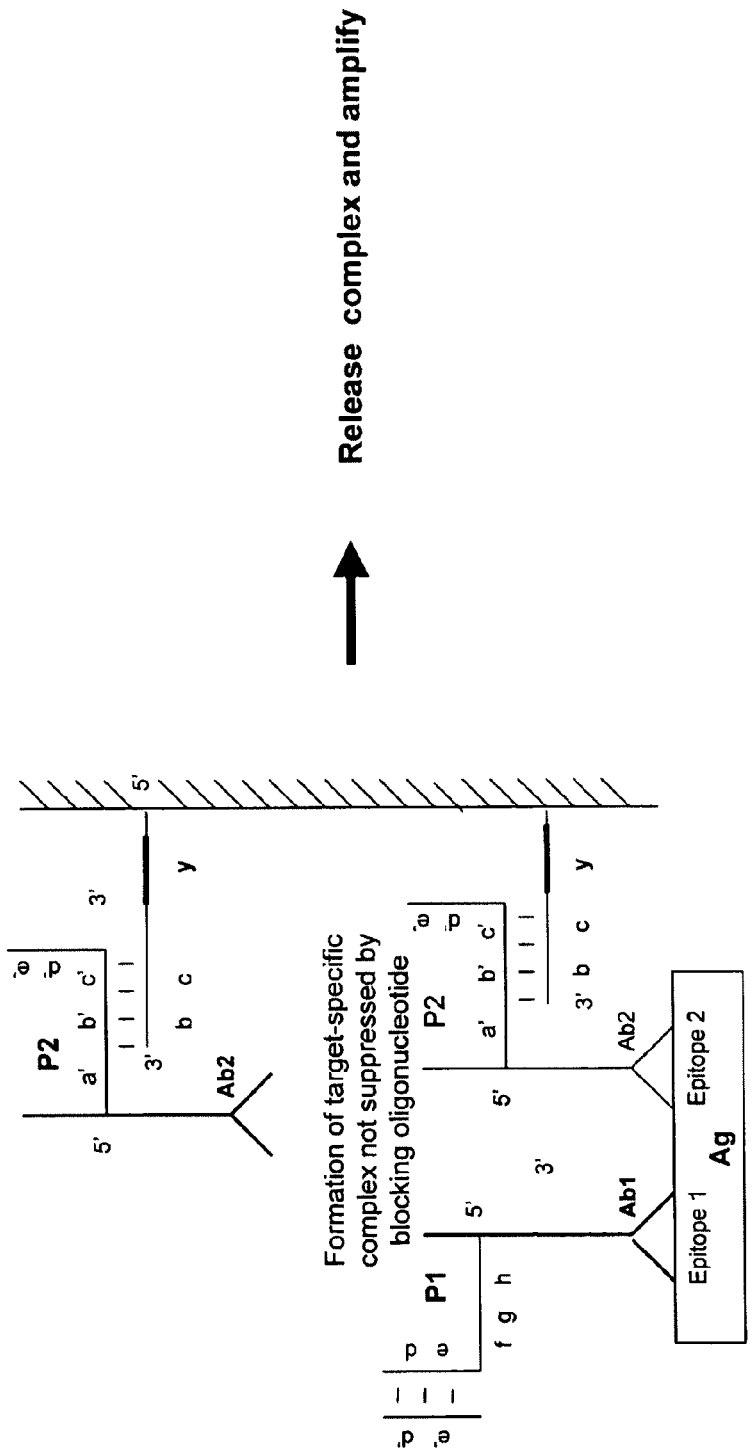

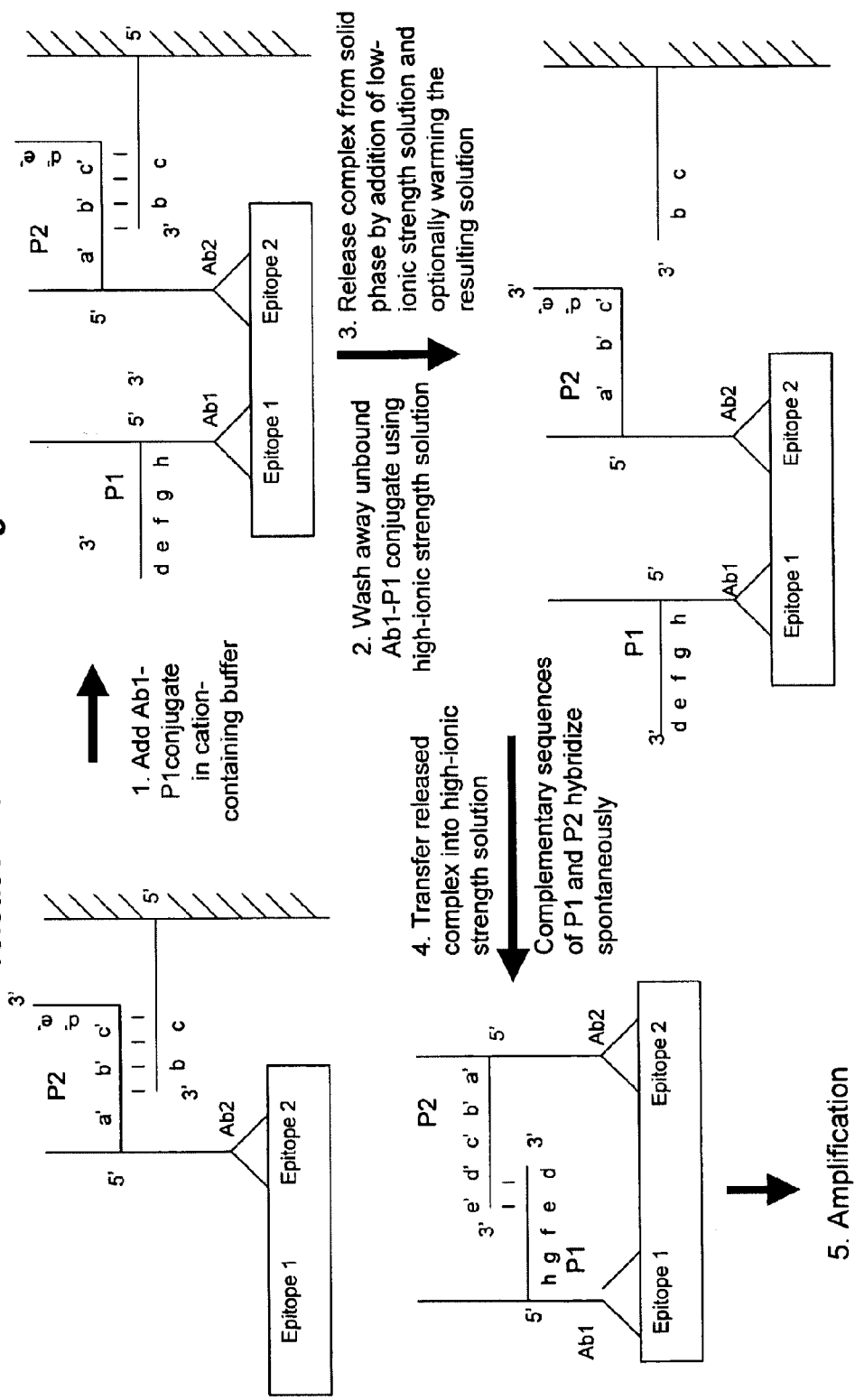

Heterogeneous formation and displacement of amplifiable complex

Heterogeneous immuno-amplification

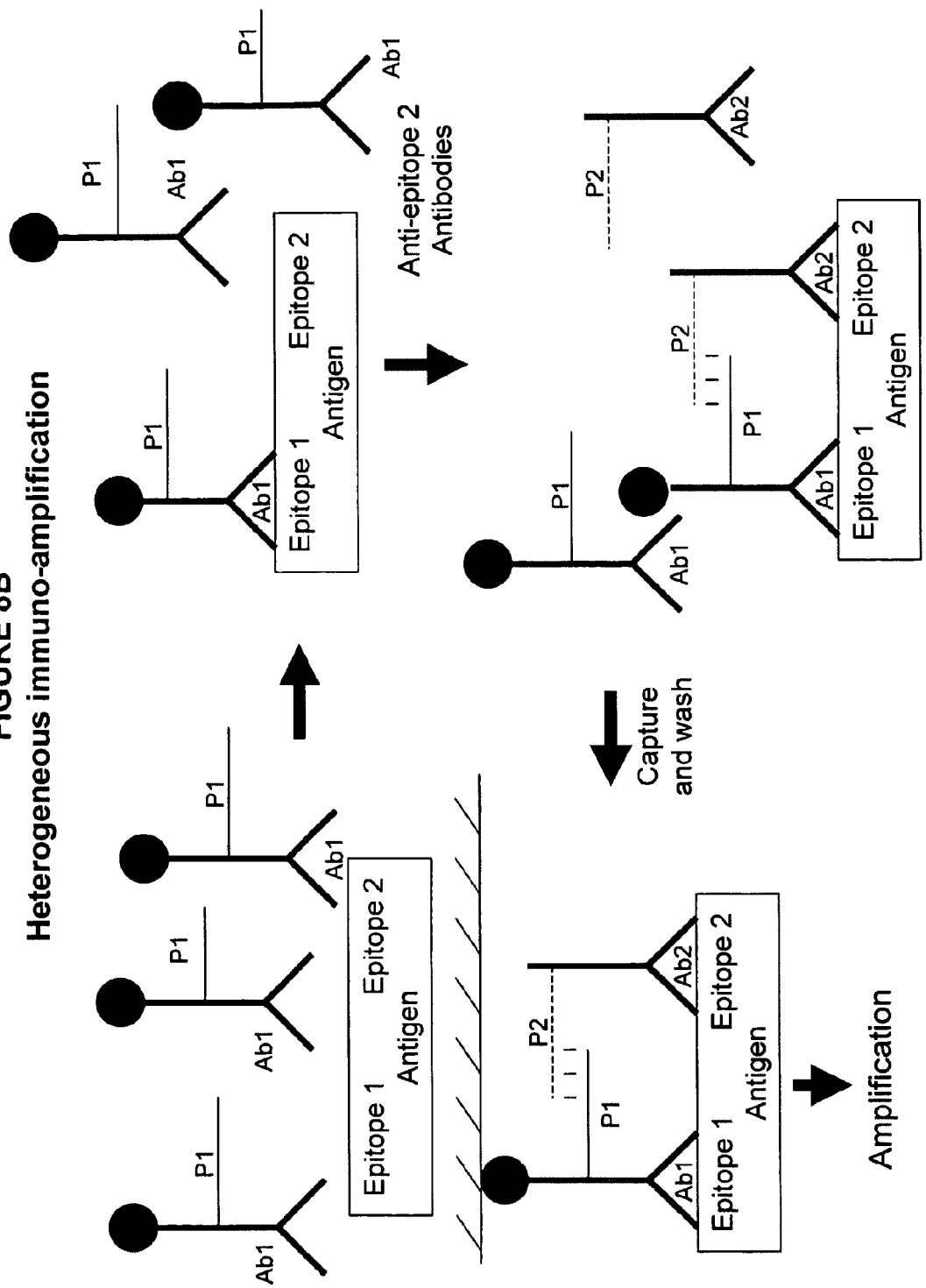

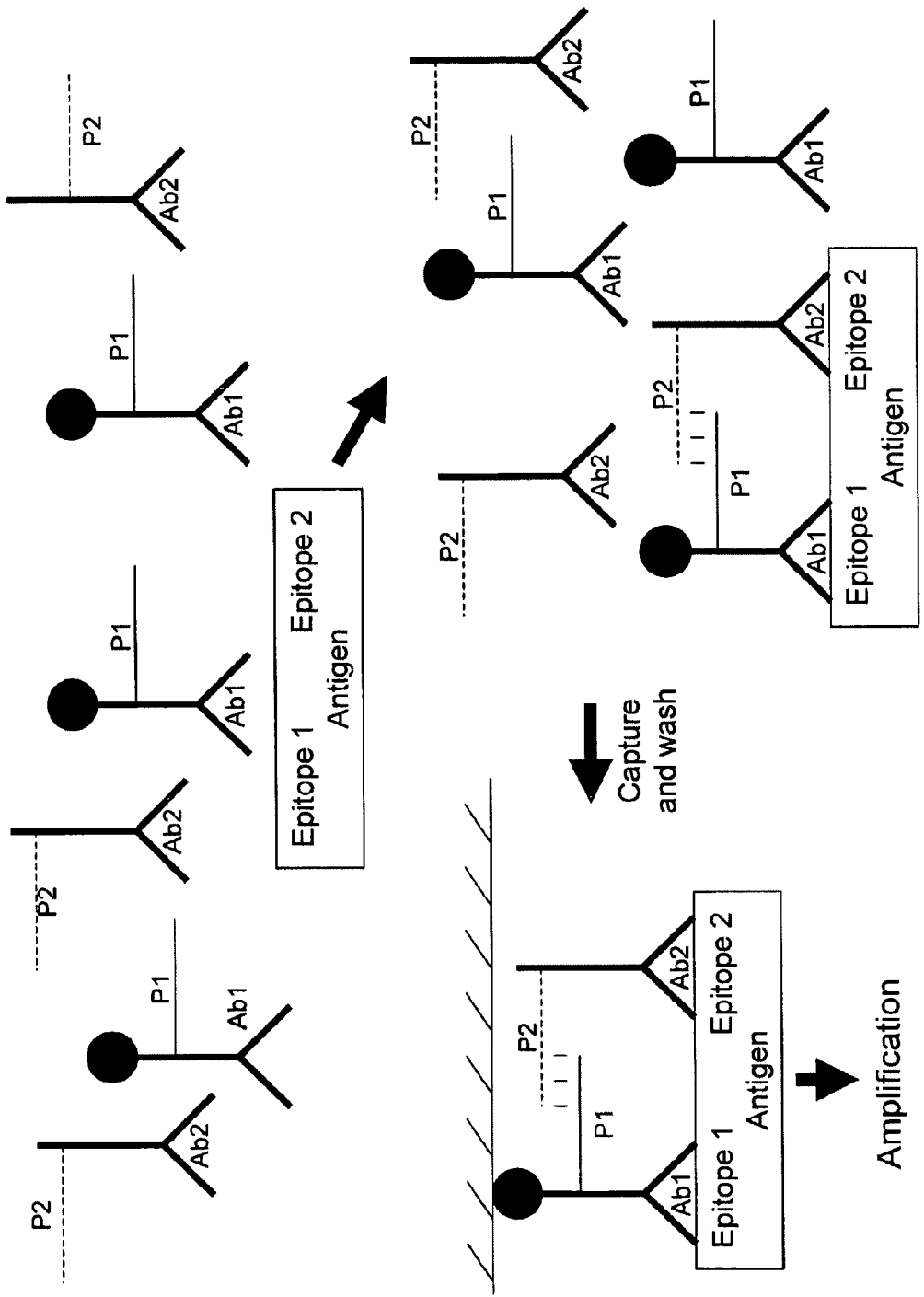
FIGURE 8C: Heterogeneous immuno-amplification

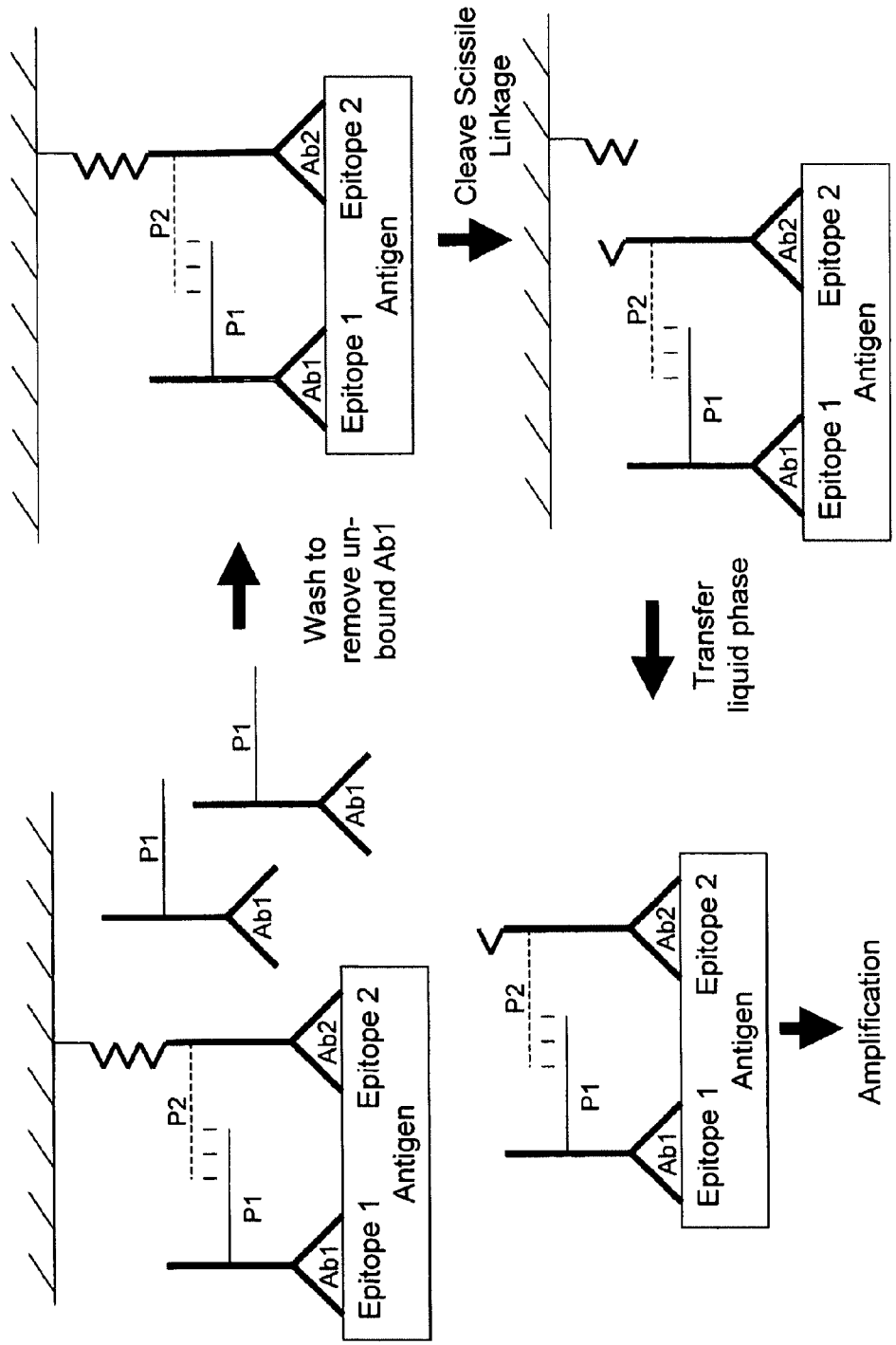

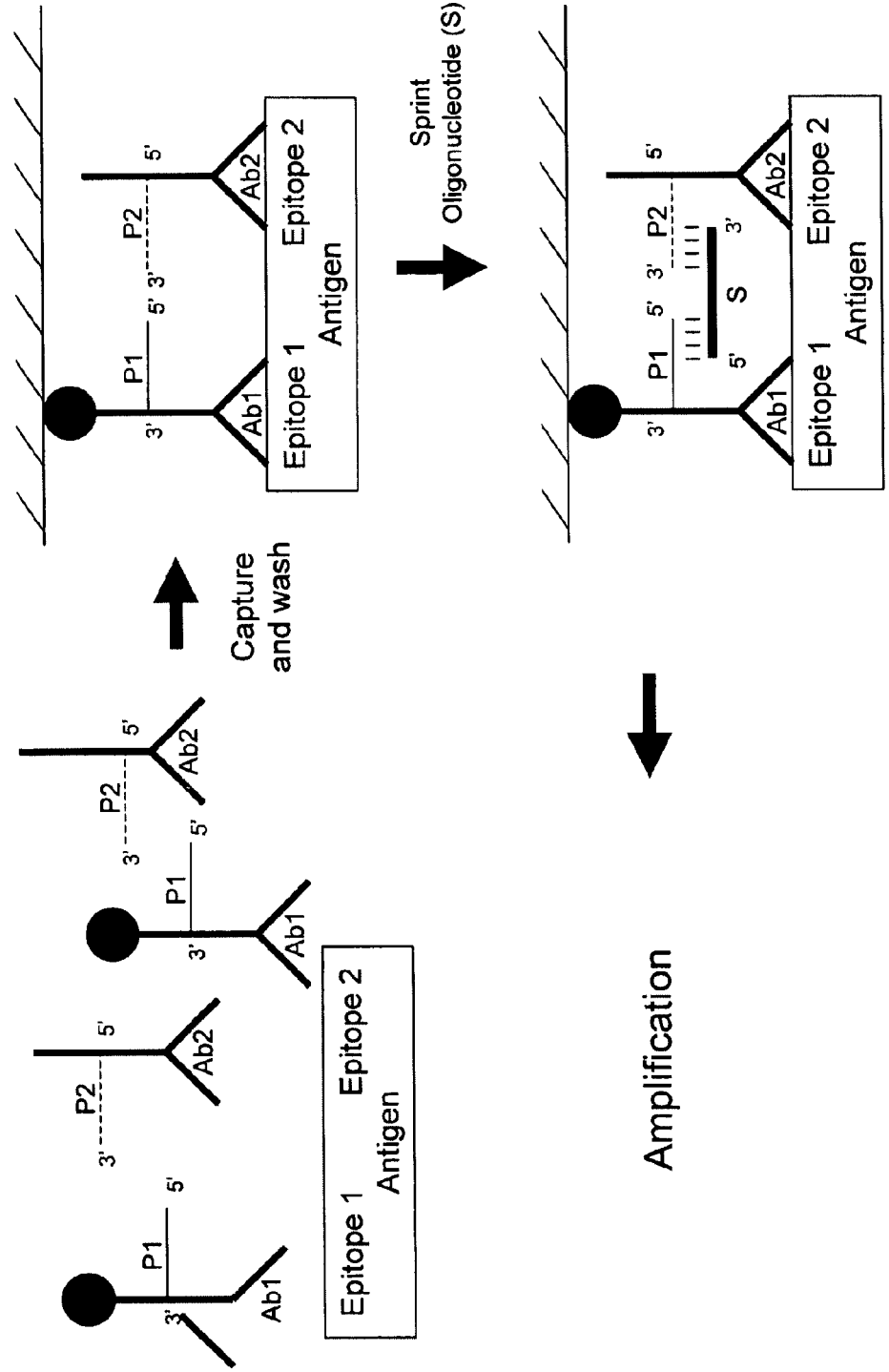

Universal immuno-amplification system

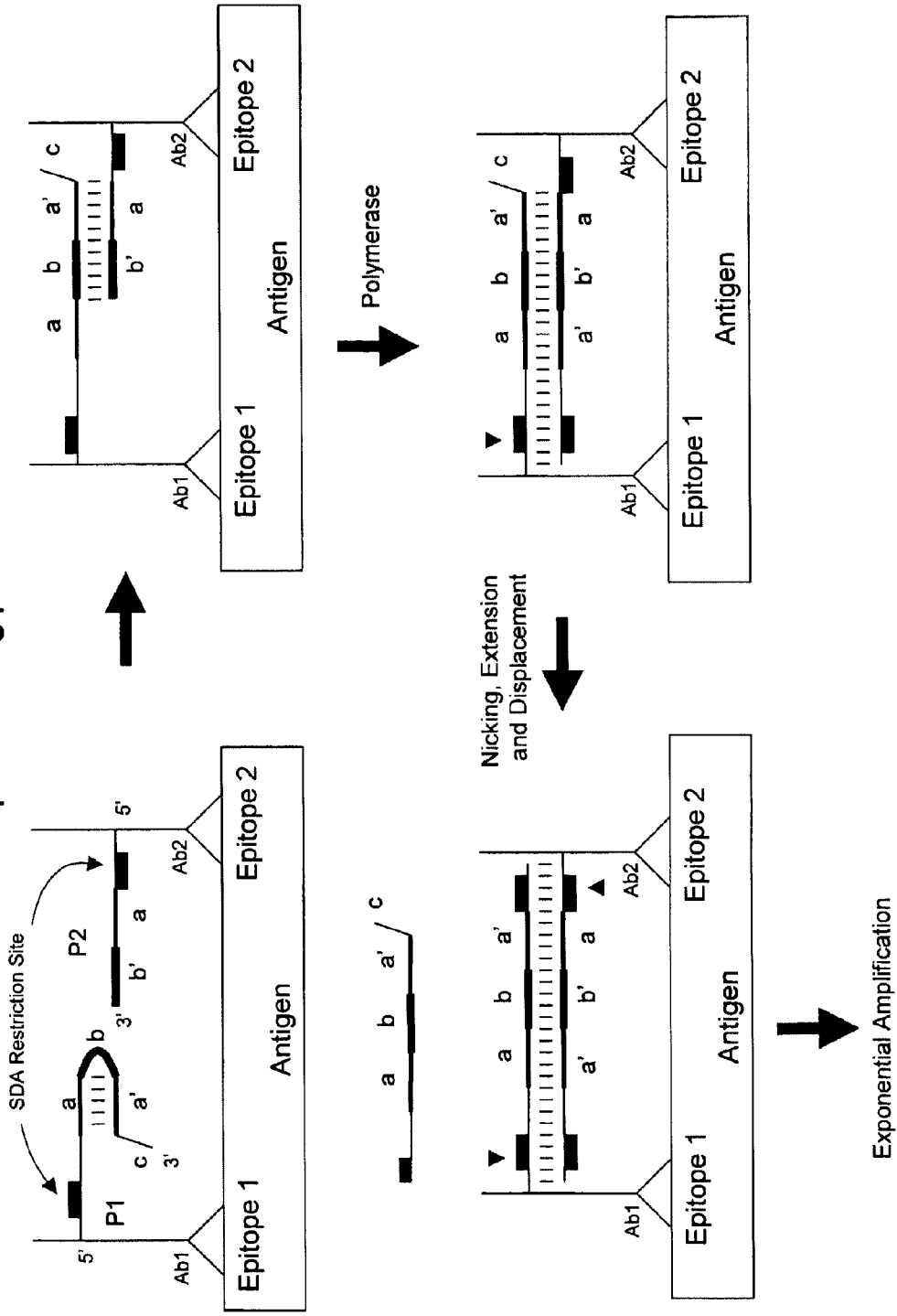

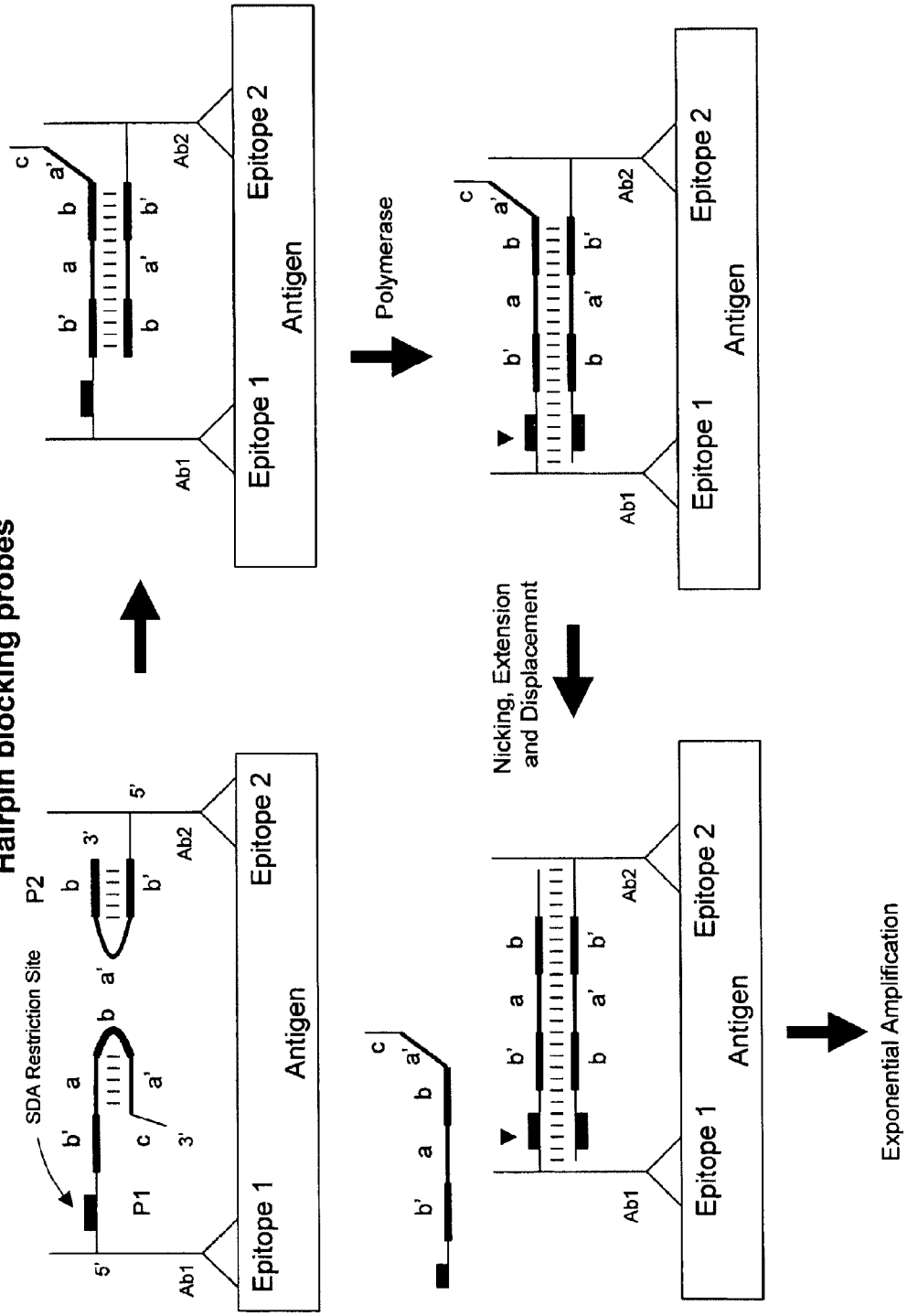

Displacement of hairpin blocking probes

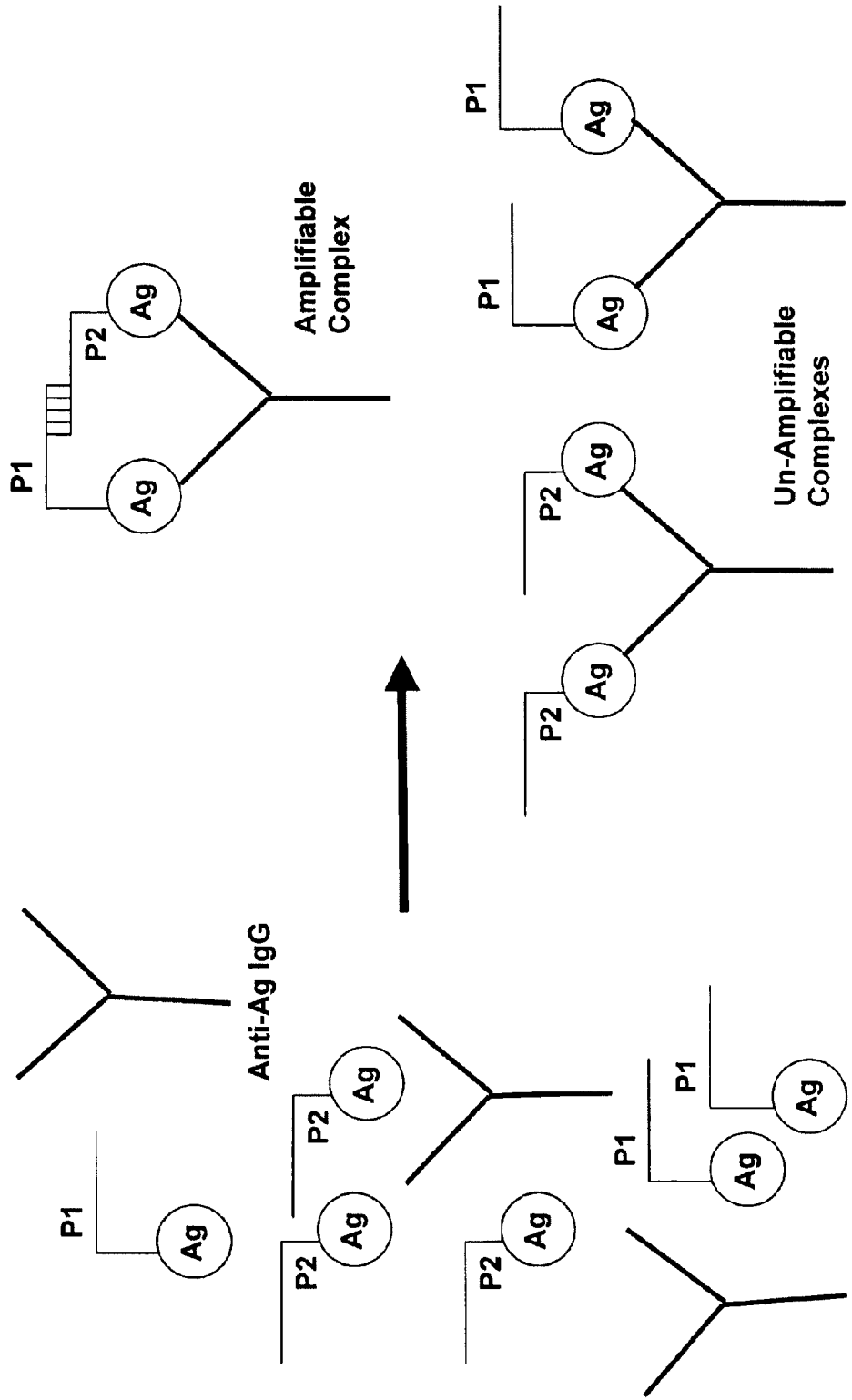

Map of probes, primers, tether oligos for binary immuno-SDA

Immuno-SDA using capped oligonucleotide probes: Mixing of antigens and oligonucleotide-conjugated antibodies Hybridization of adjacent probes Polymerase extension and restriction enzyme nicking Extension from nick and displacement of 3'-capped fragment

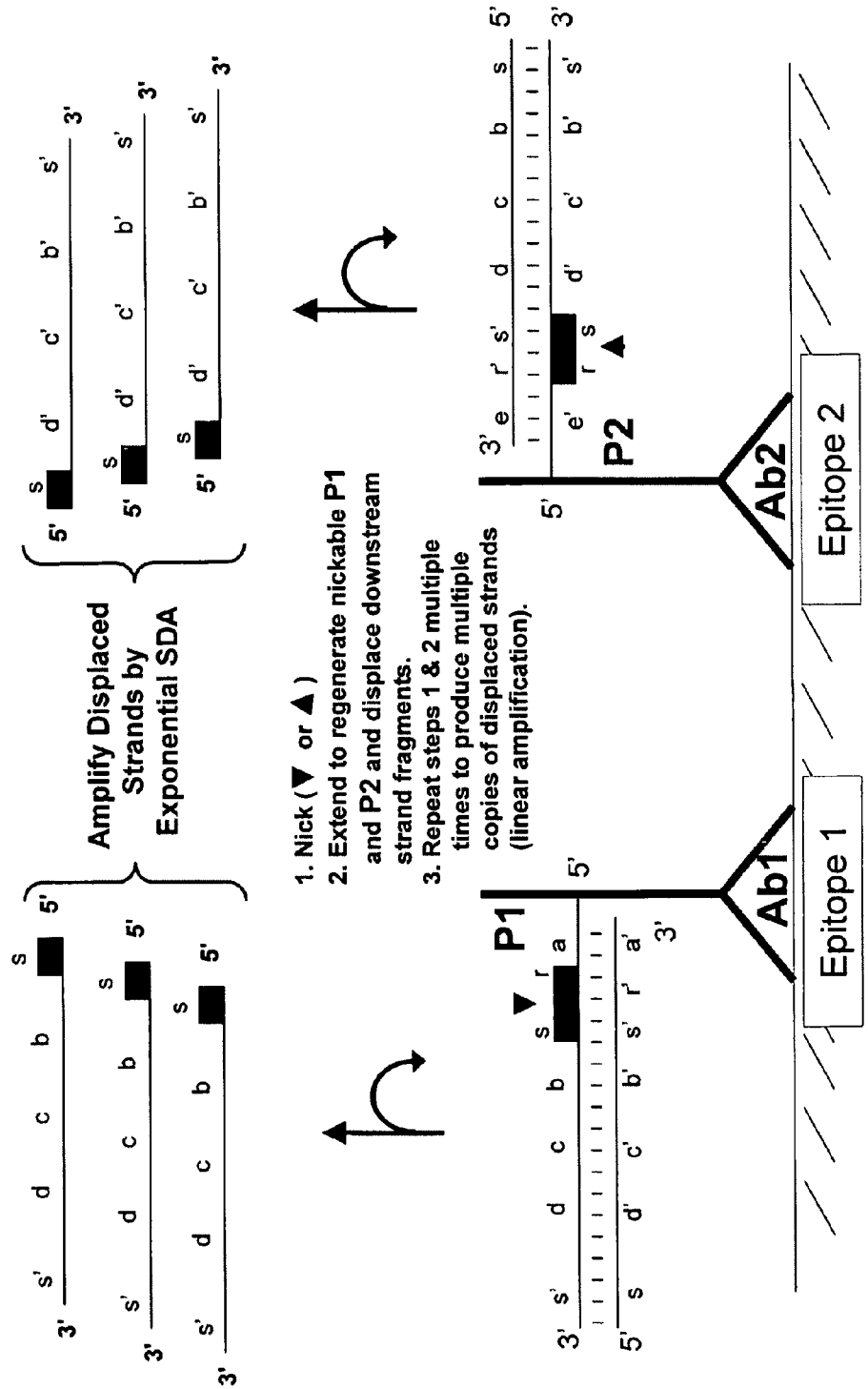
FIGURE 14E: Nicking, extension and displacement to produce amplifiable strands

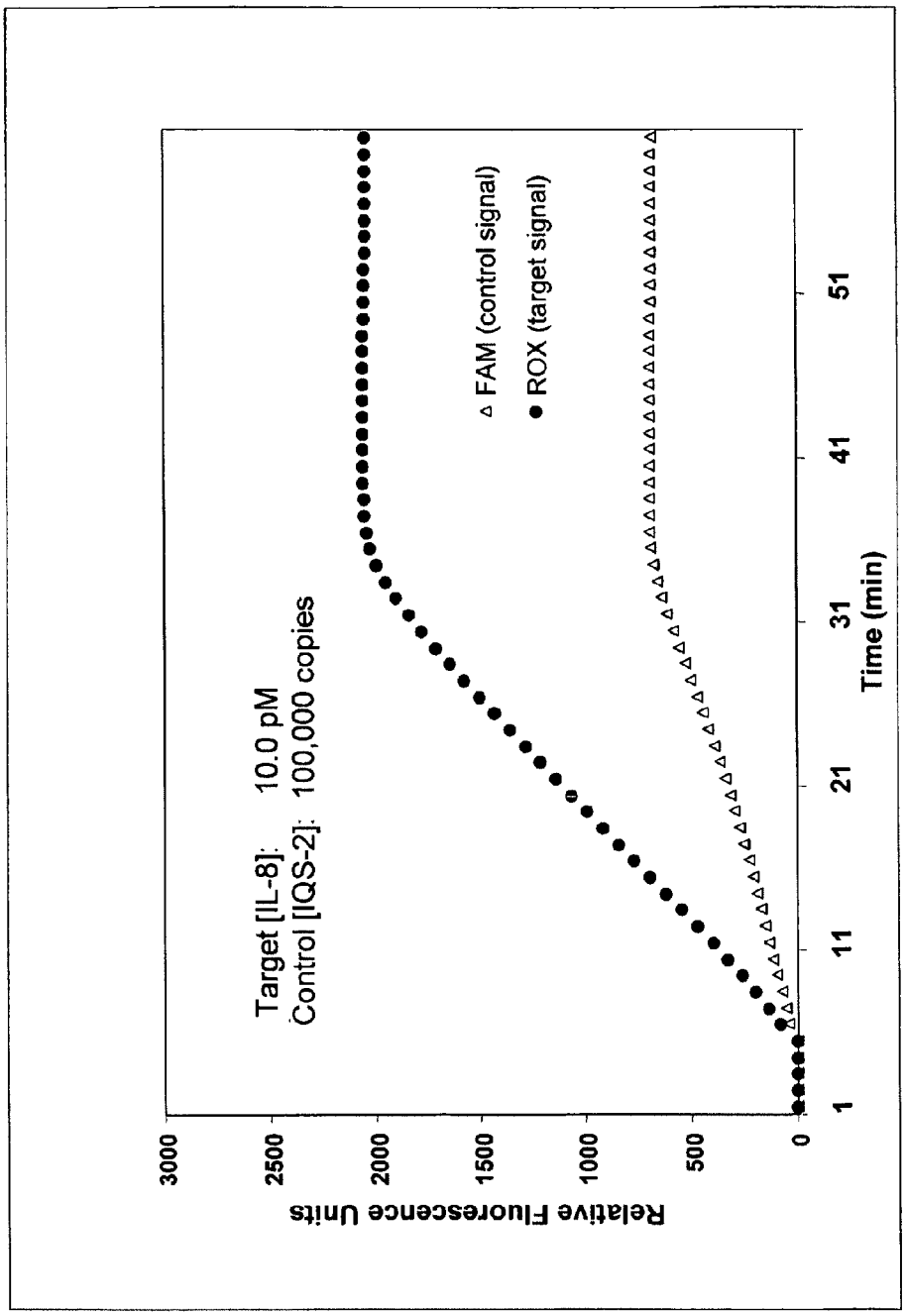

Calibration line for quantification of IL-8

IMMUNO-AMPLIFICATION

CROSS-REFERENCE TO RELATED APPLICATIONS

This application is a divisional of U.S. patent application Ser. No. 10/826,654, filed on Apr. 19, 2004, now 7,932,060 B2, issued Apr. 26, 2011, which claims the benefit of the filing date of U.S. Provisional Patent Application No. 60/463,712, filed Apr. 18, 2003, the disclosures of which are incorporated herein by reference.

FIELD OF THE INVENTION

The invention relates to the novel application of analyte-specific binding components and nucleic acid amplification to provide an ultra-sensitive, high-throughput assay to detect and quantify an analyte in solution.

BACKGROUND OF THE INVENTION

A primary goal in the areas of detection and quantification of analytes of interest is to develop a highly specific and sensitive assay system, capable of detecting minute quantities of an analyte in a complex milieu, such as blood, serum, plasma, urine or other bodily fluids. Because diagnostically significant molecules may constitute or be present in extremely minute amounts relative to the other components in a bodily fluid, an acceptable assay format must discriminate analytes that may represent a fraction of a percent of total biomaterial within a sample. Conventional procedures use analyte-specific antibodies to provide the requisite discrimination, but antibodies are limited by their cross-reactivity with other non-targeted analytes. Even for antibodies with high specificities, a small degree of cross-reactivity could pose insurmountable problems if the analyte is present at minute quantities in a milieu rich in an analyte that binds the antibody with a low affinity.

Immuno-amplification has been used as a means of increasing the sensitivity of immunoassays. In this procedure, an antigen is contacted with an antibody that is conjugated to a DNA marker molecule, which can be amplified. Instead of detecting the presence of the antibody by conventional procedures, such as labeling the antibody-antigen complex with a detectably labeled anti-antibody, the antigen-antibody-marker conjugate is detected indirectly through the amplification of the DNA marker by a polymerase chain reaction ("PCR"). The amplified DNA then may be detected through conventional methods, such as the use of dyes that fluoresce when they intercalate into double-stranded DNA. This method, known as "immuno-PCR," has been used to increase the theoretical sensitivity of immunoassays by over 10,000-fold relative to conventional assays that use anti-antibodies for detection; however, in practice the sensitivity of immuno-PCR is limited by non-specific binding of the antibody-nucleic acid conjugate to other analytes or to the surfaces of the supports used to house the reaction. Further, samples may become contaminated by residual amplified labels ("amplicons") left over from previous reactions. This is problematic for applying this technique to clinically acceptable, high-throughput assays.

Several efforts have been made to alleviate these problems. For instance, investigators have used an immobilized antibody to capture the antibody-nucleic acid-antigen complex to a solid support, which facilitates the removal of non-complexed antigens and unbound antibody-nucleic acid conjugates prior to DNA amplification. In another case, two antibodies that are specific for different determinants of an antigen can be brought into proximity by binding the antigen. Each antibody is modified with a single-stranded oligonucleotide moiety that may hybridize with an oligonucleotide of an adjacent antibody-oligonucleotide conjugate to form a double-stranded region. The hybridization of the oligonucleotide moieties is facilitated by the proximity of the two antibodies when they are bound to the same antigen. The double-stranded region of DNA is then targeted for amplification to produce a detectable signal that indicates the presence of the antigen. This technique advantageously improves the sensitivity of detection because non-specific binding of either antibody alone is insufficient to allow the formation of the amplicon; however, the sensitivity of this method may be limited by, among other things, the non-specific interaction of the antibody moieties with each other, which leads to spurious, antigen-independent amplicon formation.

Accordingly, there is a continuing need in the art to provide even more sensitive methods of analyte detection and quantification. Methods that are useful in a clinical environment preferably are extremely selective for the desired analyte and easily adapted to high-throughout screening methodologies.

SUMMARY OF THE INVENTION

The present invention meets these needs by providing a high sensitivity, low background assay that offers a streamlined workflow suitable for high-throughput assays. The assay of the present invention detects and quantifies analytes by forming an analyte-specific amplicon through the interaction of two "analyte-specific binding entities," such as antibodies (a "proximity pair"), to different epitopes of the same analyte or to epitopes in analytes in close proximity. Each member of the proximity pair (a "proximity member") comprises an analyte-specific binding entity that is conjugated to a single-stranded nucleic acid, preferably DNA (an "oligonucleotide moiety" or "probe"). The oligonucleotide moieties form an amplicon, directly or indirectly, when the proximity members are brought into close contact through the interaction with a target or analyte(s) ("target" and "analyte" are used interchangeably throughout). Interaction of the proximity members with the analyte brings the oligonucleotide moieties into close proximity, raising their effective local concentration relative to the concentration of the oligonucleotide moieties of proximity members that are not bound to an analyte. This concentration effect greatly facilitates the interaction of the two oligonucleotide moieties to form an amplicon relative to the oligonucleotide moieties of unbound proximity members. The proximity pair-analyte complex then is detected by amplification of the amplicon, using DNA amplification technologies that are well-known in the art. Amplicon formation, therefore, is highly sensitive to the presence of the target because oligonucleotide moieties that have not interacted with other oligonucleotide moieties are incapable of being amplified, and the formation of the amplicon is greatly facilitated by the increase in local concentration of oligonucleotide moieties in the proximity pair-analyte complex.

The sensitivity of the assay of the present invention is advantageously improved by preventing spurious and unwanted amplicon formation between proximity members in solution that are not complexed with an analyte. The present invention accomplishes this goal in part by providing one or more hybridization blocker oligonucleotides (or "hybridization blockers"), which hybridize to one or both of the oligonucleotide moieties of the proximity members. The hybridization blocker advantageously prohibits amplicon formation in solution between proximity members that are not complexed with an analyte. A method of using hybridization blockers comprises contacting an analyte with a first and second proximity member in a reaction mixture, where the oligonucleotide moiety of at least one of the proximity members hybridizes to the hybridization blocker. The mixture is warmed or the ionic strength is reduced sufficiently to cause the hybridization blocker to dissociate, and the mixture is then cooled or the ionic strength of the mixture is increased, allowing amplicons to form between analyte-bound proximity members. In one embodiment, a majority of the analyte-bound proximity members remain bound to the analyte during the warming step. In another embodiment, the hybridization blocker is added in molar excess over the oligonucleotide moieties of the proximity members. In yet another embodiment, the hybridization blocker hybridizes to a "splint oligonucleotide," making the splint oligonucleotide unable to hybridize to an oligonucleotide moiety of a proximity member. In a further embodiment, the hybridization blocker is removed from the oligonucleotide moiety of a proximity member by hybridizing with a complementary sequence, also referred to as a "deblocker oligonucleotide" (or a "deblocker"). That is, the deblocker, when added in excess, sequesters the hybridization blocker in a duplex so that the hybridization blocker is not as capable of hybridizing to the oligonucleotide moiety or to a splint oligonucleotide. The deblocker, therefore, reduces the presence of a hybrid between the hybridization blocker oligonucleotide and its complementary sequences.

The hybridization blocker may comprise a hairpin loop at one of its termini, where the hairpin structure serves as a double-stranded "primer" for DNA polymerase. For the purposes of the present invention, a "primer" is defined as a short stretch of nucleotides, typically of DNA, that can hybridize to one strand of a template nucleic acid. The double-stranded hybrid between the primer and its complementary sequence provides an initiation site for the extension of the primer by a DNA polymerase or reverse transcriptase, or for synthesis of RNA molecules by RNA polymerase. The hybridization blocker may hybridize to the oligonucleotide moiety at a region downstream of the hairpin structure, so that extension by DNA polymerase removes the hybridization blocker from the oligonucleotide moiety by strand displacement. This embodiment advantageously allows the hybridization blocker to be removed from the oligonucleotide moiety or splint oligonucleotide without the necessity of warming the reaction mixture, thereby avoiding or reducing dissociation of the proximity member with the analyte. In another embodiment, the hybridization blocker is added after the formation of a proximity pair-analyte complex and after the oligonucleotide moieties of the proximity pair have hybridized with each other. The hybridization blocker hybridizes to the oligonucleotide moiety of at least one of the proximity members still in solution, thereby preventing analyte-independent formation of amplicons by proximity pairs not bound to an analyte. In this embodiment as well, heating of the reaction mixture to reduce background signal is not required. Hairpin structures may also be used elsewhere. For example, one or both of the oligonucleotide moieties of the proximity members may comprise a hairpin structure that blocks the formation of the amplicon. Hybridization of oligonucleotide moieties through unpaired bases in the loop of the hairpin or adjacent to the hairpin (or, alternatively, gentle heating) disrupts the hairpin structure, thereby allowing amplicon formation and amplification.

The background signal may be advantageously further reduced by providing a solid phase capture oligonucleotide that either prevents amplicon formation until a specific release-oligonucleotide is provided or captures the proximity pair/analyte complex to allow removal of unbound components.

Further advantages are provided by using universal reagents that can be harnessed to detect any analyte that can be bound by antibodies. For example, oligonucleotide moieties can be coupled to anti-Fc antibodies or proteins A or G, which react with the immunoglobulin constant regions of the antibody-analyte complex. In some embodiments, one or both antibodies are replaced with any suitable specific analyte-targeting entity, such as an aptamer, a ligand specific for a receptor analyte, or a receptor that is specific for a ligand analyte. This replacement of one or both antibody moieties reduces spurious amplicon formation that would otherwise result from non-specific interactions between the antibody moieties. Among other suitable specific analyte-targeting entities are functional fragments of antibodies, such as Fc, Fv, Fab' or F(ab')$_2$ fragments. The reduction in the size of the antibody structure not involved in antigen binding is believed to reduce the non-specific interactions of antibodies with each other without reducing the specific interaction with antigens or analytes.

The advantages provided by the present invention allow a high-throughout and extremely sensitive assay that can be used to detect and quantify analytes in clinically relevant samples, such as blood and other bodily fluids. Analytes that may be detected and quantified by the methods of the present invention may occur in unprecedented minute quantities in a complex mixture (e.g., a bodily fluid). In one embodiment, the present invention is used to detect about 80 fg/ml of an analyte such as a cytokine. This translates to an ability to detect a molar concentration of at least about 10 fM of such small molecular weight analytes.

The present invention accordingly provides various methods to detect and/or quantify target analytes, as well as compositions that are useful in carrying out the methods of the present invention. For example, any suitable method of amplification may be used in the methods of the invention. Such methods include, but are not limited to, PCR (described in U.S. Pat. Nos. 4,683,195; 4,683,202; 4,800,159; and 4,965,188), Strand Displacement Amplification ("SDA"; see Walker et al., Proc. Nat'l Acad. Sci. USA 89: 392 (1992); Walker et al., Nucl. Acids Res. 20: 1691 (1992); and U.S. Pat. No. 5,270,184, the disclosure of which is hereby incorporated in its entirety by reference), thermophilic Strand Displacement Amplification ("tSDA"; see U.S. Pat. Nos. 5,648,211 and 5,744,311, the disclosures of which are hereby incorporated in their entirety by reference), Self-Sustained Sequence Replication ("3SR"; see Guatelli et al., Proc. Nat'l Acad. Sci. USA 87: 1874-78 (1990)), Nucleic Acid Sequence-Based Amplification ("NASBA"; see U.S. Pat. No. 5,130,238), Qβ replicase system (see Lizardi et al., BioTechnology 6:1197 (1988)); Ligase Chain Reaction ("LCR"; see U.S. Pat. No. 5,427,930); transcription-mediated amplification ("TMA"; Hirose et al., Clin. Chem. 44:2446-2452 (1998)); and transcription-based amplification (see Kwoh et al., Proc. Nat'l Acad. Sci. USA 86: 1173-77 (1989)). A preferred method of amplification is SDA.

The amplicon itself may be formed by a number of methods, including the hybridization of adjoining oligonucleotide moieties of the proximity pair. For example, adjoining oligonucleotide moieties may hybridize over all or a segment of their length. If adjoining oligonucleotides hybridize at a portion of the respective termini, then the resulting duplex may be extended, using a DNA polymerase. When the amplification reaction comprises a SDA reaction, restriction endonuclease recognition sites may be incorporated on one or both of the oligonucleotide moieties of the proximity members or their extension products.

The amplicon also may be formed by contacting the oligonucleotide moieties of the proximity pair with an oligonucleotide "splint" that hybridizes to the respective termini of the oligonucleotide moieties. The oligonucleotide splint may further comprise a restriction endonuclease recognition site and a first sequence that is complementary to a first oligonucleotide probe. The oligonucleotide moiety of a first proximity member additionally may comprise a second sequence that is complementary to a second oligonucleotide probe. The splint may be used in a method that comprises adding the first and second probes and extending the sequence complementary to the oligonucleotide moieties with a DNA polymerase. The oligonucleotide moiety of the second proximity member is displaced, leaving the amplicon attached to the first proximity member through the conjugation with the oligonucleotide moiety of the first proximity member. For the purpose of the present invention, a displaced oligonucleotide moiety that is not amplified is referred to as a "tether oligonucleotide." "Displacing," for the purpose of the present invention, may be accomplished by such methods as strand displacement or hydrolysis of the displaced strand catalyzed by a polymerase having a 3'-5' exonuclease activity. The method further comprises amplifying the amplicon through any of the well-known methods of amplification, such as SDA.

In another embodiment, the amplicon advantageously is released from the complex of the proximity pair and the analyte, which reduces the background by eliminating signal from antibody-oligonucleotide conjugates that are absorbed to the assay support surfaces. In this embodiment, two oligonucleotide splints are used to form the amplicon, and both of the oligonucleotide moieties of the proximity members are tether oligonucleotides. A first bridging probe hybridizes to the 5' end of the oligonucleotide moiety of a first proximity member, and a second bridging probe hybridizes to the 5' end of the oligonucleotide moiety of a second proximity member. The first and second bridging probes hybridize with each other at their respective 3' ends. Upon extension with a polymerase, the oligonucleotide moieties of the first and second proximity members are displaced, and the amplicon is released from the remaining components of the proximity pair-analyte complex. The amplicon is then amplified by any of the well-known methods of amplification.

In an alternative embodiment, the proximity pair-analyte complex is immobilized on a solid support. The amplicon is released from the complex into solution, using the method set forth above, while the remaining components of the proximity pair-analyte remain bound to the solid support. In this embodiment, the solution containing the amplicon can be removed entirely from the remaining components of the complex prior to amplification, which reduces background even further.

The use of two splint oligonucleotides in the manner set forth above allows a method of target-mediated probe cycling. This method comprises contacting a proximity pair with first and second splint oligonucleotides, extending the complement of the oligonucleotide moieties with DNA polymerase, thereby displacing the amplicon from the proximity pair, amplifying the amplicon, and contacting the proximity pair with additional first and second splint oligonucleotides. The splint oligonucleotides optionally may hybridize to the 3' end of the oligonucleotide moiety of a first proximity member and the 5' end of the oligonucleotide moiety of a second proximity member. The splint oligonucleotides optionally may hybridize to the 3' end of the oligonucleotide moiety of a first proximity member and the 3' end of the oligonucleotide moiety of a second proximity member. Both of the splint oligonucleotides optionally may hybridize to complementary sequences of a third splint oligonucleotide that forms a bridge between the first and second splint oligonucleotides.

In a further embodiment, an oligonucleotide splint may comprise a sequence encoding a RNA polymerase promoter in a region of the probe that does not hybridize with an oligonucleotide moiety and that is upstream, i.e., located in a 5' orientation, of a first sequence that is complementary to a first oligonucleotide probe. The oligonucleotide moiety of a first proximity member additionally may comprise a second sequence that is complementary to a second oligonucleotide probe. The splint may be used in a method that comprises adding the first and second probes and extending the sequence complementary to the oligonucleotide moieties with a DNA polymerase. The oligonucleotide moiety of the second proximity member is displaced by the extended strand, leaving the amplicon attached to the first proximity member, where the amplicon comprises a now intact, double-stranded RNA polymerase binding site. The method further comprises transcribing single-stranded RNAs by contacting the RNA polymerase binding site with an RNA polymerase. The RNAs may be detected by means well-known in the art, including hybridization with labeled probes. In addition to strand displacement, the oligonucleotide moiety of the second proximity member also may be removed by using a DNA polymerase with 5'-3' exonuclease activity, such as Taq DNA polymerase.

Alternatively, the single-stranded RNA transcript is contacted with a primer that hybridizes to the RNA at its 3' region, allowing transcription of the RNA by reverse transcriptase to generate a DNA-RNA hybrid. Digesting this DNA-RNA hybrid with RNase H yields a complementary DNA strand. Contacting this DNA strand with a primer, which comprises the complement to the RNA polymerase binding site, regenerates the intact double-stranded RNA polymerase binding site. The DNA strand is contacted with an RNA polymerase, which catalyzes the synthesis of a single-stranded RNA transcript. The steps of contacting the transcript with a primer, contacting the primer-transcript hybrid with a reverse transcriptase, digesting the DNA-RNA hybrid, and contacting the resulting single-stranded DNA with a primer that reconstitutes the RNA polymerase binding site may be repeated, resulting in exponential amplification of the amplicon.

The amplification method of the present invention may be conducted entirely in solution in a "homogeneous format," or it may comprise the immobilization of components of the reaction to a solid support in a "heterogeneous format." For a method of amplification using the heterogeneous format, a proximity member, an analyte or a complex between a proximity member or pair and an analyte is immobilized to a solid support, such as a particle or the surface of a reaction vessel. For this purpose, a proximity member or analyte comprises an oligonucleotide moiety complementary to an oligonucleotide conjugated to the support (a "capture oligonucleotide"). The hybrid formed between the oligonucleotide moiety of the proximity member or analyte and the capture oligonucleotide may comprise a restriction endonuclease recognition site. The captured proximity member or analyte is released from the solid support by a method comprising contacting the recognition site with the appropriate restriction endonuclease. Alternatively, the method to release the bound proximity member or analyte comprises denaturing the hybrid between the capture oligonucleotide and the oligonucleotide moiety of the proximity member or analyte by such means as increasing the temperature, decreasing ionic strength, changing the pH of the reaction mixture, or adding chelating agents that promote hybrid denaturation. In yet another embodiment, the capture oligonucleotide comprises a scissile linkage that is particularly susceptible to cleavage by, for example, physical, enzymatic, chemical or photochemical means. In a further embodiment, the capture oligonucleotide or the oligonucleotide moiety of the proximity member or analyte comprises a complementary sequence to a primer. The primer is capable of hybridizing to the hybrid formed between the capture oligonucleotide and the oligonucleotide moiety of the proximity member or analyte. The oligonucleotide moiety of the proximity member or analyte then may be displaced from the hybrid by polymerase chain extension and strand displacement. In a related embodiment, the capture oligonucleotide is capable of forming a hairpin structure that forms a template for polymerase extension, causing release of a captured proximity member or analyte by strand displacement.

The hybrid between the capture oligonucleotide and the oligonucleotide moiety of the proximity member or analyte optionally may comprise an RNA sequence. The proximity member or analyte is released from the surface by contacting the hybrid with an RNase, such as RNase H. In one embodiment, the oligonucleotide moiety of a proximity member that hybridizes to the capture oligonucleotide is the oligonucleotide moiety that is involved in forming the amplicon. The oligonucleotide moiety cannot form an amplicon as long as it remains hybridized to the capture oligonucleotide, but release of the oligonucleotide moiety from the hybrid by strand displacement, for example, allows the amplicon to form.

Amplification using the heterogeneous format may comprise contacting an analyte with a first proximity member in a reaction mixture, adding a second proximity member that is immobilized to a solid support or is capable of being immobilized to a solid support under conditions sufficient to form a proximity pair-analyte complex that comprises an amplicon, washing the bound proximity pair-analyte complex to remove proximity members that are not immobilized to the solid support, amplifying the amplicon, and detecting the amplification product. The second proximity member may be added before, after or simultaneously with the first proximity member. Optionally, the second proximity member may be immobilized to the solid support by a scissile linkage, which is cleaved after washing but prior to amplification. The method of immobilizing the proximity member to a solid support and cleaving the proximity member from the solid support that are set forth above may be used. Further, any of the methods for forming the amplicon set forth above, such as the method that comprises adding a splint oligonucleotide, may be used in the heterogeneous format.

The present invention advantageously provides universal components that can be used in any of the amplification methods set forth above. In a preferred embodiment, an analyte is contacted with a first antibody that binds a first epitope and a second antibody that binds a second epitope, where the first and second epitopes and antibodies may be the same or different. Optionally, the first and second antibodies may each be labeled with a different hapten moiety (e.g., biotin, fluorescein, digoxigenin, trinitrophenol, dinitrophenol and the like). The antibodies are contacted with a universal component that comprises one or more proximity members that specifically bind the first and/or second antibodies to form a proximity pair comprising an amplicon. The universal component may be, for example, protein A or protein G, conjugated to a oligonucleotide moiety. Alternatively, the universal component may be an anti-immunoglobulin constant region antibody that is conjugated to an oligonucleotide. If the first and second antibodies are labeled with hapten moieties, then the universal component may be antibodies (or other agents such as streptavidin) that are specific for the particular hapten label. The use of universal components advantageously eliminates the necessity of modifying each analyte-specific analyte-binding entity with an oligonucleotide moiety.

The proximity members may be antigens that are conjugated to two different oligonucleotide moieties. The analyte in this embodiment is an antigen-specific antibody, which may be an IgG or any other type of antibody. The binding of the antigen-oligonucleotide conjugates by the antibody forms a proximity pair that may comprise an amplicon, when the bound antigen-oligonucleotide conjugates comprise different oligonucleotide moieties. This method, therefore, can be used to detect the presence of particular antibodies with great sensitivity.

The invention also provides a kit, which may comprise individual or combined components and reagents that are useful for carrying out the method of the present invention, such as buffers, chemical reagents, enzymes, oligonucleotides, proximity members, and instructions for the use of these components or reagents. For example, the kit may comprise oligonucleotide amplification primers that are suitable for carrying out the amplification and detection methods described herein. The kit may additionally comprise reagents and solutions for detecting amplified nucleic acids, such as radiolabels, enzyme substrates, antibodies, and the like. Suitable solutions and reagents are well-known and are described in Sambrook et al., Molecular Cloning, A Laboratory Manual (3rd ed., 2001), for example. The components of the kit are packaged together in a common container, typically including instructions for performing embodiments of the methods disclosed herein.

BRIEF DESCRIPTION OF THE DRAWINGS

FIG. 4A shows a simple competitive hybridization blocker.

FIG. 4C shows a disabling hybridization blocker.

FIG. 4EE shows the use of a 3' probe tail to stabilize a probe-blocker duplex.

FIG. 4G shows a disabling hybridization blocker in a binary immuno-SDA reaction.

FIG. 4H shows step-wise blocking in a binary immuno-SDA reaction.

FIG. 4I shows the post-binding addition of hybridization blockers in a binary immuno-SDA reaction.

FIG. 7C shows, the formation of an immobilized two-site "sandwich" by the binding of a second proximity member to the immobilized complex between the target analyte and the first proximity member.

FIGS. 7E-H show the use of a hybridization blocker oligonucleotide to suppress probe-probe interactions that lead to target-independent amplicon formation.

FIG. 7I shows the release of an immobilized complex between a target analyte and two proximity members using low ionic strength.

FIGS. 8A-C show heterogeneous immuno-amplification.

FIG. 8D shows heterogeneous immuno-amplification with a scissile linkage.

FIG. 9 shows heterogeneous immuno-amplification with splint oligonucleotides.

FIG. 11A shows hairpin release probes.

FIG. 11B shows hairpin hybridization blocker probes.

FIG. 12 shows detection of antigen-specific immunoglobulin.

FIGS. 14A-E show the use of a 3' capped oligonucleotide moiety to form amplicons attached to a first proximity member and to a second proximity member, but not to both proximity members simultaneously.

FIG. 15A shows a two-color, real-time fluorescence profile for immuno-SDA detection of IL-8.

DETAILED DESCRIPTION OF THE PREFERRED EMBODIMENTS

Figure 1A:
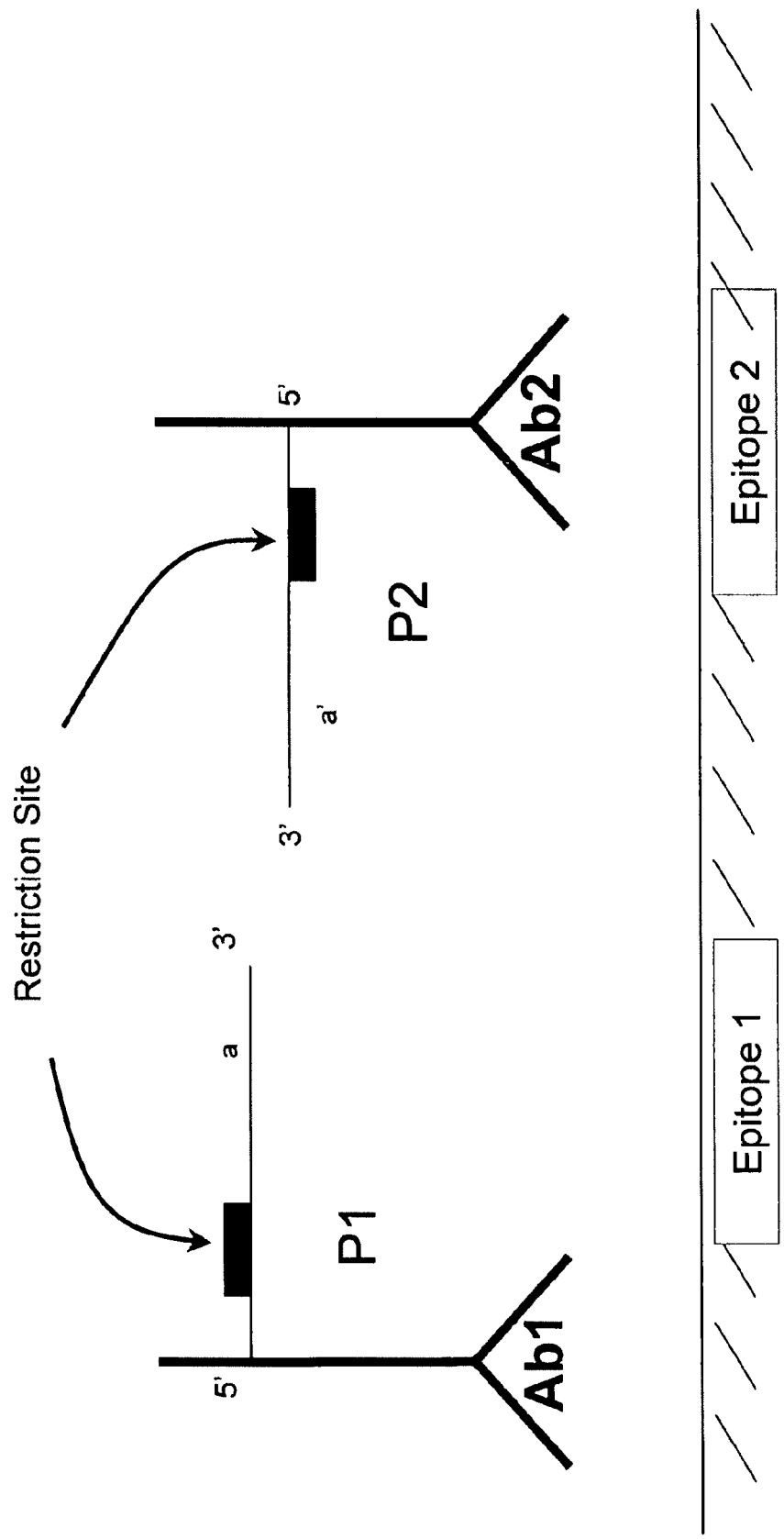
FIG. 1A shows mixing of antigens and oligonucleotide-conjugated antibodies.
Figure 1B:
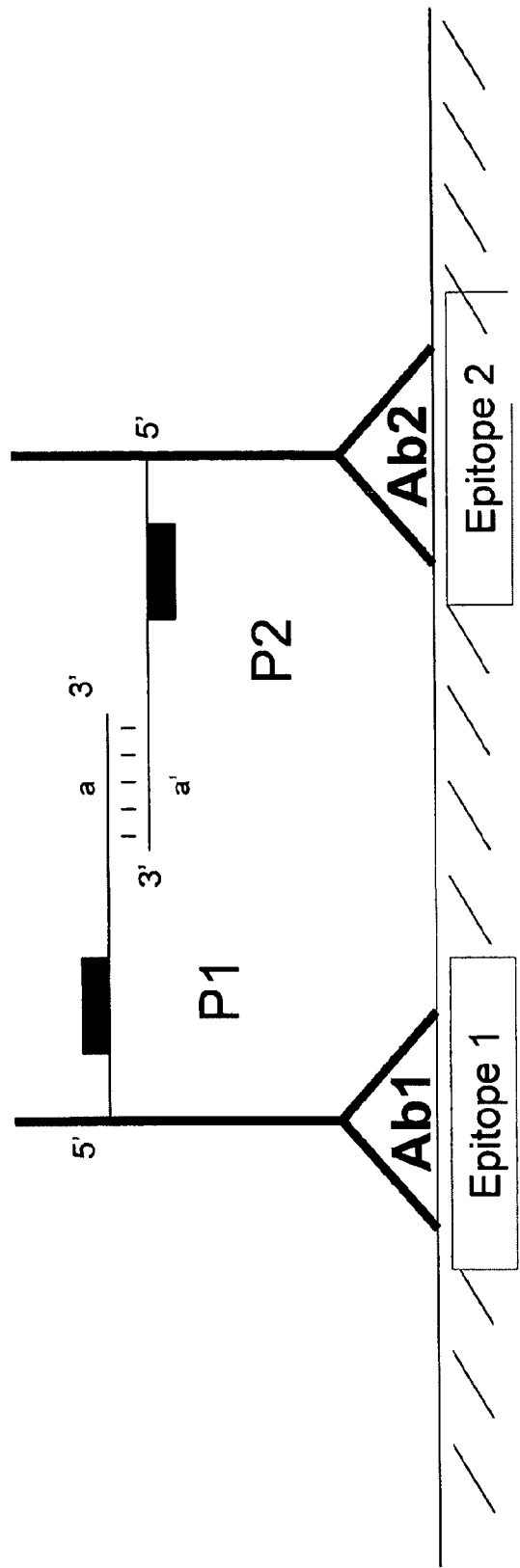
FIG. 1B shows hybridization of adjacent probes.
Figure 1C:
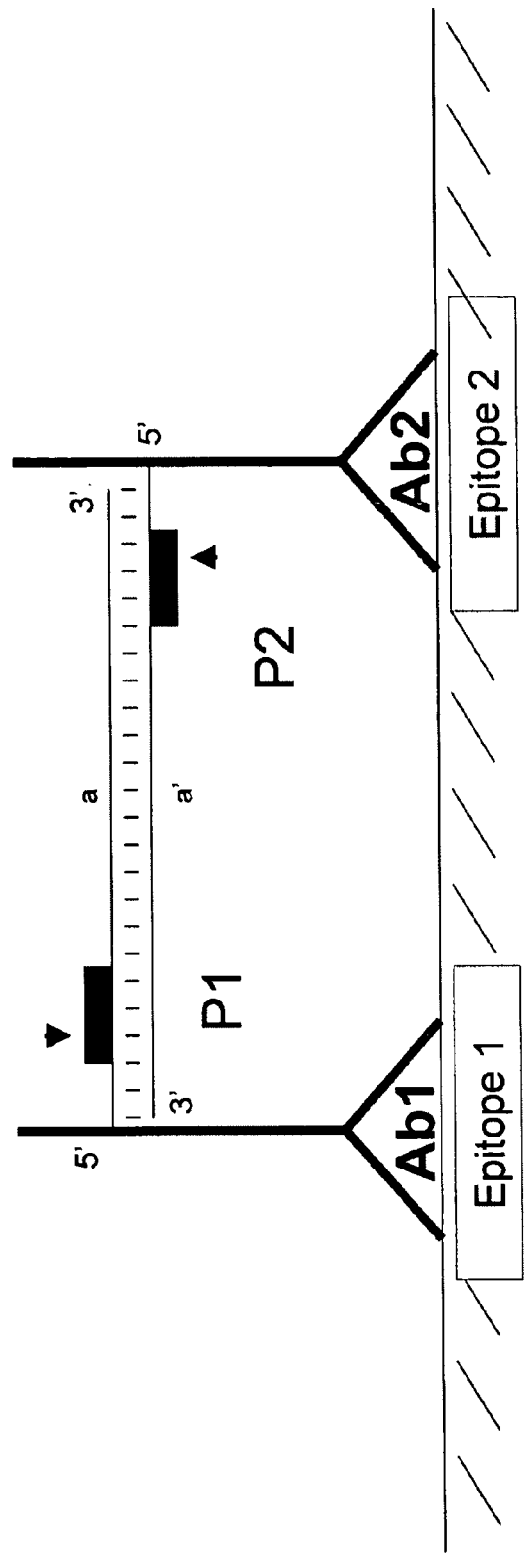
FIG. 1C shows a polymerase extension and restriction enzyme nicking.

Minute quantities of an analyte may be detected with great sensitivity by the present invention. The invention provides conjugates of analyte-specific binding factors, such as antibodies, conjugated to oligonucleotide moieties that can form an amplicon. The conjugation between antibodies and other proteins with oligonucleotides is known in the art and taught, for example, in U.S. Pat. Nos. 5,849,878 and 5,665,539, which are incorporated by reference in their entirety herein. If the analyte-specific binding factor is a nucleic acid, for example, an aptamer, then the analyte-specific binding factor and the oligonucleotide or probe moiety may be synthesized in one contiguous strand using chemical synthesis methods known in the art. The term "conjugate" still applies to such aptamer-probe entities. The conditions for establishing an amplicon by adjoining oligonucleotides that are each conjugated to an antibody are also known and taught in U.S. Pat. No. 6,511,809, for example. Conditions and methodologies for amplifying amplicons and for detecting their presence are also known in the art, as taught in U.S. Pat. No. 6,511,809 and U.S. Patent Application Publication No. 2002/00674779, both incorporated herein by reference in their entirety. The use of labeled probes for the detection of amplification products, for example, also is taught in U.S. Pat. Nos. 5,928,869, 5,919,630; 5,935,791; 6,316,200; and 6,379,888, all incorporated herein by reference in their entirety. U.S. Pat. No. 5,840,487 teaches the use of internal controls for isothermal nucleic acid amplification reactions and is also incorporated herein by reference in its entirety.

According to the present invention, a preferred method of amplification by SDA is detailed in FIG. 1. Ab1 and Ab2 are antibodies that recognize adjacent epitopes 1 and 2 and that are conjugated to oligonucleotide probes P1 and P2, respectively (FIG. 1A). The antibodies are representative, but not limiting examples, of the analyte-specific binding components that are useful in the present invention. For instance, useful analyte-specific binding components known in the art include functional fragments of antibodies, such as Fc, Fv, Fab' and F(ab')$_2$ fragments. Other examples of analyte-specific binding components include aptamers, ligands specific for a receptor analyte, or a receptor that is specific for a ligand analyte. Further, it will be understood by the skilled artisan that various different types of analyte-specific binding components may be used in combination. "Oligonucleotide probes" and "oligonucleotide moieties" are used synonymously for the purposes of the present invention. The term "oligonucleotide" should not be understood as placing an upper size limit on the nucleic acid moieties for the purpose of this invention; therefore, "oligonucleotide" is synonymous with "polynucleotide," as used herein. For the purposes of the present invention, an oligonucleotide may be composed in whole or in part by DNA, RNA or an analogue or derivative thereof. In this embodiment, P1 and P2 comprise complementary 3' terminal sequences and upstream SDA nick sites. The use of nick sites for SDA and the conditions for SDA in general are described in U.S. Pat. Nos. 5,919,630; 5,846,726; and 6,054,729, which are incorporated herein by reference in their entirety. The 3' ends of P1 and P2 hybridize to one another when the two antibodies to which they are linked are held in close proximity by binding to their respective epitopes (FIG. 1B). Conditions conducive to nucleic acid hybridization, including the number of base pairs or mismatches in the hybridized portion of a nucleic acid and the temperature and ionic strength of the buffer in which the hybridization occurs, are well-known in the art and are generally described, for example, in Sambrook et al., Molecular Cloning, A Laboratory Manual (3rd ed., 2001). The bulk solution concentration of Ab1 and Ab2 is relatively low compared with that at the surface of the antigen, such that antigen-independent hybridization of P1 and P2 is minimized. DNA polymerase is then used to fill in the recessed 3' ends of the P1:P2 hybrid (FIG. 1C). This serves to generate double-stranded restriction sites that are recognized by the SDA nicking enzyme. A nicking enzyme catalyzes the cleavage of only one strand of the double-stranded DNA template. Nicking and polymerase extension from the site of the nick displaces the downstream DNA strand into solution and regenerates the nick site (FIG. 1D). Repeated cycling of the nicking and extension/displacement steps may be used to produce multiple copies of the displaced strand. The displaced strand is captured by a complementary SDA primer (FIG. 1E). Extension from the 3' ends of the captured strand and hybridized SDA primer produces a double-stranded DNA molecule that may be exponentially amplified through a series of intermediates. In an alternative embodiment, only one of the oligonucleotide probes P1 and P2 comprises an SDA nick site.

Figure 1D:
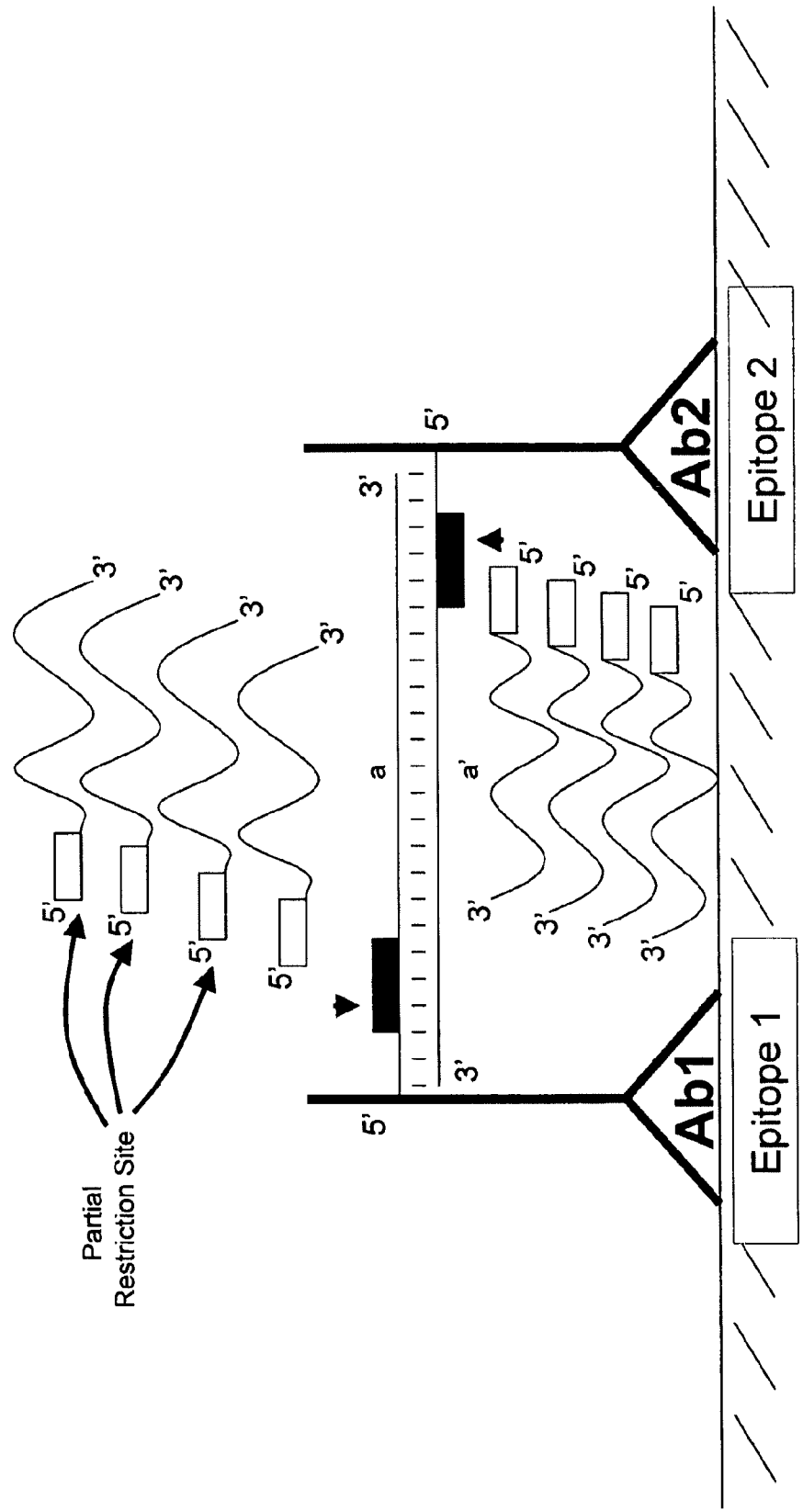
FIG. 1D shows extension, displacement and linear amplification.
Figure 1E:
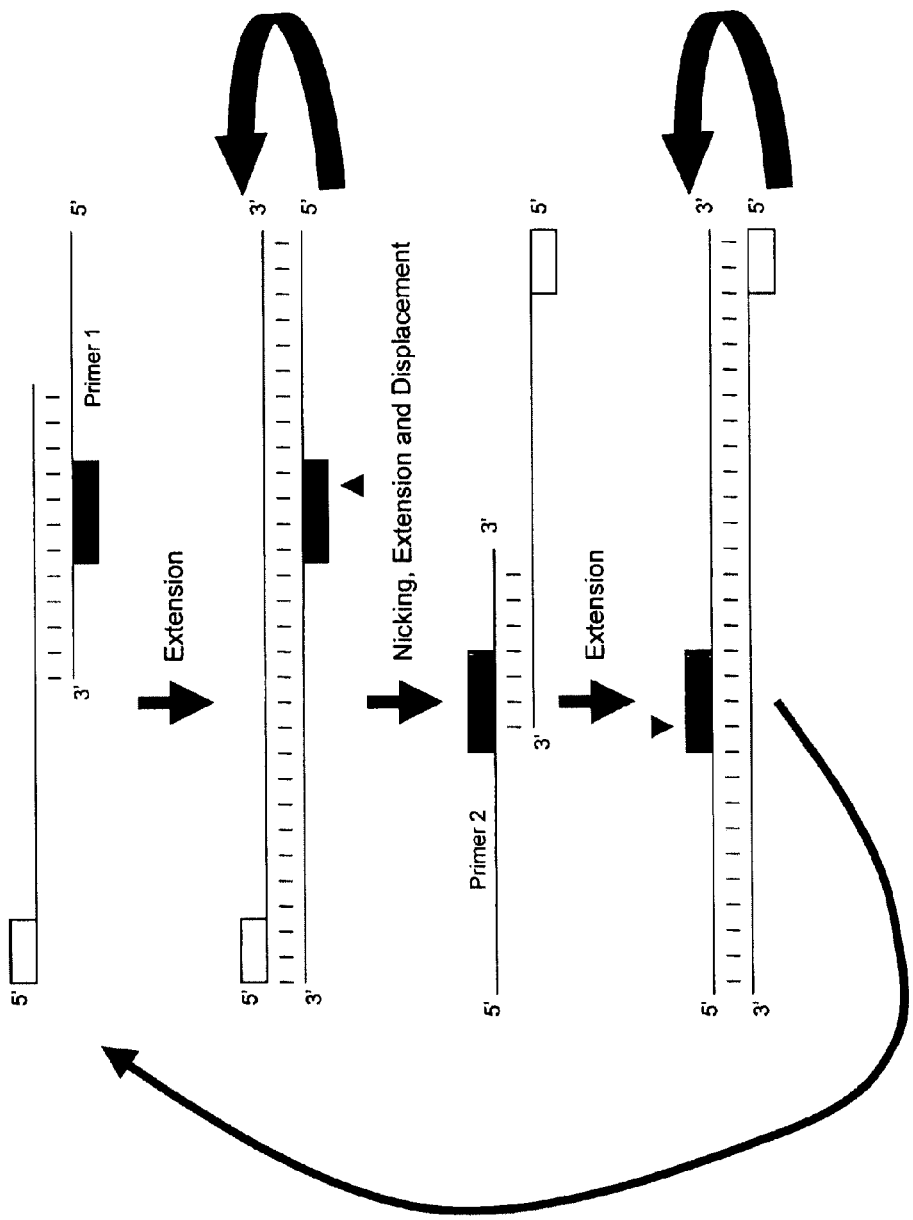
FIG. 1E shows hybridization, polymerase extension, nicking and exponential amplification.
Figure 1F:
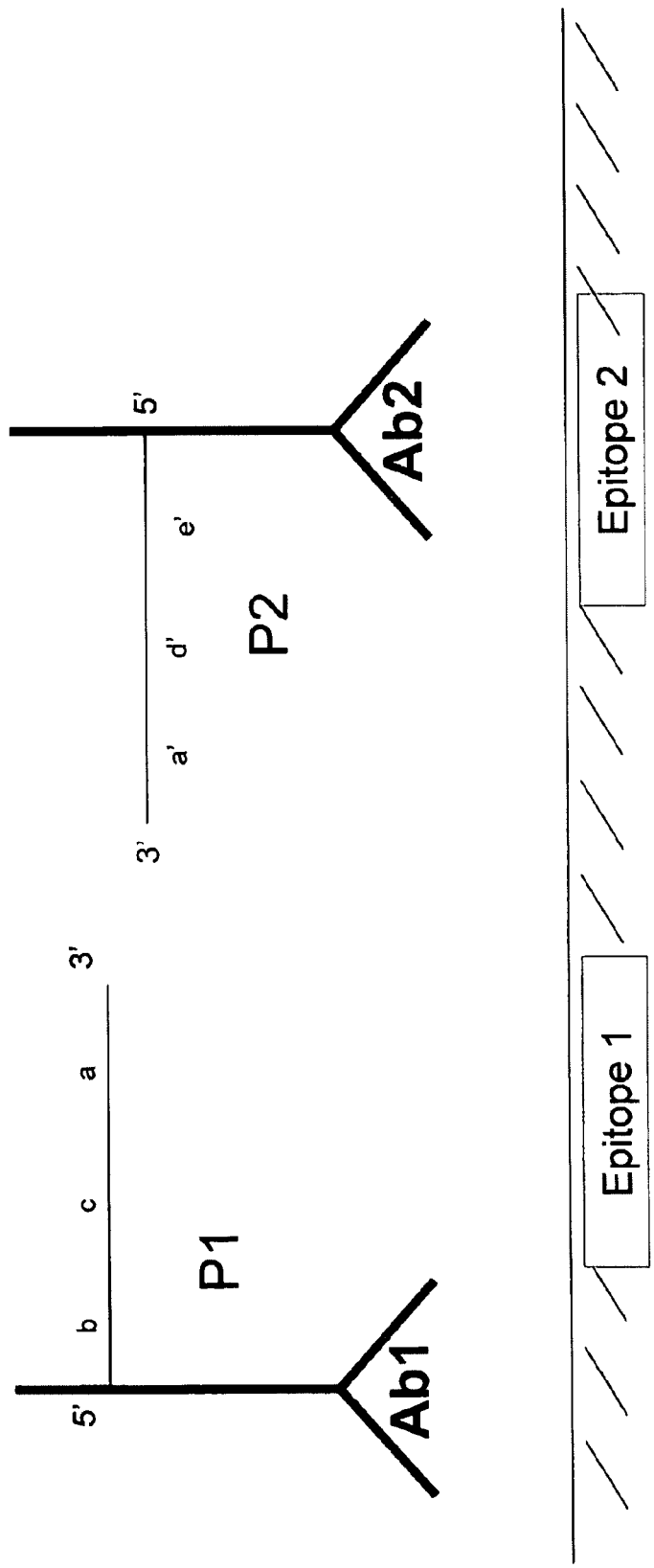
FIG. 1F shows mixing of antigens and oligonucleotide-conjugated antibodies.
Figure 1G:
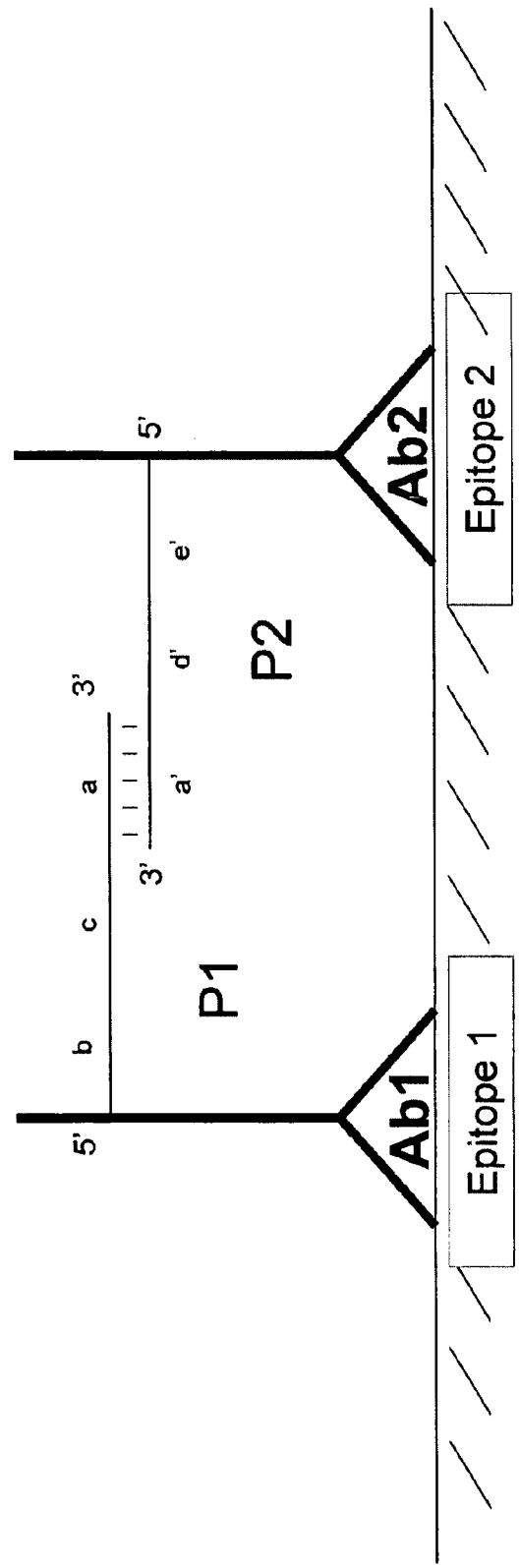
FIG. 1G shows hybridization of adjacent probes.
Figure 1H:
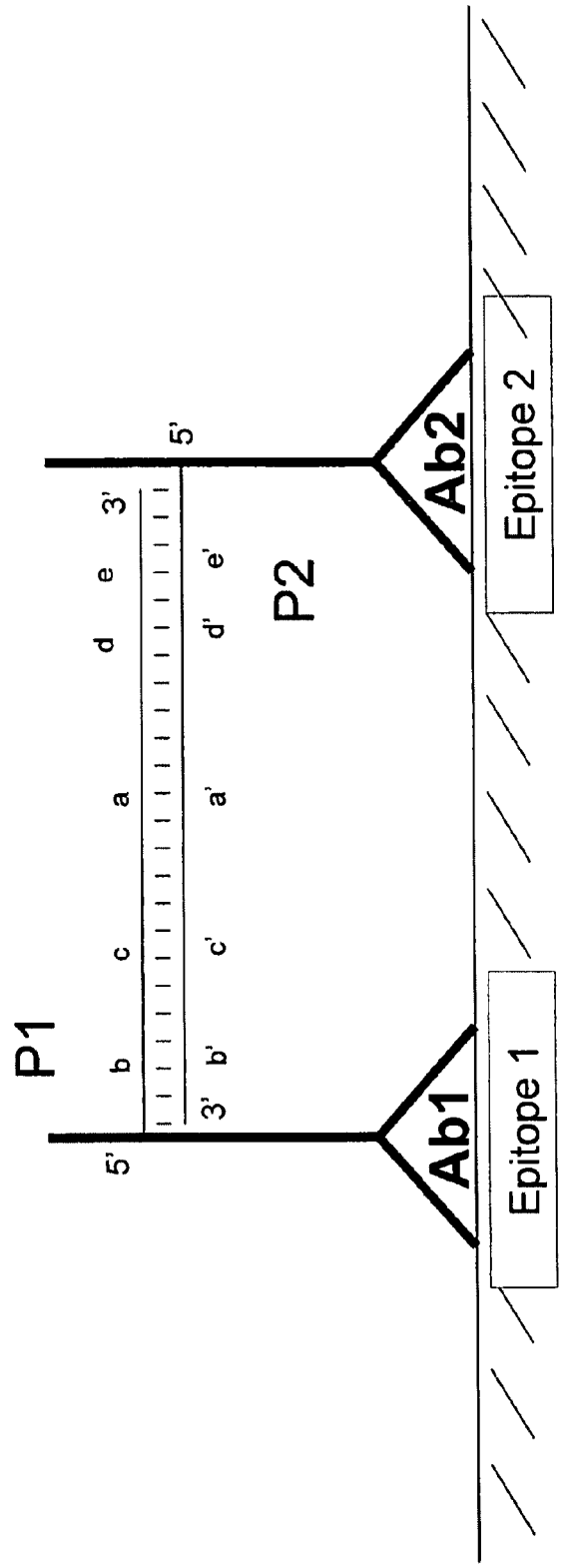
FIG. 1H shows extension of probes with a polymerase.
Figure 1I:
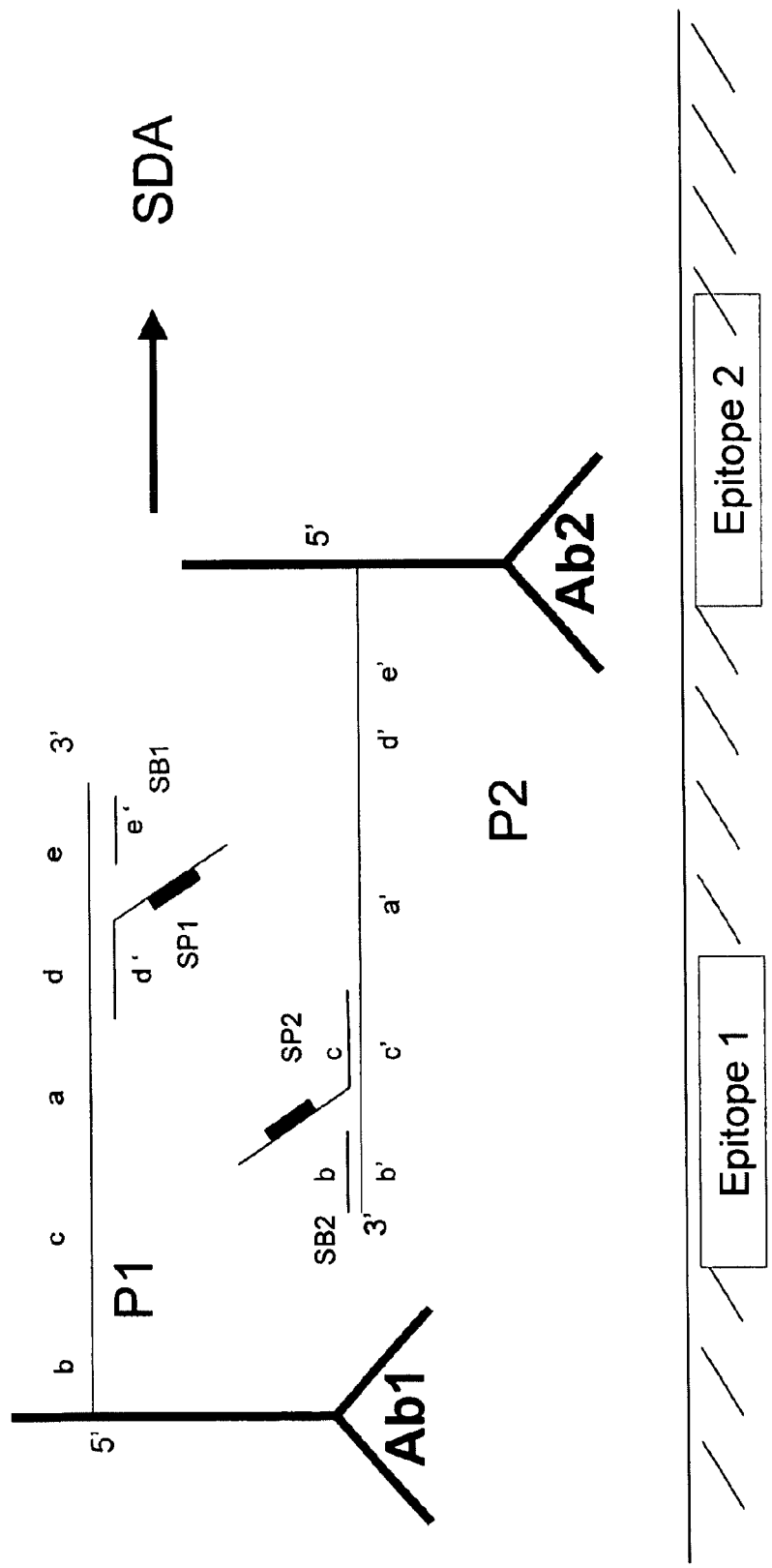
FIG. 1I shows denaturation of a probe-extension duplex and the binding of SDA primers.

In another embodiment (FIG. 1F-I), probes P1 and P2 lack SDA nick sites, but comprise instead sequences c and d', which also are present on SDA primers SP2 and SP1, respectively (see FIG. 1I). Extension of the 3' ends of P1 and P2 creates a duplex containing complementary sequence d on the extension product of P1 and complementary sequence c' on the extension product of P2 (see FIG. 1H). The strands of the duplexed extension products are then separated by, for example, heating, whereupon SDA primers SP1 and SP2 hybridize to the complement of the newly synthesized sequences d and c' of the extended probes. The extended probes optionally may comprise a sequence located 3' to the binding sites of the SDA primers, shown as sequence e of extended P1 and sequence b' of extended P2. These sequences hybridize with bumper primers SB1 and SB2 (see FIG. 1I). During SDA, the SDA primers SP1 and SP2 are extended by polymerase (not shown). Extension of the bumper primers, if present, serves to displace the SDA primer extension products from the probe strands, and the displaced strands are then amplified by SDA, as described in U.S. Pat. Nos. 5,270,184; 5,919,630; 5,846,726; and 6,054,729. In the event that the extended probes do not contain sequences 3' to the SP1 and SP2 binding sites (not shown), the 3' ends of the probes that are hybridized to SDA primers are extended by polymerase, creating nickable restriction sites that allow subsequent nicking and strand displacement by SDA as described above.

In preceding embodiments, oligonucleotide moieties (P1 and P2) were conjugated to their respective analyte binding entities (Ab1 and Ab2) through linkages located at or near their 5' termini. In an alternative embodiment illustrated in FIG. 1J, conjugate Ab1-P1 is formed through a linkage located at or near the 3' terminus of P1, while conjugate Ab2-P2 is formed through a linkage located at or near the 5' terminus of P2. P1 comprises sequence (a b c d e f) (read 5' to 3'), and P2 comprises sequence (j' i' h' g' f' e') (read 5' to 3'). Ab2-P2 further comprises an extendible 3' end (i.e., a 3' terminal hydroxyl group). As shown, sequence (e f) of P1, which is capable of hybridizing to sequence (f' e') of P2, is located 5' of the site at which P1 is conjugated to Ab1, whereas (f' e') is located 3' of the site at which P2 is conjugated to Ab2. Probes P1 and P2 are, therefore, said to be linked to their respective analyte binding entities (Ab1 or Ab2) in opposite sequence orientations. When P1 and P2 are brought into close proximity, for example, through binding of their respective proximity members to the same target analyte molecule, sequence (e f) of P1 hybridizes with (f' e') of P2, as depicted on the left side of FIG. 1J. Polymerase may then be used to extend the 3' end of P2 to create an extension product (i.e., amplicon) P2-ext containing the new sequence, as shown. P2-ext may then be detected by methods known in the art, making use of all or part of the new sequence (d' c' b' a') to distinguish P2-ext from unconverted P2. For example, P2-ext may be amplified by nucleic acid amplification methods described above. P2-ext may be separated from P1 by heating the solution, and a primer may hybridize to the new sequence at the 3' end of P2-ext and be extended to create a complement of P2-ext. Subsequent rounds of amplification may involve separation of the complement from P2-ext and hybridizing to the complement a different primer comprised of a sequence located near the 5' end of P2. In a preferred embodiment, sequence b will contain the single-strand component of a recognition sequence for an SDA-compatible restriction enzyme. Formation of P2-ext then creates a double-stranded recognition sequence that is nicked by the restriction enzyme. Extension from the nick creates a new strand that is complementary to P2-ext, regenerating the nickable recognition sequence. This product may be amplified and detected by SDA methods referred to above. Optionally, sequence i' of P2 may also comprise the single-strand component of a recognition sequence for SDA and, if so, the duplex formed between P2-ext and its full-length complementary strand will contain two nickable restriction enzyme recognition sequences. In another embodiment, sequence b may be a single-strand component of an RNA polymerase promoter site. Formation of P2-ext then creates a double-stranded RNA polymerase promoter, which may be used to direct the activity of an RNA polymerase to synthesize RNA molecules that are complementary to sequence (j' i' h' g' f' e' d' c') of P2-ext. These RNA molecules may be detected directly, or they may be further amplified by methods such as 3SR, NASBA, TMA, or transcription-based amplification. Optionally, sequence i' of P2 may comprise the single-strand component of an RNA polymerase promoter. In this case, extension of a primer hybridized to the 3' end of P2-ext would create a double-stranded promoter site that can be used to direct the activity of the RNA polymerase to synthesize RNA molecules comprising the sequence (h' g' f' e' d' c' b' a'), which may be detected directly or amplified using the aforementioned methods. Regardless of the method of detection Or amplification of P2-ext, the embodiments depicted in FIG. 1J comprise probe moieties P1 and P2 that are linked to their respective analyte-binding elements Ab1 and Ab2 in opposite sequence orientations, and the two probes hybridize to each other in a target-mediated process, creating a duplex with an extendible 3' end that is subsequently extended to create an amplicon. In the absence of target-analyte, P1 and P2 will not be brought into close proximity, and P2-ext will not form except through spurious (i.e., target-independent) interactions mentioned below, which may be suppressed by hybridization blocking oligonucleotides, also described below. P2-ext is, therefore, produced as a consequence of the presence of target analyte and in proportion to the quantity of target analyte present. Determination of the quantity of P2-ext produced may, therefore, be used to determine the quantity of target analyte present in a sample.

Figure 2A:
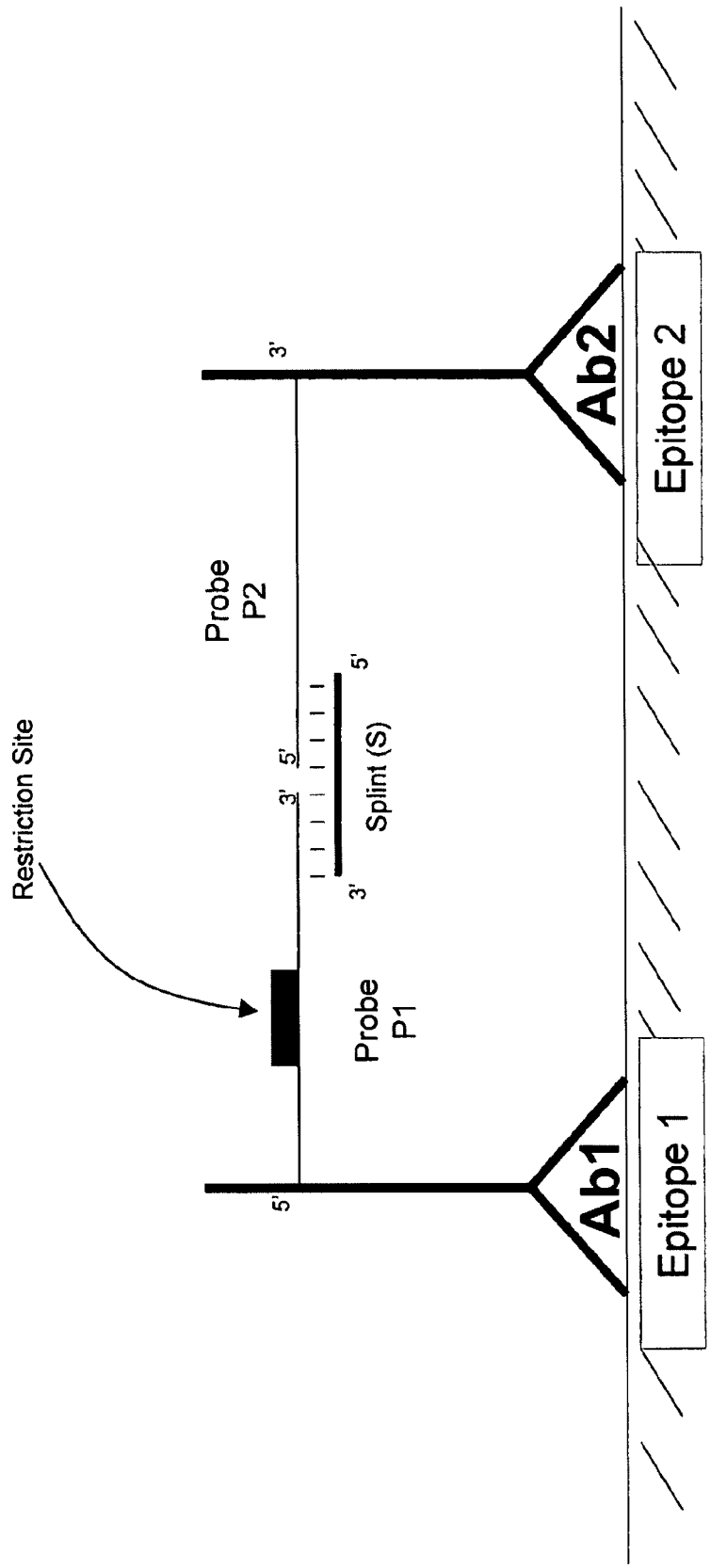
FIG. 2A shows hybridization of a splint oligonucleotide.
Figure 2B:
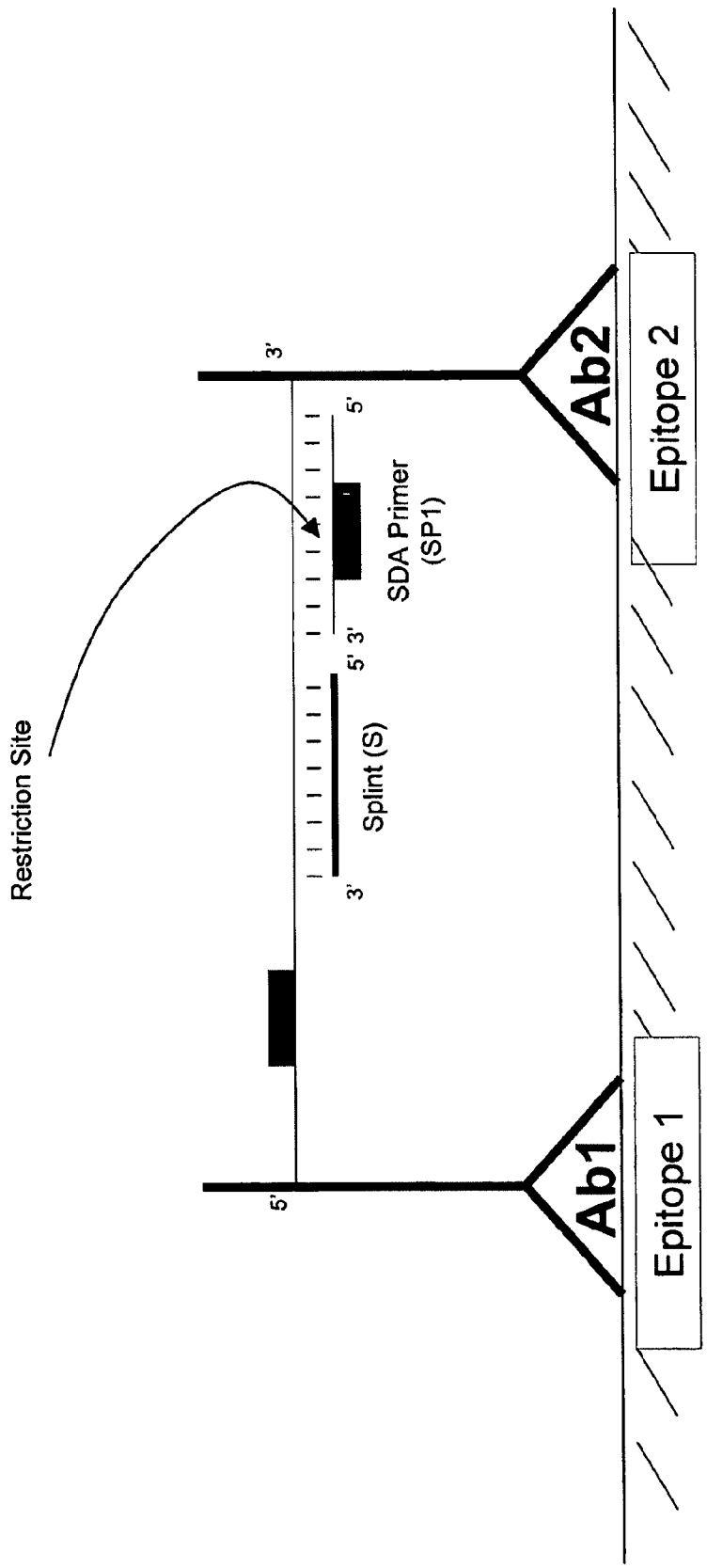
FIG. 2B shows ligation of adjacent probes.
Figure 2C:
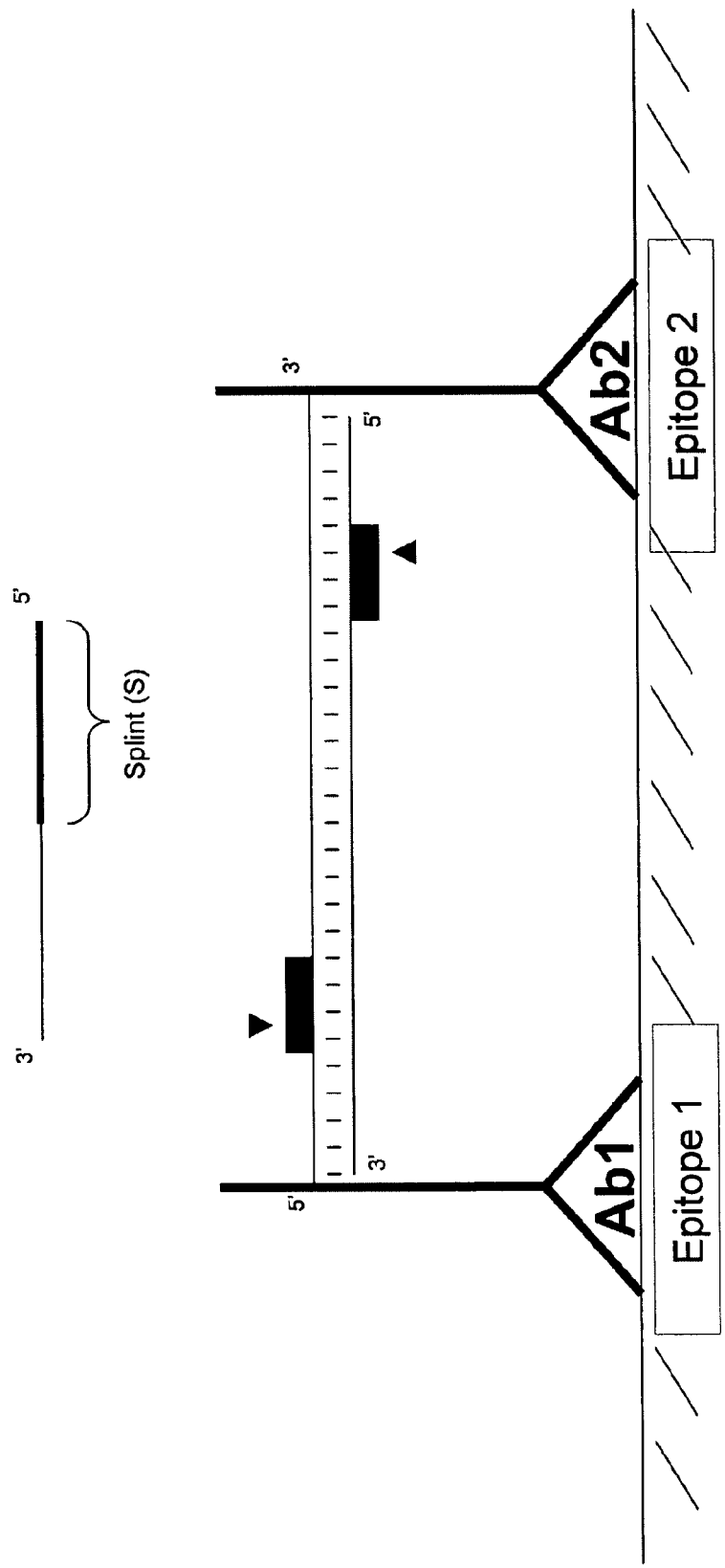
FIG. 2C shows DNA polymerase extension and displacement.

FIGS. 2A-C detail a representative use of a splint oligonucleotide. Ab1 and Ab2 are antibodies that recognize adjacent epitopes 1 and 2 and are conjugated to oligonucleotide probes P1 and P2, respectively (FIG. 2A). P1 is conjugated to Ab1 through a linkage located at or near its 5' terminus, and it comprises a 3' terminal hydroxyl group and upstream SDA nick site. Probe P2 is conjugated to Ab1 at its 3' end, and it comprises an SDA primer binding site and 5' terminal phosphate group. The sequence of the splint oligonucleotide S is complementary to the 3' end of probe P1 and the 5' end of probe P2 such that, when held in close proximity by binding of the antibodies to their respective epitopes, oligonucleotides P1 and P2 form a double-stranded hybrid with the splint S. When hybridized to the splint oligonucleotide S, the 3'-OH of P1 and 5'-PO$_4$ of P2 are adjacent, and DNA ligase is used to catalyze the formation of a phosphodiester bond linking the P1 and P2 sequences (FIG. 2B). SDA primer SP1 hybridizes to probe P2 upstream of splint oligonucleotide S. A strand-displacing DNA polymerase extends from the 3' ends of primer SP1 and splint oligonucleotide S. Extension of primer SP1 displaces the extension product of splint oligonucleotide S (FIG. 2C) and creates a double-stranded DNA molecule with SDA restriction enzyme nick sites at either end. This molecule is analogous to that depicted in FIG. 1C. Nicking, polymerase extending from the nick, and displacing the downstream strand leads to exponential amplification (FIGS. 1D-E). In one embodiment, the probe P1 does not comprise a SDA nick site. In another embodiment, the splint oligonucleotide S comprises a 3' cap to prevent 3' extension of the splint S.

Figure 1J:
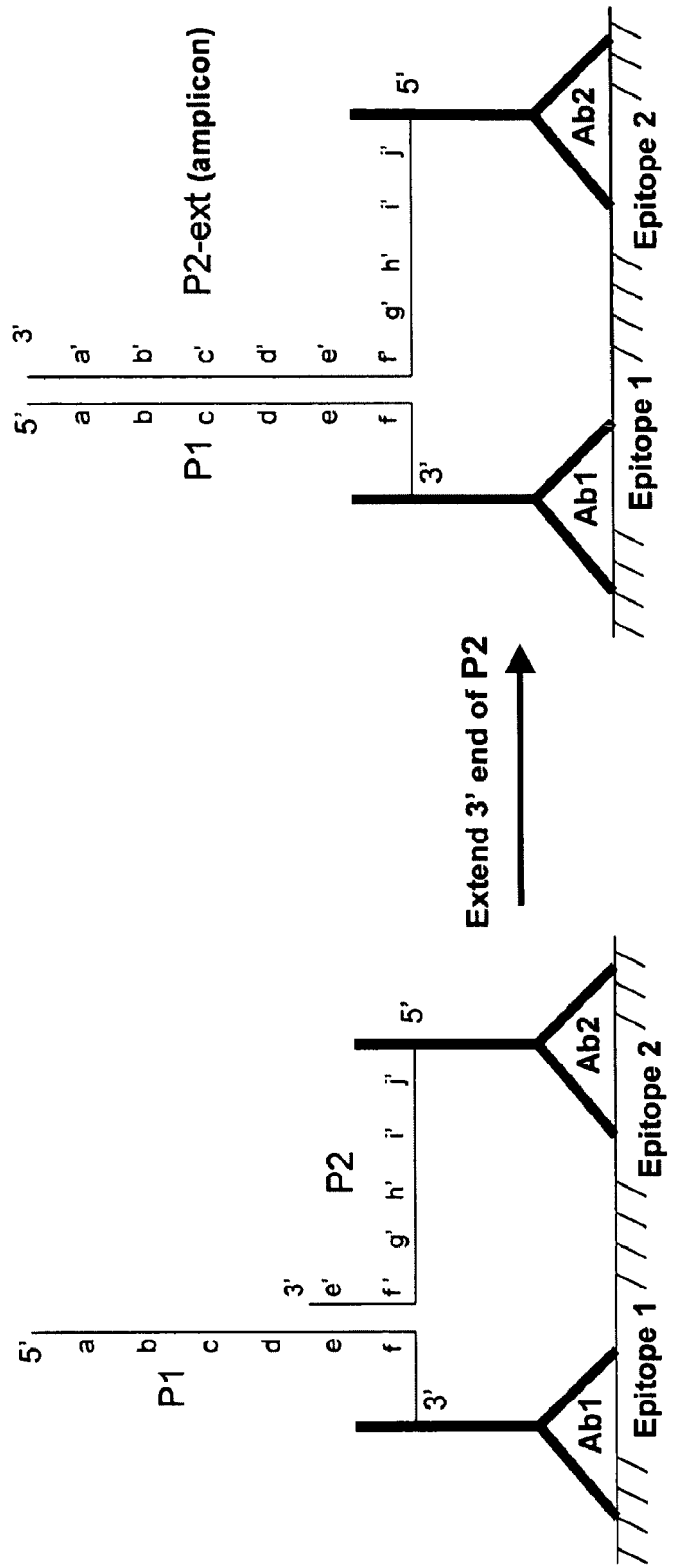
FIG. 1J shows amplicon formation from hybridized probes of opposite sequence orientation.
Figure 2D:
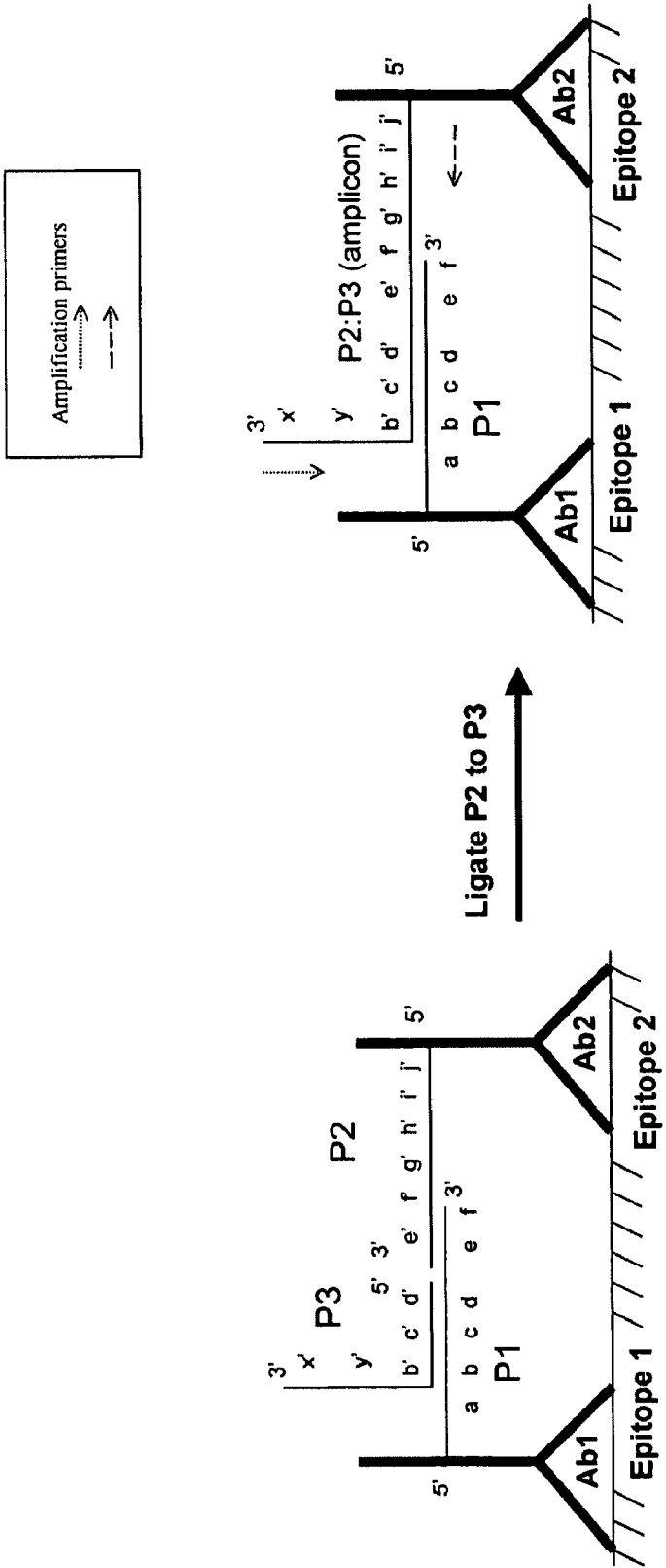
FIG. 2D shows the use of two hybridized proximity probes to ligate a third probe.
Figure 2E:
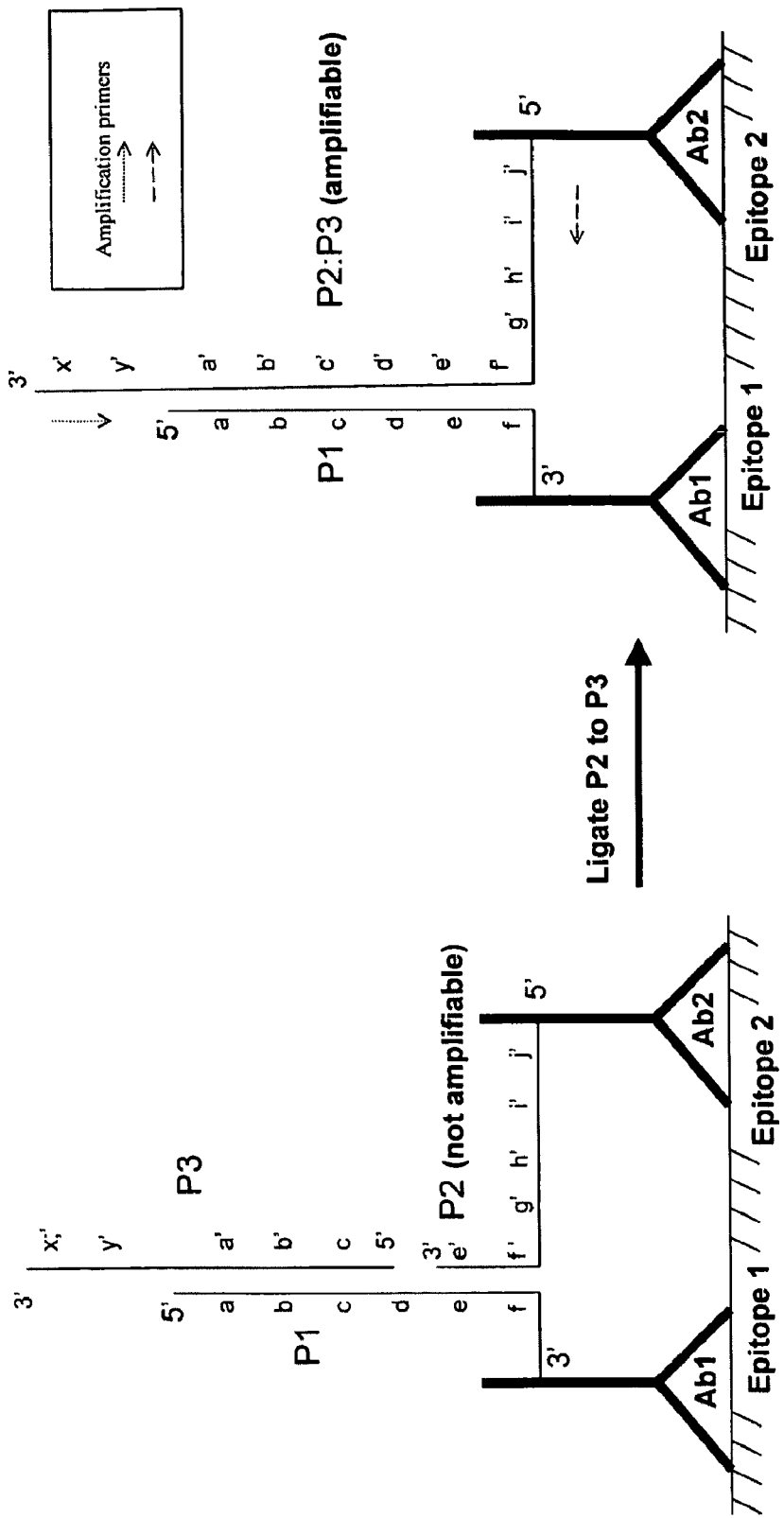
FIG. 2E shows the use of two hybridized proximity probes in opposite sequence orientation to ligate a third probe.

FIGS. 2D and 2E illustrate an alternative embodiment for target-mediated, ligase-catalyzed amplicon formation using a pair of proximity members. Probes P1 and P2 are linked, or conjugated, to their respective antibodies (or other analyte binding entities) Ab1 and Ab2. Conjugation may occur through linkages at or near the 5' termini of both probes, as shown in FIG. 2D, or one of the two probes (P1) may be conjugated through a linkage located at or near the 3' end of the probe. P1 comprises sequence (a b c d e f) (read 5' to 3'), and P2 comprises sequence (j' i' h' g' f' e') (read 5' to 3'). Conjugate Ab2-P2 further comprises a 3' terminal hydroxyl group. In configurations depicted by either FIG. 2D or 2E, sequences (e f) of P1 and (f' e') of P2 are capable of hybridizing to each other. A third probe P3 comprises sequence (d' c' b' x' y') and further comprises a 5' terminal phosphate group. P3 is capable of hybridizing to sequence (b c d) of probe P1 (adjacent to sequence (e f) of P1). In the presence of target analyte, P1 and P2 are brought into close proximity and form a duplex through hybridization of sequences (e f) and (f' e'). Probe P3 may be hybridized to P1, as shown, either before or after P1 and P2 hybridize. In either case, the 5' nucleotide of P3 is positioned adjacent to the 3' nucleotide of P2 and, in this configuration, P2 and P3 may be covalently linked together by DNA ligase (or other ligation mechanism) to form the amplicon P2:P3, as shown. P2:P3 may then be detected by various methods, including amplification, such as those described above for embodiments depicted in FIG. 1J. In this case, however, sequence x' and/or y' will be used as sites for primer hybridization. In the absence of target analyte, P1 and P2 will not be brought into close proximity, and P2:P3 will not form, except through spurious (i.e., target-independent) interactions between P1 and P2 mentioned below, which may be suppressed by hybridization blocking oligonucleotides also described below. P2:P3 is, therefore, produced as a consequence of the presence of target analyte and in proportion to the quantity of target analyte present. Determination of the quantity of P2:P3 produced may, therefore, be used to determine the quantity of target analyte present in a sample. Hybridization blockers are not required during amplification of amplicons formed by ligating oligonucleotide moieties of proximity members because probes that can be joined by ligation typically do not form hybrids with each other and therefore do not have the potential to undergo spurious probe conversion during amplification involving 3' extension of oligonucleotides.

FIG. 3 shows a representative embodiment of the present invention that comprises a splint oligonucleotide designed to bridge the gap between two oligonucleotide moieties of proximity members. In one embodiment (FIG. 3A), one of the proximity antibodies Ab1 is conjugated through a linkage at or near the 3' end of a tether-oligonucleotide. Hereafter, a "tether oligonucleotide" denotes an oligonucleotide moiety that is displaced from the amplicon but remains conjugated to the analyte-specific binding moiety. The tether oligonucleotide TO is complementary to a segment (preferably at or near the 5' end) of the splint oligonucleotide P1. Splint oligonucleotide P1 may further comprise a primer sequence to facilitate amplification of the converted probe and a detector region to facilitate detection of the converted probe. P1 may also comprise a restriction recognition sequence to facilitate amplification by SDA. In addition, the 3' sequence of the splint oligonucleotide is complementary to the 3' end of probe P2 that is conjugated through its 5' terminus to antibody Ab2. As depicted in FIG. 3A, the 5' end of P1 is complementary to the tether oligonucleotide TO, which is attached to Ab1. Optionally, the tether oligonucleotide may be complementary to a sequence not on the 5' end of P1. When antibodies Ab1 and Ab2 are bound to their respective epitopes, splint oligonucleotide P1 is able to hybridize to both TO and P2 (FIG. 3A). Extension from the 3' ends of probe P2 and the splint oligonucleotide displaces tether oligonucleotide TO and creates a double-stranded DNA molecule linked to antibody Ab2 (FIG. 3B). Nicking of this double-stranded product, extending with polymerase, and displacing the downstream strand generates a single-stranded oligonucleotide that may form a hybrid with a complementary SDA primer (FIG. 3C). This leads to exponential amplification through a succession of intermediate nicking, extending, displacing and priming events (FIG. 3D).

Figure 3A:
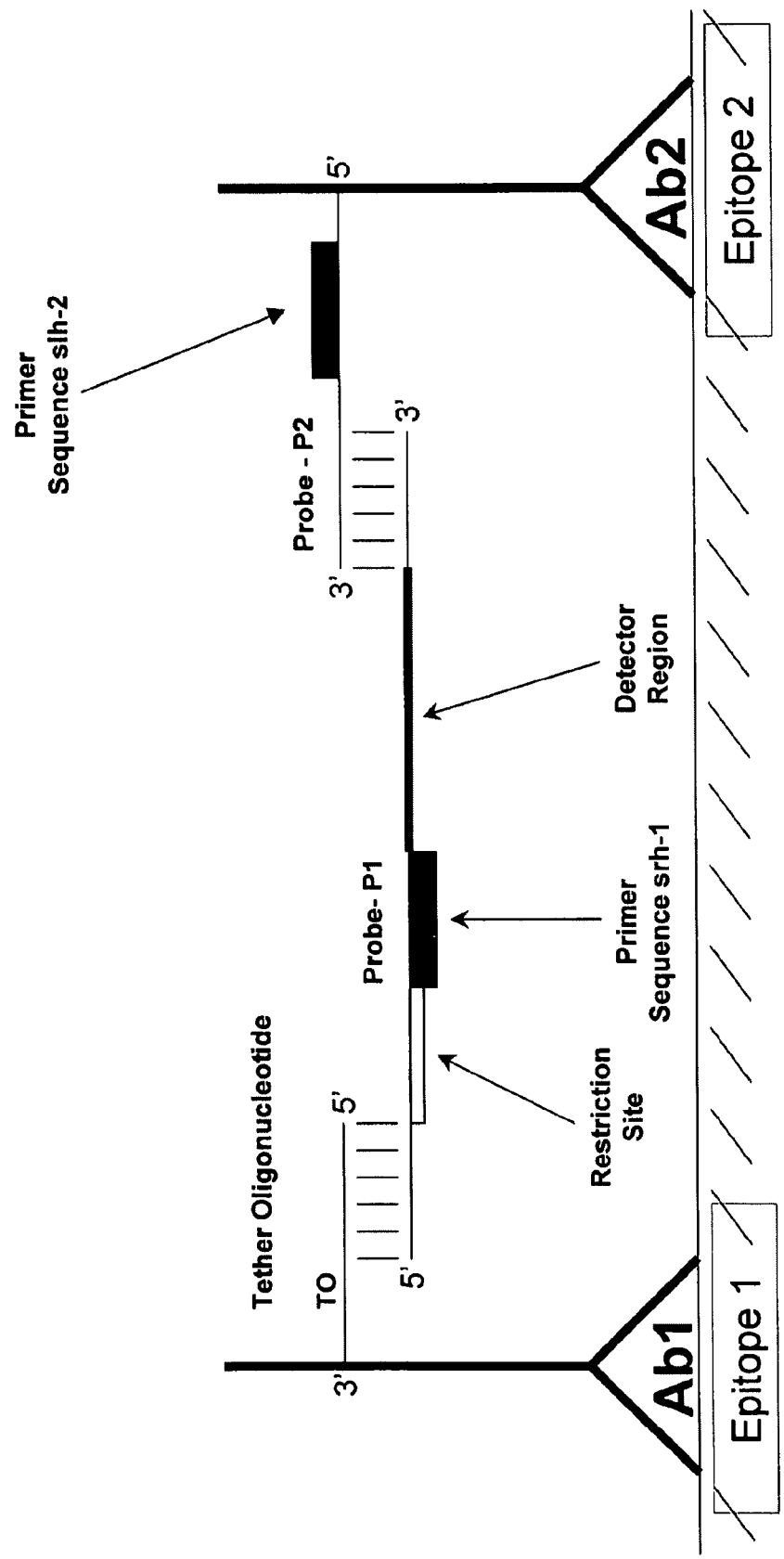
FIG. 3A shows a single-tether probe.
Figure 3B:
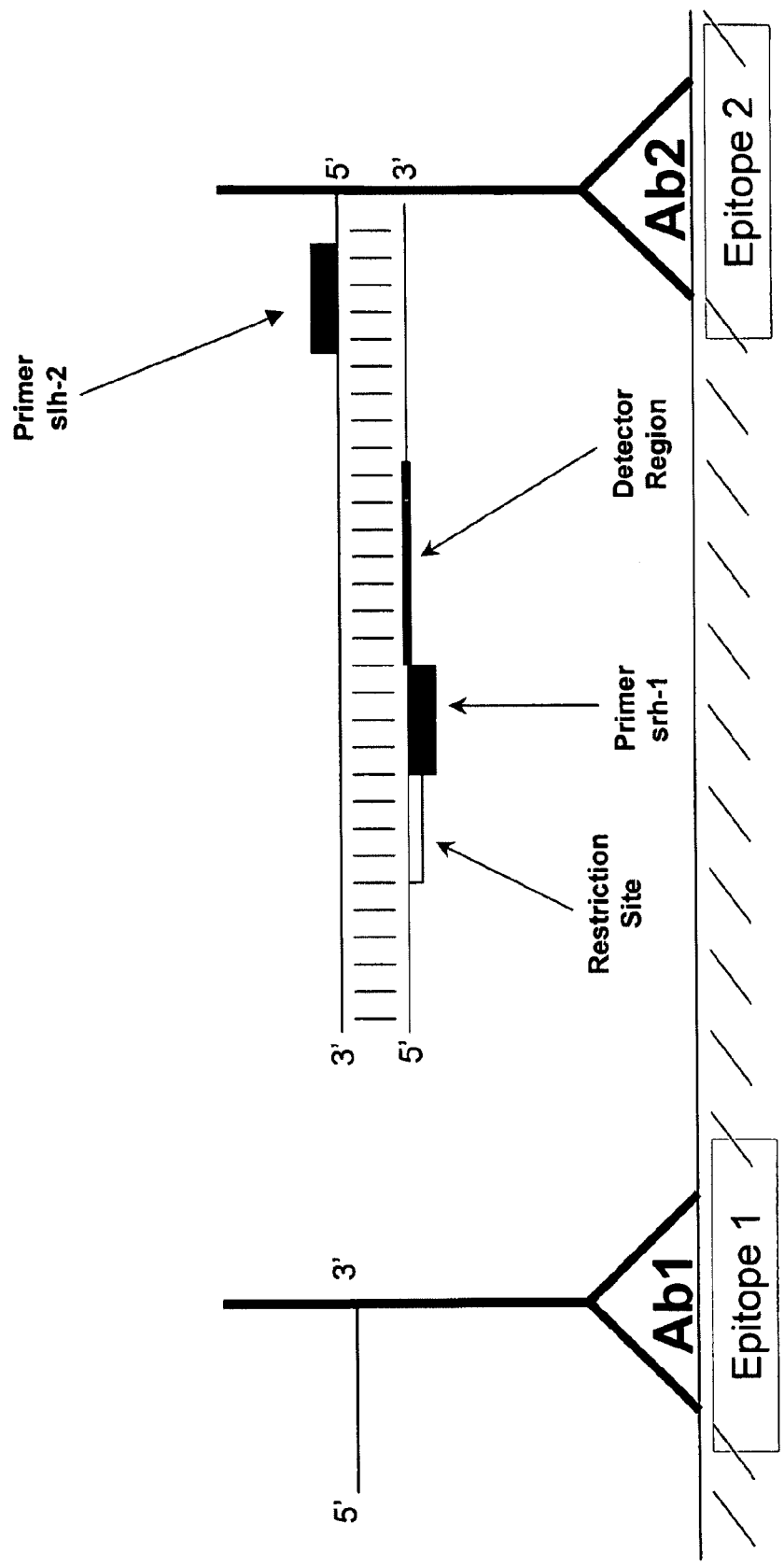
FIG. 3B shows extension and displacement of a single-tether probe.
Figure 3D:
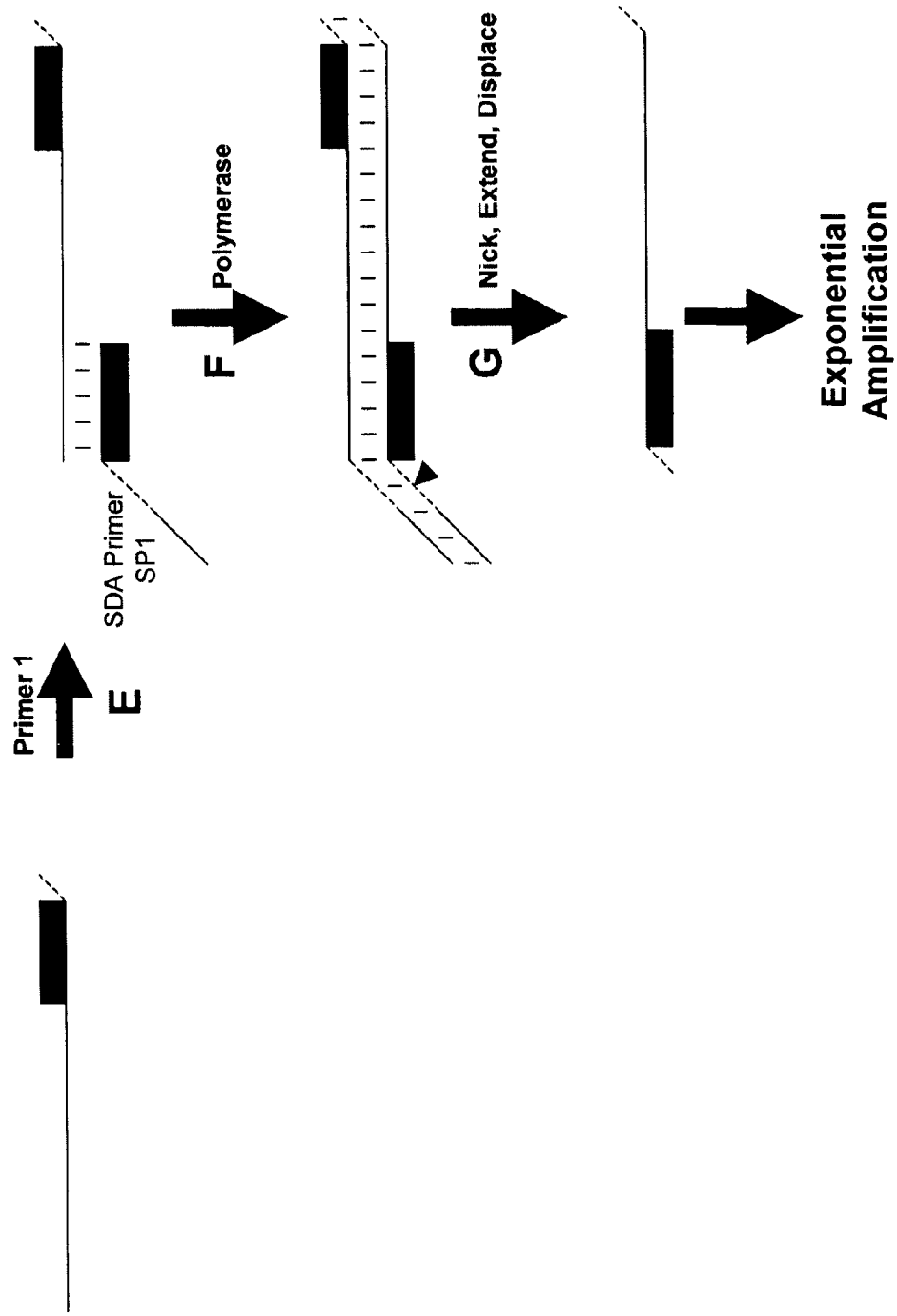
FIGS. 3C and D show nicking, extension, displacement and capture.
FIG. 3E shows splint oligonucleotides having a 3'/3' configuration.
FIG. 3F shows extension/displacement of splint oligonucleotides.
FIG. 3G shows target-mediated probe cycling.
FIG. 3H shows splint oligonucleotides having a 5'/3' configuration.
FIG. 3I shows splint oligonucleotides having a 5'/5' configuration.
FIG. 3J shows splint oligonucleotides having a 3'/3' configuration.
FIG. 3K shows splint oligonucleotides having a 3'/3' configuration.
FIG. 3L shows displacement of splint oligonucleotides from a captured complex.
Figure 3E:
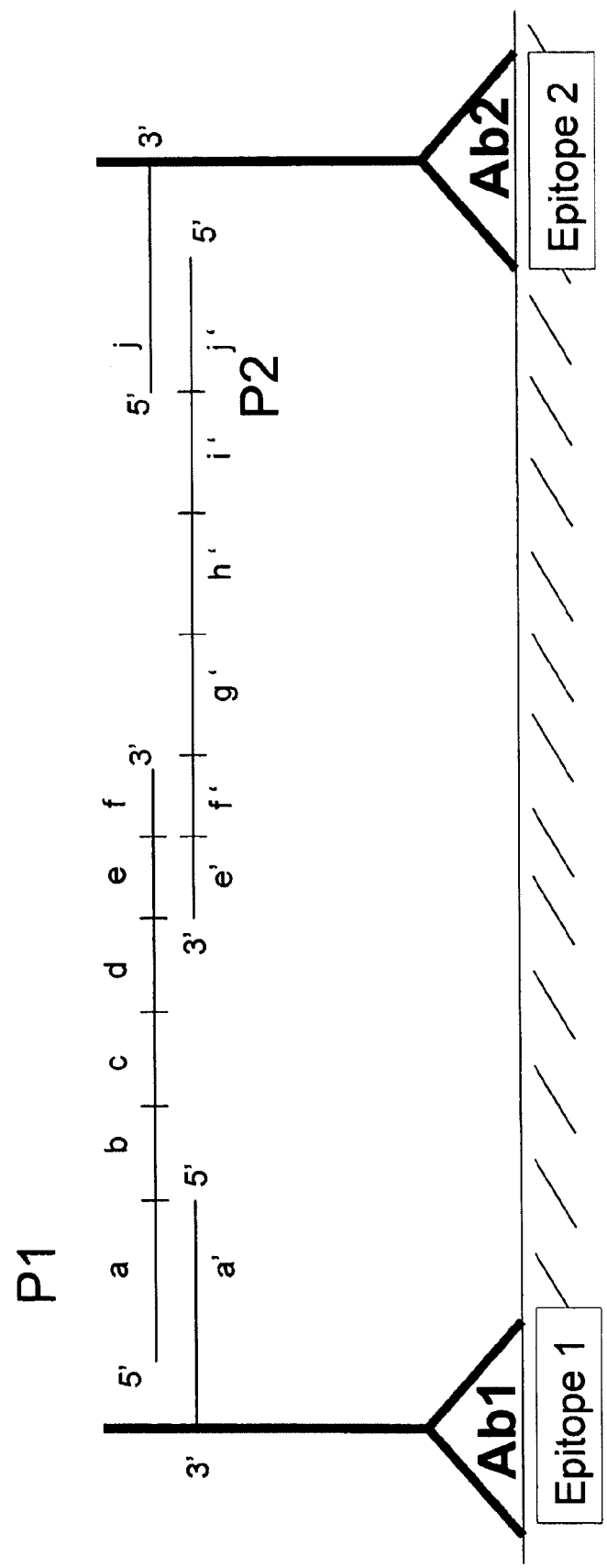

FIG. 3E depicts a second embodiment for bridging the gap between antibodies. In this configuration, each antibody (Ab1 and Ab2) is conjugated with a different tether oligonucleotide, a' for Ab1 and j for Ab2. Typically, the tether oligonucleotide of the antibody Ab1 differs from the tether oligonucleotide of the second antibody Ab2. In this case, a' and j are not equivalent in sequence. Splint oligonucleotides P1 and P2 each contain a sequence (optionally near the 5' end) that is complementary to the oligonucleotide sequences a' and j. For example, P1 contains sequence a, and P2 contains sequence j'. Sequence a of probe P1 hybridizes to sequence a' of Ab1, and sequence j of Ab2 hybridizes to sequence j' of P2. In this embodiment, P1 and P2 each contain a short 3' sequence that is complementary to the other probe; therefore, sequence (e f) of P1 is complementary to (f' e') of P2. Appreciable hybridization of these complementary 3' sequences of P1 and P2 occurs with high efficiency only when the probes P1 and P2 are brought into spatial proximity by consequence of also being hybridized to tether oligonucleotides (a' and j) of the antibodies bound to proximate epitopes. Hybridization of the 3' ends of P1 and P2 creates a short duplex with recessed 3' ends, which may then be extended by polymerase. In one embodiment, extension of the 3' ends serves to displace the splint oligonucleotides P1 and P2 from the tether oligonucleotides (and antibodies), while simultaneously creating a duplex comprised of the extension products (P1-ext and P2-ext) of both probes (FIG. 3F). P1 and P2 extension products may then be detected by a variety of amplification methods known in the art, including PCR, SDA, ligase chain reaction, 3SR, Qβ replicase-based amplification, solid phase amplification and NASBA. Sequences contained on the probes, e.g., sequences (b, c, d, e, f) of P1, and (e', f', g', h', i', j') of P2, or probe extension products may be used to facilitate amplification and detection of the probes. Special sequences that may be used to facilitate amplification include primer binding sites, restriction endonuclease sites, sequences capable of hybridizing with hybridization blocker oligonucleotides, RNA promoter sites, and the like. Detection of amplified products may occur by heterogeneous or homogeneous methods well-known in the art. Alternatively, duplex II of FIG. 3F may be detected directly without amplification by methods well-known in the art. If the method employs a DNA polymerase that possesses a 5'-3' exonuclease activity, e.g., Taq DNA polymerase, the tether oligonucleotide (a' or j) may be degraded during the extension process, and the degradation products may be detected as an indication of the presence of target antigen.

Figure 3H:
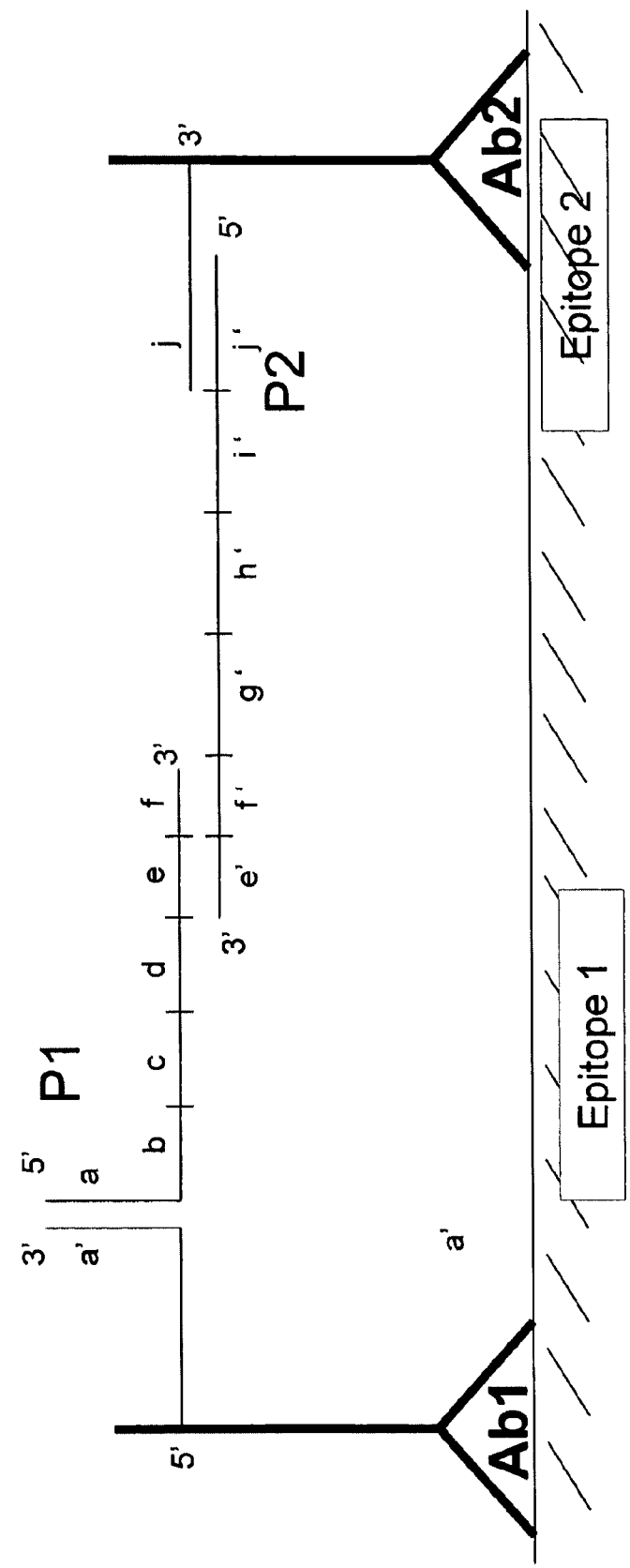
Figure 3I:
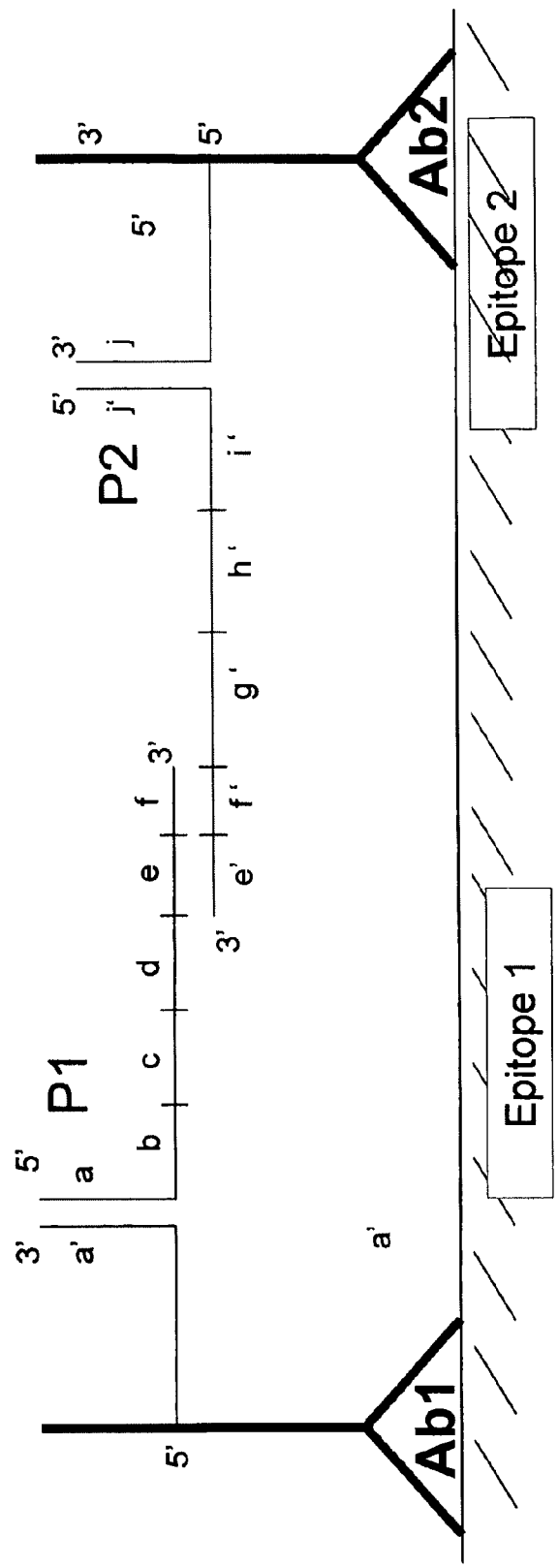

While FIGS. 3E and 3F depict antibodies conjugated to the 3' ends of the tether oligonucleotides, FIG. 3H depicts alternative configurations in which both antibodies of a proximity pair are conjugated to the 5' ends of the tether oligonucleotides. Likewise, FIG. 3I depicts an embodiment in which one tether oligonucleotide is conjugated to an antibody through a 5' linkage and the other oligonucleotide is conjugated through a 3' linkage. In each of these latter two configurations, 3' extension of the probe sequences P1 and P2 results in displacement of the probes from the tether oligonucleotides and creation of a double-stranded duplex identical to that shown in FIG. 3F.

If the tether oligonucleotides are not degraded during the displacement process, second set of probe molecules P1 and P2 may hybridize to the vacated tether oligonucleotides of the target-bound proximity members (FIG. 3G). As before, the 3' ends of P1 and P2 anneal, and extension again results in displacement of the probes and creation of a duplex comprised of P1-ext and P2-ext. The vacated tether oligonucleotides again anneal to a new pair of unextended probes (P1 and P2) if present, and the cycle of 3' hybridization, extension, displacement, and subsequent binding of unextended probes continues as long as Ab1 and Ab2 remain bound to the proximate epitopes and a supply of P1 and P2 exists. As a result of this cycling process, multiple copies of detectable probe extension duplexes are formed from each target present.

In all the examples shown in FIGS. 3A-3L, initial hybridization of the probes to the tether oligonucleotides may occur either before or after the antibody has bound to the target molecule, depending on the experimental protocol used. In one embodiment, at least one of the antibodies Ab1 and Ab2 is or may be covalently or non-covalently linked to a paramagnetic particle (FIG. 9) or other solid surface (FIG. 3L), e.g., the inner wall of a microwell. In configurations where at least one of the antibodies is linked to a bead, solid surface or other solid matrix, and both probes P1 and P2 (FIG. 3L) are attached indirectly to the antibodies by hybridization to tether oligonucleotides, extension of the probes creates a duplex that is displaced from the antibody-target complex, while the complex itself remains attached to the bead, solid surface or other solid matrix. If desired, the solution containing the displaced duplex then may be removed and analyzed or amplified in a separate well or compartment, leaving behind the complex and any material bound non-specifically to the matrix surface.

Figure 3J:
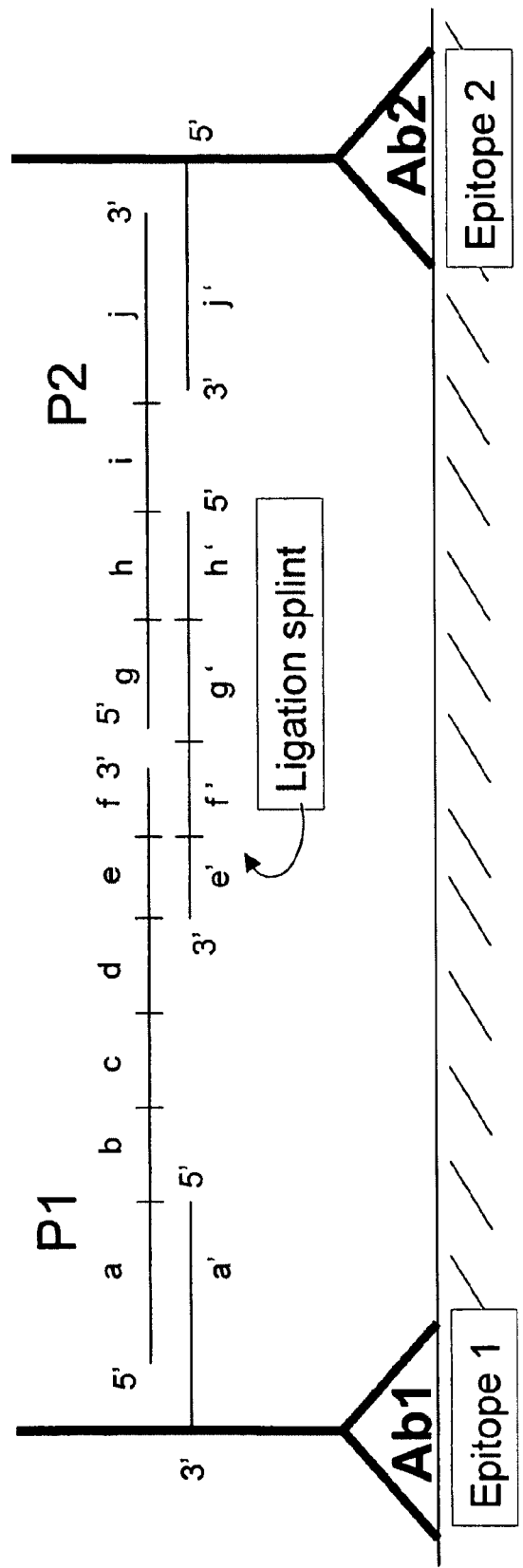

In another embodiment of the present invention, a ligation splint oligonucleotide may be complementary to a portion of both splint oligonucleotides P1 and P2 as shown, for example, in FIG. 3J. When hybridized to the ligation splint oligonucleotide, probes P1 and P2 may be ligated as described in FIG. 2 so that the 3' end of P1 is covalently joined to the 5' end of P2 (FIG. 3J), which may then be amplified as described in FIG. 2.

Figure 3K:
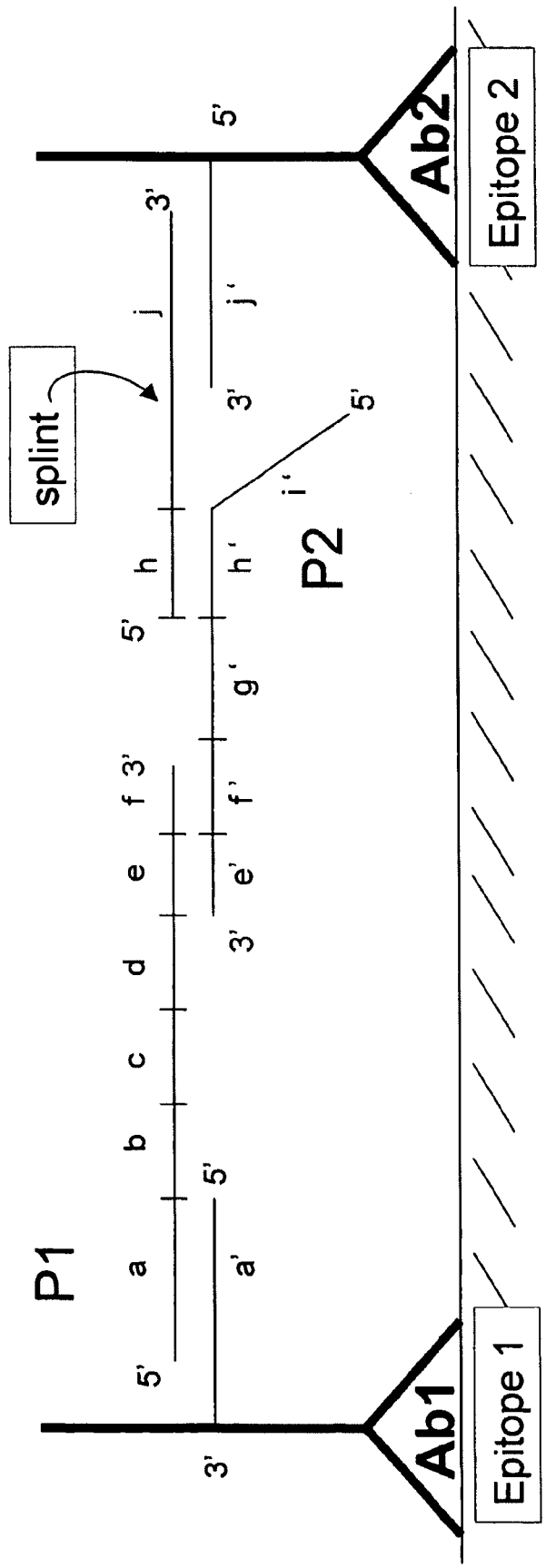
Figure 3L:
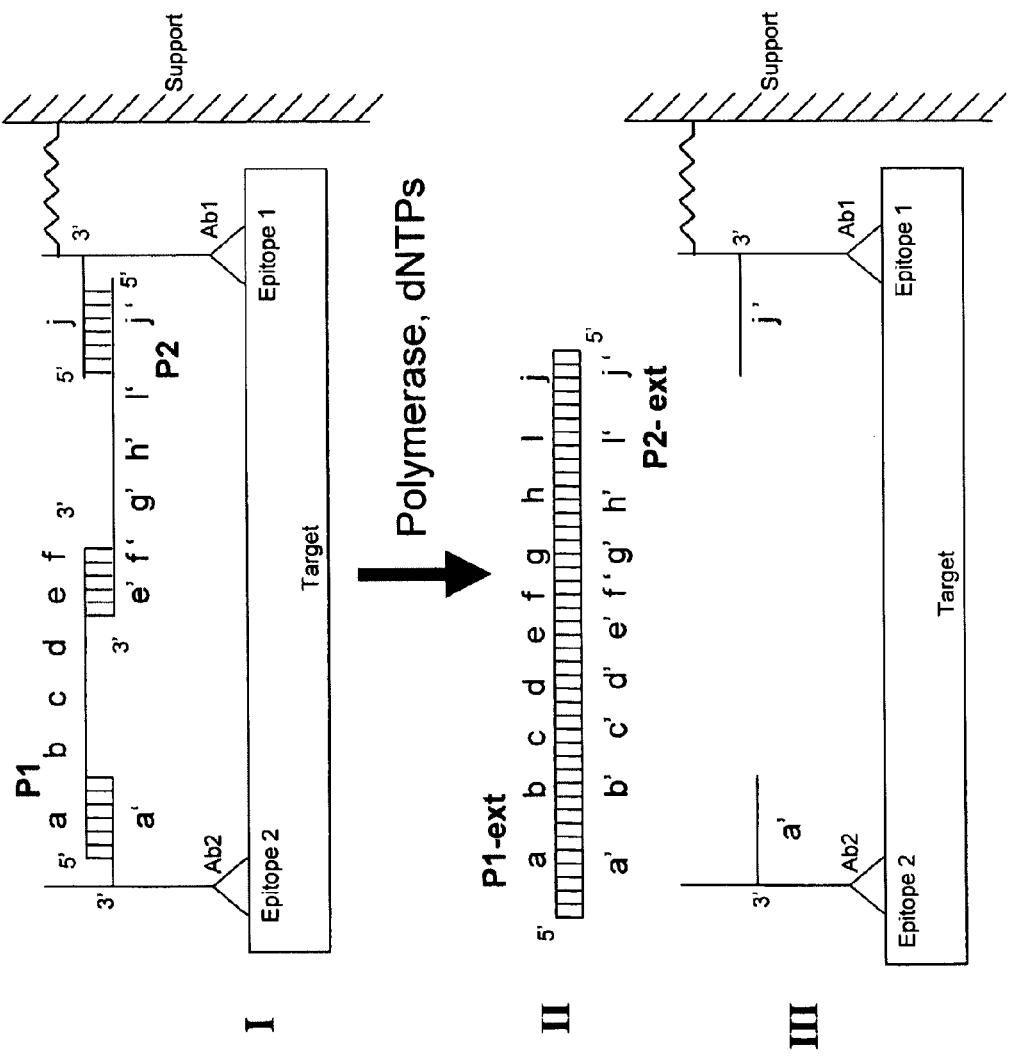

In an alternative embodiment, the splint oligonucleotide hybridizes to a tether oligonucleotide (j') and to one probe molecule P2, as exemplified in FIG. 3K. The 3' end of the splint-bound P2 may then hybridize with the complementary 3' end of spatially proximate P1. 3' extension of the probes displaces the probes from the splint and tether oligonucleotides and forms a full-length, amplifiable duplex analogous to that produced in the earlier examples shown in FIG. 3.

FIG. 4 shows hybridization blocker oligonucleotides that are designed to reduce the prevalence of hybridization between probe molecules linked to antibodies that are not bound to proximate epitopes. Such target-independent hybridization is a source of background signal because it results in probe extension products that are indistinguishable from those produce by bona fide target binding events, and background signal reduces the overall sensitivity of the detection method. The current invention comprises the use of hybridization blocker oligonucleotides (or "hybridization blockers") to reduce spurious, target-independent probe interactions that lead to background signal. FIG. 4A depicts the basic principle underlying the use of hybridization blockers in proximity-based amplification methods. Short sequences of mutual complementarity (e f and f' e') (read 5' to 3') comprise the 3' ends of P1 and P2. These sequences may hybridize to each other to form a duplex with 5' overhangs as shown. The number of probe molecules populating the duplexed versus single-stranded state depends on the total probe concentration and on the intrinsic stability of the duplex, which in turn is related to duplex length and composition. The interaction between P1 and P2 can be diminished or reversed by the addition of a hybridization blocker oligonucleotide, preferably in molar excess over the probes, which upon hybridization to P1 competitively blocks the interaction between the two probes. The blocker need not be complementary to P1 across the entire subsequence that interacts with P2. Partial complementarity across this site also diminishes hybridization of P1 to P2.

Figure 4B:
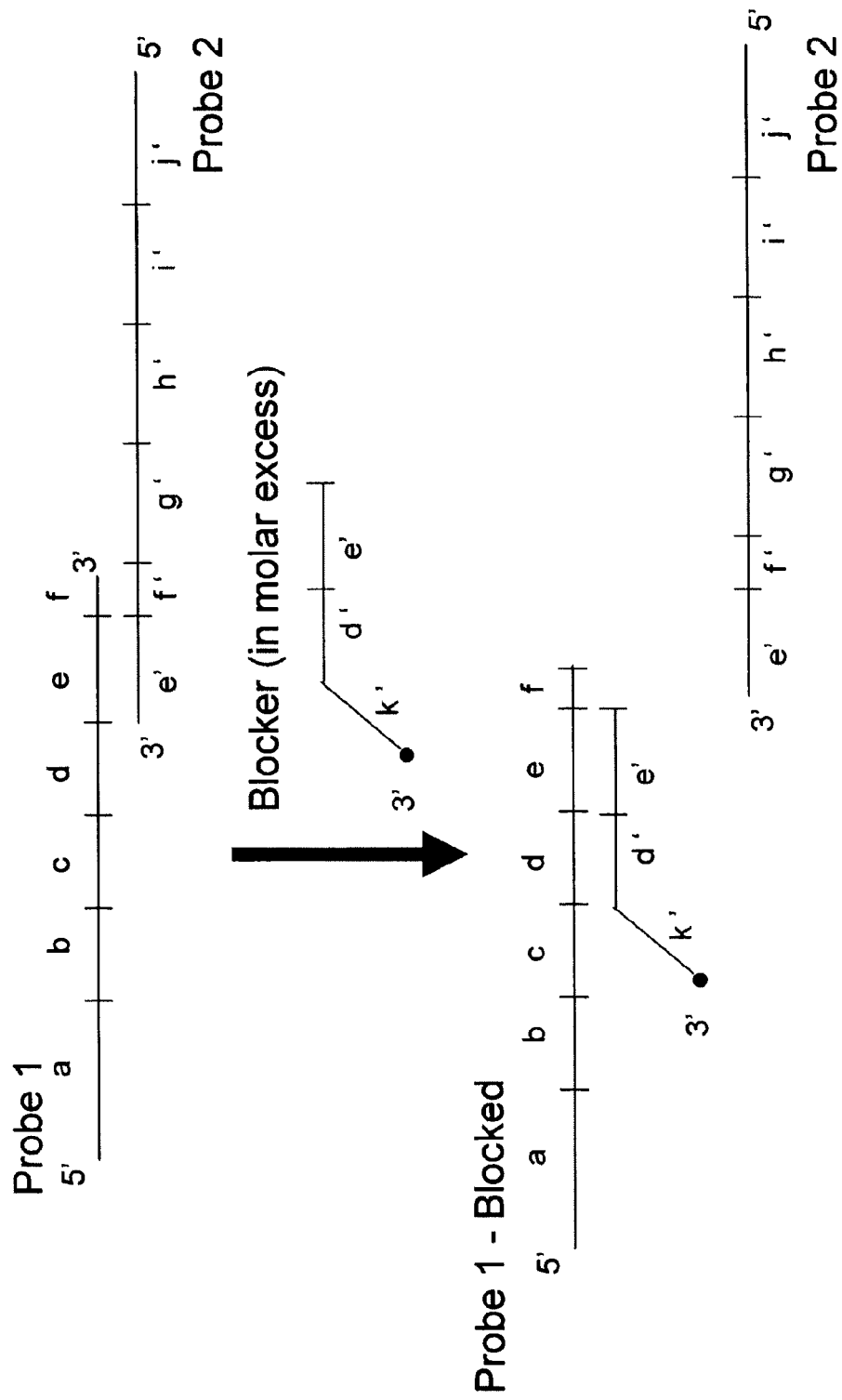
FIG. 4B shows a recessed competitive hybridization blocker.

In one embodiment, the hybridization blocker oligonucleotide comprises a first subsequence (e' or f' e') that is identical to part or all of that portion of P2 that is complementary with P1 (subsequence e f). In a second embodiment (FIG. 4B), the hybridization blocker oligonucleotide comprises the first subsequence, defined above, and a second subsequence (d' in FIG. 4B) that is complementary to a segment of P1, but not identical to a subsequence of P2. The second subsequence of the hybridization blocker stabilizes the blocker-P1 interaction relative to the P1-P2 interaction, thereby improving blocking efficiency. The second subsequence also may serve as a site for nucleation of the P1-blocker duplex in the event that P2 molecule is already hybridized to P1. Following nucleation, formation of the full P1-blocker duplex then displaces P2 from P1. The P1 subsequence d of this embodiment may be directly adjacent to the probe subsequence e, as shown in FIG. 4B, or it may be located some nucleotides away from subsequence e (not shown). In the latter case, the hybridization blocker subsequence d' may be linked indirectly to hybridization blocker subsequence e' through a spacer, comprising additional nucleotides and/or a non-nucleotide linker, such as a tetraethylene glycol (TEG) moiety.

In a third embodiment (FIG. 4C), the hybridization blocker oligonucleotide may comprise a first subsequence (defined above), optionally a second subsequence (defined above), and a third subsequence (t' s' in FIG. 4C), which is located 5' of the first subsequence and which may serve as a template for the 3' extension of P1. The third subsequence optionally may contain a suitable non-nucleotide moiety m' (i.e., a "5' cap"), which are well known in the art, to prevent the addition of non-templated nucleotides to the 3' extension product of P1 and to discourage binding of polymerase to the blunt-ended duplex formed by extension of P1 (see FIG. 4C). Preferably, the 3' extension of P1 on the blocker-template yields a P1-extension product containing a new sequence (s t) at its 3' end that is not complementary to the P2 sequence. Addition of the 3' sequence (s t), therefore, serves to disable P1 as a functioning primer for DNA synthesis on a P2 template. Addition of the sequence (s t) also serves to stabilize the blocker-P1 interaction by increasing the number of complementary base pairs between the two molecules. Optionally, the new 3' sequence (s t) produced in this embodiment is entirely or partially complementary to a segment of P1, such that, if the extended P1 and hybridization blocker dissociate, the extended P1 will fold into a stem-loop (hairpin) structure, diminishing any interaction with P2. In this case, the 3' end of the P1 hairpin optionally may be extended to lengthen the stem of the hairpin, and this extension optionally may create a nickable or cleavable restriction endonuclease site within the P1 molecule.

Figure 4D:
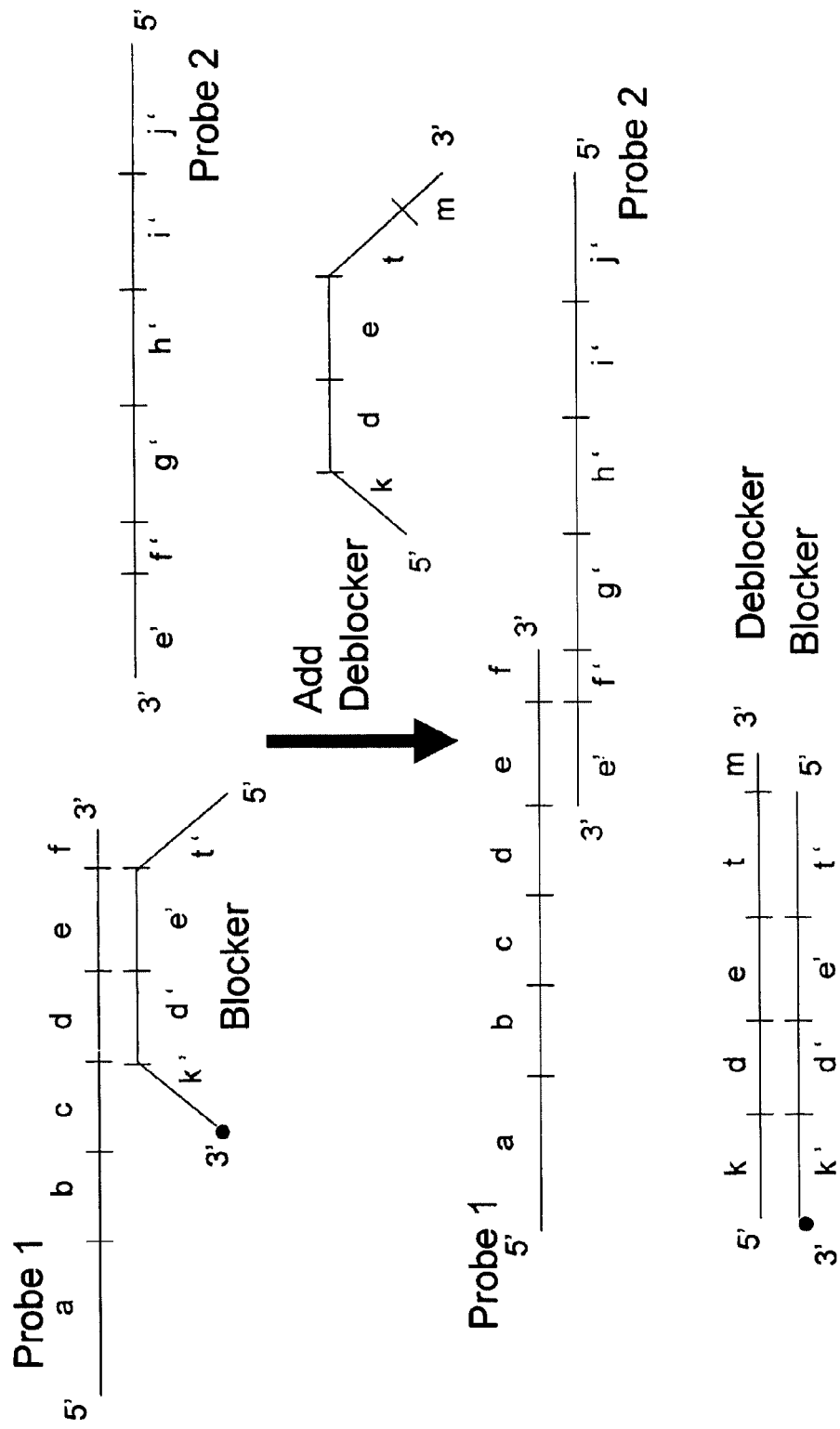
FIG. 4D shows a displaceable hybridization blocker.
Figure 4E:
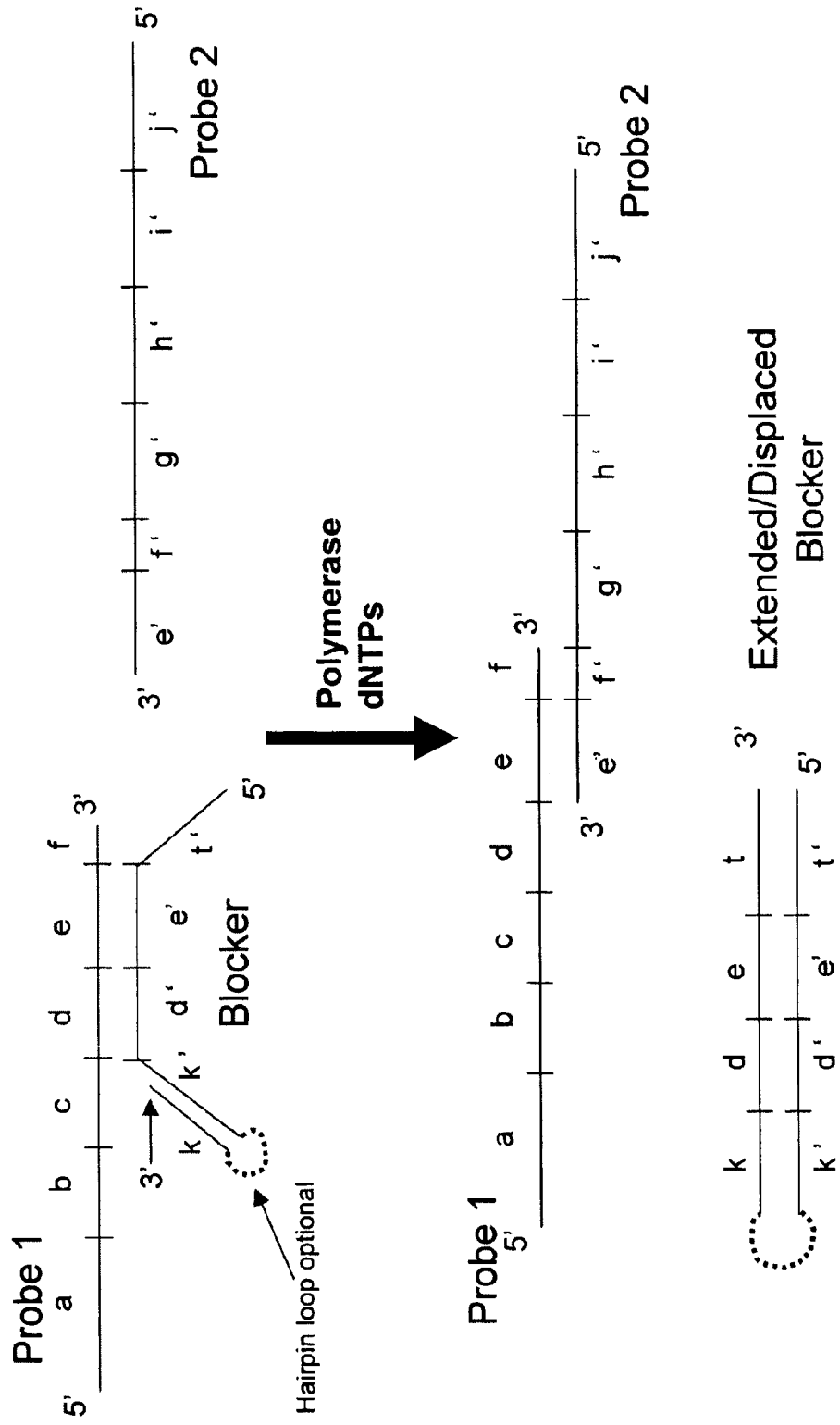
FIG. 4E shows a self-displacing hybridization blocker.
Figure 4E:
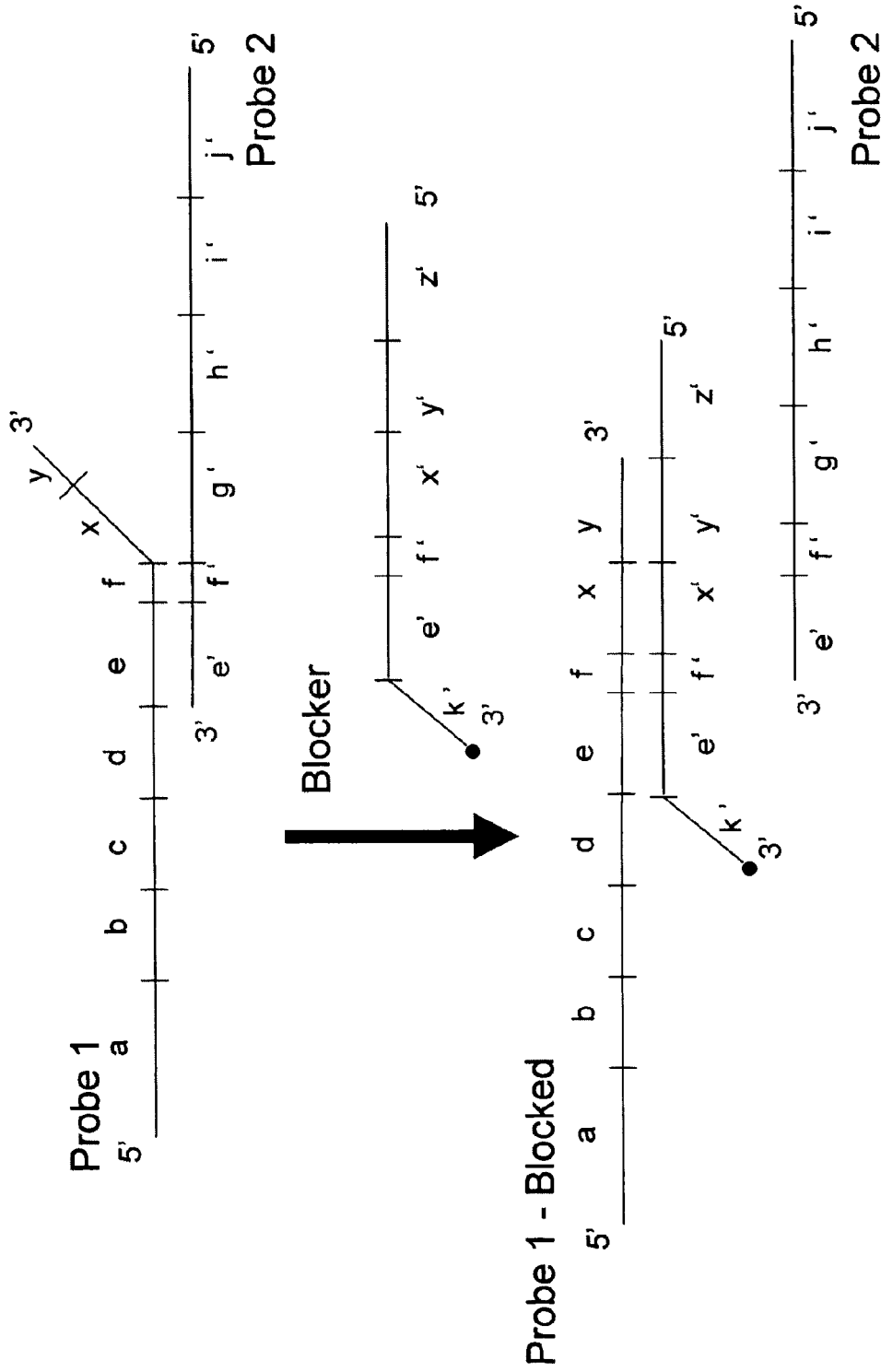

In a fourth embodiment, it may be desirable to block reversibly the interaction between P1 and P2 during a certain phase of a process. FIG. 4D depicts a hybridization blocker design that allows reversible blocking. In this embodiment, the hybridization blocker comprises a subsequence (e' d') that is complementary to the probe to be blocked (P1 in FIG. 4D) and one or more tail sequences (t' and/or k') that are not complementary to the probe. Hybridization of the hybridization blocker to P1 precludes P1-P2 interactions. At the desired time, a deblocking oligonucleotide may be added to displace the hybridization blocker oligonucleotide from P1, freeing the latter to interact with P2. The deblocking oligonucleotide comprises one or more tail sequences (t and/or k) that are complementary to the tail sequences of the hybridization blocker. The tail sequences serve as a site of nucleation for the blocker-deblocker hybridization. Once hybridization of the complementary tail sequences is nucleated, additional base-pairs form between the hybridization blocker and deblocker until the blocker is displaced from P1. To ensure displacement of the blocker from the probe, the overall thermodynamic stability of the blocker-deblocker complex must be higher than the probe-blocker complex. The deblocking oligonucleotide need not be perfectly complementary to the hybridization blocker oligonucleotide, provided that the thermodynamic stability of the blocker-deblocker duplex is higher than the stability of probe-blocker duplex. For instance, it may be desirable for the deblocker to contain one or more nucleotides that form mismatches with the hybridization blocker oligonucleotide, provided that the resulting blocker-deblocker duplex is more stable than the probe-blocker duplex. In particular, it may be desirable for sequence e of the deblocker to contain one or more nucleotides that form one or more mismatches with sequence e' of the blocker. The primary function of these mismatching nucleotides of the deblocker is to destabilize potential interactions between sequence e of the deblocker and sequence e' of P2. In a variation of this embodiment, the hybridization blocker may be displaced by polymerase-catalyzed extension of sequence k as shown in FIG. 4E. In this case, the deblocking sequence is synthesized directly upon the blocking sequence, and no separate deblocker oligonucleotide need be added. In yet another embodiment, a probe may comprise a 3' stem-loop structure at or near its 3' end that serves to, block interactions between probe molecules (see FIG. 11).

To prevent 3' extension of the blocker by polymerase, all hybridization blocker oligonucleotides described above, except the hybridization blocker with the hairpin structure depicted in FIG. 4E, may comprise a cap on the 3' terminal nucleotide. Hybridization blocker oligonucleotides with 3' caps are referred to as "capped oligonucleotides." Such 3' caps are well-known in the art and include inverted nucleotides, 2'-3' dideoxyribonucleotides, and 3' deoxyribonucleotides. Hybridization blocker oligonucleotides may contain a 3' tail sequence that does not form complementary base-pairs with the probe nucleotides when the hybridization blocker forms a duplex with the probe. The non-base-paired 3' tail also serves to prevent 3' extension of the blocker when the hybridization blocker is duplexed with the probe and, therefore, serves as a "3' cap" as well.

FIG. 4EE illustrates the use of a 3' tail on Probe 1 (P1) to facilitate stabilization of the P1 blocker duplex. The 3' tail of P1 is comprised of sequence x y and is located 3' of sequence (e f), which is capable of hybridizing with sequence (f' e') of Probe 2 (P2). The 3' tail of P1 does not hybridize to P2. The hybridization blocker comprises sequence (y' x' f') and optionally e'. The hybridization blocker is, therefore, capable of hybridizing to P1 to form a duplex covering the 3' tail of P1, as well as all or part of sequence e f of P1. Formation of the blocker:P1 duplex will reduce the prevalence of P1:P2 hybrids as described above. Base-pairing between (x y) of P1 and (y' x') of the hybridization blocker serves to stabilize the blocker:P1 duplex. The hybridization blocker optionally comprises sequence z' located 5' of sequence (y' x'). Sequence z' may serve as a site for initiating hybridization of the deblocker oligonucleotides in methods described above.

Figure 4F:
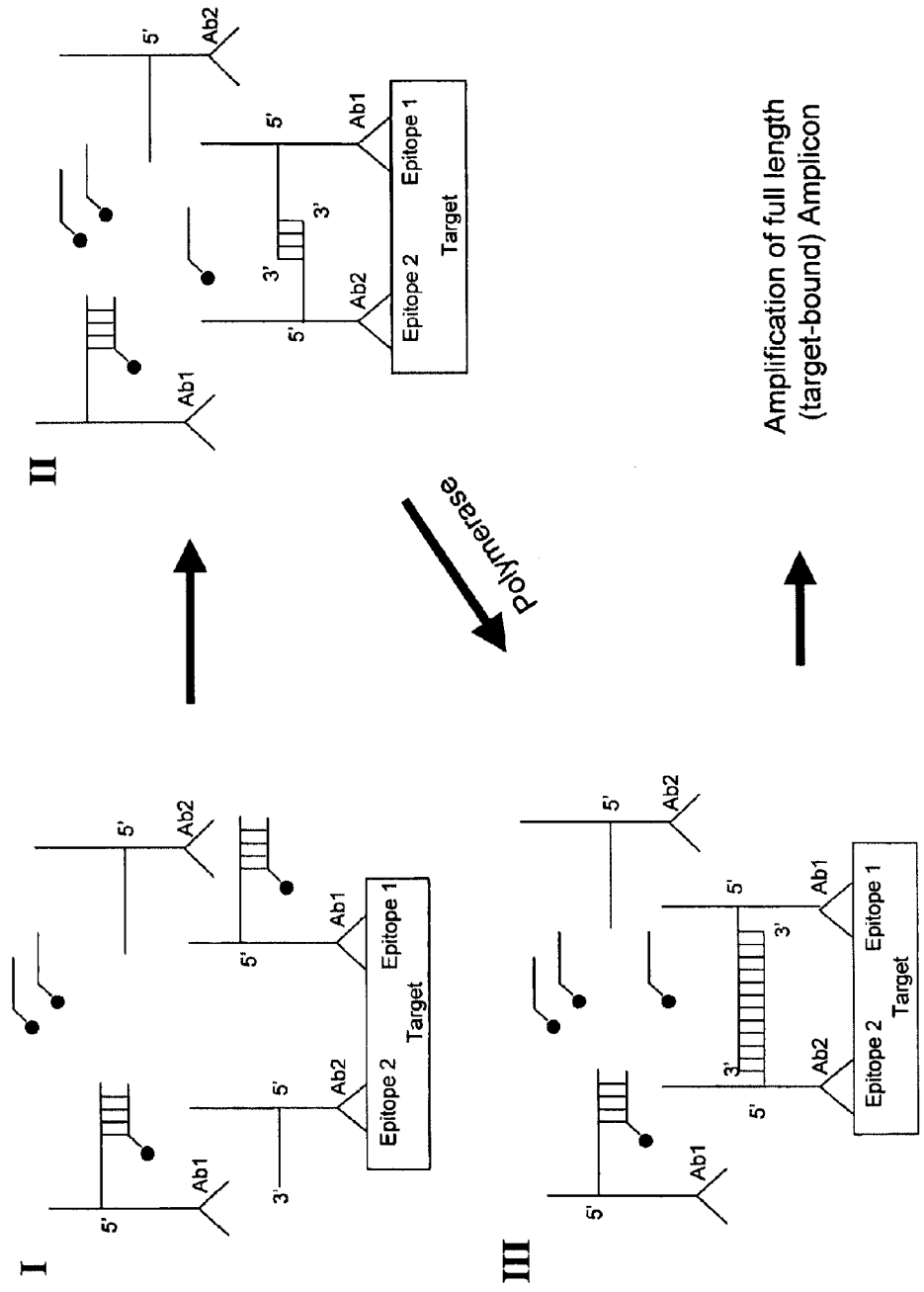
FIG. 4F shows competitive hybridization blocker in a binary immuno-SDA reaction.
Figure 5A:
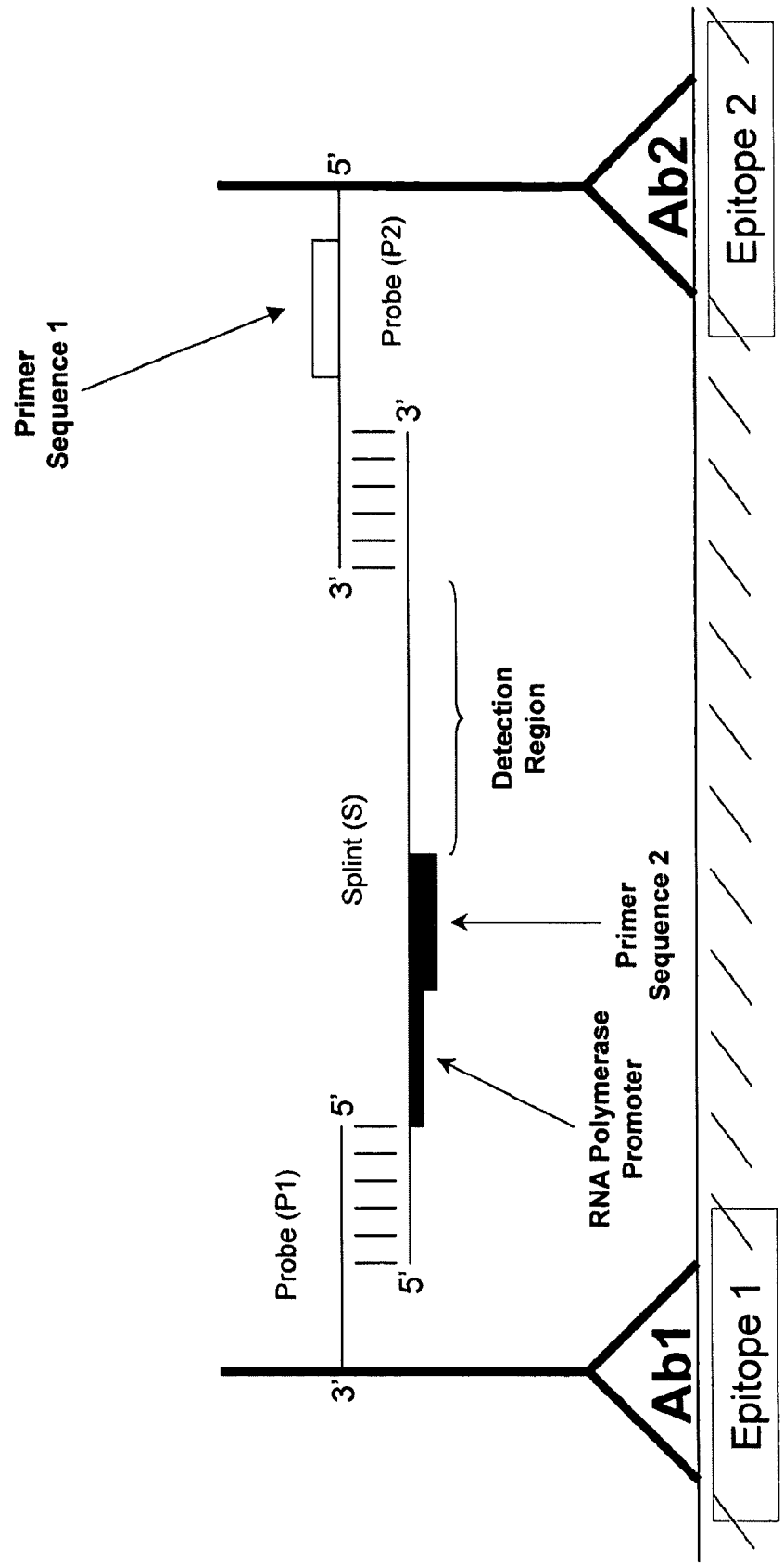
FIG. 5A shows a splint oligonucleotide hybridization.
Figure 5B:
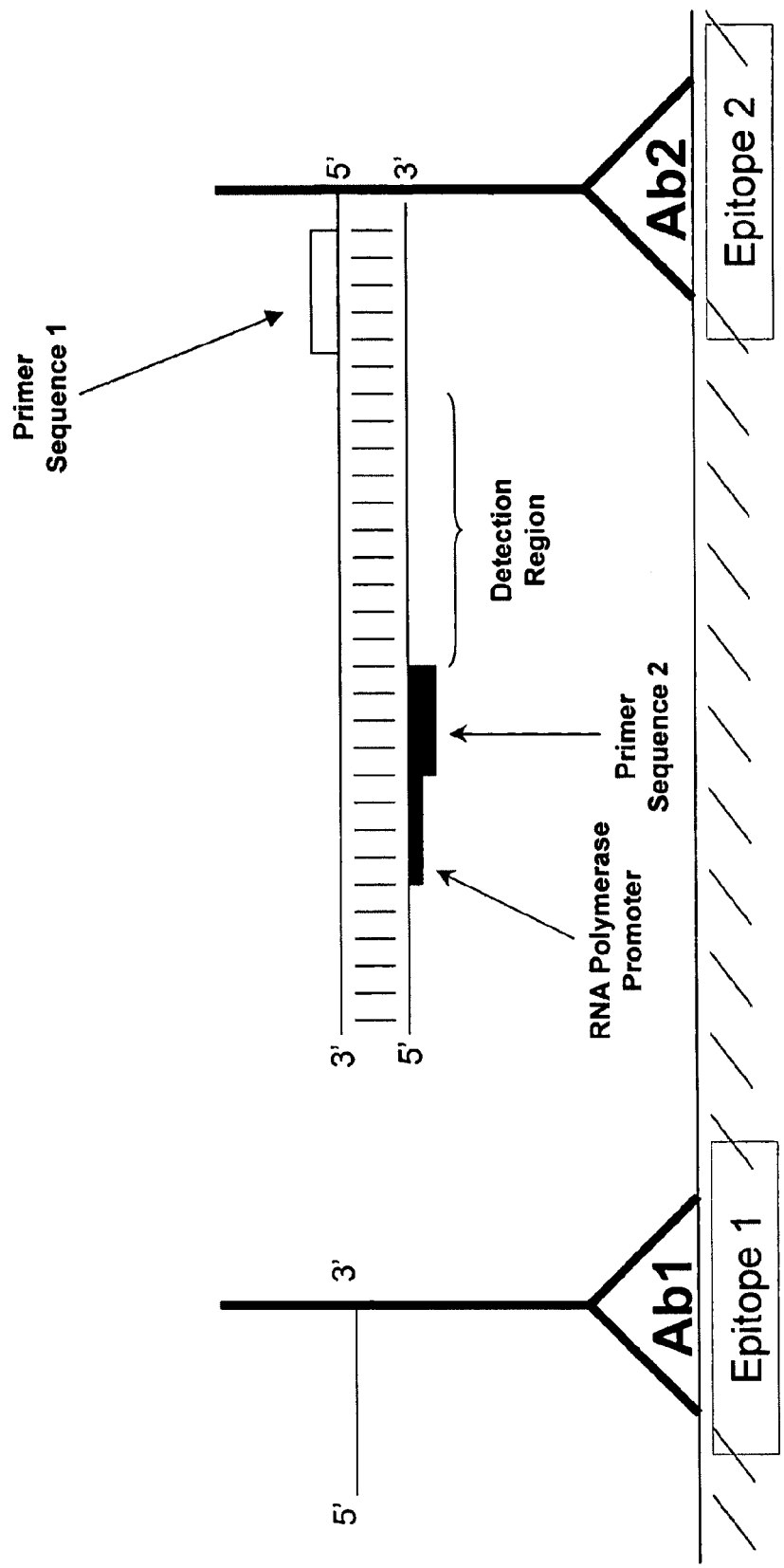
FIG. 5B shows extension and displacement.
Figure 5C:
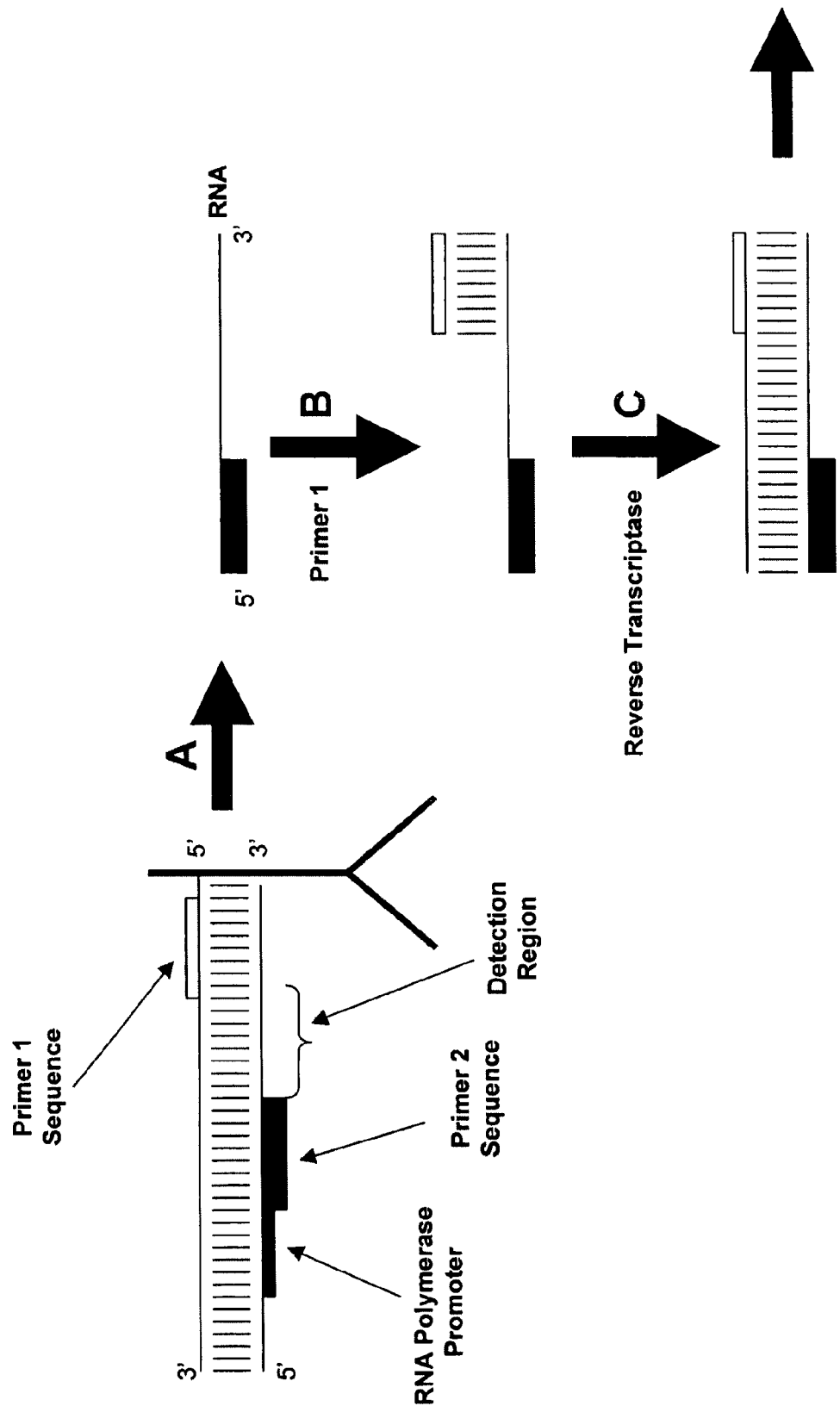
FIG. 5C shows RNA polymerase activity, hybridization and extension.
Figure 5D:
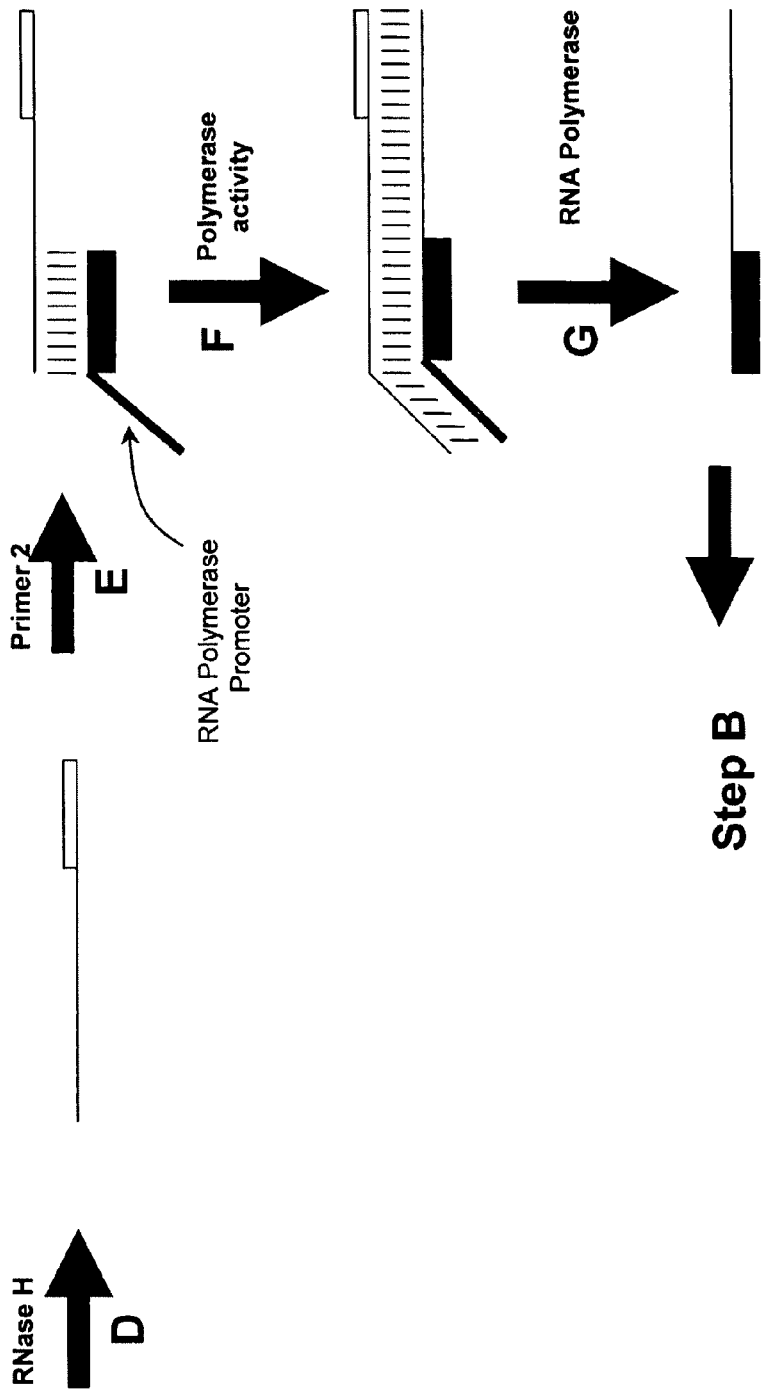
FIG. 5D shows RNase H activity, hybridization and extension.

FIG. 4F illustrates the use of hybridization blocker oligonucleotides in a binary immuno-amplification reaction. P1 and P2 are conjugated directly to antibodies Ab1 and Ab2, respectively. The same principles apply regardless if the probes are bound to an antibody indirectly via hybridization to a tether oligonucleotide, or if the analyte-specific binding components are aptamers or other analyte-specific binding molecules other than antibodies. As depicted, a hybridization blocker oligonucleotide hybridizes to the 3' end of P1, precluding its interaction with P2. Hybridization of the hybridization blocker does not interfere with binding of the antibody to the target analyte, and initially the hybridization blocker is hybridized to P1 strands whether or not Ab1 is complexed with the analyte or free in solution (state I). Typically, the concentration of free Ab1 and Ab2 (and the conjugated probes) in bulk solution is between 1 fM and 10 nM. Because hybridization blocker concentrations typically are 10- to 100,000-fold higher than probe concentrations, blocker-P1 interactions predominate over P1-P2 interactions for probes that are conjugated to antibodies that are not target-bound; however, when epitopes 1 and 2 of a target molecule are bound to Ab1 and Ab2, respectively, the effective local concentration of P1 relative to P2 on the ternary target-antibody complex becomes much higher (typically 1-100 µM) than the concentration of probes and hybridization blockers in bulk solution. As a result, the P1:P2 duplex prevails over the P1:blocker duplex for probes linked to target-bound antibodies (state II). Polymerase-catalyzed extension of the 3' ends of the P1:P2 hybrids, therefore, results in an amplifiable duplex on the target-Ab1-Ab2 complex (state III), while probes not linked to target complexes remain blocked, unextended and incapable of being amplified. While FIG. 4F depicts the use of a single hybridization blocker that hybridizes with only one of the probes, a second hybridization blocker that hybridizes with the other probe may be used in conjunction with the first blocker.

FIG. 4G depicts a similar reaction scheme, employing hybridization blockers capable of "disabling" P1 molecules by functioning as a template for extension (see FIG. 4C above). For the reasons set forth above, the blocker:P1 duplex predominates over the P1:P2 duplex for probes in bulk solution, whereas the P1:P2 duplex prevails on the ternary, target-antibody complex. Polymerase-catalyzed extension of the blocker:P1 duplex results in a "disabled" P1 extension product (see FIG. 4C), while extension of the of the P1:P2 duplex results in an amplifiable duplex as in FIG. 4F.

FIG. 4H depicts a step-wise blocking process, in which a displaceable hybridization blocker A hybridizes to P2, forming a blocker A:P2 duplex. Optionally, hybridization blocker A in this scheme may have a sufficient length or concentration to make the blocker A:P2 duplex more stable than the P1:P2 duplex, both in bulk solution and on the ternary, target-Ab1-Ab2 complex. A second hybridization blocker B that is complementary to a segment of P1 and a deblocker D that is complementary to displaceable hybridization blocker A are added to the solution, resulting in displacement of A from P2, formation of P1:blocker B duplexes in bulk solution, and formation of P1:P2 duplexes on the ternary, target-antibody complex. Optionally, hybridization blocker B may comprise a "disabling" sequence to disable P1 as described above (see FIGS. 4C and 4F). As before, polymerase-catalyzed extension of the probe-probe hybrid results in an amplifiable duplex, while optional extension of the P1:blocker B duplexes results in a "disabled" P1 extension product.

FIG. 4I depicts a reaction scheme in which the P1:P2 duplex is allowed to form both in bulk solution and on the ternary, target-antibody complex. Addition of a hybridization blocker then preferentially disrupts P1:P2 duplexes in bulk solution compared to those on the ternary target complex because of the different effective probe concentration in bulk solution versus the ternary complex (see FIG. 4F).

In one embodiment, the hybridization blocker oligonucleotide may be covalently or non-covalently linked to a paramagnetic particle or other solid surface and further may be used to reversibly bind proximity members to the surface (see FIG. 6). In another embodiment of the present invention, at least one of the antibodies Ab1 and Ab2 is, or may be, covalently or non-covalently linked to a paramagnetic particle (see FIG. 9) or other solid surface.

The embodiment of the present invention depicted in FIG. 5 comprises a splint oligonucleotide that is designed to bridge the gap between two proximity members. In one embodiment, the splint oligonucleotide S comprises an RNA polymerase promoter sequence, a downstream primer binding sequence, and a detector region (FIG. 5A). The 5' sequence of splint S is complementary to the 5' end of P1, which is conjugated to antibody Ab1 at its 3' terminus. In addition, the 3' sequence of splint S is complementary to the 3' end of probe P2, which is conjugated to antibody Ab2 at its 5' end. When antibodies Ab1 and Ab2 are bound to their respective epitopes, splint oligonucleotide S is able to hybridize to both P1 and P2 (FIG. 5A). Extension from the 3' ends of probe P2 and splint S displaces probe P1 and creates a double-stranded molecule linked to antibody Ab2, which possesses a functional RNA polymerase promoter (FIG. 5B). RNA polymerase produces single-stranded RNAs, using this double-stranded promoter sequence. In one embodiment (not shown), the single-stranded oligonucleotides are detected directly by any suitable method known in the art. In a second embodiment, the single-stranded RNA molecules hybridize to complementary primers that in turn are extended to generate DNA:RNA hybrids (FIG. 5C). Digestion of the RNA strand of these hybrids with an RNase produces single-stranded DNA molecules to which primers containing an RNA polymerase promoter may hybridize (FIG. 5D). Extension from the 3' ends of the hybridized primers and their target strands generates double-stranded RNA polymerase promoter sequences, leading to exponential amplification.

Another aspect of the present invention, illustrated in FIG. 6, comprises different methods for attaching antibodies, antigens or antigen-antibody complexes to solid surfaces by oligonucleotide hybridization to a capture oligonucleotide that is attached directly to a support, which may be a solid surface, polymer, hydrogel, or other surface. Suitable supports for the invention, such as a particle or microtiter well surface, are well-known in the art. Methods of stably conjugating oligonucleotides to various supports are well-known in the art as well. The capture oligonucleotide may interact by hybridization with an oligonucleotide moiety or it may interact with another oligonucleotide that is conjugated to an analyte-binding moiety of a proximity member. The invention further comprises methods of selectively releasing the captured molecules from the surfaces by a variety of chemical, physical or enzymatic means.

Figure 6A:
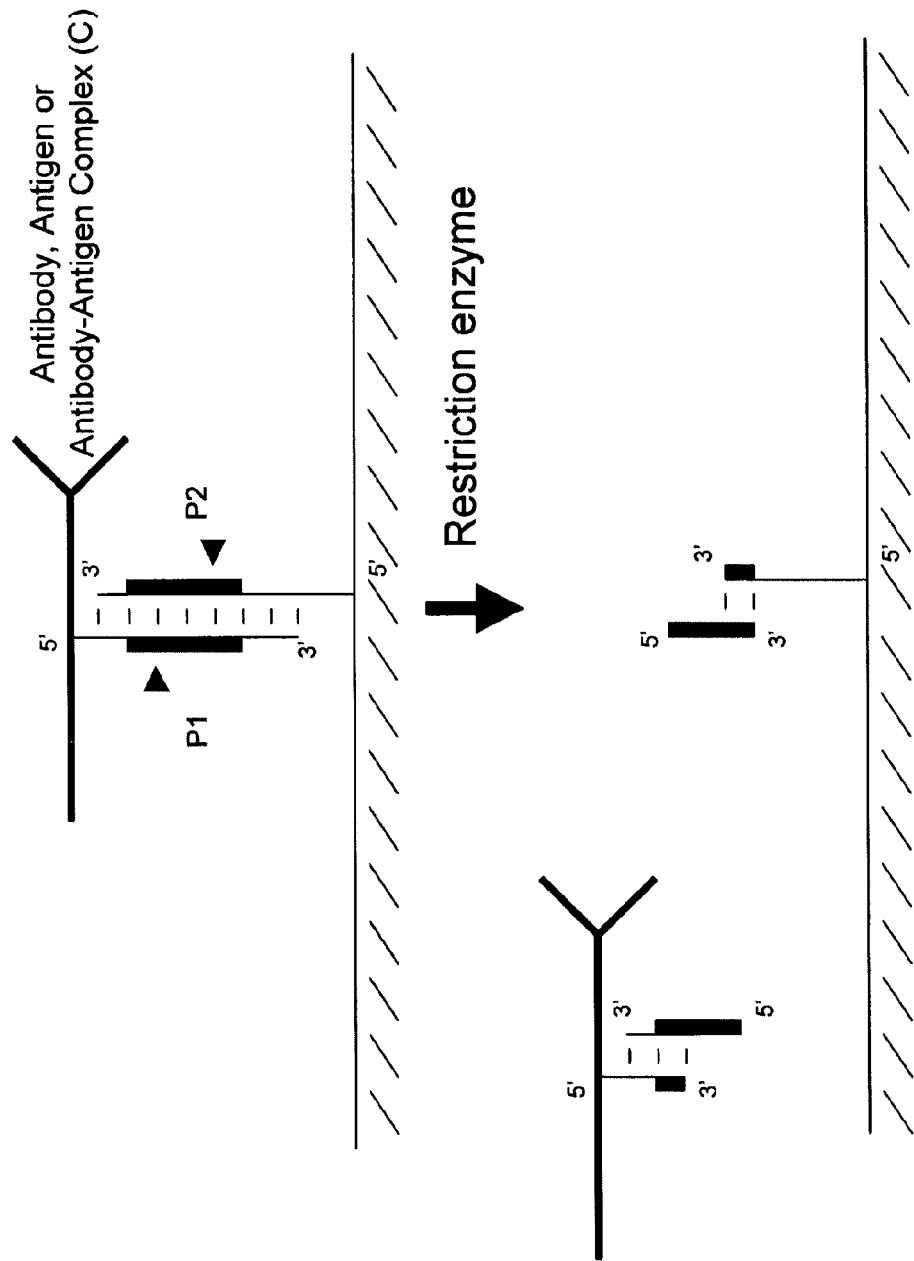
FIGS. 6A-C show restriction endonuclease-mediated release of an attached conjugate.

As shown in FIG. 6A, the antibody, antigen or antibody-antigen complex C may be conjugated to P1 via its 5' terminus. The conjugated oligonucleotide comprises a restriction enzyme recognition sequence and optional flanking sequences and hybridizes to a complementary oligonucleotide P2, which is attached by its 5' terminus to a solid surface. Release of the complex C from the solid phase occurs through the specific activity of a restriction enzyme that cleaves the double-stranded recognition sequence formed by hybridization of P1 and P2. P1 in all the panels of FIG. 6 may be the amplifiable oligonucleotide moiety of the proximity member (see FIG. 6N), or it may be another oligonucleotide that is conjugated to the analyte-specific binding moiety.

As shown in FIG. 6B, the antibody, antigen or antibody-antigen complex C may be conjugated to P1 via its 5' terminus. The conjugated oligonucleotide comprises a restriction enzyme recognition sequence and optional flanking sequences and hybridizes to a complementary oligonucleotide P2 attached by its 5' terminus to a solid surface. P2 comprises the complement of oligonucleotide P1 and a 3' non-complementary tail. Release of complex C from the solid phase occurs through the specific activity of a restriction enzyme that cleaves the double-stranded recognition sequence formed upon hybridization of oligonucleotides P1 and P2. The cleaved P1 oligonucleotide is rendered single-stranded through hybridization of the displacement oligonucleotide D.

As shown in FIG. 6C, the antibody, antigen or antibody-antigen complex C may be conjugated to P1 via its 3' terminus. The conjugated oligonucleotide comprises a restriction enzyme recognition sequence and optional flanking sequences and hybridizes to a complementary oligonucleotide P2 attached by its 3' terminus to a solid surface. Release of the complex C from the solid phase occurs through the specific activity of a restriction enzyme that cleaves the double-stranded recognition sequence formed upon hybridization of P1 and P2.

Figure 6D:
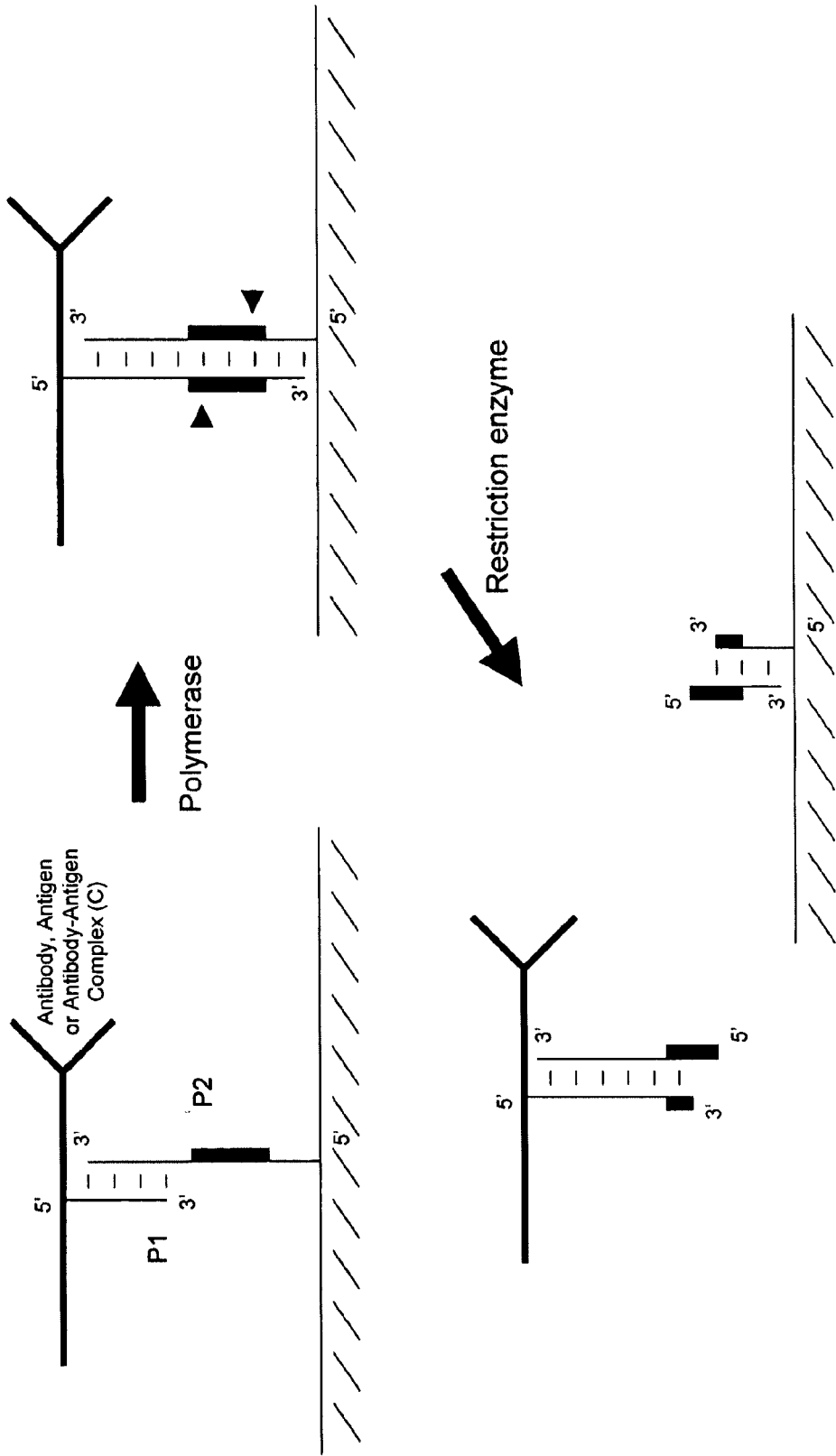
FIGS. 6D and E show polymerase- and restriction endonuclease-mediated release.

As shown in FIG. 6D, the antibody, antigen or antibody-antigen complex C is conjugated to P1 via its 5' terminus. The conjugated oligonucleotide comprises a sequence that is complementary to the 3' end of an oligonucleotide P2 that is attached through its 5' terminus to a solid surface. P2 comprises a restriction enzyme recognition sequence and optional flanking sequences. DNA polymerase extension from the 3' end of P1 results in synthesis of the complement of P2 and the formation of a double-stranded restriction enzyme recognition sequence that may be cleaved selectively to release complex C. In a further embodiment, the 3' end of oligonucleotide P2 may be capped to prevent extension.

As shown in FIG. 6E, the antibody, antigen or antibody-antigen complex C is conjugated to an oligonucleotide P1 via its 5' terminus. The conjugated oligonucleotide comprises a restriction enzyme recognition sequence together with optional flanking DNA and a sequence that is complementary to the 3' end of an oligonucleotide P2, which is attached through its 5' terminus to a solid surface. DNA polymerase extension from the 3' end of P2 results in synthesis of the complement of oligonucleotide P1 and formation of a double-stranded restriction enzyme recognition sequence that may be cleaved selectively to release complex C. In a further embodiment, the 3' end of oligonucleotide P1 may be capped to prevent extension.

As shown in FIG. 6F, the antibody, antigen or antibody-antigen complex C is conjugated to an oligonucleotide P1 via its 5' terminus. The conjugated oligonucleotide comprises a sequence that is complementary to another oligonucleotide P2 that is attached by its 5' terminus to a solid surface. Release of the complex C from the solid phase occurs through a change in the physical environment such as a reduction in ionic strength, the addition of chelating agent(s), a change in pH or an increase in temperature or a combination of these factors. Under appropriate conditions, physical release of complex C is reversible.

As shown in FIG. 6G, the antibody, antigen or antibody-antigen complex C is conjugated to an oligonucleotide P1 via its 5' terminus. The conjugated oligonucleotide comprises a sequence that is complementary to another oligonucleotide P2, which is attached by its 5' terminus to a solid surface. The sequence of P2 comprises at least a partial complement of P1 and a scissile linkage that may be cleaved by physical, chemical or photochemical means to release complex C into solution. Examples of scissile linkages include, but are not limited to, disulfide bonds (cleaved, for example, by DTT) and cis-hydroxyl groups (cleaved by periodate). In FIG. 6GG, the probe P1 bearing antibody, antigen, antibody-antigen complex is attached to a solid-surface through a scissile linkage, e.g., disulfide, cis-glycol, etc. Physical, enzymatic, chemical or photochemical cleavage of linkage may be used to liberate the P1-bearing complex from the surface.

Figure 6H:
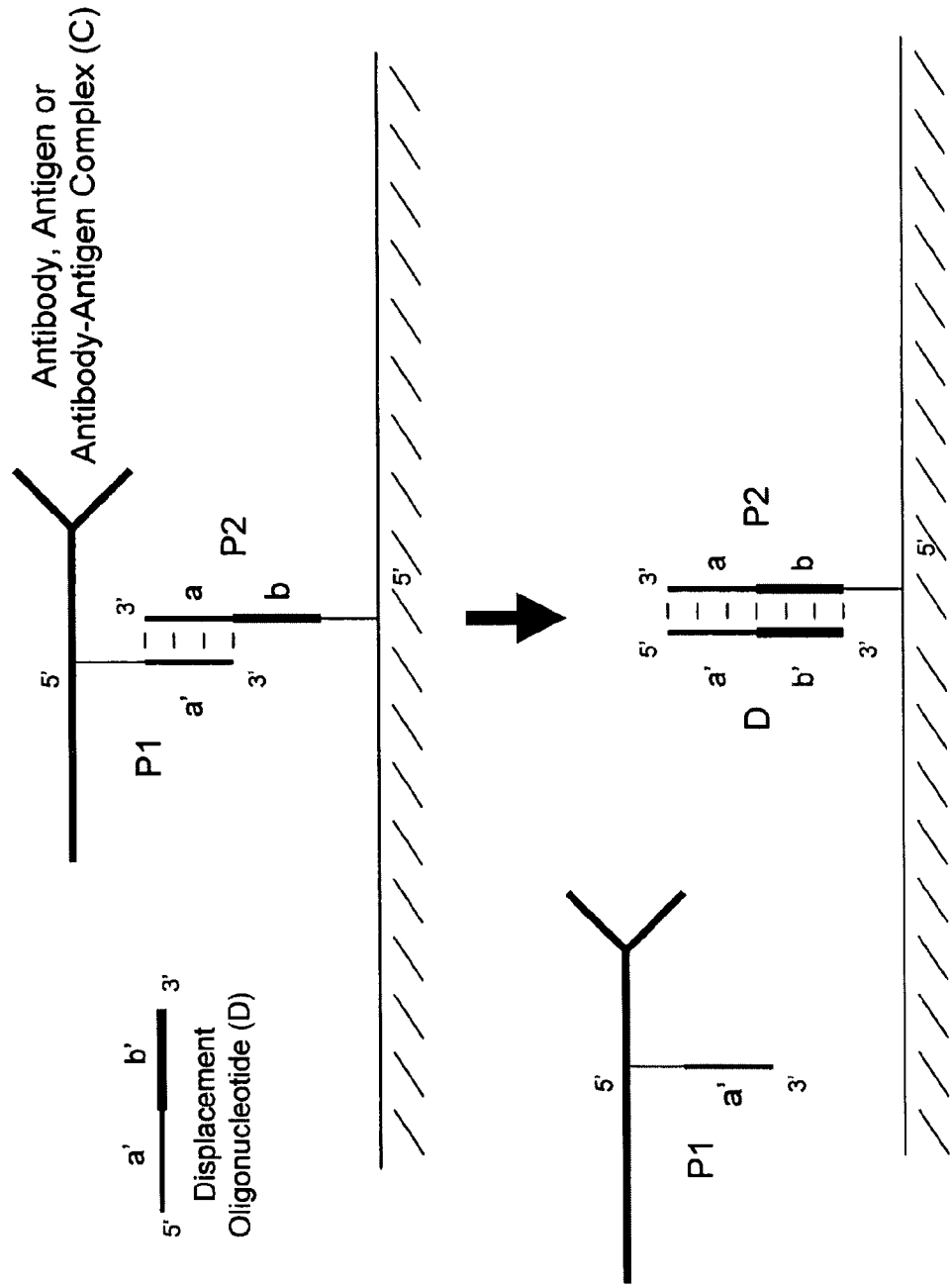
FIG. 6H shows oligonucleotide displacement.

As shown in FIG. 6H, the antibody, antigen or antibody-antigen complex C is conjugated to an oligonucleotide P1 via its 5' terminus. The conjugated oligonucleotide comprises an optional 5' sequence and 3' sequence a'. Oligonucleotide P2 is attached via its 5' terminus to a solid support and comprises sequence a and upstream sequence b. Hybridization of a and a' attaches complex C to the support. Selective release of complex C is achieved through the addition of the displacement oligonucleotide D, which comprises sequences a' and b'. Hybridization of D to sequences a and b of P2 is thermodynamically favored over hybridization of sequences a and a' alone, resulting in displacement of P1 and release of complex C into solution. In a second embodiment, the displacement probe may be complementary to all or part of P1. In a third embodiment, the antibody or antibody-antigen complex may be linked to the surface-bound oligonucleotide P2 indirectly through a splint oligonucleotide (not shown), which comprises sequences complementary to both surface-bound oligonucleotide and the P1. In this latter case, displacement may occur by hybridization of oligonucleotide D to either P1, P2, or the splint oligonucleotide.

As shown in FIG. 6I, the antibody, antigen or antibody-antigen complex C is conjugated to an oligonucleotide P1 via its 5' terminus. The conjugated oligonucleotide comprises an optional 3' sequence a'. Oligonucleotide P2 is attached via its 5' terminus to a solid support, and P2 comprises sequence a and downstream sequence b. Hybridization of sequence a of oligonucleotide P2 and sequence a' of oligonucleotide P1 attaches complex C to the surface. Selective release of complex C is achieved through the hybridization of the displacement oligonucleotide D, comprising sequence b', to sequence b of P2 and extension of oligonucleotide D from its 3' end using a strand-displacing DNA polymerase. In a further embodiment, the polymerase used for the extension reaction may possess 5'-3' exonuclease activity, which degrades sequence a' of P1 and releases the hybridized P2 oligonucleotide. In an alternative embodiment, P2 may comprise a 3' hairpin structure (FIG. 6M), so that extension of the 3' end of the hairpin by polymerase results in displacement of P1. In this embodiment, displacement oligonucleotide D is not required. Optionally, a splint oligonucleotide may be used in the embodiments depicted by FIGS. 6I and 6M.

Figure 6J:
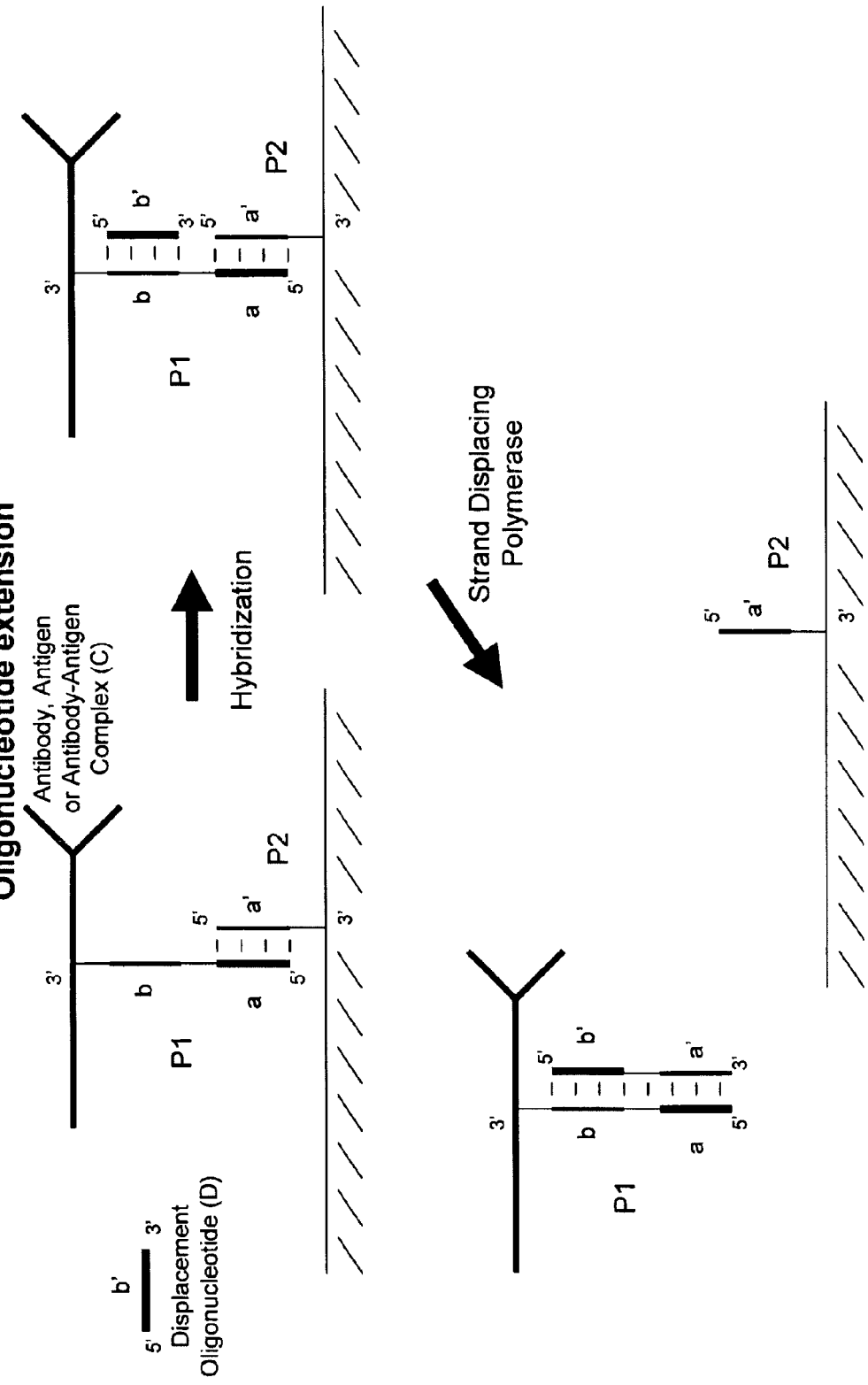
FIG. 6F shows physical release.
FIGS. 6G and 6GG show scissile linkages and chemical cleavage.
FIGS. 6I and J show oligonucleotide extension.
FIGS. 6K and L show RNase H release.
FIG. 6M shows a self-priming capture/displacement oligonucleotide.
FIG. 6N shows the involvement of the displaced probe moiety in the formation of an amplicon.

As shown in FIG. 6J, the antibody, antigen or antibody-antigen complex C is conjugated to an oligonucleotide P1 via its 3' terminus. The conjugated oligonucleotide comprises 3' sequence b and 5' sequence a. Oligonucleotide P2 is attached via its 3' terminus to a solid support and comprises sequence a' and an optional downstream sequence. Hybridization of a of oligonucleotide P1 and a' of oligonucleotide P2 attaches complex C to the surface. Selective release of complex C is achieved through the hybridization of the displacement oligonucleotide D to sequence b of P1 and extension from the 3' end using a strand displacing DNA polymerase. In a further embodiment, the polymerase used for the extension reaction may possess 5'-3' exonuclease activity, which degrades the sequence a' of P2 and releases the hybridized P1 oligonucleotide.

In FIG. 6K, the antibody, antigen or antibody-antigen complex C is conjugated to an oligonucleotide P1 via its 5' terminus. The conjugated oligonucleotide comprises an optional 5' sequence b and a 3' sequence a. Oligonucleotide P2 is made of RNA, is attached via its 5' terminus to a solid support and comprises sequence a'. Hybridization of sequence a of oligonucleotide P1 and sequence a' of oligonucleotide P2 attaches complex C to the surface. Release of complex C is achieved through the addition of an RNase, such as RNase H, which selectively degrades the RNA strand of a DNA:RNA hybrid.

In an alternative embodiment, conjugation of P1 to Ab1 and attachment of P2 to the solid support occurs via the 3' terminus of the respective oligonucleotides.

Figure 6L:
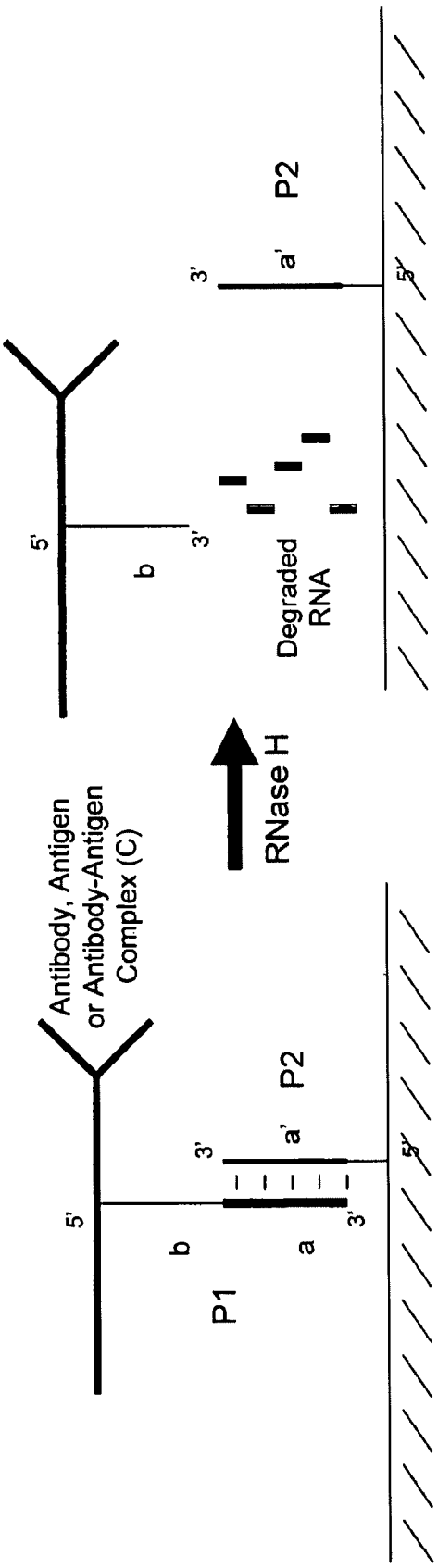
Figure 6M:
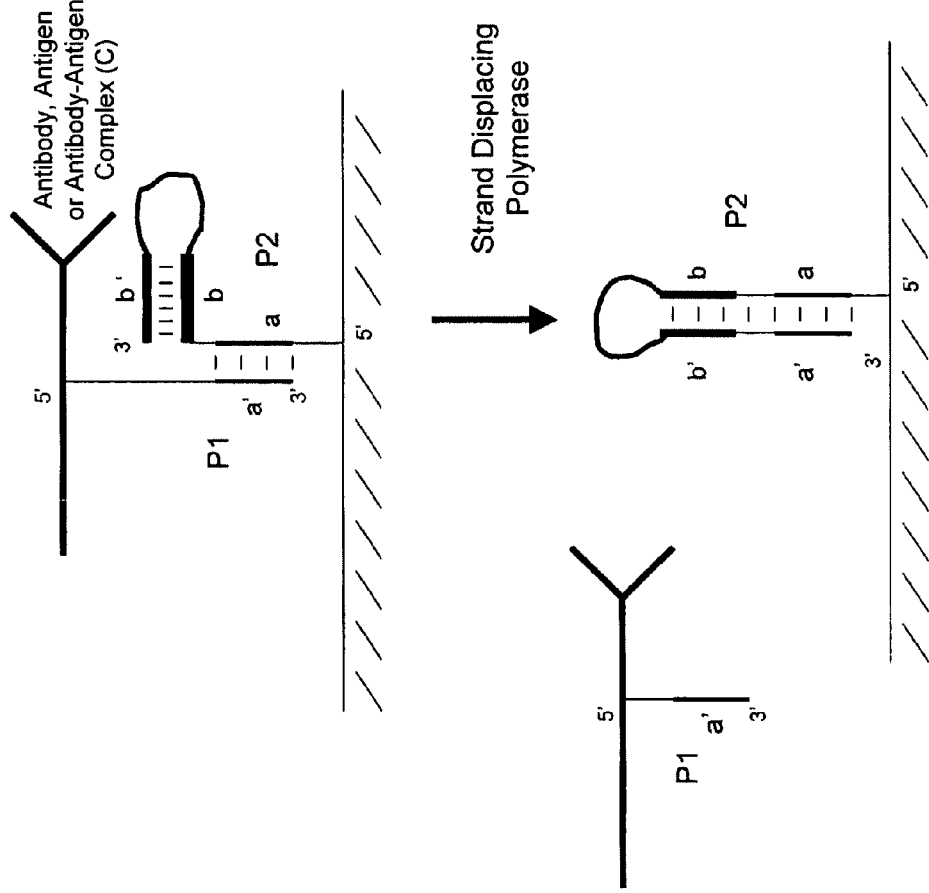

In FIG. 6L, the antibody, antigen or antibody-antigen complex C is conjugated to an oligonucleotide P1 via its 5' terminus. The conjugated oligonucleotide is made of RNA and comprises an optional 5' sequence b and 3' sequence a. Oligonucleotide P2 is attached via its 5' terminus to a solid support and comprises sequence a'. Hybridization of sequence a of oligonucleotide P1 and sequence a' of oligonucleotide P2 attaches complex C to the surface. Release of complex C is achieved through the addition of an RNase, such as RNase H, that selectively degrades the RNA strand of the DNA:RNA hybrid. In an alternative embodiment, conjugation of P1 to Ab1 and attachment of P2 to the solid support occurs via the 3' terminus of the respective oligonucleotides.

Figure 6N:
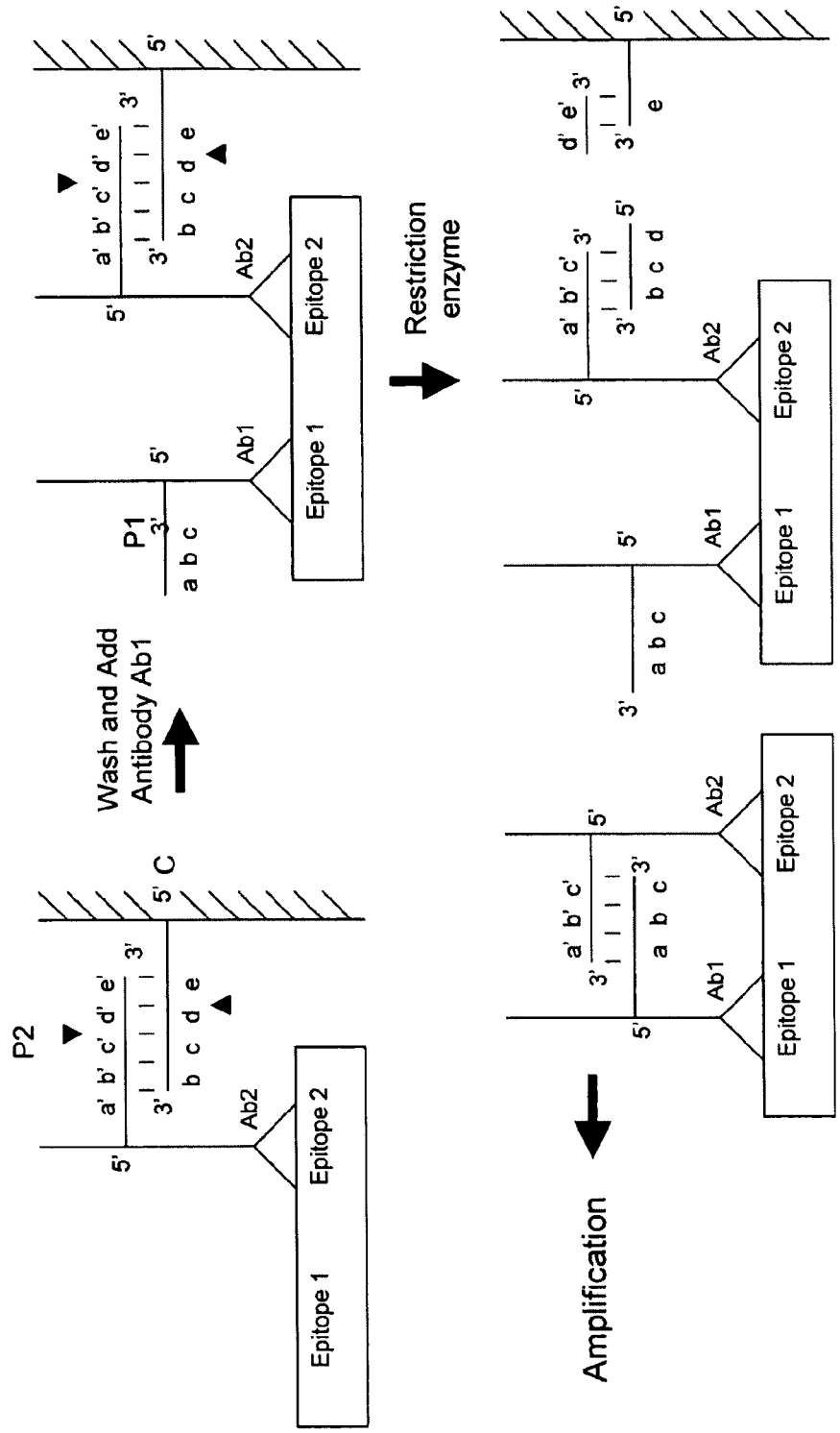

In the embodiment illustrated by FIG. 6N, the immobilized proximity member is released by cleavage with a restriction endonuclease. Ab1 is conjugated to an oligonucleotide P1 that comprises sequence (a b c). Antibody Ab2 is conjugated to oligonucleotide P2 that comprises the sequence (a' b' c' d' e'), where the region d corresponds to a restriction endonuclease recognition site. Antibody Ab2 is bound to its specific epitope, and the antibody-antigen complex is captured to a solid support by hybridization of oligonucleotide P2 to a complementary capture oligonucleotide C, which is attached to the surface. The support optionally is washed to remove unbound antigen and other components of the sample. Antibody Ab1 is then added, whereupon it binds epitope 1. The degree of complementarity between oligonucleotide P2 and capture probe C is greater than that between P2 and oligonucleotide P1; therefore, hybridization between P1 and capture probe C is thermodynamically favored over hybridization of oligonucleotides P1 and P2. The antigen-antibody complex is released upon cleavage of the restriction endonuclease recognition site d. The remaining fragment of oligonucleotide P2, attached to antibody Ab2, comprises the sequence (a' b' c') and is complementary to probe P1 on antibody Ab1. Hybridization of (a' b' c') to its complement is thermodynamically favorable and results in the linkage of antibodies Ab1 and Ab2 through an oligonucleotide hybrid with extendible 3' ends. This complex may be used in a suitable amplification reaction, such as that depicted in FIG. 1.

Figure 7A:
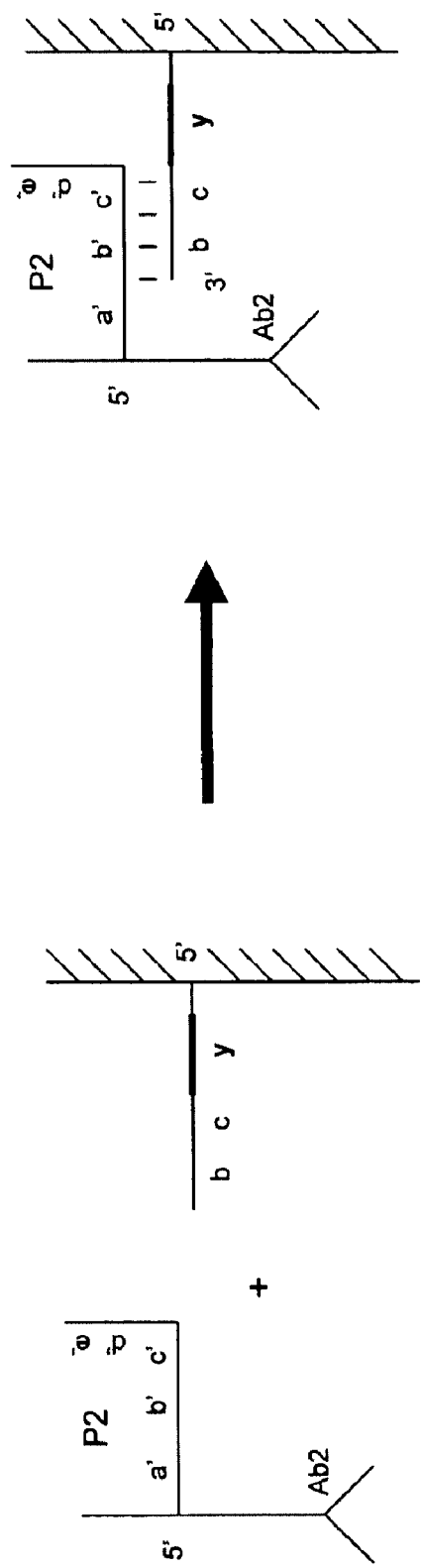
FIG. 7A shows immobilization of a first proximity member by hybridization of an oligonucleotide moiety of the first proximity member with a capture oligonucleotide.
Figure 7B:
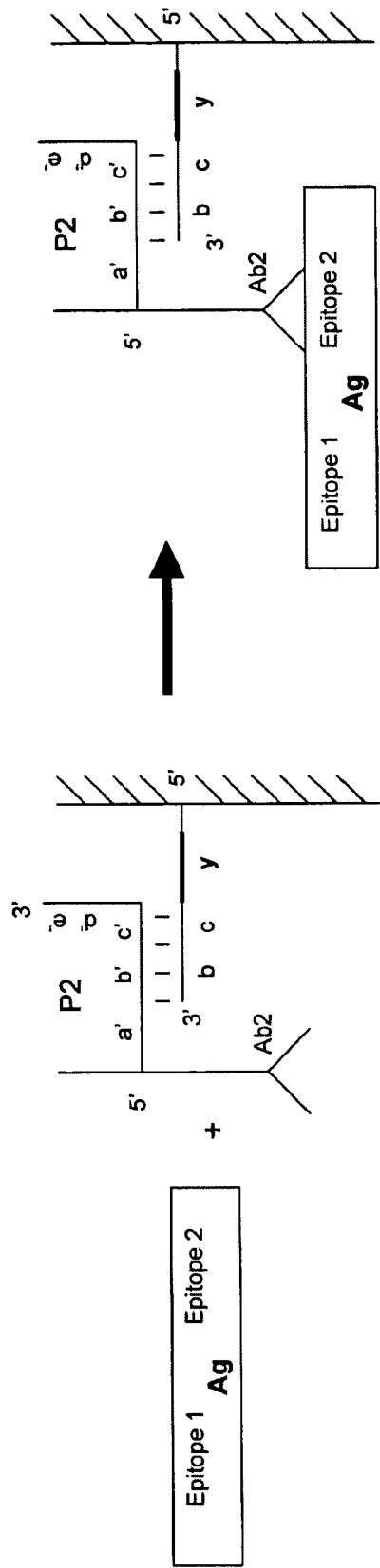
FIG. 7B shows the binding of a target analyte to the immobilized first proximity member.

FIG. 7A shows immobilization of a proximity member through an interaction of the oligonucleotide moiety with a capture oligonucleotide, where the oligonucleotide moiety is capable of forming an amplicon when the oligonucleotide moiety is released from the capture oligonucleotide. The capture oligonucleotide, comprising regions b, c and y, is shown conjugated to the solid support by its 5' end, although it also may be attached via its 3' end. Regions b and c interact by hybridization with regions b' and c', respectively, of an oligonucleotide moiety P1. Region y represents a site that promotes release by any of the methods described above, including those shown in FIGS. 6A-6N. Ab2 may be immobilized on the solid support before or after it binds to the analyte Ag. FIG. 7B shows an embodiment in which Ab2 is immobilized before Ab2 binds the analyte Ag. In one embodiment, the bound proximity member-analyte complex is washed prior to amplification to reduce the background signal by removing unbound molecules. The complete complex between Ab2, Ab1, and the target analyte is shown in FIG. 7C.

Figure 7D:
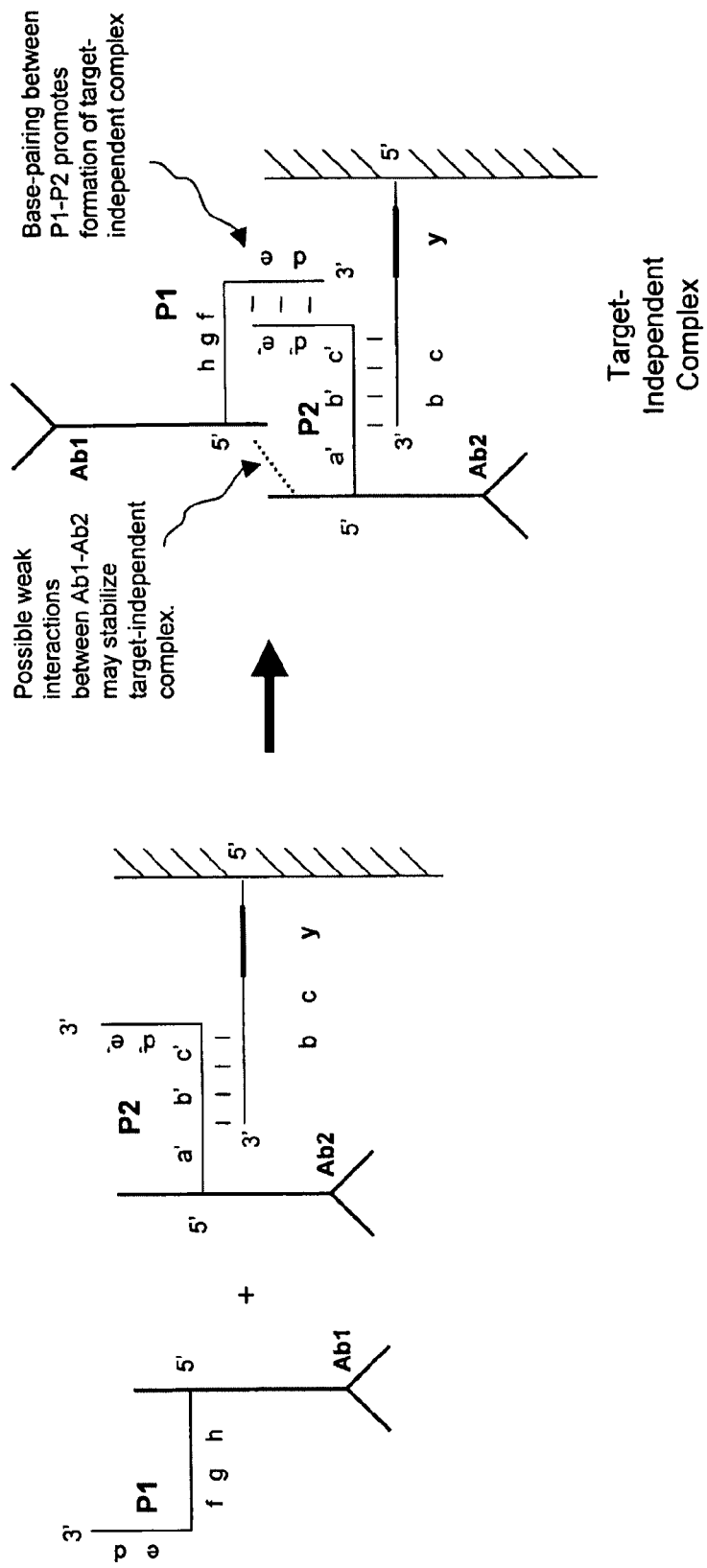
FIG. 7D shows a mechanism by which a target-independent amplicon may form.
Figure 7F:
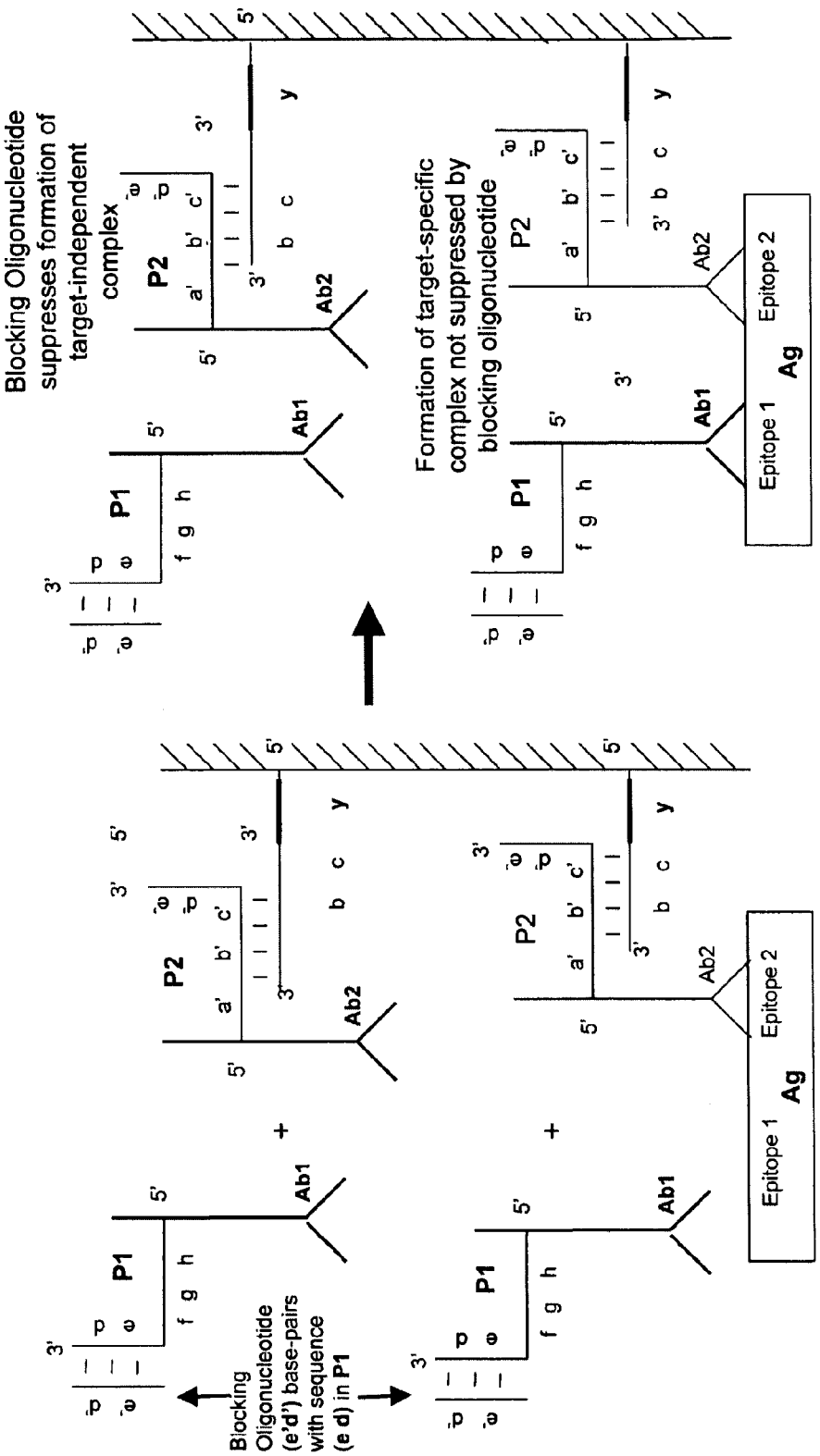
Figure 7G:
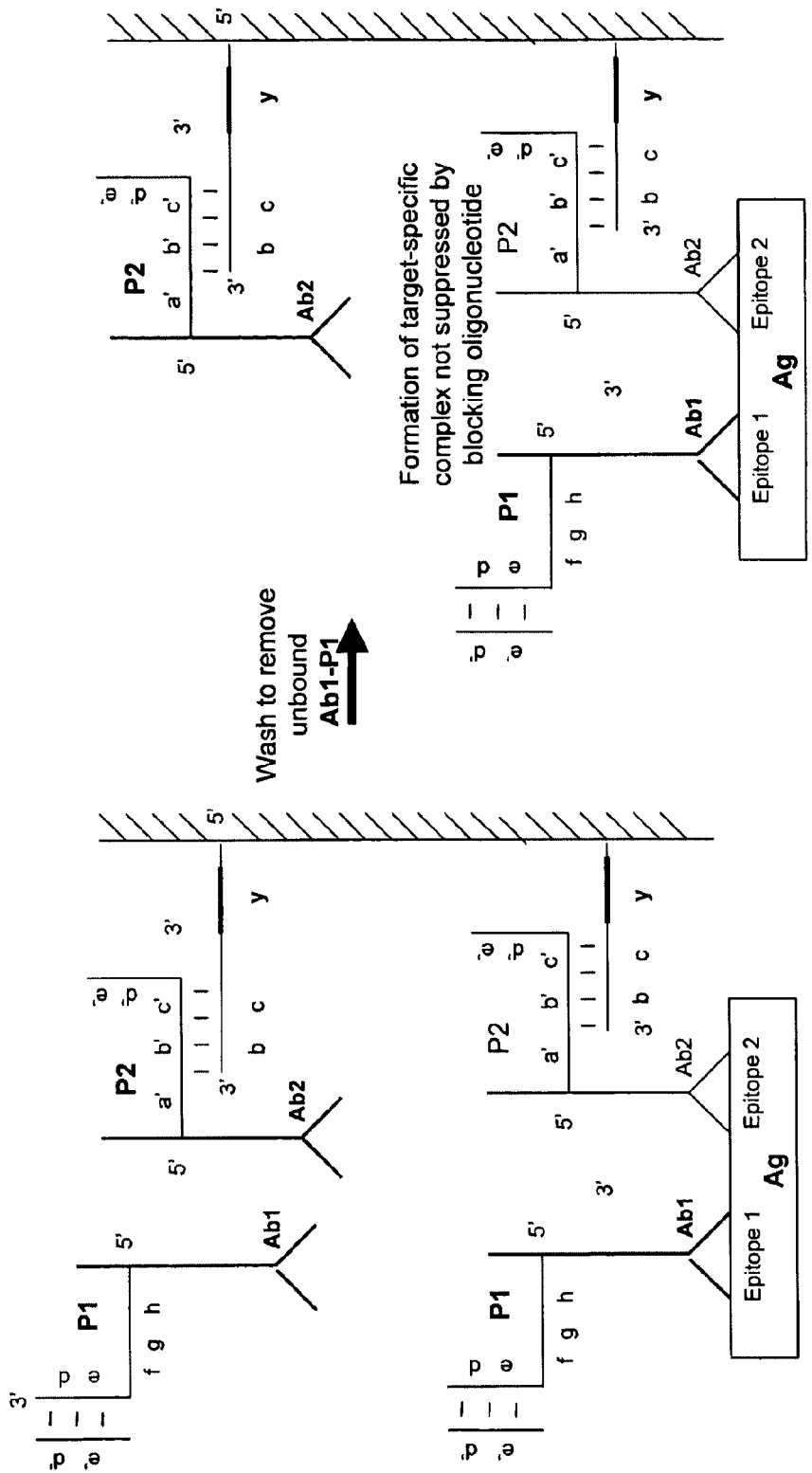

FIG. 7D illustrates what is believed to be a source of target-independent amplification arising through non-specific interactions between two proximity members. As shown, this non-specific interaction takes place between Ab1 and Ab2, although other sources of non-specific interactions are possible. The interaction between Ab1 and Ab2 promotes the interaction of P1 and P2 via complementary regions, in this case regions (d e) and (d' e'), respectively, which are used to form the amplicon. Formation of the P1:P2 interaction likewise may promote the continued association between Ab1 and Ab2; therefore, destabilization of the P1:P2 interaction may decrease the overall target-independent signal. This can be accomplished by providing a hybridization blocker oligonucleotide that interacts with region (d e) of P1, for example, to prevent the interaction of this region with its complement (d' e') in P2.

Figure 7J:
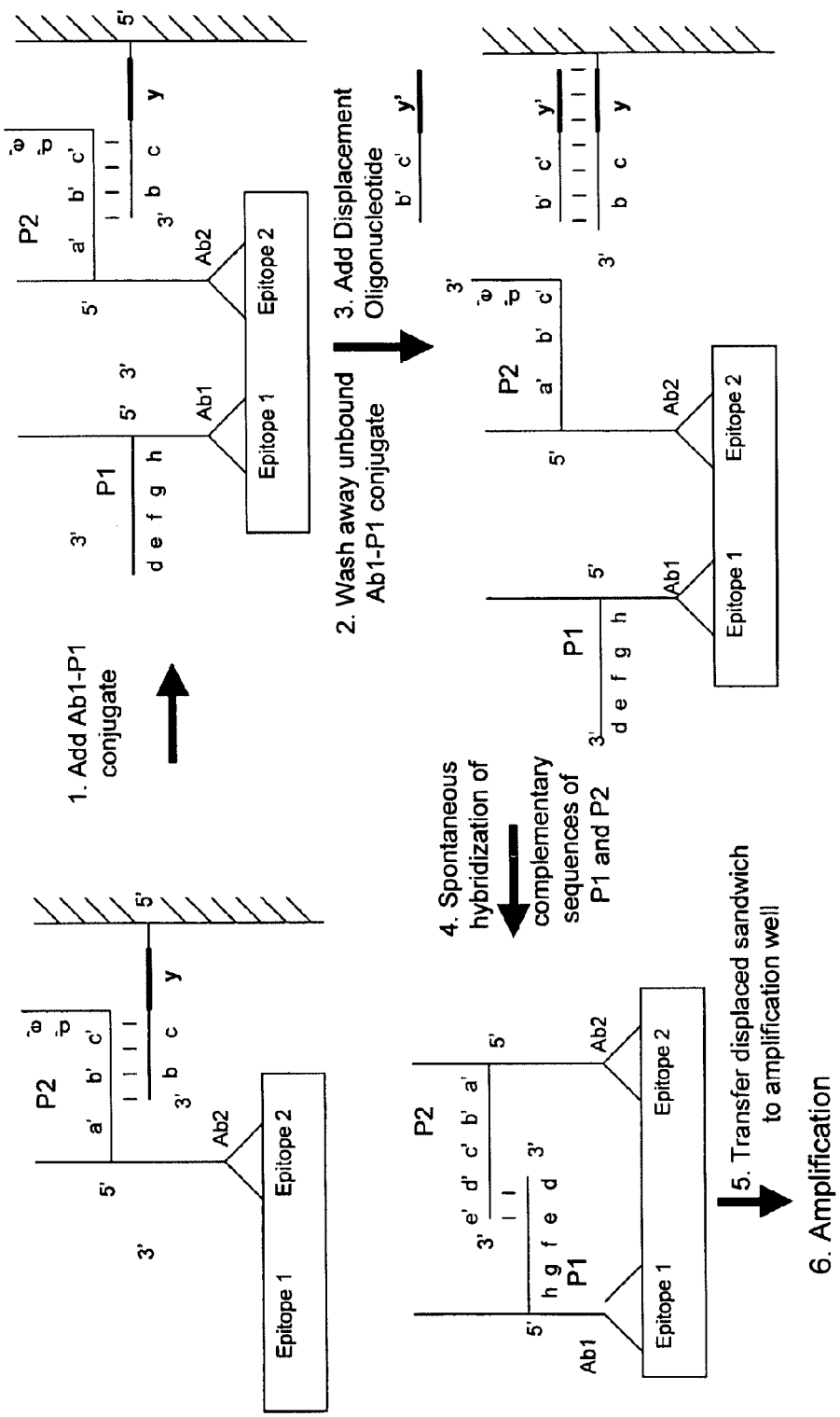
FIG. 7J shows the use of a capture oligonucleotide and release in a heterogeneous assay format.

The use of a hybridization blocker oligonucleotide in a method to detect an analyte by amplification is illustrated in FIGS. 7E-7H. Ab2 is bound to epitope 2 of an analyte before the addition of Ab1 or simultaneously with the addition of Ab1 to the reaction mixture, and Ab2 is immobilized to a surface by interaction with a capture oligonucleotide. The capture oligonucleotide in this embodiment hybridizes with region (b' c') of P2. Optionally, the bound complex is washed before or after complex formation between Ab2 and the analyte to remove unbound molecules. Ab1 is added in the presence of a hybridization blocker oligonucleotide comprising a region (d' e') that is hybridized with the region (d e) of P1 to suppress the interaction of Ab1 and Ab2, as described above. Unbound Ab1 may be washed from the reaction vessel after Ab1 has formed a complex with epitope 1 of the analyte. As shown in FIGS. 7E-7H, the hybridization blocker oligonucleotide does not interfere with the formation of a target-specific complex. The release of P2 from the capture oligonucleotide allows region (d' e') of P2 to interact with region of (d e) of P1 to form a double-stranded initiation site for amplification. P2 may be released from the capture oligonucleotide by any of the means described above. For example, as depicted in FIG. 7I, P2 is released by changing the ionic strength of the buffer (see FIG. 6F, which shows physical release from the capture oligonucleotide). As shown in FIG. 7I, once P2 is released, it is free to interact with P1 to form a double-stranded sequence that may be amplified. Alternatively, a displacement oligonucleotide may be used to dissociate P2 from the capture oligonucleotide, along the lines shown in FIG. 7J (see also FIG. 6H).

FIG. 7I illustrates how changes in ionic strength may be used selectively to release P2 and promote the subsequent interaction of P1 and P2. In FIG. 7I, the formation of a complex among Ab1-P1, Ab2-P2, and a target analyte is achieved in a buffer that may have an ionic strength optimal for the formation of the ternary complex. Unbound or non-specifically bound Ab1-P1 may be washed away in a high-ionic strength buffer, which weakens non-specific interactions but maintains the duplex formed between sequences (b' c') of P2 and the capture oligonucleotide, as well as the complex formed between Ab1, Ab2, and the target analyte. Shifting the ionic strength of the buffer to a low-ionic strength has the effect of melting the duplex between P2 and the capture oligonucleotide. The degree of destabilization of a nucleic acid duplex by lowering ionic strength can be calculated for any sequence of nucleotides using the methods set forth in Sambrook et al., Molecular Cloning, A Laboratory Manual (3rd ed., 2001), for example. Shifting the ionic strength back to high ionic strength after the complex is dissociated from the capture oligonucleotide allows P1 and P2 to hybridize to form an amplifiable sequence.

Figure 8A:
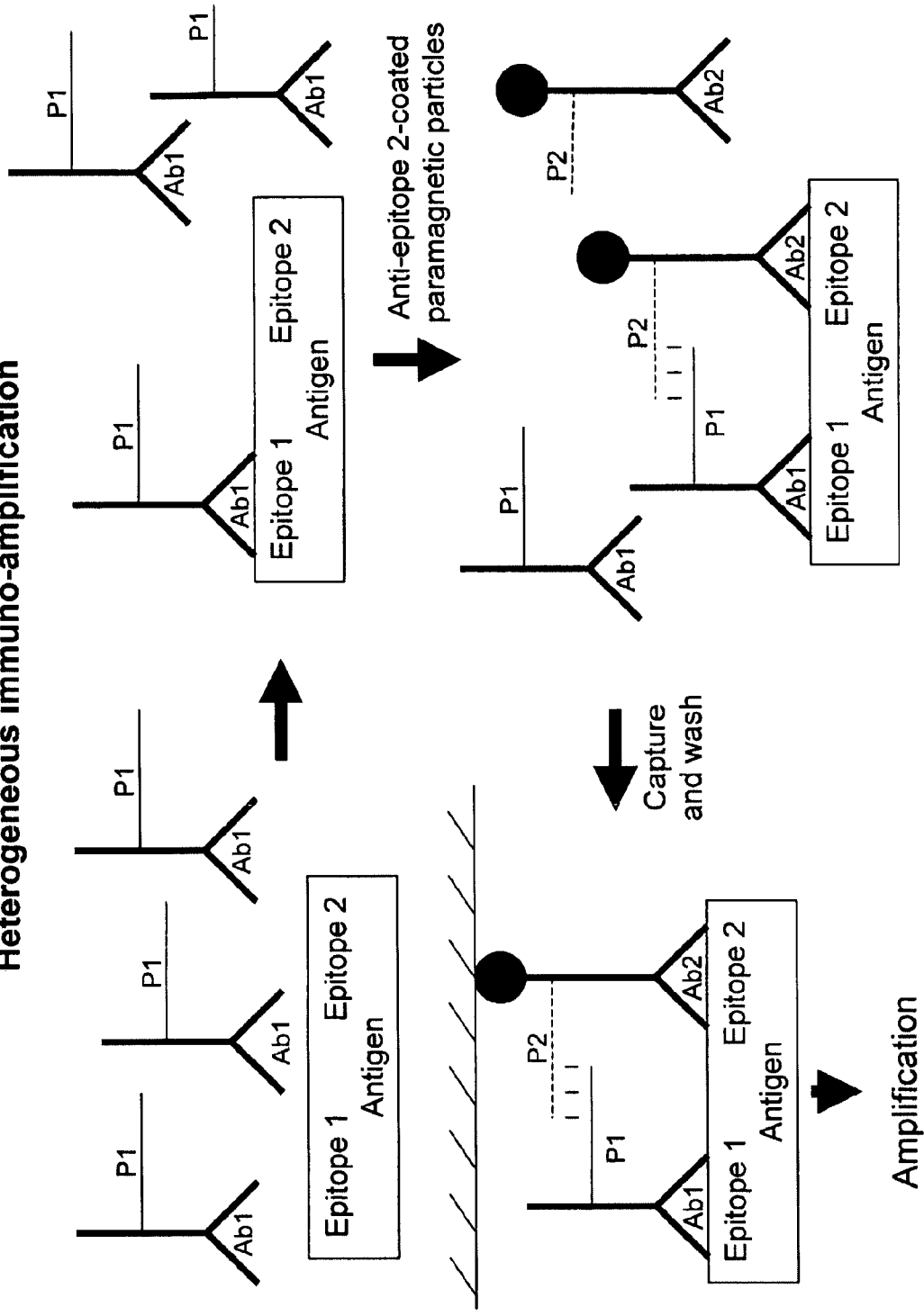

In FIG. 8A, antibodies Ab1 and Ab2 recognize adjacent antigenic epitopes and are conjugated via 5' terminal linkages to oligonucleotides P1 and P2, respectively. The 3' ends of P1 and P2 are complementary, and antibody Ab2 is also linked either covalently or non-covalently to a paramagnetic particle. Antibody Ab1 is allowed to bind to its specific epitope prior to addition of paramagnetic particles that are coated with Ab2. Binding of Ab2 adjacent to Ab1 permits hybridization of the 3' ends of oligonucleotides P1 and P2. The concentration of Ab1 and Ab2 in solution is low relative to that bound to the surface of the antigen, such that antigen-independent hybridization of P1 and P2 is minimized. The antibody-antigen complex is captured by application of a magnetic field, and unbound Ab1 antibody is removed by washing. The P1:P2 hybrid may then be used in a suitable amplification reaction, such as that depicted in FIG. 1.

In FIG. 8B, antibodies Ab1 and Ab2 recognize adjacent antigenic epitopes and are conjugated via 5' terminal linkages to oligonucleotides P1 and P2, respectively. The 3' ends of P1 and P2 are complementary, and antibody Ab1 is also linked either covalently or non-covalently to a paramagnetic particle. Antibody Ab1 is allowed to bind to its specific epitope prior to addition of antibody Ab2. Binding of Ab2 adjacent to Ab1 permits hybridization of the 3' ends of oligonucleotides P1 and P2. The concentration of Ab1 and Ab2 in solution is low relative to that bound to the surface of the antigen, such that antigen-independent hybridization of P1 and P2 is minimized. The antibody-antigen complex is captured by application of a magnetic field, and unbound Ab2 antibody is removed by washing. The P1:P2 hybrid may then be used in an amplification reaction.

In FIG. 8C, antibodies Ab1 and Ab2 recognize adjacent antigenic epitopes and are conjugated via 5' terminal linkages to oligonucleotides P1 and P2, respectively. The 3' ends of P1 and P2 are complementary, and antibody Ab1 is also linked either covalently or non-covalently to a paramagnetic particle. Both antibodies Ab1 and Ab2 are allowed to bind to their specific epitopes simultaneously. Binding of Ab2 adjacent to Ab1 permits hybridization of the 3' ends of oligonucleotides P1 and P2. The concentration of Ab1 and Ab2 in solution is low relative to that bound to the surface of the antigen, such that antigen-independent hybridization of P1 and P2 is minimized. The antibody-antigen complex is captured by application of a magnetic field, and unbound Ab2 antibody is removed by washing. The P1:P2 hybrid may then be used in an amplification reaction.

In FIG. 8D, antibody Ab2 bearing probe P2 is attached or attachable to a surface, e.g., a bead or a microwell wall, through a scissile linkage (see FIG. 6GG). Antibody Ab1 bearing P1 binds to epitope 1 of the target antigen, and this complex is immobilized by binding of epitope 2 to the surface-linked Ab1. Unbound Ab1 is washed away, and the scissile linkage is then cleaved, liberating the ternary complex from the surface. The solution phase containing the detached ternary complex is then transferred to a second reaction well for amplification, leaving behind any Ab1 that is non-specifically bound to original surface.

Another aspect of the invention is illustrated in FIG. 9. Antibodies Ab1 and Ab2 recognize adjacent antigenic epitopes. Oligonucleotide P1 is conjugated by its 3' end to antibody Ab1. Oligonucleotide P2 is conjugated via its 5' terminus to antibody Ab2. Antibody Ab1 is linked either covalently or non-covalently to a paramagnetic particle. The two antibodies are mixed with the antigen and allowed to bind to their respective epitopes. The resulting antibody-antigen complex is captured by the application of a magnetic field, and unbound Ab2 antibodies and other components of the sample matrix are removed by washing. Splint oligonucleotide S, which is complementary to the 5' end of probe P1 and the 3' end of probe P2, is then added. Hybridization between the splint oligonucleotide S and the 5' end of probe P1 and 3' end of probe P2 bridges the gap between the two antibodies. The P1:L:P2 hybrid then may be used in an amplification reaction as depicted in FIG. 3. Other linker configurations depicted in FIG. 3 may be used as well. In addition, Ab1 may be attached to the paramagnetic or other particle through a cleavable linkage as described in FIGS. 6A-6L.

Figure 10:
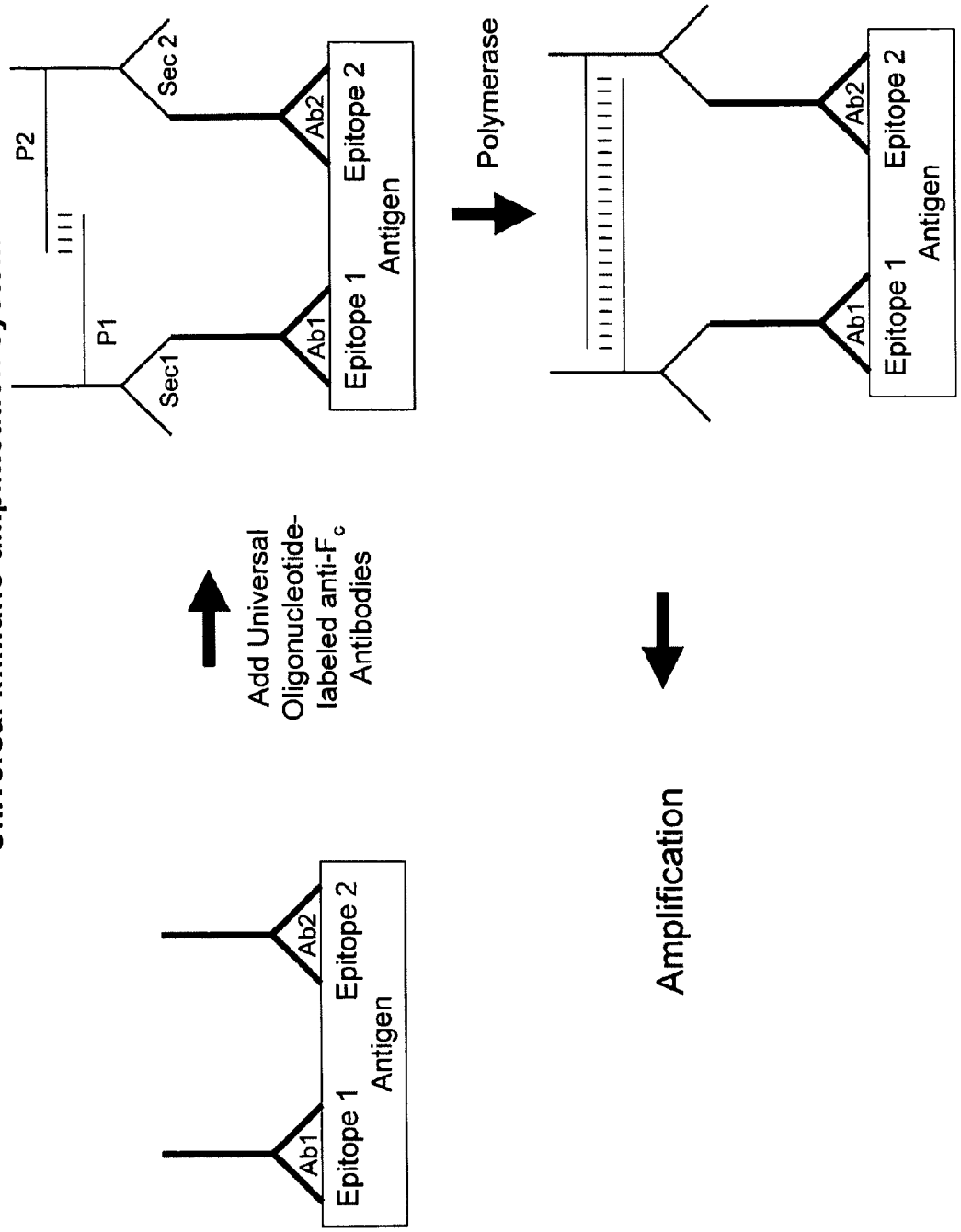
FIG. 10 shows a universal immuno-amplification system.

Yet another aspect of the invention is set forth in FIG. 10. Unlabeled Ab1 and Ab2 bind to proximate epitopes on the target antigen. Secondary antibodies Sec1 and Sec2, e.g., anti-Fc1 and anti-Fc2, are labeled respectively with oligonucleotide probes P1 and P2, which comprise mutually complementary 3' ends. The secondary antibodies then bind to the unlabeled primary antibodies Ab1 and Ab2, bringing the oligonucleotide probes into close proximity, whereupon hybridization and extension of the 3' ends converts the probes into amplifiable strands. Optionally, Ab1 and Ab2 may be labeled with hapten moieties (e.g., biotin, fluorescein, digoxigenin, trinitrophenol, dinitrophenol and the like). In this case, probe-labeled secondary antibodies Sec1 and Sec 2 possess binding specificities against the respective hapten labels of Ab1 and Ab2.

In a further embodiment, the secondary antibodies are labeled with probes that can be ligated when mutually base-paired to a ligation splint oligonucleotide (FIG. 2). When a pair of secondary antibodies binds to a pair of unlabeled antibodies that are bound to proximate epitopes, the probes mutually base-pair with the ligation splint oligonucleotide and ligation occurs.

In a third embodiment, the labeled secondary antibodies are combined with (and may bind to) the primary antibodies prior to or during incubation with the antigen. In a fourth embodiment, at least one of the secondary antibodies is linked to a solid surface, e.g., a microwell wall or a magnetic bead. In a fifth embodiment, the secondary antibody is reversibly linked to a solid surface (FIGS. 6A-6L, 7A-7D, and 8A-8D). In a sixth embodiment, the surface-linked antibody is released from the solid surface, and the released antibody is subjected to an amplification reaction. In a seventh embodiment, Ab1 and/or Ab2 may be an aptamer, receptor, or other epitope binding entity, and Sec1 and Sec2 are probe-labeled recognition molecules that bind to Ab1 and Ab2. In an eight embodiment, the Sec1 and/or Sec2 may be a Fab' fragment, an aptamer, an antibody against an antibody, or any molecule that specifically recognizes Ab1 or Ab2.

Protein G or Protein A optionally can be substituted for the Sec1 and Sec2, as illustrated in FIG. 10. Protein G and Protein A bind to most IgG molecules and to the Fc region, with one Protein G or Protein A binding per IgG molecule. Specifically, Protein G or Protein A can be modified with "universal oligonucleotide" probes (labeled P1 and P2 in FIG. 10). The modified Protein G molecules, for example, can be pre-bound to the antibodies that recognizing epitope 1 and epitope 2. In this case, Protein G or Protein A modified with P1 would be pre-bound to Ab1. Likewise, Protein G or Protein A modified with P2 would be pre-bound to Ab2. Alternatively, the probe-modified Protein G or Protein A molecules could be mixed together and used as depicted in FIG. 10.

This approach has certain advantages. First, only one reagent, namely Protein G or Protein A, needs to be modified. Second, almost any primary detector antibody can be used to attach to the antigen, e.g., a rat, mouse, or rabbit antibody. Third, pre-binding the modified Protein G or Protein A to the primary antibodies are specifically tagged reagents available for general use with any Ab1 or Ab2. The resulting standardization of the assay components is expected to improve quantification and reproducibility.

In some instances it may be advantages to use a Protein A/Protein G fusion product in place of Protein A or Protein G. It should also be understood that "Protein A" or "Protein G" can refer to either the natural bacterial product or to genetically engineered or recombinant versions that have been designed for optimal binding to the IgG molecules, for example, by eliminating the albumin binding capability of Protein G.

Another aspect of the present invention is shown in FIG. 11, in which the present invention comprises oligonucleotide-labeled antibodies for use in immuno-amplification reactions that are precluded from participation in non-specific primer-primer interactions through the incorporation of hairpin structures. Antibody Ab1 is conjugated to oligonucleotide P1, which comprises an SDA restriction enzyme nicking site and a downstream sequence (a b a' c), where a and a' are complementary sequences that hybridize to form a hairpin structure. The Tm of the hairpin is sufficiently low so that a proportion of the oligonucleotide label exists in an open, relaxed form under the conditions of the amplification reaction. The $T_m$ of a nucleic acid duplex can be calculated by methods well-known in the art for any sequence of nucleotides under a given set of temperatures and ionic strengths, using one of the methods described in Sambrook et al., Molecular Cloning, A Laboratory Manual (3rd ed., 2001), for example. The 3' terminal sequence c does not form part of the hairpin structure and is designed to prevent self-priming of DNA polymerase extension. Antibody Ab2 is conjugated to oligonucleotide P2, which comprises an SDA restriction enzyme nicking site and downstream sequence (a b'). When antibodies Ab1 and Ab2 bind to their respective epitopes, breathing of the hairpin of probe P1 permits base pairing to occur between the two oligonucleotide labels. The $T_m$ of the P1:P2 hybrid formed by pairing of sequences (b a') and (a b') is greater than that of the P1 hairpin; therefore, hybridization of P1 and P2 is thermodynamically favored. DNA polymerase then extends the 3' end of P2 to generate a double-stranded restriction site that is capable of being nicked. Nicking, extension and strand displacement leads to formation of a double-stranded DNA molecule with nickable restriction sites at either end. This construct may be used in an exponential SDA reaction.

In another embodiment, antibody Ab1 may be conjugated to oligonucleotide P1, which comprises an SDA restriction enzyme nicking site and downstream sequence (b' a b a' c), where a and a' are complementary sequences that hybridize to form a hairpin structure. Sequences b and b' are also complementary, but they form a less stable structure than that formed by hybridization of a and a'. Formation of the a:a' hairpin is, therefore, favored. The 3' terminal sequence c does not form part of the hairpin structure and is designed to prevent self priming of DNA polymerase extension. Antibody Ab2 is conjugated to oligonucleotide P2, which comprises sequence (b' a' b), where b and b' are complementary and form a hairpin structure. Probe P2 lacks an SDA nicking site. Thus, if DNA polymerase extension occurs from the 3' end, a dead-end product is generated that cannot undergo linear amplification. The Tm of the a:a' and b:b' hairpins is sufficiently low so that a proportion of each oligonucleotide exists in an open, relaxed form under the conditions of the reaction. When antibodies Ab1 and Ab2 bind to their respective epitopes, breathing of the hairpins of probes P1 and P2 permits base pairing to occur between the two oligonucleotide labels. The Tm of the P1:P2 hybrid formed by pairing of sequences (b' a b) and (b a' b') is greater than that of the either hairpin structure; therefore, hybridization of P1 and P2 is thermodynamically favored. DNA polymerase then extends the 3' end of P2 to generate a nickable double-stranded restriction site. Nicking, extension and strand displacement leads to formation of a double-stranded DNA molecule that may be fed into an exponential SDA reaction.

Figure 11C:
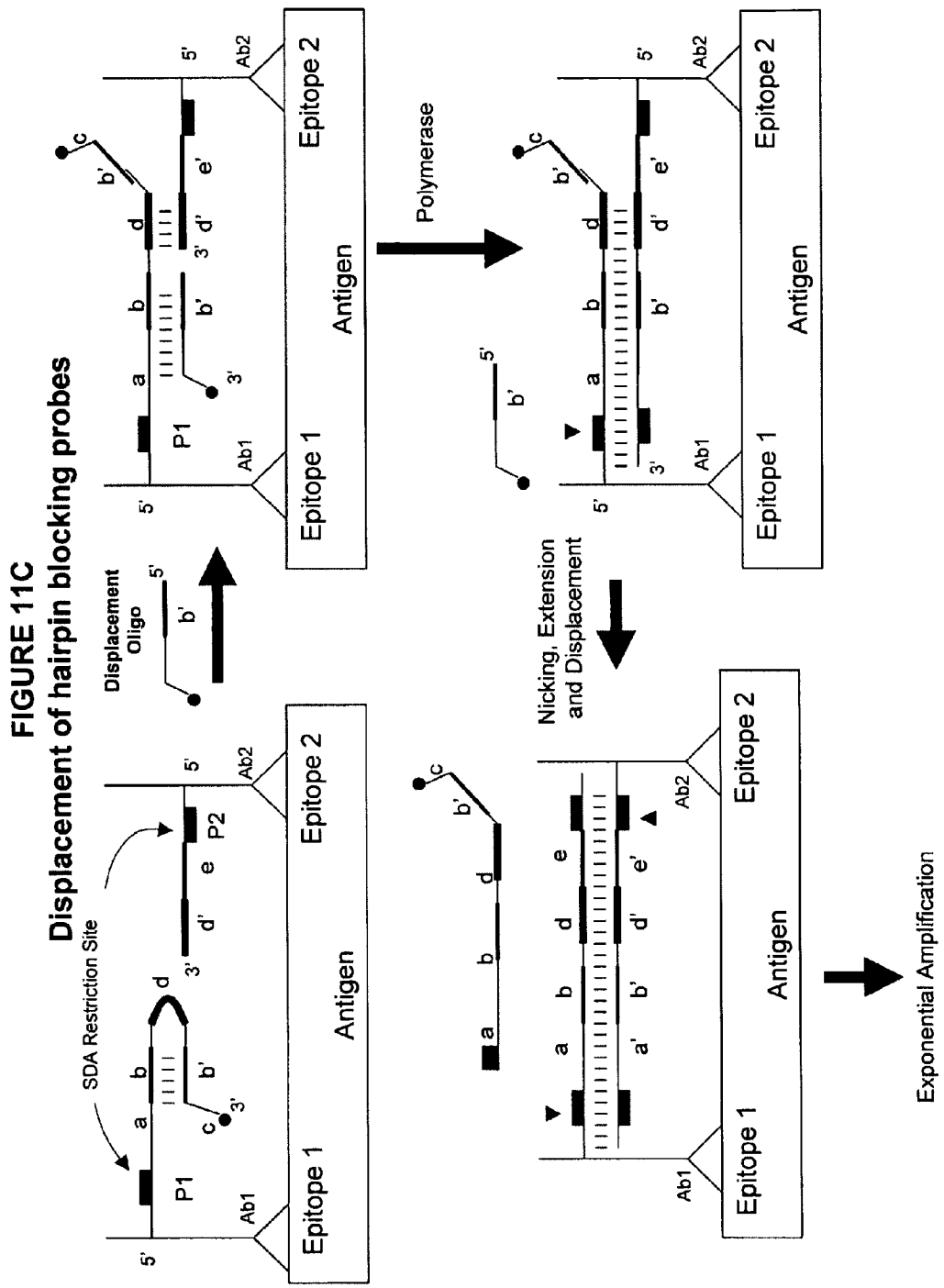
FIG. 11C shows displacement of hairpin hybridization blocker probes.

A further embodiment is depicted in FIG. 11C. Probe P1 comprises hairpin sequences b, d, b', sequence a, which is 5' of the hairpin sequences, and sequence c, which is 3' of the hairpin sequences and which optionally contains a non-extendible 3' cap. Sequences b and b' are complementary and hybridize to form the stem of a hairpin structure. Sequence d forms the loop of the hairpin. Optionally, part of sequence d may base pair with itself to form part of the stem structure along with b and b'. Probe P2 comprises sequence d', which is complementary to sequence d of P1. The presence of the hairpin structure precludes hybridization of d and d'. Addition of a displacement oligonucleotide D opens the hairpin by first hybridizing to sequence a of P1 and subsequently displacing the b' arm of the stem. Sequence d' of P2 then hybridizes with the unfolded sequence d of P1, and P2 is extended by polymerase, displacing oligonucleotide D and creating a nickable double-stranded restriction site on P1. Amplification then follows in a manner analogous to the embodiment depicted in FIG. 11B.

FIG. 12 depicts a method for detecting the presence of antigen-specific immunoglobulin antibodies in a test sample. Probes P1 and P2 are conjugated to an antigen molecule Ag, such that each Ag molecule is labeled with either P1 or P2, but not both. The labeled antigens are mixed with the test sample and bind to the Ag-specific immunoglobulin as shown. Complexes that contain both P1 and P2 will be amplifiable, detectable and indicative of the presence of an Ag-specific immunoglobulin. In the absence of an Ag-specific immunoglobulin, no detectable complex will form. A similar approach may be used to detect any ligand-receptor interaction comprising either two or more identical ligand binding sites or binding sites to two or more different ligands. In the latter case, each ligand is labeled with a different probe sequence. For example, Protein G, which binds to the Fc region of IgG, may be labeled with P1, and Ag may be labeled with P2. Binding of the labeled Ag and protein G to the same IgG molecule would create a complex that is amplifiable and detectable by the methods of the present invention.

Figure 13:
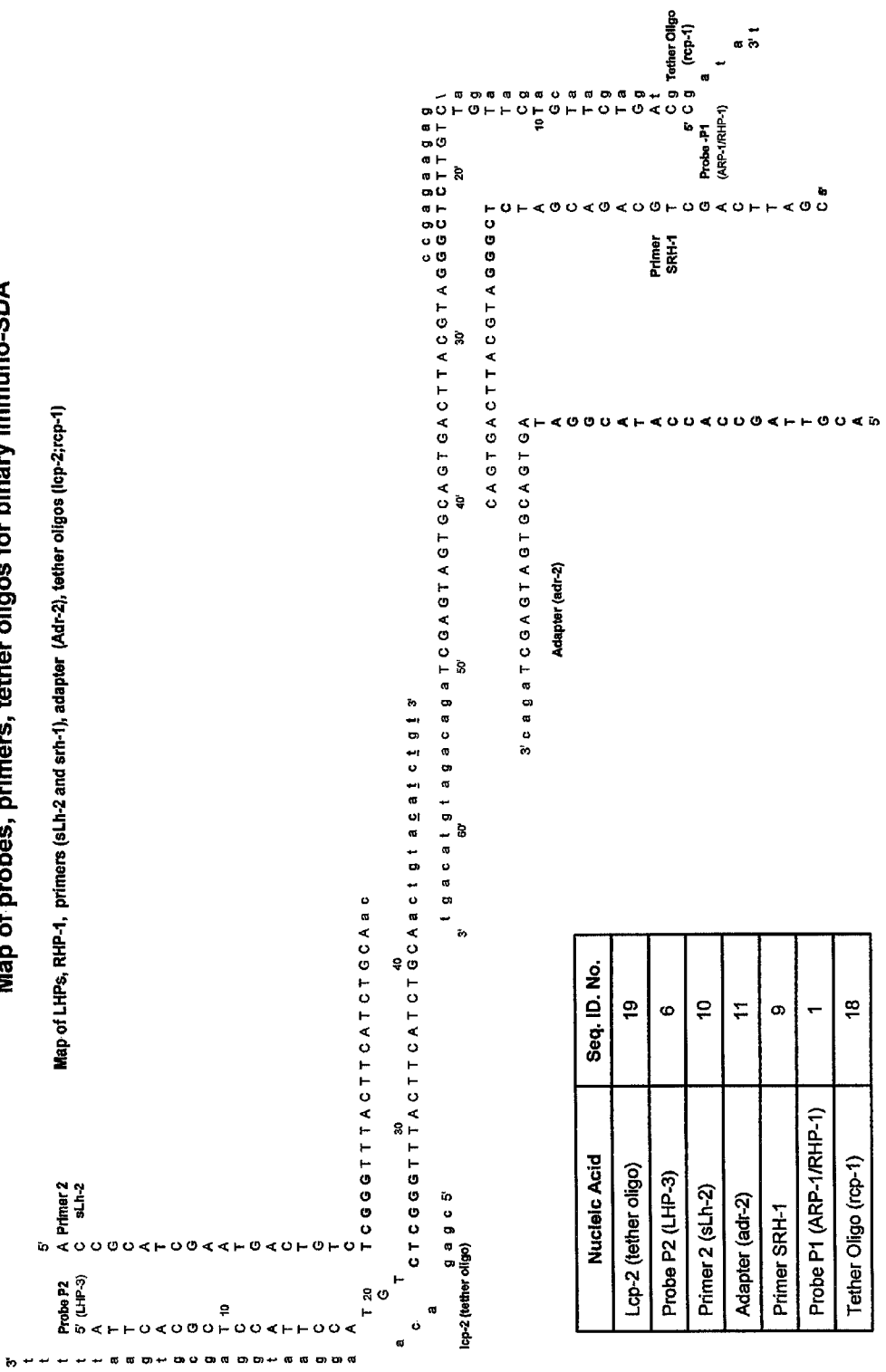
FIG. 13 presents a map of representative probes, primers, and tether oligonucleotides for binary immuno-SDA (see SEQ ID NOS.:19, 6, 10, 11, 9, 1 and 18, respectively, in order of appearance).
Figure 14A:
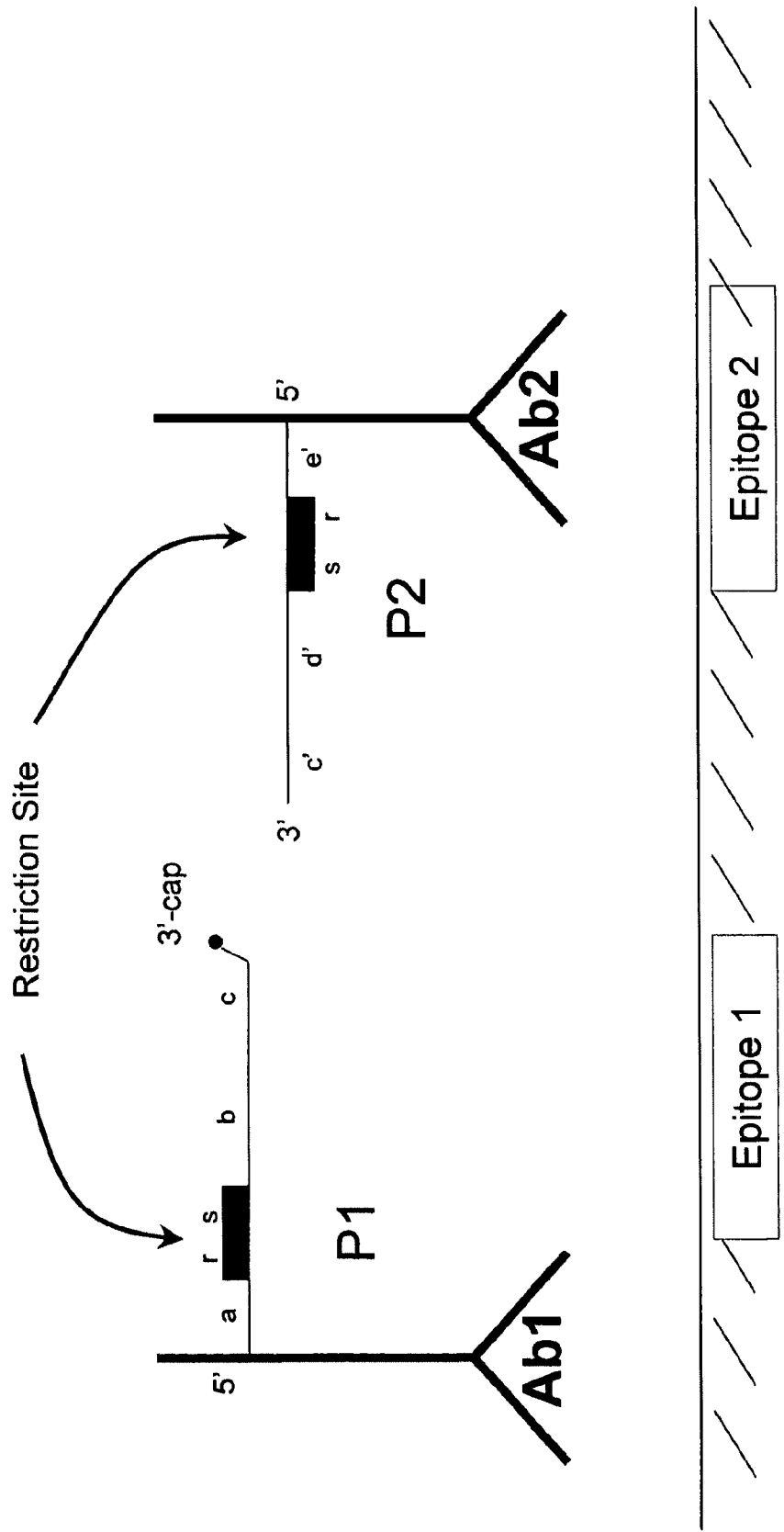
Figure 14B:
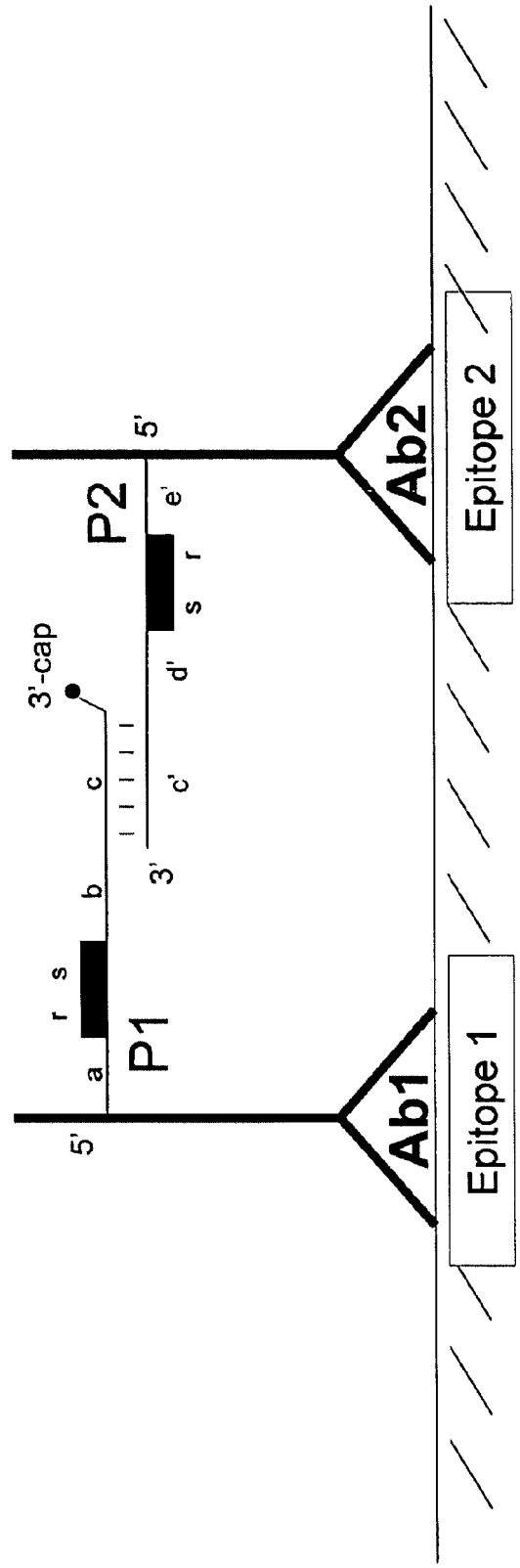
Figure 14C:
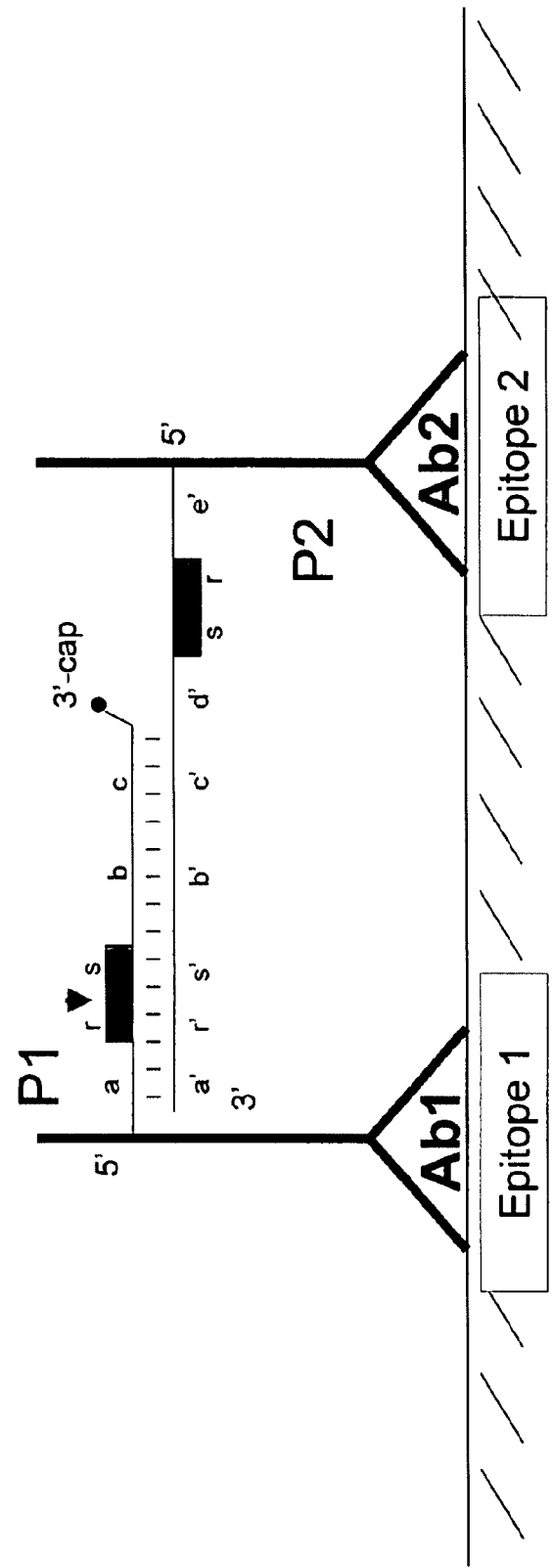
Figure 14D:
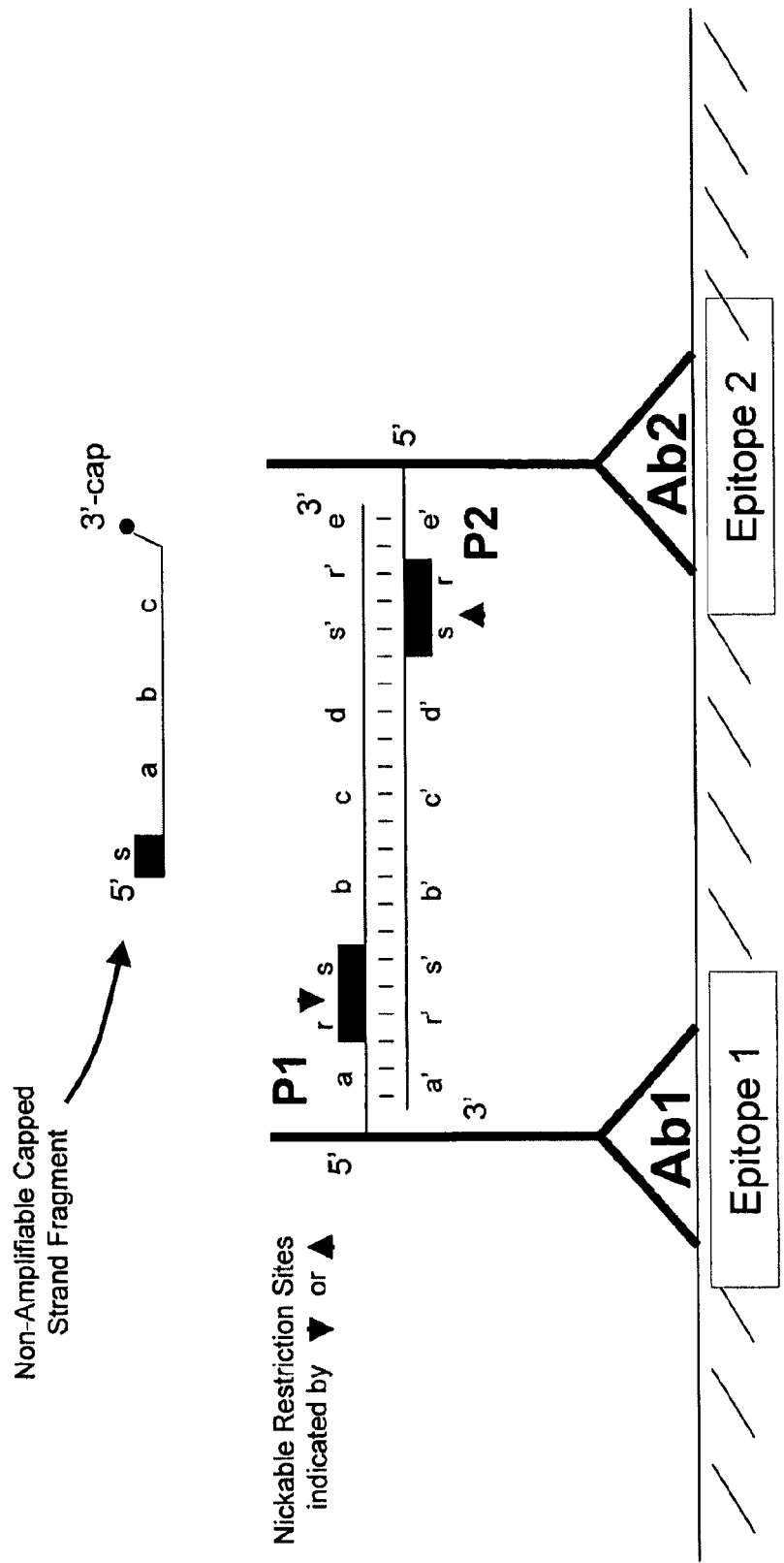

FIG. 13 shows representative probes, primers, adapters, reporters and tether oligonucleotides that are useful for binary immuno-SDA. The structure of these oligonucleotides and a method of their use is set forth in the following Examples. The following. Examples are in no way intended to limit the scope of the invention.

EXAMPLE 1

Representative Sequences of Probes, Primers, Adapters, Reporters Useful for Binary Immuno-SDA The sequences of some of the probes, primers, adapters, and reporters shown below are set forth in FIG. 13.
Probes (P1, P2)

RHP-1 (right hand probe; sequence in bold is common with primer SRH-1, below):

(SEQ ID NO.: 1)
5' CCA GTC TTG TCT TGT CTG TTC TCG GGA TGC ATT

CAG TGA CGT GAT GAG CTA GAC AGA TGT ACA GT

RHP-3 (right hand probe; sequence in bold is common with primer SRH-1, below):

(SEQ ID NO.: 2)
5' CCA GTC TTG TCT TGT CTG TTC TCG GGA TGC ATT CAG TGA CGT GAT GAG CTA GAC AGA TGT AC

RBD-3v3 (right hand probe; X=biotin-labeled dT; sequence in bold is common with primer SRH-1, below):

(SEQ ID NO.: 3)
5' CCA GTC TTG TCT TGT CTG TTC TCG GGA TGC ATT CAG TGA CGT GAT GAG CTA GAC AGA TGT AC TTT TXT

LHP-1 (left hand probe; underlined bases are complementary with the 3' end of RHP-1):

(SEQ ID NO.: 4)
5' ATT CAC GCT TCC ATT CCA TGT CTC GGG TTT ACT TCA TCT GCA <u>ACT GTA C</u>

LHP-2 (left hand probe; underlined bases are complementary with the 3' end of RHP-1):

(SEQ ID NO.: 5)
5' ATT CAC GCT TCC ATT CCA TGT CTC GGG TTT ACT TCA TCT GCA <u>ACT GTA CAT</u>

LHP-3 (left hand probe; underlined bases are complementary with the 3' end of RHP-1):

(SEQ ID NO.: 6)
5' ATT CAC GCT TCC ATT CCA TGT CTC GGG TTT ACT TCA TCT GCA <u>ACT GTA CAT CTG T</u>

LHP-4 (left hand probe; underlined bases are complementary with the 3' end of RHP-1):

(SEQ ID NO.: 7)
5' ATT CAC GCT TCC ATT CCA TGT CTC GGG TTT ACT TCA TCT GCA <u>ACT GTA CAT CTG TCT</u>

LHP-5 (left hand probe; underlined bases are complementary with the 3' end of RHP-1):

(SEQ ID NO.: 8)
5' ATT CAC GCT TCC ATT CCA TGT CTC GGG TTT ACT TCA TCT GCA <u>ACT GTA CAT CT</u>

Primers

SRH-1 (right-hand primer; sequence in bold is common with RHP-1):

(SEQ ID NO.: 9)
5' CGA TTC AGC TGC AGA CGA TCT CGG GAT GCA TTC AGT GAC

SLH-2 (left-hand primer; sequence in bold is common with LHP-1, 2, 3, 4 and 5; underlined bases are complementarity with the 3' end of RHP-1):

(SEQ ID NO.: 10)
5' ACC GCA TCG AAT GAC TGT CTC GGG TTT ACT TCA TCT GCA <u>AC</u>

Adapters

ADR-2 (underlined bases are identical to the 3' end of TBD10.2 [D/R]):

(SEQ ID NO.: 11)
5' <u>ACG TTA GCC ACC ATA CGG ATA</u> GTG ACG TGA TGA GCT AGA C

ADR-5 (underlined bases are identical to the 3' end of TBD10.2 [D/R]):

(SEQ ID NO.: 12)
5' <u>ACG TTA GCC ACC ATA CGG ATG</u> ATG AGC TAG AC

ADR-8 (underlined bases are identical to the 3' end of TBD10.2 [D/R]):

(SEQ ID NO.: 13)
5' <u>ACG TTA GCC ACC ATA CGG ATG</u> TGA CGT GAT GAG C

ADIQS-1 (IQS adapter):

(SEQ ID NO.: 14)
5' ACG TTA GCC ACC ATA CGG ATG ATG AGC ATC TG

ADQS-2 (adapter for IQS-2; underlined bases are identical to 3' end of altD6.9(F/D)):

(SEQ ID NO.: 15)
5' <u>AGC TAT CCG CCA TAA GCC AT</u> AC TCA GAG TGA TCA AGT

Reporters

TBD10.2 (D/R) (underlined bases are identical to the 5' end of ADR-2 and ADR-5):

(SEQ ID NO.: 16)
5' (dabcyl)-TAG CGC CCG AGC GCT <u>ACG TT</u>(rox)<u>A GCC ACC ATA CGG AT</u> altD6.9 (F/D):

(SEQ ID NO.: 17)
5' (fam)-AGT TGC CCC GAG GCA ACT(dabcyl) AGC TAT CCG CCA TAA GCC AT Tether Oligonucleotides RCP-1 (tether oligonucleotide; UPPER CASE bases are complementary to the 5' end of RHP-1):

(SEQ ID NO.: 18)
5' CCG AGA ACA GAC AAG ACA AGA CTG Gat at

LCP-2 (tether oligonucleotide; UPPER CASE bases are complementary to the 5' end of LHP 1-5):

(SEQ ID NO.: 19)
5' CGA GAC ATG GAA TGG AAG CGT GAA Ttt tt

LCP-4 (tether oligonucleotide; UPPER CASE bases are complementary to the 5' end of LHP 1-5):

(SEQ ID NO.: 20)
5' t tta ttt tat CGA GAC ATG GAA TGG AAG CGT GAA T

Capture and Displacement Oligos

RCP-13v1 (capture oligonucleotide; UPPER CASE bases are complementary to a sequence near the 5' end of RHP-3; underlined bases are complementary to DO-13v1; X=tetra-ethylene glycol; Z=hexa-ethylene glycol; X is linked to Z through a phosphodiester moiety; and Z is linked to the 5' end of the oligonucleotide through a phosphodiester moiety):

(SEQ ID NO.: 21)
5' biotin-X-Z-cct ggt acg agt ttc tat cct AA TGC ATC aCG AGA ACA GAC AAG ACA AG t DO-13v1 (displacement oligonucleotide [cap]=3' deoxyruidine):

(SEQ ID NO.: 22)
5' CTT GTC TTG TCT GTT CTC GTG ATG CAT TAG GAT AGA AAC TCG TAC CAG G-[cap] 3'

RCP-9v2.2 (capture oligonucleotide; UPPERCASE bases are complementary to bases near the 5' end of RHP-3; underlined bases are complementary to displacement oligo CMPR-9v2; X=tetra-ethylene glycol; Z=hexa-ethylene glycol; X is linked to Z through a phosphodiester moiety; and Z is linked to the 5' end of the oligonucleotide through a phosphodiester moiety):

(SEQ ID NO.: 23)
5' biotin-X-Z-t tta CAC TGA ATG CAT tCC tAG AAC AGA CAA GAC AAG ACT ccg tgg cAg cgt CMPR-9v2 (capture oligonucleotide; UPPER CASE bases are complementary to the 5' end of RHP-3; [cap]=3' deoxyuridine):

(SEQ ID NO.: 24)
5' ACG CTG CCA CGG AGT CTT GTC TTG TCT GTT CTt GGA ATG CAT TCA GT-[cap] 3'

Blocking Oligonucleotides ([cap]=2',3' dideoxycytidine)

LBK-1 (UPPERCASE bases are complementary to 3' end of LHP-3):

(SEQ ID NO.: 25)
5' ACA GAT GTA CAG Taa ttt-[cap] 3'

RDB-3p5 (UPPER CASE bases are complementary to 3' end of RHP-1; underlined bases are complementary to 3' end of RHP-3):

(SEQ ID NO.: 26)
5' cag ttc agc acA CTG TAC ATC TGT CTA GC aa-[cap] 3'

RDB-3p8 (UPPER CASE bases are complementary to 3' end of RHP-1; underlined bases are complementary to 3' end of RHP-3):

(SEQ ID NO.: 27)
5' cag ttc agc acA CTG TAC ATC TGT CTA GCT CA aa-[cap] 3'

RDB-3p10 (UPPER CASE bases are complementary to 3' end of RHP-1; underlined bases are complementary to 3' end of RHP-3):

(SEQ ID NO.: 28)
5'cag ttc agc acA CTG TAC ATC TG T CTA GCT CAT Cta-[cap] 3'

RDB-3z8 (UPPER CASE bases are complementary to 3' end of RHP-3):

(SEQ ID NO.: 29)
5' cag ttc agc ac aa GTA CAT CTG TCT AGC TCA aac-[cap] 3'

RDB-3z0 (UPPER CASE bases are complementary to 3' end of RHP-3):

(SEQ ID NO.: 30)
5' cag ttc agc ac aa GTA CAT CTG T aac-[cap] 3'

Quantification Standards and Quality Control ("QC") Nucleotides

LTAR-1 (QC oligonucleotide from Epoch Biosciences (Bothell, Wash.); underlined bases differ from IQS-1):

(SEQ ID NO.: 31)
5' TTT TAC TTC ATC TGC AAC TGT ACA TCT GTC TAG CTC ATC ACG TCA CTG AAT GCA T

IQS-1 (internal quantification standard; underlined bases differ from LTAR-1):

(SEQ ID NO.: 32)
5' TT TAC TTC ATC TGC AAC ACA TGA TCT CAG ATG CTC ATC ACG TCA CTG AAT GCA TC

IQS-2 (internal quantification standard; lower case bases differ from target-derived amplicon):

(SEQ ID NO.: 33)
5' TTA CTT CAT CTG CAA C at ctg tca ctt gat cac tct ga G TCA CTG AAT GCA TC

EXAMPLE 2

Experimental Demonstration of Homogeneous Immuno-SDA

In the following series of experiments, the analyte-specific binding moieties of the proximity members were biotin moieties, and the chosen test analyte was streptavidin ("SA"). Biotin was linked to the 5' end of the oligonucleotide moieties P1 (RHP-1) and P2 (LHP-1 or LHP-3). (See EXAMPLE 1, above.) P1 and P2 were each at 1 μM concentration and were mixed with 10 mM Tris-EDTA buffer and bovine serum albumin (BSA) and optionally SA at 0.25 μM. After 10 minutes at room temperature, the mixtures were serially diluted so that the final probe concentrations were in the pM range. The diluted mixtures were then mixed with SDA primers (SRH1, SLH2), an adapter (ADR-5), and a reporter probe (TBD10.2), and the mixtures were heated to 72° C. for 10 minutes. The samples were cooled to 52° C. and added to "amplification wells," containing a dried cocktail of SDA components that included dNTPs. Final probe concentrations were either 1 fM or 10 fM, and final SA concentration was either zero or one-half the respective probe concentrations. BsoBI restriction endonuclease and Bst DNA polymerase (BD Diagnostic Systems, Baltimore, Md.) were then added to the mixtures, and isothermal amplification was carried out for 1 hour at 52° C. Amplification was monitored by observing the fluorescence increase associated with conversion of the fluorescein-labeled reporter probe, TBD10.2, as described in U.S. Pat. No. 6,316,200.

MOTA values (a measure of fluorescence intensity integrated over the course of the 1 hour reaction) are reported in TABLE 1. When P2 is LHP-3, which forms a 13 bp duplex when hybridized to P1 (RHP-1), MOTA values are 100-1000-fold higher for samples containing the analyte SA than for the controls that did not contain SA, demonstrating the ability of this SDA-based binary probe system to detect the SA protein at sub-fM concentration.

TABLE 1

| Streptavidin | | | | | |
| --- | --- | --- | --- | --- | --- |
| 0 | 2.5 fM | 0 | 0.25 fM | 0 | 0.025 fM |
| Concentration of each RHP-1 and LHP-3 (13 bp overlap) | | | | | |
| 10 fM | 10 fM | 1 fM | 1 fM | 0.1 fM | 0.1 fM |

| | | | | | | |
| --- | --- | --- | --- | --- | --- | --- |
| MOTA | 300 | 198,090 | 0 | 161,570 | 10 | 10 |
| Score | 320 | 136,430 | 80 | 109,990 | 0 | 32,880 |
| | 0 | 166,240 | 630 | 146,010 | 0 | 86,240 |
| | 30 | 171,020 | 890 | 157,530 | 0 | 71,780 |
| | 0 | 154,760 | 150 | 114,840 | 330 | 350 |
| | 150 | 143,390 | 160 | 135,800 | 160 | 0 |
| Mean | 133 | 161,655 | 318 | 137,623 | 83 | 31,877 |
| % Control | 111% | 14% | 112% | 16% | 164% | 122% |

| 0 | 2.5 fM | 0 | 0.25 fM |
| --- | --- | --- | --- |
| Concentration of each RHP-1 and LHP-3 (7 bp overlap) | | | |
| 10 fM | 10 fM | 1 fM | 1 fM |

| | | | | |
| --- | --- | --- | --- | --- |
| MOTA | 1,830 | 170 | 80 | 10 |
| Score | 8,680 | 0 | 990 | 70 |
| | 20 | 180 | 430 | 140 |
| | 110 | 120 | 5,680 | 0 |
| | 100 | 320 | 990 | 10 |
| | 12,870 | 10 | 140 | 10 |
| Mean | 3,935 | 133 | 1,385 | 40 |
| % Control | 140% | 90% | 155% | 138% |

EXAMPLE 3

Experimental Demonstration of Heterogeneous Immuno-SDA

In this experiment, RHP-1, bearing either a 5' biotin or a 5' aminolinker and no biotin, served as P1. LHP-1, bearing either a 5' biotin or a 5' amino linker and no biotin, served as P2. 100 nM probes were mixed with SA-coated beads (Promega, Madison, Wis.) and incubated with occasional agitation for 45 minutes at room temperature. The beads were then gathered to the sides of the tube, and the solution was removed. The beads were resuspended in 0.1 mg/mL BSA before gathering them to the side of the tube and discarding the solution phase. These washing steps were repeated four times before the beads were finally resuspended in SDA reaction buffer. The resulting suspension was added to a mixture containing SDA primers (SLH-2, SRH-1), an adapter (ADR-5), and reporter (TBD.10.2). Final concentrations of bead-bound SA in these mixtures was 40 or 400 fM. SDA was then carried out as described in EXAMPLE 2, above.

The results are shown in TABLE 2. As expected, strong MOTA values were observed for reactions containing biotinylated probes and SA at either 40 or 400 fM, indicative of conversion of SA-bound probes into amplifiable extension products. By contrast, MOTA values were very low for control reactions containing SA and probes that were labeled with 5' aminolink groups instead of biotin. As expected for these control reactions, the probes lacking biotin were unable to bind to the bead-linked SA and were consequently eliminated during the wash steps and, therefore, were not converted to amplifiable extension products. The low signal that appears in the control reactions may result from non-specific binding of aminolinked probes to the bead surface.

TABLE 2

| | Biotin Probes | | Amino-Linked Probes | |
| --- | --- | --- | --- | --- |
| [SA] | 400 fM | 40 fM | 400 fM | 40 fM |
| MOTA | 103,550 | 47,240 | 420 | 450 |
| Score | 115,900 | 970 | 0 | 0 |
| | 91,580 | 0 | 250 | 40 |
| | 105,410 | 8,890 | 0 | 90 |
| | −47* | 20,040 | 370 | 310 |
| | 91,310 | 49,910 | 8,510 | 0 |
| Mean | 101,550 | 21,175 | 1,592 | 148 |

| | No Probes | | No Probes | |
| --- | --- | --- | --- | --- |
| [SA] | 400 fM | 40 fM | No SA | |
| MOTA | 120 | 110 | 160 | |
| Score | 0 | 310 | 540 | |
| | 200 | 0 | 250 | |
| | 120 | 410 | 0 | |
| | −45* | 270 | 50 | |
| | 230 | 380 | 1,430 | |
| Mean | 134 | 247 | 405 | |

EXAMPLE 4

Experimental Demonstration of Immuno-SDA with a Single Tether Oligonucleotide

In this experiment, un-biotinylated RHP-1 (see above) served as P1, LHP-3 (bearing a 5' biotin) served as P2, and RCP-1 (bearing a 3' biotin) served as a tether oligo, TO. Probes P1 and P2 and tether oligo TO were mixed in equimolar ratios and added to tubes that either contained or lacked SA. The tubes were incubated briefly at room temperature, and the contents of the tube were then serially diluted to give probe concentrations in the pM range. The diluted mixtures were then mixed with SDA primers (SRH1, SLH2), an adapter (ADR-5) and a reporter probe (TBB10.2) for a final concentration of SA of either 0 or 0.25 fM and a concentration of 1 fM each for P1, P2 and TO. The mixtures were then either subjected to a "heat-spike" (72° C. for 10 minutes) or incubated at 52° C. for 10 minutes ("no heat spike"). The P1:TO duplex, which has an estimated $T_m$ of 64° C., is expected to be stable at 52° C. and disrupted by incubation at 72° C. Upon disruption, the P1:TO duplex will reform only very slowly ($t_{1/2}$>100 hours) at the diluted (1 fM) probe concentrations. The samples were subjected to SDA by addition of BsoBI restriction endonuclease, Bst DNA polymerase and a dried cocktail of dNTPs, followed by incubation at 52° C. in a ProbeTec™ ET instrument. When probes P1 and P2 are bound through TO or biotin, respectively, to a common SA molecule, their complementary 3' ends hybridize and are extended, creating hybridization sites for the SDA primers (SLH-2 and SRH-1) and adapter ADR-5. This enables simultaneous amplification and detection of the extended P1 and P2 molecules. Amplification was monitored by observing the adapter-mediated fluorescence increase associated with conversion of the fluorescein-labeled reporter probe, TBD10.2 (see U.S. Pat. No. 6,316,200 for details of adapter mediated reporter probe conversion).

The results are shown in TABLE 3. "No heat spike" samples that contained the analyte 0.25 fM SA and 1 fM probes showed a strong increase in fluorescence (average MOTA=166,000), while control samples lacking SA but containing 1 fM probes displayed average MOTA values of just 3,000, which is comparable to values obtained from samples in which the P1:TO duplex was disrupted by the 72° C. heat spike prior to SDA. In samples lacking SA, MOTA values remain low because formation of a P1-P2 duplex does not occur with appreciable efficiency at 1 fM probe concentration.

TABLE 3

|  | Heat Spike | | No Heat Spike | |
| --- | --- | --- | --- | --- |
|  | NO SA | SA | No SA | SA |
| MOTA | 290 | 50 | 4740 | 177230 |
|  | 22360 | 250 | 20 | 168210 |
|  | 30 | 380 | 1660 | 175550 |
|  | 190 | 210 | 8240 | 193620 |
|  | 27730 | 8100 | 350 | 139080 |
|  | 160 | 60 | 1500 | 145330 |
| MEAN | 10120 | 1798 | 3002 | 166503 |
| % CV | 136% | 196% | 116% | 12% |

EXAMPLE 5

Analyte Quantification by Binary Immuno-SDA

Levels of target analyte in a sample may be determined quantitatively by including an internal standard (e.g., IQS-1 of EXAMPLE 1), which is co-amplified with target-mediated probe extension products. The internal standard and target-dependent probe-extension products are amplified by common pairs of SDA primers but are detected by different and distinguishably labeled reporter probes (e.g., TBD10.2 and AltD6.9 of EXAMPLE 1). By comparing the relative signals of the two reporter probes, one can deduce the concentration of the probe-specific extension products relative to the known quantity of internal standard. In determining absolute concentrations of analyte, it may be advantageous to produce a "standard curve" of the ratio of background-corrected target/control signals versus target analyte signals. The ratio of signals observed for the test sample may then be compared against the standard curve to produce absolute analyte concentration. Similar methods of quantifying nucleic acid target levels are known in the art (see, e.g., Nadeau et al., "Real-time Sequence-specific Detection of Nucleic Acids during Strand Displacement Amplification," Anal. Biochem. 276: 177-187 (1999)).

EXAMPLE 6

Experimental Demonstration of Immuno-SDA with Two Tether Oligonucleotides

In this experiment, unbiotinylated RHP-1 (see above) served as P1, and unbiotinylated LHP-3 served as P2, while RCP-1 (bearing a 3' biotin) and LCP-4 (bearing a 5' biotin) served as tether oligonucleotides. The interaction between P1, P2 and the t ether oligonucleotides is shown diagrammatically in FIG. 3H. Probes P1 and P2 and tether oligonucleotides were mixed in equimolar ratios (where the molarity was determined with respect to only the tether oligonucleotide moieties of the proximity members) and added to tubes that either contained or lacked SA. Reactions were carried out as described in EXAMPLE 4, except no 72° C. "heat spike" experiment was performed. The results are shown in TABLE 4. Samples containing SA showed strong fluorescence increases (average MOTA values=136,000), while samples lacking SA displayed negligible increases (MOTA=533).

TABLE 4

|  | NO SA | SA |
| --- | --- | --- |
| MOTA | 680 | 156740 |
|  | 470 | 138080 |
|  | 260 | 133150 |
|  | 200 | 137820 |
|  | 1200 | 127070 |
|  | 390 | 126840 |
| MEAN | 533 | 136617 |
| % CV | 69% | 8% |

EXAMPLE 7

Experimental Demonstration of Homogeneous Immuno-SDA with IL-8 as the Analyte

MAb G265-8 (Ab1; BD Bioscience Pharmingen), directed against human IL-8, was covalently coupled to SA to yield an anti-IL-8 IgG-SA conjugate (Ab1-SA) containing one SA moiety per IgG. MAb G265-8 and SA were conjugated using methods well-known in the art. A mixture containing 20 nM 5' biotin-labeled probe RHP-3 (P1), 10 nM Ab1-SA conjugate, 10 nM Tris-EDTA buffer, and 0.1 mg/ml BSA was prepared and incubated overnight at 4° C. to permit the biotinylated oligonucleotide to bind the Ab1-SA conjugate to form Ab1-SA-P1.

MAb G265-5 (Ab2; BD Bioscience Pharmingen), which binds an IL-8 epitope distinct from that of MAb G265-8, was covalently coupled directly to an amino-modified form of probe LHP-3 (P2) to produce Ab2-P2 conjugates having an average of 2.5 P2 moieties per Ab2. MAb G265-5 and LHP-3 were conjugated essentially as described in U.S. Pat. No. 6,511,809 B1, where LHP-3 comprised a primary aliphatic amine group linked the 5' terminus.

Ab1-SA-P1 and Ab2-P2, each with an Ab-probe conjugate concentration of 1 nM, were mixed with 10 mM Tris-EDTA buffer and BSA and optionally 0.01-1 nM IL-8. After 30 minutes at room temperature, the mixtures were serially diluted so that the final concentration of Ab-probe conjugate was in the fM range. The diluted mixtures were then mixed with SDA primers SRH-1 and SLH-2, adapter ADR-5, and reporter probe TBD10.2. After the mixtures were warmed to 37° C. for 10 minutes, a portion of each sample was added to amplification wells at 52° C., as described in EXAMPLE 2, where each amplification reaction contained BsoBI restriction enzyme and Bst DNA polymerase. The final concentration of the Ab-probe conjugates was 1 fM, and the final IL-8 concentration was 0, 0.01, 0.1 or 1 fM. The concentrations of other components were as described in EXAMPLE 2. The samples were immediately transferred to a ProbeTec™ ET instrument, where isothermal amplification was carried out for 1 hour at 52° C. Amplification was monitored by observing the fluorescence increase as described in EXAMPLE 2.

Average MOTA values are reported in TABLE 5. Low MOTA values were obtained for samples lacking IL-8, while higher levels of IL-8 resulted in increased MOTA values, confirming detection of IL-8 by the homogenous immuno-SDA method. In this experiment, no hybridization blocker oligonucleotide was employed, but samples were diluted about a million-fold after formation the proximity pair-IL-8 complex to reduce the occurrence of target-independent probe amplification.

TABLE 5

Detection of IL-8 by homogeneous immuno-SDA

| IL-8 concentration in binding mixture (pM) | Average MOTA (n = 6) |
|---|---|
| 0 | 492 |
| 10 | 3,983 |
| 100 | 73,883 |
| 1,000 | 128,847 |

EXAMPLE 8

Experimental Demonstration of Background Suppression by Use of a Hybridization Blocker Oligonucleotide This experiment illustrates the use of a hybridization blocker oligonucleotide to suppress target-independent amplification resulting from base-pairing between P1 and P2 molecules not associated with target analyte. In this experiment, probe P1 is 5' biotinylated RHP-3, and probe P2 is 5' biotinylated LHP-3 (see above). The 10 nucleotide sequences comprising the 3' ends of P1 and P2 are complementary to each other. As in EXAMPLE 2, the target analyte is SA, which contains four biotin binding sites in its tetrameric form. The hybridization blocker oligonucleotide is RDB-3p8 (EXAMPLE 1), which comprises an 18-nucleotide sequence that is complementary to the 3' end of RHP-3. A duplex formed between P1 and hybridization blocker RDB-3p8, therefore, will include the 10 nucleotides at the 3' end of P1 that are complementary to P2, as well as an additional eight nucleotides of P1 that are not complementary to P2. RDB-3p8 further comprises a 5' tail sequence of 14 nucleotides (the bases 5' of the underlined bases of RDP-3p8 in EXAMPLE 1), which serve as a disabling template upon which the 3' end of RHP-3 may be extended (depicted in FIG. 4C). A characteristic feature of the hybridization blockers of the present invention is that they do not become covalently attached or ligated to oligonucleotide moieties of proximity members. In methods of the present invention that rely on extension of 3' ends of oligonucleotide moieties to produce analyte-specific amplicons, it is necessary for hybridization blocker-probe duplexes to remain stable during polymerase-catalyzed amplification methods (such as SDA and PCR) that require extension of 3' ends and that typically occur at elevated temperatures where duplexes become less stable. The elevated temperatures typically employed in polymerase-based amplification methods (e.g. PCR and SDA) can reduce the prevalence of probe-blocker hybrids to the point where suppression of spurious probe conversion becomes ineffective. This difficulty is overcome in the present invention by selecting hybridization blockers capable of forming probe-blocker hybrids that are more stable than hybrids formed between probes, and by making use of the disabling template, which stabilizes probe-blocker templates at elevated temperatures.

Analysis of SA-containing solutions by immuno-SDA was carried out as follows. Solutions were prepared containing 20 pM each of 5' biotin-labeled probe RHP-3 (P1) and 5' biotin-labeled LHP-3 (P2), 50 nM RDB-3p8 hybridization blocker oligonucleotide, 10 mM Tris-EDTA buffer, and 0.1 mg/ml BSA. Each solution also contained SA at 0, 0.1, 1, 10, or 100 fM. The solutions were incubated for 2 hours at 37° C., and the mixtures were diluted 10-fold in immuno-SDA buffer. 100 µL of the diluted samples were then mixed with 20 µL of a priming solution containing 1.5 µM SRH-1 SDA primer, 3.75 µM SLH-2 SDA primer, 2.25 µM ADR-8 adapter, 3.75 µM TBD10.2 reporter probe, and 0.375 µM RDB-3p8 hybridization blocker oligonucleotide. The resulting mixtures were incubated at 37° C. for 10 minutes. The sequences of all oligonucleotides may be found in EXAMPLE 1. To initiate an immuno-SDA reaction, 80 µL of each mixture were transferred to an amplification microwell containing 20 µL of the SDA enzyme solution pre-equilibrated at 52° C. and comprised of Bst DNA polymerase, BsoBI restriction enzyme and other SDA components including potassium phosphate, BSA and dNTPs. The microwells then were sealed quickly, placed in a ProbeTec™ ET instrument, and maintained at 52° C. for 1 hour as the fluorescence of each microwell was monitored. A series of control reactions that did not contain the RDB-3p8 hybridization blocker oligonucleotide were prepared, along with those described above, and were monitored concurrently in the ProbeTec™ ET instrument.

After accounting for dilution of the original binding mixtures, each immuno-SDA mixture contained 1.3 pM P1 and P2 and SA concentrations of either 0, 0.6, 6, 66, 666 or 6666 aM. The immuno-SDA reactions also contained 30 mM potassium phosphate (pH 7.6), 75 mM bicine, 50 mM potassium hydroxide, 3.5% dimethylsulfoxide (DMSO), 5 mM magnesium acetate, 50 µg/ml BSA, 500 nM SLH-2, 200 nM SRH-1, 50 nM RDB-3p8, 300 nM ADR-8, 500 nM TBD10.2, 0.1 mM dATP, 0.1 mM dGTP, 0.1 mM dTTP, 0.5 mM 2'-deoxycytidine 5'-O-(1-thiotriphosphate) S-isomer (dCTPαS), approximately 8 units of Bst DNA polymerase and 18 units of BsoBI restriction enzyme. Amplification of products resulting from mutual hybridization and extension of P1 and P2 (see FIG. 1) were detected by monitoring the increase in ROX fluorescence associated with amplification of the TBD10.2 reporter oligonucleotide through the adapter-mediated process described in U.S. Pat. No. 6,316,200. For each well, one ROX reading was made every minute during the course of the reaction. The ROX fluorescence readings for each sample were plotted over a time period of 60 minutes.

MOTA values are reported in TABLE 6. For target-free reactions (i.e., 0 aM SA) without the hybridization blocker oligonucleotide, a relatively high average MOTA value of 49,382 was obtained. This background signal significantly limits the sensitivity of immuno-amplification and is believed to arise from target-independent hybridization of P1 with P2 and subsequent extension of their 3' ends, which converts the probes into amplifiable products even in the absence of target analyte. Background signal is dramatically reduced, however, when a hybridization blocker oligonucleotide is included in the reaction mixtures, as revealed by the low average MOTA value of 376 obtained from the target-free mixtures with RDB-3p8. In these reactions, the hybridization blocker oligonucleotide binds competitively to the 3' end of P1, thereby preventing P2 from hybridizing to P1 and essentially eliminating target-independent conversion of the probes into amplifiable products.

Reaction mixtures containing both the target analyte SA and the RDB-3p8 hybridization blocker oligo-nucleotide exhibit high MOTA values, indicating efficient amplification of target bound probes even in the presence of the hybridization blocker oligonucleotide. The inventors estimate that concurrent binding of probes P1 and P2 to the same molecule of SA increases the local concentration of the two probes by over 10 million-fold relative to unbound probes in bulk solution. The estimated effective local concentration of the two probes on the SA molecule is greater than 10 µM, which greatly exceeds the 50 nM concentration of hybridization blocker oligonucleotide in bulk solution. The high local concentration of target-bound P1 and P2 promotes mutual hybridization of the probes and conversion of the probes into amplifiable products, despite the presence of the competing hybridization blocker oligonucleotide. By contrast, probes P1 and P2 not bound to target have a concentration in bulk solution of 1.3 pM, and mutual hybridization of these unbound probes is efficiently suppressed by competitive hybridization of the hybridization blocker oligonucleotide with P1. While some suppression of target-bound probe conversion appears to occur, as revealed by reduced MOTA scores for the SDA reactions at 666 aM SA containing the hybridization blocker compared with reactions at 666 aM SA without the blocker, the ratio of target signal/background signal is nearly 200-fold greater for reactions containing the hybridization blocker.

TABLE 6

MOTA values from SDA-based detection of SA with or without a hybridization blocker oligonucleotide

| SA concentration in SDA reaction (aM) | MOTA with 50 nM hybridization blocker oligo- nucleotide RDB-3p8 | MOTA without RDB-3p8 |
| --- | --- | --- |
| 0 | 376 | 49,382 |
| 0.6 | 1,037 | N.D. |
| 6 | 6,075 | N.D. |
| 66 | 38,815 | N.D. |
| 666 | 73,175 | 109,142 |
| 6666 | 98,790 | N.D. |

In general, reaction mixtures containing higher concentrations of unbound probes P1 and P2 will require increased concentrations of hybridization blocker oligonucleotide to provide the same degree of background suppression as samples containing lower probe concentrations. The concentration of hybridization blocker oligonucleotide may be adjusted empirically to determine the concentration needed to provide an adequate degree of background suppression. Because high concentrations of hybridization blocker oligonucleotide also may suppress amplification of target-bound probes to some degree, the lowest concentration of a hybridization blocker oligonucleotide found to give adequate background suppression will generally be optimal.

The hybridization blocker oligonucleotide employed in this example, RDB-3p8, contains an 18-nucleotide sequence that is complementary to the 3' end of probe P1, RHP-3, such that hybridization of RDB-3p8 to RHP-3 creates an 18-base pair duplex and unpaired, single-stranded tails on the 5' ends of each oligonucleotide. Hybridization blocker oligonucleotides having a complementary sequence either longer or shorter than RDB-3p8 (e.g., RDB-3p10 or RDB-3p5, respectively) also may be employed. In general, for a given concentration, hybridization blocker oligonucleotides with shorter segments of probe complementarity will form duplexes with P1 that are of lower stability (lower $T_m$) than those with longer segments of probe complementarity. Hybridization blocker oligonucleotides that form less stable duplexes with a given probe generally will need to be employed at higher concentrations to provide the same degree of background suppression as hybridization blocker oligonucleotides that form more stable duplexes with the probe. The stability of the P1:P2 duplex also will affect the efficiency of a given hybridization blocker oligonucleotide. In general, the more stable the P1:P2 duplex, the higher the concentration of a given hybridization blocker oligonucleotide that must be employed to impart a suitable level of background suppression. Likewise, the more stable the P1:P2 duplex, the more stable the probe-blocker duplex must be to impart the same degree of background suppression for a fixed concentration of hybridization blocker oligonucleotide. The stability of the duplex formed between a hybridization blocker oligonucleotide and probe can be modulated by changing the length or sequence composition of the hybridization blocker oligonucleotide sequence that is complementary to the probe. Software for estimating the duplex stability from parameters such as oligonucleotide sequence and concentration are well-known in the art, such as OLIGO® (Cambio, United Kingdom) and Mfold (copyright 1996 Dr. M. Zuker) (see http://www.bioinfo.rpi.edu/applications/mfold, described in Zuker, *Nucl. Acids. Res.* 31:3406-15 (2003), incorporated herein by reference).

Two hybridization blocker oligonucleotides, one specific for each probe, may be employed simultaneously to suppress background signal. In general, lower concentrations of hybridization blocker oligonucleotides are required to impart the same degree of background suppression obtained with a single hybridization blocker oligonucleotide.

EXAMPLE 9

Homogeneous Detection of Sub-Picomolar IL-8 Concentrations by Immuno-SDA

Antibody-probe conjugates Ab1-SA-P1 and Ab2-P2 were as described in EXAMPLE 7. 50 µL samples containing 10 mM Tris-EDTA buffer, 20 pM Ab1-SA-P1, 100 pM Ab2-P2, 1 mg/mL BSA, 0.1 mg/mL mouse gamma globulin, 50 nM hybridization blocker oligonucleotide RDB-3z8, and IL-8 at 0, 0.005, 0.010, or 0.025 µM were prepared. After incubating for 3 hours at room temperature, an 5 µL aliquot of each sample was diluted 1:10 (v/v) into Tris-EDTA buffer containing 0.1 mg/mL BSA and then further diluted 1:10 (v/v) into a 100 µL solution containing SDA primers SRH-1 (100 nM) and SLH-2 (500 nM), 300 nM adapter primer ADR-8, 500 nM reporter probe TBD10.2(D/R), and 50 nM hybridization blocker RDB-3z8. Four such diluted mixtures were prepared from each original sample. The diluted mixtures were then incubated at 37° C. for approximately 10 minutes before an 80 µL aliquot of each mixture was transferred into a separate microwell containing 20 µL of SDA enzyme solution that had been pre-warmed to 52° C. The microwells were sealed, placed into a ProbeTec™ ET instrument and incubated at 52° C. for 1 hour. Amplification was monitored by observing the fluorescence increase associated with conversion of the fluorescein-labeled reporter probe, TBD10.2, as described in U.S. Pat. No. 6,316,200, herein incorporated by reference. Resulting MOTA values are reported in TABLE 7. Average MOTA values for binding mixtures containing IL-8 concentrations as low as 0.005 pM are significantly higher than the values from the zero IL-8 samples, confirming the ability of the current homogeneous method to detect analyte concentrations in the low femtomolar range without separating bound from unbound antibodies.

Background signals, represented by MOTA scores in the zero IL-8 samples, are thought to result from spurious amplicon formation arising through weak interactions between antibodies not bound to target (see EXAMPLE 16). Background levels are higher in this example than in EXAMPLE 7 because antibody concentrations in SDA reactions of the current example were at least 200-fold higher than in the earlier example.

TABLE 7

Homogeneous detection of sub-picomolar IL-8 concentrations by immuno-SDA

| [IL-8] in binding mix | Average MOTA (n = 4) standard error |
|---|---|
| 0.000 pM | 12,800 ± 3,800 |
| 0.005 pM | 27,300 ± 4,300 |
| 0.010 pM | 47,600 ± 12,000 |
| 0.025 pM | 96,500 ± 2,900 |

EXAMPLE 10

Experimental Demonstration of Immuno-SDA Employing a Tether Oligonucleotide and a Bridging Probe to Detect IL-8

10 nM of the Ab1-SA conjugate of EXAMPLE 9 was mixed with 20 nM 3'-biotin labeled RCP-1 tether oligonucleotide (TO) in 0.1 M Tris-EDTA buffer containing 0.1 mg/mL BSA. This mixture was incubated overnight at 4° C. to permit the biotinylated oligonucleotide to bind the Ab1-SA conjugate, forming Ab1-SA-TO.

Mixtures containing 1 nM Ab1-SA-TO, 1 nM RHP-3 with no biotin label (P1), 1 nM Ab2-P2 (see EXAMPLE 8), 10 mM Tris-EDTA buffer, 0.1 mg/mL BSA, and IL-8 at 0, 10 or 100 pM were prepared. After incubating for 30 minutes at room temperature, the mixtures were serially diluted so that the final concentration of Ab-probe conjugates was in the fM range. The diluted mixtures then were mixed with SDA primers SRH-1 and SLH-2, adapter ADR-5, and reporter probe TBD10.2, and the mixtures were warmed to 37° C. for 10 minutes. A portion of each diluted sample was added to dried amplification wells at 52° C. as described in EXAMPLE 2, which also contained the BsoBI restriction enzyme and Bst DNA polymerase. The concentrations of Ab-probe conjugates in resulting SDA mixture were 1 fM, and the IL-8 concentration was either 0, 0.01, or 0.1 fM. The samples were immediately transferred to a ProbeTec™ ET instrument, where isothermal amplification was carried out for 1 hour at 52° C. Amplification was monitored by observing the fluorescence increase as described in EXAMPLE 2 above.

MOTA values are reported in TABLE 8. Low MOTA values were obtained for samples lacking IL-8, while higher levels of IL-8 resulted in increased MOTA values, confirming detection of IL-8 by an immuno-SDA method in which P1 is employed as a splint oligonucleotide linked indirectly to analyte binding moiety Ab1 through hybridization with a tether oligonucleotide TO, as depicted in FIG. 3A. In this experiment, no hybridization blocker oligonucleotide was employed, and samples were diluted about a million-fold after formation the proximity pair-IL-8 complex to reduce the occurrence of target-independent probe amplification.

TABLE 8

Detection of IL-8 by homogeneous immuno-SDA with tether oligonucleotide

| IL-8 concentration in binding mixture (pM) | Average MOTA (n = 6) |
|---|---|
| 0 | 345 |
| 10 | 505 |
| 100 | 32,227 |

EXAMPLE 11

Experimental Demonstration of Immuno-SDA Employing a Fab' Fragment as Analyte Binding Moiety in the Detection of IL-8

MAb G265-8 (see EXAMPLE 9) was digested with pepsin to yield F(ab')$_2$ fragments and fragments of the Fc region. F(ab')$_2$ was purified and further treated with dithiothreitol (DTT) to reduce the disulfide bridges linking the Fab' fragments. The resulting Fab' fragment (Ab1) was coupled to two RHP-3 oligonucleotides (P1) to form an Ab1-P1 conjugate.

Mixtures containing 0.1 nM Ab1-P1, 0.1 nM Ab2-P2 (see EXAMPLE 8), 10 mM Tris-EDTA buffer, 0.1 mg/mL BSA, 10 nM hybridization blocker oligonucleotide RDB-3p8 (see EXAMPLE 1), and IL-8 at 0, 0.1 or 1 pM were prepared. After incubating 3 hours at 37° C., the mixtures were serially diluted so that the resulting concentration of Ab-probe conjugates was in the fM range. The diluted mixtures were then mixed with SDA primers SRH-1 and SLH-2, adapter ADR-5, additional hybridization blocker RDB-3p8 to a final concentration of 10 nM, and reporter probe TBD10.2. The resulting mixtures were maintained at 37° C. for 10 minutes. A portion of each sample was then added to dried amplification wells at 52° C. as described in EXAMPLE 2, which also contained the BsoBI restriction enzyme and Bst DNA polymerase. In the resulting SDA mixtures, the concentrations of the Ab-probe conjugates were 100 fM and the IL-8 concentration was either 0, 0.1 or 1 fM (TABLE 9). The samples were immediately transferred to a ProbeTec™ ET instrument, where isothermal amplification was carried out for 1 hour at 52° C. Amplification was monitored by observing the fluorescence increase, as described in EXAMPLE 2.

TABLE 9

Detection of IL-8 by homogeneous immuno-SDA with Fab'-P1 conjugate

| IL-8 concentration in binding mixture (pM) | Average MOTA (n = 6) |
|---|---|
| 0 | 1,920 |
| 0.1 | 4,713 |
| 1 | 19,710 |

Average MOTA values for four replicates are reported in TABLE 9. Low MOTA values were obtained for samples lacking IL-8, while higher levels of IL-8 resulted in increased MOTA values, confirming detection of IL-8 by the immuno-SDA method in which a Fab' is employed as the analyte binding moiety of Ab1-P1.

EXAMPLE 12

Target-Mediated Amplicon Formation Using Reversibly Immobilized Proximity Member, Combined with Background Suppression Using a Hybridization Blocker Oligonucleotide The buffers used in this example are as follows:
TBS: 25 mM Tris (pH 7.6), 150 mM NaCl;
Diluent A: Diluent B plus 0.01% Tween-20, 800 µM D-biotin and 5 mM EDTA;
Diluent B: TBS, 0.5% Skim Milk Powder (Oxoid Ltd., United Kingdom), 0.1 mg/mL molecular biology grade DNA (Roche Molecular Systems, Pleasanton, Calif.);
Blocking Solution: TBS, 4.5% Skim Milk Powder, 1 mg/mL molecular biology grade DNA, 2 mg/mL sodium azide, 5 mM EDTA;
Wash Buffer: TBS, 5 mM EDTA, 0.05% Tween-20;
SDA Reaction Buffer (Concentrated): 90 mM bicine, 60 mM KOH, 12 mM potassium phosphate, 6.57% glycerol, 4.23% DMSO;
SDA Primer Mix: 7.5 µM SRH-1, 37.5 µM SLH-2, 300 µM ADR-5, 37.5 µM TBD10.2 in water; and
SDA Enzyme Mix: 18 units BsoBI restriction endonuclease and 8 units Bst polymerase (BD Diagnostic Systems) in 75 mM Bicine, 50 mM potassium hydroxide, 10 mM potassium phosphate (pH 7.6).

The chosen target analyte is IL-8, and MAbs G265-5 and G265-8 are the analyte-binding moieties. MAb G265-5 was conjugated to probe LHP-3 to produce Ab1-P1. MAb G265-8 was conjugated with SA, and this conjugate was mixed with the 5' biotinylated probe RHP-3 at a ratio of two probes per Ab molecule to produce Ab2-P2.

A capture oligonucleotide was immobilized to a solid support according to the following procedure. SA-coated 96-microwell plates (Pierce Cat. No. 15121) were rinsed three times in TBS and incubated overnight in Blocking Solution before being washed four times with Wash Buffer. A 100 µL solution containing 80 nM of 5'-biotinylated RCP-9v2.2 capture oligonucleotide was added to each well and incubated for 1 hour at room temperature. The plates were then washed four times with Wash Buffer containing 800 µM D-biotin.

Hybridization of the Ab2-P2 conjugate to the immobilized capture oligonucleotide was performed as follows: 100 µL of 0.1 nM Ab2-P2 in Diluent A was added to each microwell and incubated at room temperature for 1 hour. The microwells were then washed four times with Wash Buffer. 100 µL of a sample solution containing either 0 or 50 pM IL-8 in Diluent B was then added to each microwell and incubated at room temperature for 1 hour. The microwells were then washed four times with Wash Buffer. This step resulted in a complex formed between IL-8 and the immobilized Ab2-P2.

Binding of Ab1-P1 to the complex between IL-8 and the immobilized Ab2-P2 was performed as follows: a 100 µL solution of 0.1 nM Ab1-P1 conjugate in Diluent A, containing either 1 µM LBK-1 hybridization blocker oligonucleotide or no hybridization blocker oligonucleotide, was added to the microwells containing the complex between IL-8 and Ab2-P2 and incubated at room temperature for 1 hour. Microwells containing the LBK-1 hybridization blocker oligonucleotide were then washed five times in Wash Buffer containing 1 µM LBK-1, followed by two washes with Wash Buffer devoid of LBK-1. Microwells not exposed to the hybridization blocker oligonucleotide were washed seven times with Wash Buffer. For both sets of wells, two final washes were carried out with TBS.

The captured complexes prepared as described above were eluted from the support by addition of 120 µL of SDA Reaction Buffer (Concentrated) and incubated at room temperature for 20 minutes. A 100 µL volume containing the eluted complexes was transferred from each microwell to a new microwell containing 20 µL of the SDA Primer Mix. The microwells were incubated for 20 minutes at room temperature and then placed on a 37° C. heat block for 10 minutes. To initiate amplification by SDA, 80 µL was removed from each 37° C. microwell and transferred to a separate microwell containing 20 µL of SDA Enzyme Mix that had been preheated to 52° C. The microwells then were quickly placed into a BD ProbeTec™ ET instrument and maintained at 52° C. for 1 hour while fluorescence intensity was monitored during the course of amplification. The MOTA value for each amplification reaction was determined from the kinetic fluorescence profile obtained during the course of the reaction.

As depicted in FIG. 7D, base-pairing between the probe moieties P1 and P2 of antibody-probe conjugates Ab1-P1 and Ab2-P2 promotes formation of target-free binary complexes between the two antibody-probe conjugates. Inclusion of hybridization blocker oligonucleotide LBK-1 in binding mixtures suppresses formation of the target-free complexes by precluding base-pairing between P1 and P2. The presence of target-free binary complexes in the absence of the hybridization blocker oligonucleotide resulted in high levels of background signal during immuno-amplification reactions, as revealed in TABLE 10 by the high average MOTA value associated with binding mixtures that contained no IL-8 and no LBK-1 hybridization blocker oligonucleotide. By contrast, the presence of 1 µm LBK-1 hybridization blocker oligonucleotide reduces the average MOTA value for the "no IL-8" binding mixtures by 20-fold, indicating substantial reduction in the formation of the target-free complexes. The presence of the hybridization blocker oligonucleotide reduces the intensity of the IL-8 specific signal slightly (compare MOTA values of the 50 pM IL-8 mixtures with and without LBK-1); however, the ratio of specific signal to background signal is 12-fold higher for binding mixtures that contained the hybridization blocker oligonucleotide than for those that did not.

The results further demonstrate the use of an immobilized proximity member (Ab2-P2) to capture or immobilize a target antigen (IL-8) and to form an immobilized ternary complex comprising the target antigen and both members of a proximity pair (Ab1-P1 and Ab2-P2), as depicted in FIGS. 7A-7G. This example also reveals that a detectable number of the immobilized ternary complexes become detached from the solid-phase during the 20-minute room temperature elution period following addition of the concentrated SDA buffer, even though the estimated half-life of the immobilizing hybrid (the duplex formed between capture oligonucleotide and probe moiety P2) is much longer (many days) than the 20-minute elution time.

TABLE 10

Average MOTA values (n = 6) from immuno-SDA detection of IL-8 using immobilize proximity member with or without a hybridization blocker oligonucleotide

| IL-8 concentration in Binding Mixture (pM) | With 1 µM LBK-1 hybridization blocker oligonucleotide | Without hybridization blocker oligonucleotide |
|---|---|---|
| 0 | 1,533 | 31,829 |
| 50 | 66,404 | 112,451 |

EXAMPLE 13

Target-Mediated Amplicon Formation Using Reversibly Immobilized Proximity Member: Release of Immobilized Complex by Application of Low-Ionic Strength Solution The MAbs, analyte and buffers used in this example are the same as those described in EXAMPLE 12. Biotinylated RCP-9v2.2 capture oligonucleotide was immobilized on a support in the same manner as described in EXAMPLE 12. Hybridization of the Ab2-P2 conjugate to the immobilized capture oligonucleotide was performed as described in EXAMPLE 12. 100 µL Diluent B containing either 0 or 10 pM IL-8 then was added to each microwell, which were incubated at room temperature for 1 hour. The microwells then were washed four times with Wash Buffer. Diluent A containing 0.1 nM of the Ab1-P1 conjugate and 1 µM of the LBK-1 hybridization blocker oligonucleotide was then added to each microwell, and the microwells were incubated at room temperature for 1 hour. Microwells then were washed as described in EXAMPLE 12, except that the final two wash steps contained 10 mM NaCl rather than TBS.

To release the resulting immobilized complex between IL-8 and the Ab1-P1 and Ab2-P2 conjugates, each microwell was treated with either 75 µL water or non-concentrated SDA Buffer. After incubating for 20 minutes at room temperature, 70 µL of this solution was removed and analyzed by SDA as described in EXAMPLE 12.

This example demonstrates the use of a low-ionic strength solution to release intact the immobilized ternary complex comprised of an IL-8 molecule bound simultaneously to the proximity pairs Ab1-P1 and Ab2-P2. The results of this example are shown in TABLE 11. The average MOTA value obtained for samples containing 10 pM IL-8 that were eluted with water (low ionic strength) is nearly 10-fold higher than the average MOTA value for samples eluted with SDA buffer (moderate ionic strength), confirming the release of the ternary complex by application of a low-ionic strength solution as depicted in FIG. 7I.

TABLE 11

Average MOTA values (n = 6) from immuno-SDA detection of IL-8 using an immobilized proximity member: Elution at low ionic strength or at moderate ionic strength

| IL-8 concentration in Binding Mixture (pM) | Elution with water (low ionic strength) | Elution with SDA buffer (moderate ionic strength) |
|---|---|---|
| 0 | 148 | 220 |
| 10 | 46,584 | 4,888 |

EXAMPLE 14

Target-Mediated Amplicon Formation Using Reversibly Immobilized Proximity Member: Release of Immobilized Complex by Application of a Displacement Oligonucleotide The MAbs, analyte and buffers are the same as those described in EXAMPLE 12. Biotinylated RCP-9v2.2 capture oligonucleotide was immobilized on a support in the same manner as described in EXAMPLE 12. Hybridization of the Ab2-P2 conjugate to the immobilized capture oligonucleotide was performed as described in EXAMPLE 12. 100 µL Diluent B containing either 0 or 10 pM IL-8 then was added to each microwell, which were incubated at room temperature for 1 hour. The microwells then were washed four times with Wash Buffer. Diluent A containing 0.1 nM of the Ab1-P1 conjugate and 1 µM of the LBK-1 hybridization blocker oligonucleotide was then added to each microwell, and the microwells are incubated at room temperature for 1 hour. Microwells then were washed as described in EXAMPLE 12.

To release the resulting immobilized complexes between IL-8 and the Ab1-P1 and Ab2-P2 conjugates, each microwell was treated with 120 µL of SDA Buffer (Concentrated) that either contained 0.1 µM of the CMPR-9v2 displacement oligonucleotide or no displacement oligonucleotide. After incubating for 20 minutes at room temperature, this solution was analyzed by SDA as described in EXAMPLE 12.

This example demonstrates the use of a displacement oligonucleotide to release intact the immobilized ternary complex comprised of an IL-8 molecule bound simultaneously to proximity pairs Ab1-P1 and Ab2-P2. The results of the current example are shown in TABLE 12. The average MOTA value obtained for samples containing 10 pM IL-8 and treated with the displacement oligonucleotide is 10-fold higher than the MOTA value for 10 pM IL-8 samples not treated with the displacement oligonucleotide, confirming the release mechanism depicted in FIG. 7J.

TABLE 12

Average MOTA values (n = 6) from immuno-SDA detection of IL-8 using an immobilized proximity member with or without a displacement oligonucleotide

| IL-8 concentration in Binding Mixture (pM) | With 0.1 µM CMPR-9v2 displacement oligonucleotide | Without displacement oligonucleotide |
|---|---|---|
| 0 pM | 97 | 220 |
| 10 pM | 54,702 | 4,888 |

EXAMPLE 15

Experimental Demonstration of Immuno-SDA Using a 3'-Capped Proximity Probe

This example provides an experimental demonstration of the process depicted in FIG. 14, namely the use of a 3'-capped, non-extendible proximity probe for detection of an analyte by immuno-amplification. The target analyte in this example is SA. The 3'-capped proximity probe P1 is LHP-3 [cap] (shown in EXAMPLE 1). LHP-3 [cap] comprises a 3' dexoyuridine moiety that prevents extension of the probe when LHP-3 [cap] is hybridized to the complementary template strand P2. In this example, the analyte binding moiety is a biotin moiety attached to the 5' end of LHP-3 [cap]. The second probe of the proximity pair, P2, is RHP-3 (shown in EXAMPLE 1), which comprises a 5' biotin moiety and an extendible 3' end. An uncapped control probe, LHP-3, comprises a 5' biotin moiety and an extendible 3' end. Amplification primers, adapter oligonucleotide, reporter probe, hybridization blocker oligonucleotide and other reaction components are the same as EXAMPLE 8.

Solutions were prepared containing 20 pM 5' biotin RHP-3, 20 pM 5' biotin LHP-3 [cap], 10 mM Tris-EDTA buffer, 5 µg/mL BSA, and either 0 or 10 fM SA. The binding mixtures optionally contained 100 nM RDB-3p5 hybridization blocker oligonucleotide (see TABLE 13). The binding mixtures were incubated at 37° C. for 2 hours and then diluted 10-fold and subjected to SDA as described in EXAMPLE 8. A control mixture, in which LHP-3 [cap] was replaced by uncapped LHP-3, was also prepared and subjected to SDA as described above. Average MOTA values from the various SDA reactions are shown in TABLE 13.

TABLE 13

Average MOTA values (n = 4) from immuno-SDA detection of SA using 3'-capped or uncapped P1 probe

| SA concentration in Binding Mix (fM) | Concentration of RDB-3p5 hybridization blocker oligonucleotide | | | |
|---|---|---|---|---|
| | 0 P1 = LPH-3 [cap] | 100 nM P1 = LPH-3 [cap] | 0 P1 = LPH-3 (no cap) | 100 nM P1 = LPH-3 (no cap) |
| 0 | 36,355 | 2,985 | 55,588 | 4,683 |
| 10 | N/D | 133,325 | N/D | 115,143 |

As indicated by MOTA values for samples without SA, reactions in which the proximity probe P1 contained a 3'-extension cap (LHP-3 [cap]) exhibited significantly lower background signal than reactions containing the uncapped probe (LHP-3). For both capped and uncapped probes, the presence of a hybridization blocker oligonucleotide suppressed background signal by about 12-fold relative to the same reaction mixtures devoid of the hybridization blocker oligonucleotide. While the background signal was lower with the capped probe, signal in the presence of 10 fM SA was slightly higher for the capped probe versus the uncapped probe, indicating efficient conversion of the capped P1 and uncapped P2 probes into amplifiable products in the presence of the target analyte. This example further demonstrates that analyte-specific amplicon formation can occur when only one of the overlapping 3' ends formed by a probe-probe hybrid comprises a 3' OH group.

EXAMPLE 16

Experiment Revealing Antibody-Antibody Interactions as a Source of Target-Independent Amplicon Formation This example demonstrates that the interaction between the Ab moieties of the proximity members contributes to target-independent amplification. Four test solutions were prepared containing the components listed below, as described in EXAMPLE 9, in a solution of 10 mM Tris-EDTA buffer and 0.1 mg/mL BSA:
Test Solution 1: 1 nM Ab1-P1 and 1 nM Ab2-SA-P2;
Test Solution 2: 1 nM Ab1-P1, 1 nM unconjugated Ab2 and 2 nM unconjugated P2;
Test Solution 3: 1 nM unconjugated Ab1, 2 nM unconjugated P1 and 1 nM Ab2-P2; and
Test Solution 4: 2 nM unconjugated-P1 and 2 nM unconjugated P2.

The test solutions were incubated for 30 minutes at 37° C. and then serially diluted so that the resulting concentrations of antibodies, probes and conjugates were in the pM range. The diluted mixtures were then mixed with SDA primers and enzymes and subjected to SDA as described in EXAMPLE 9, except that the SDA reaction mixtures optionally contained 50 nM RDB-3p8 hybridization blocker oligonucleotide. Further, the unconjugated probes were used at twice the molar ratio of antibody-probe conjugates to reflect the known probe:antibody ratio of 2:1 in the conjugates. No target analyte was present in the reactions, so MOTA values produced are attributable solely to target-independent probe conversion.

The average MOTA values from the various test solutions are reported in TABLE 14. In reaction mixtures without hybridization blocker oligonucleotides, average MOTA values exceeded 100,000 for all test solutions. In Test Solution 4, containing 50 nM RDB-3p8 hybridization blocker oligonucleotide, average MOTA values were reduced to below 20,000, indicating a greater than 5-fold suppression of background signal. By contrast, the MOTA values for Test Solution 1 were reduced only about 2-fold to ~59,000 by the presence of the hybridization blocker oligonucleotide, indicating that blocking efficiency provided by RDB-3p8 is lower in the presence of two intact antibody probe conjugates than in the presence of the unconjugated probes P1 and P2. The higher MOTA values of Test Solution 1 compared with Test Solution 4 implies the occurrence of antibody-mediated amplicon formation in Test Solution 1 and further suggests that target-independent adherence of Ab1 and Ab2 to each other brings the attached probe moieties into sufficiently close proximity to facilitate spurious amplicon formation. Apparently, because the local probe concentration in mutually adhering antibody pairs is much higher than the overall probe concentration in bulk solution, hybridization blocker oligonucleotides cannot suppress target-independent probe conversion in Test Solution 1 as effectively as in Test Solution 4, where adhering antibody pairs cannot form. This is consistent with the results of Test Solutions 2 and 3, which exhibit MOTA values comparable to those of Test Solution 4, indicating that both probe moieties of a proximity pair must be antibody-conjugated to produce the high MOTA values attributed to the antibody-mediated probe conversion seen in Test Solution 1.

TABLE 14

Background signal (average MOTA values, where n = 6) produced by various combinations of proximity components

| Test Solution | Proximity components | With 50 nM RDB-3p8 hybridization blocker oligonucleotide | Without hybridization blocker oligonucleotide |
|---|---|---|---|
| 1 | Ab1-P1 + Ab2-P2 | 59,309 | 133,521 |
| 2 | Ab1-P1 + Ab2 + P2 | 14,444 | 110,704 |
| 3 | Ab1 + P1 + Ab2-P2 | 17,185 | 121,298 |
| 4 | P1 + P2 | 19,674 | 103,114 |

EXAMPLE 17

Detection of IL-8 by Immuno-SDA Employing a Probe with Reversed Opposite Sequence Orientation This example provides an experimental demonstration of the concept depicted in FIG. 1J. Antibody conjugates Ab1-SA and Ab2-P2 were as described in EXAMPLE 7. Ab1-SA was incubated overnight at 4° C. with probe RBD-3v3 at a probe: antibody ratio of 2:1 to form Ab1-SA-P1. As noted in EXAMPLE 1, RBD-3v3 contains a biotin-moiety near its 3' terminus. Samples containing 10 mM Tris-EDTA buffer, 20 pM Ab1-SA-P1, 100 pM Ab2-P2, 1 mg/mL BSA, 50 nM hybridization blocker oligonucleotide RDB-3z8, and IL-8 at 0, 0.1, 0.25, 0.5 and 1.0 µM were prepared. After incubating for 3 hours at room temperature, an aliquot of each standard sample was diluted 1:10 (v/v) into Tris-EDTA buffer containing 0.1 mg/mL BSA and further diluted 1:10 (v/v) into a solution containing SDA primers (SRH-1 and SLH-2), adapter primer (adr-8), reporter probe (TBD10.2(D/R)), and 50 nM hybridization blocker (RDB-3z8). In the SDA reactions, primer, adapter and reporter concentrations were as described in EXAMPLE 18, and hybridization blocker RDB-3z8 concentration was 50 nM. Four replicates of these diluted mixtures were prepared from each original sample. The diluted mixtures were then incubated at 37° C. for approximately 10 minutes before an 80 µL aliquot of each mixture was transferred into a separate microwell containing 20 µL of SDA enzyme solution that had been pre-warmed to 52° C. The microwells were sealed, placed into a ProbeTec™ ET instrument and incubated at 52° C. for 1 hour. Amplification was monitored by observing the fluorescence increase as described in EXAMPLE 9.

Average MOTA values are reported in TABLE 15. Low MOTA values were obtained for samples lacking IL-8, while increasing levels of IL-8 resulted in progressively higher MOTA values, confirming detection of IL-8 by an immuno-SDA method in which one of the probes is joined to an antibody through a linkage near its 3' end as depicted in FIG. 1J. The results further confirm that a probe-probe (P1-P2) duplex comprising only one extendible 3' OH group can produce an analyte-specific amplicon.

TABLE 15

Detection of IL-8 by homogeneous immuno-SDA with reversed probe (rbd-3v3)

| IL-8 concentration in binding mixture (pM) | Average MOTA (n = 4) |
| --- | --- |
| 0 | 3,069 |
| 0.1 | 23,098 |
| 0.25 | 81,641 |
| 0.5 | 118,338 |
| 1.0 | 128,724 |

EXAMPLE 18

Quantification of IL-8 by Immuno-SDA Employing an Internal Nucleic Acid Control and Proximity Pair This example illustrates absolute quantification of a target analyte (in this case IL-8) in a test sample using the ratio of two fluorescence signals resulting from co-amplification of a nucleic acid control and a target amplicon produced from analyte-bound proximity members, respectively. According to the present invention, a plurality of standard samples and at least one test sample are initially formed. The plurality of standard samples each contain a known starting quantity of a nucleic acid control sequence, a known starting quantity of target analyte, and a quantity of proximity pairs of the invention. Typically, different members of the plurality of the standard samples will have different known quantities of target analyte. The test sample contains a known starting quantity of the nucleic acid control sequence, an unknown quantity of a non-nucleic acid target analyte, and a quantity of the proximity pair. It is this unknown quantity of the target analyte that is to be determined by the absolute quantification method.

In standard and test samples, the oligonucleotide moieties of proximity members that are bound concurrently to the same target analyte molecule are converted into amplicons by any of the methods of the invention described above. The resulting amplicons and nucleic acid control sequences in each standard and test sample are then co-amplified. Within each sample, amplification of amplicons and control sequences may produce separately detectable fluorescence emissions, so that the amplification of the amplicons and control nucleic acid within the same sample may be monitored independently at different fluorescence emission wavelengths during the course of amplification.

The fluorescence values obtained during amplification may be displayed as a two-dimensional graph, termed a "real-time fluorescence profile," with measurement time points assigned to the abscissa and the fluorescence values assigned to the ordinate. FIG. 15A shows an example of a two-color, real-time fluorescence profile of a sample resulting from co-amplification of target and control amplicons in the experiments described below. The detection wavelengths used in the current example were those characteristic for the fluorescent dyes rhodamine and fluorescein, which were used to label the reporter oligonucleotides that are specific for the target amplicon and control nucleic acid, respectively.

For each of the standard and test samples, fluorescence intensities were measured at the two independent detection wavelengths over a plurality n of time-points, which comprise the amplification interval. For a given sample i, each time-point (tp) has two associated fluorescence values, one corresponding to amplified target amplicon $FT(tp)_i$ and the other to amplified control nucleic acid $FC(tp)_i$. These two readings, gathered from the same sample at the same time interval, are referred to as a "matched pair" of fluorescence values.

For purposes of analysis, real-time fluorescence profiles of two or more different samples are assumed to be temporally coherent; that is, the same time-point from two or more different samples corresponds to the same measure of elapsed time following initiation of amplification in the respective samples. These equivalent time-points from different samples are said to be "coincident." In the event that raw fluorescence profiles of different samples are not temporally coherent, methods known in the art may be employed to construct temporally coherent "normalized" profiles from the raw data (see, e.g., U.S. Pat. Nos. 5,863,736 and 6,066,458, the disclosures of which are incorporated herein by reference in their entirety).

For each time-point (tp) within the real-time fluorescence profile of a given sample i, each matched pair of fluorescence values may be used to compute a signal ratio, $SR(tp)_i$ according to the relationship (Equation 1):

$$SR(tp)_i = [FT(tp)_i - FT(base)_i] / [FC(tp)_i - FC(base)_i] \quad \text{Equation 1,}$$

in which the baseline fluorescence measurements, $FT(base)_i$ and $FC(base)_i$, correspond to the respective fluorescence intensities prior to detectable amplification of target and control amplicons. In practice, $FT(base)_i$ is taken as the average value of the target amplicon fluorescence measured over the first several time-points during amplification of sample i, and FC(base)$_i$ is taken as the average nucleic acid control fluorescence measured over those same time-points, although other approximations of baseline fluorescence may also be employed.

Each pair of real-time target and control fluorescence profiles resulting from an amplified sample will, therefore, give rise to n signal ratios, where n is the number of time-points in the profile. Likewise, each time-point that is coincident across a plurality of k samples will have k "coincident" signal ratios, SR(tp)$_i$, associated with it, where each signal ratio corresponds to a sample i at the coincident time-point tp.

To correlate between the signal ratios produced by a sample and the quantity of analyte (IL-8) contained in the sample, signal ratios determined for a plurality of k standard samples containing various known quantities of IL-8 were analyzed as follows. Each set of coincident signal ratios (i.e., signal ratios derived from the same time-point, tp, across all k standard samples) was first subjected to linear regression against the known analyte concentrations according to Equation 2, which defines a "calibration" line relating the quantities log(SR(tp)$_i$) and log([IL-8]$_i$) and possessing slope, m(tp), and intercept, b(tp), values determined by the regression routine:

$$\log(SR(tp)_i) = \{m(tp)\log([IL-8]_i)\} + b(tp) \quad \text{Equation 2.}$$

Figure 15B:
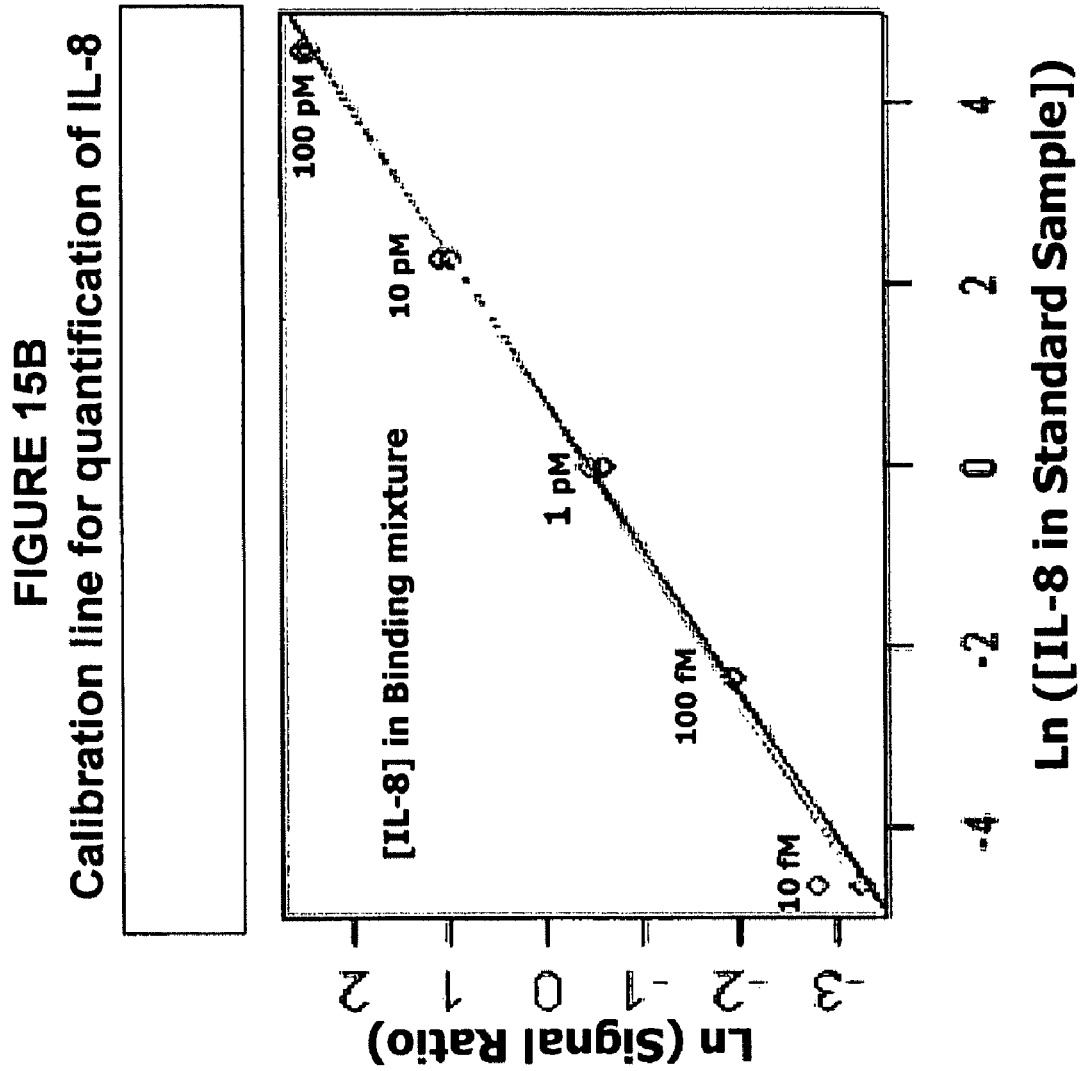
FIG. 15B shows a calibration line for quantification of IL-8.

This operation is repeated for each of the n sets of coincident signal ratios, producing n calibration lines defined by n pairs of slope and intercept values, each pair corresponding to a different coincident time-point across the plurality of k standard samples. One of the n calibration lines obtained from this analysis (tp=8 min) is shown in FIG. 15B.

A "best" measurement time-point (tp$_{best}$), corresponding to "best" pair of slope and intercept values, is then selected based on a goodness-of-fit criterion, and the signal ratio for the test sample is computed according to Equation 1 from fluorescence measurements obtained at the time-point coincident with the selected "best" time point. The quantity of analyte IL-8 in a test sample j can then be calculated from the signal ratio of the test sample at best measurement time-point, SR(tp$_{best}$)$_j$, and "best" pair of slope, m (tp$_{best}$), and intercept, b(tp$_{best}$), values by means of Equation 3:

$$\log([IL-8]_j) = \{\log(SR(tp_{best})) - b((tp_{best})\}/m((tp_{best}) \quad \text{Equation 3.}$$

Various statistical criteria may be employed to determine a "best" calibration line, or a corresponding "best" measurement time, tp$_{best}$. A number of these statistical criteria have been described in U.S. Pat. Nos. 5,863,736 and 6,066,458. Other statistical methods for selecting a best time also may be employed.

Experimental procedures were performed as follows. Antibody-probe conjugates Ab1-SA-P1 and Ab2-P2 were as described in EXAMPLE 7. Standard samples containing 10 mM Tris-EDTA buffer, 20 pM Ab1-SA-P1, 100 pM Ab2-P2, 1 mg/mL BSA, 25 nM hybridization blocker oligonucleotide RDB-3p8, and IL-8 at 0.01, 0.1, 1.0, 10.0 and 100 pM were prepared. After incubating for 3 hours at room temperature, an aliquot of each standard sample was diluted 1:10 (v/v) into Tris-EDTA buffer containing 0.1 mg/mL BSA and then further diluted 1:100 (v/v) into a solution containing SDA primers (SRH-1 and SLH-2), adapter primers (adr-8 and adqs-2), reporter probes (TBD10.2(D/R) and ALTD6.9(F/D)), 50 nM hybridization blocker (RDB-3p8), and 100,000 copies of control nucleic acid (IQS-2). Two such diluted mixtures were prepared from each original standard sample. The diluted standard mixtures were then incubated at 37° C. for approximately 10 minutes before an 80 μL aliquot of each mixture was transferred into a separate microwell containing 20 μL of SDA enzyme solution that had been pre-warmed to 52° C. The microwells were then sealed, placed into a ProbeTec™ ET instrument and incubated at 52° C. for 1 hour. During this 1-hour incubation, the fluorescence of each microwell was recorded through two optical channels, one specific for rhodamine fluorescence and the other specific for fluorescein fluorescence. A pair of fluorescence readings (one fluorescein and one rhodamine) was recorded at each 1-minute interval during the 1-hour course of the reaction, resulting in 60 pairs of fluorescence readings for each SDA reaction.

A set of test samples containing IL-8 concentrations of 0.01, 0.1, 1.0, 10.0, and 100.0 pM were prepared and subjected to competitive two-color SDA, as described above for the standard samples. The quantity of control oligonucleotide (IQS-2) was equivalent to those in the standard samples.

In the present example, two-color fluorescence data from a total of 10 duplicate SDA reactions for each of the five IL-8 standard samples were used to construct a calibration equation as follows. For each of the 10 amplified standard samples (i), signal ratios, SR(tp)$_i$, were calculated according to Equation 1 for each of the 60 time points (tp). Each set of coincident signal ratios from the standard samples was subjected to linear regression against the known IL-8 concentration as described in Equation 2 above, yielding slope (m(tp)) and intercept (b(tp)) values corresponding to a different "calibration" line for each of the 60 time-points. A goodness-of-fit criterion was applied to the calibration lines to determine that the best measurement time for this plurality of standard samples was tp=8 minutes. A plot of log (SR(tp=8 min)) versus log([IL-8]) and the corresponding calibration line are shown in FIG. 15B, which reveals a linear relationship between signal ratio and IL-8 concentration over a 10,000-fold range of analyte concentration.

Signal ratios were computed from fluorescence data (tp=8 minutes) for the various test samples noted above. Equation 3 was then used to calculate IL-8 concentrations of the test samples, using the best slope and intercept values, corresponding to the tp=8 minutes calibration line derived from the standard curves.

The results shown in TABLE 16 reveal close agreement between calculated and actual IL-8 concentrations, confirming the accurate quantification of target analyte by methods of the present invention.

TABLE 16

Quantification of IL-8 in Test samples by immuno-SDA

| Test Sample | Actual IL-8 Concentration | Calculated IL-8 Concentration |
|---|---|---|
| 1 | 0.01 pM | 0.02 pM |
| 2 | 0.1 pM | 0.09 pM |
| 3 | 1.0 pM | 0.9 pM |
| 4 | 10 pM | 6.8 pM |
| 5 | 100 pM | 92.0 pM |

Having now fully described the invention with reference to certain representative embodiments and details, it will be apparent to one of ordinary skill in the art that changes and modifications can be made thereto without departing from the spirit or scope of the invention as set forth herein. All the methods and procedures set forth herein are readily practicable by the artisan of ordinary skill in this field.

What is claimed is:

1. A method of detecting an analyte, comprising:
   (i) combining:
      (a) an analyte;
      (b) a first proximity member, comprising a first analyte-specific binding entity that is capable of forming a complex with the analyte and that is conjugated to a first oligonucleotide comprising a first portion and a second portion;
      (c) a second proximity member, comprising a second analyte-specific binding entity that is capable of forming a complex with the analyte and that is conjugated to a second oligonucleotide comprising a portion that is capable of hybridizing to the first portion of the first oligonucleotide; and
      (d) a support comprising a capture oligonucleotide that is capable of hybridizing to the second portion of the first oligonucleotide, thereby forming a complex comprising the analyte, the first proximity member, the second proximity member and the capture oligonucleotide on the support, wherein each of the first analyte-specific binding entity and the second analyte-specific binding entity is an antibody or a functional fragment thereof that binds the analyte, wherein the complex further comprises a hybrid comprising the first portion of the first oligonucleotide and the portion of the second oligonucleotide;
   (ii) the first portion of the first oligonucleotide moiety and the portion of the second oligonucleotide moiety; extending the 3' terminus of the first oligonucleotide and/or the second oligonucleotide in the complex and producing an amplicon;
   (iii) amplifying the amplicon and producing an amplification product; and
   (iv) detecting the analyte by the detection of the amplification product.

2. The method of claim 1, wherein the first and second portions of the first oligonucleotide comprise no overlapping bases.

3. The method of claim 1, wherein the first and second portions of the first oligonucleotide have identical base sequences.

4. The method of claim 1, wherein said step (ii) further comprises a ligation step.

5. The method of claim 1, further comprising washing the support after said step (i).

6. The method of claim 5, further comprising releasing the first proximity member from the support after said washing the support.

7. The method of claim 6, wherein a hybrid formed by the capture oligonucleotide and the first oligonucleotide in the complex comprises a restriction endonuclease recognition site, and wherein the releasing step comprises cleaving the site by a restriction endonuclease.

8. The method of claim 6, wherein the complex comprises a hybrid formed by the capture oligonucleotide and the first oligonucleotide, further comprising a polymerase-catalyzed extension of the hybrid thereby forming a restriction endonuclease recognition site, and the releasing step comprises cleaving the site by a restriction endonuclease.

9. The method of claim 6, wherein the releasing step is performed by physical dissociation of a hybrid formed by the capture oligonucleotide and the first oligonucleotide in the complex.

10. The method of claim 6, wherein the releasing step is performed by physical, chemical or enzymatic cleavage.

11. The method of claim 6, wherein the capture oligonucleotide comprises a double-stranded portion and a single stranded portion, the releasing step comprises extending the double-stranded portion of the capture oligonucleotide to displace the first oligonucleotide from a hybrid formed by the capture oligonucleotide and the first oligonucleotide in the complex.

12. The method of claim 11, wherein the capture oligonucleotide comprises a hairpin loop.

13. The method of claim 6, wherein the first oligonucleotide comprises a double-stranded portion and a single stranded portion, the releasing step comprises extending the double-stranded portion of the first oligonucleotide to displace the capture oligonucleotide from a hybrid formed by the capture oligonucleotide and the first oligonucleotide in the complex.

14. The method of 13, wherein the first oligonucleotide comprises a hairpin loop.

15. The method of claim 6, wherein one or both strands of a hybrid formed by the capture oligonucleotide and the first oligonucleotide in the complex comprises or comprise RNA, and wherein the releasing step comprises degrading said RNA of said one or both strands with a RNase.

16. The method of claim 1, wherein the amplifying step is performed using a method or system selected from the group consisting of polymerase chain reaction, strand displacement amplification, thermophilic strand displacement amplification, self-sustained sequence replication, nucleic acid sequence-based amplification, a Q replicase system, ligase chain reaction, and transcription mediated amplification.

17. The method of claim 1, wherein the detecting step is quantitative.

* * * * *

SEQUENCE LISTING

<160> NUMBER OF SEQ ID NOS: 33

<210> SEQ ID NO 1
<211> LENGTH: 65
<212> TYPE: DNA
<213> ORGANISM: Artificial Sequence
<220> FEATURE:
<223> OTHER INFORMATION: Synthetic polynucleotide sequence

<400> SEQUENCE: 1
ccagtcttgt cttgtctgtt ctcgggatgc attcagtgac gtgatgagct agacagatgt    60
acagt                                                                65

<210> SEQ ID NO 2
<211> LENGTH: 62
<212> TYPE: DNA
<213> ORGANISM: Artificial Sequence
<220> FEATURE:
<223> OTHER INFORMATION: Synthetic polynucleotide sequence

<400> SEQUENCE: 2
ccagtcttgt cttgtctgtt ctcgggatgc attcagtgac gtgatgagct agacagatgt    60
ac                                                                   62

<210> SEQ ID NO 3
<211> LENGTH: 68
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (67)
<223> OTHER INFORMATION: biotin labeled

<400> SEQUENCE: 3
ccagtcttgt cttgtctgtt ctcgggatgc attcagtgac gtgatgagct agacagatgt    60
acttttt                                                              68

<210> SEQ ID NO 4
<211> LENGTH: 49
<212> TYPE: DNA
<213> ORGANISM: Artificial Sequence
<220> FEATURE:
<223> OTHER INFORMATION: Synthetic polynucleotide sequence

<400> SEQUENCE: 4
attcacgctt ccattccatg tctcgggttt acttcatctg caactgtac                49

<210> SEQ ID NO 5
<211> LENGTH: 51
<212> TYPE: DNA
<213> ORGANISM: Artificial Sequence
<220> FEATURE:
<223> OTHER INFORMATION: Synthetic polynucleotide sequence

<400> SEQUENCE: 5
attcacgctt ccattccatg tctcgggttt acttcatctg caactgtaca t             51

<210> SEQ ID NO 6
<211> LENGTH: 55
<212> TYPE: DNA
<213> ORGANISM: Artificial Sequence
<220> FEATURE:

<223> OTHER INFORMATION: Synthetic polynucleotide sequence

<400> SEQUENCE: 6
attcacgctt ccattccatg tctcgggttt acttcatctg caactgtaca tctgt    55

<210> SEQ ID NO 7
<211> LENGTH: 57
<212> TYPE: DNA
<213> ORGANISM: Artificial Sequence
<220> FEATURE:
<223> OTHER INFORMATION: Synthetic polynucleotide sequence

<400> SEQUENCE: 7
attcacgctt ccattccatg tctcgggttt acttcatctg caactgtaca tctgtct    57

<210> SEQ ID NO 8
<211> LENGTH: 53
<212> TYPE: DNA
<213> ORGANISM: Artificial Sequence
<220> FEATURE:
<223> OTHER INFORMATION: Synthetic polynucleotide sequence

<400> SEQUENCE: 8
attcacgctt ccattccatg tctcgggttt acttcatctg caactgtaca tct    53

<210> SEQ ID NO 9
<211> LENGTH: 39
<212> TYPE: DNA
<213> ORGANISM: Artificial Sequence
<220> FEATURE:
<223> OTHER INFORMATION: Synthetic polynucleotide sequence

<400> SEQUENCE: 9
cgattcagct gcagacgatc tcgggatgca ttcagtgac    39

<210> SEQ ID NO 10
<211> LENGTH: 41
<212> TYPE: DNA
<213> ORGANISM: Artificial Sequence
<220> FEATURE:
<223> OTHER INFORMATION: Synthetic polynucleotide sequence

<400> SEQUENCE: 10
accgcatcga atgactgtct cgggtttact tcatctgcaa c    41

<210> SEQ ID NO 11
<211> LENGTH: 40
<212> TYPE: DNA
<213> ORGANISM: Artificial Sequence
<220> FEATURE:
<223> OTHER INFORMATION: Synthetic polynucleotide sequence

<400> SEQUENCE: 11
acgttagcca ccatacggat agtgacgtga tgagctagac    40

<210> SEQ ID NO 12
<211> LENGTH: 32
<212> TYPE: DNA
<213> ORGANISM: Artificial Sequence
<220> FEATURE:
<223> OTHER INFORMATION: Synthetic polynucleotide sequence

<400> SEQUENCE: 12
acgttagcca ccatacggat gatgagctag ac    32

<210> SEQ ID NO 13

```
<211> LENGTH: 34
<212> TYPE: DNA
<213> ORGANISM: Artificial Sequence
<220> FEATURE:
<223> OTHER INFORMATION: Synthetic polynucleotide sequence

<400> SEQUENCE: 13
acgttagcca ccatacggat gtgacgtgat gagc                                    34

<210> SEQ ID NO 14
<211> LENGTH: 32
<212> TYPE: DNA
<213> ORGANISM: Artificial Sequence
<220> FEATURE:
<223> OTHER INFORMATION: Synthetic polynucleotide sequence

<400> SEQUENCE: 14
acgttagcca ccatacggat gatgagcatc tg                                      32

<210> SEQ ID NO 15
<211> LENGTH: 37
<212> TYPE: DNA
<213> ORGANISM: Artificial Sequence
<220> FEATURE:
<223> OTHER INFORMATION: Synthetic polynucleotide sequence

<400> SEQUENCE: 15
agctatccgc cataagccat actcagagtg atcaagt                                 37

<210> SEQ ID NO 16
<211> LENGTH: 35
<212> TYPE: DNA
<213> ORGANISM: Artificial Sequence
<220> FEATURE:
<223> OTHER INFORMATION: Synthetic polynucleotide sequence: see
      specification as filed for detailed description of labels and
      preferred embodiments

<400> SEQUENCE: 16
tagcgcccga gcgctacgtt agccaccata cggat                                   35

<210> SEQ ID NO 17
<211> LENGTH: 38
<212> TYPE: DNA
<213> ORGANISM: Artificial Sequence
<220> FEATURE:
<223> OTHER INFORMATION: Synthetic polynucleotide sequence: see
      specification as filed for detailed description of labels and
      preferred embodiments

<400> SEQUENCE: 17
agttgccccg aggcaactag ctatccgcca taagccat                                38

<210> SEQ ID NO 18
<211> LENGTH: 29
<212> TYPE: DNA
<213> ORGANISM: Artificial Sequence
<220> FEATURE:
<223> OTHER INFORMATION: Synthetic polynucleotide sequence

<400> SEQUENCE: 18
ccgagaacag acaagacaag actggatat                                          29

<210> SEQ ID NO 19
<211> LENGTH: 29
<212> TYPE: DNA
<213> ORGANISM: Artificial Sequence
<220> FEATURE:
```

<223> OTHER INFORMATION: Synthetic polynucleotide sequence

<400> SEQUENCE: 19
cgagacatgg aatggaagcg tgaattttt                                    29

<210> SEQ ID NO 20
<211> LENGTH: 35
<212> TYPE: DNA
<213> ORGANISM: Artificial Sequence
<220> FEATURE:
<223> OTHER INFORMATION: Synthetic polynucleotide sequence

<400> SEQUENCE: 20
tttattttat cgagacatgg aatggaagcg tgaat                             35

<210> SEQ ID NO 21
<211> LENGTH: 50
<212> TYPE: DNA
<213> ORGANISM: Artificial Sequence
<220> FEATURE:
<223> OTHER INFORMATION: Synthetic polynucleotide sequence: see
      specification as filed for detailed description of labels and
      preferred embodiments

<400> SEQUENCE: 21
cctggtacga gtttctatcc taatgcatca cgagaacaga caagacaagt              50

<210> SEQ ID NO 22
<211> LENGTH: 50
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (50)
<223> OTHER INFORMATION: 3'deoxyuridine

<400> SEQUENCE: 22
cttgtcttgt ctgttctcgt gatgcattag gatagaaact cgtaccaggn              50

<210> SEQ ID NO 23
<211> LENGTH: 52
<212> TYPE: DNA
<213> ORGANISM: Artificial Sequence
<220> FEATURE:
<223> OTHER INFORMATION: Synthetic polynucleotide sequence

<400> SEQUENCE: 23
tttacactga atgcattcct agaacagaca agacaagact ccgtggcagc gt           52

<210> SEQ ID NO 24
<211> LENGTH: 48
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (48)
<223> OTHER INFORMATION: 3'deoxyuridine

<400> SEQUENCE: 24
acgctgccac ggagtcttgt cttgtctgtt cttggaatgc attcagtn                48

<210> SEQ ID NO 25
<211> LENGTH: 19
<212> TYPE: DNA

```
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (19)
<223> OTHER INFORMATION: 2',3'deoxycytidine

<400> SEQUENCE: 25
acagatgtac agtaatttn                                                     19

<210> SEQ ID NO 26
<211> LENGTH: 32
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (32)
<223> OTHER INFORMATION: 2',3'deoxycytidine

<400> SEQUENCE: 26
cagttcagca cactgtacat ctgtctagca an                                      32

<210> SEQ ID NO 27
<211> LENGTH: 35
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (35)
<223> OTHER INFORMATION: 2',3'deoxycytidine

<400> SEQUENCE: 27
cagttcagca cactgtacat ctgtctagct caaan                                   35

<210> SEQ ID NO 28
<211> LENGTH: 37
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (37)
<223> OTHER INFORMATION: 2',3'deoxycytidine

<400> SEQUENCE: 28
cagttcagca cactgtacat ctgtctagct catctan                                 37

<210> SEQ ID NO 29
<211> LENGTH: 27
<212> TYPE: DNA
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (27)
<223> OTHER INFORMATION: 2',3'deoxycytidine

<400> SEQUENCE: 29
cagttcagca caagtacatc tgtaacn                                            27

<210> SEQ ID NO 30
<211> LENGTH: 27
<212> TYPE: DNA
```

```
<213> ORGANISM: Artificial Sequence
<220> FEATURE:
<223> OTHER INFORMATION: Synthetic polynucleotide sequence
<220> FEATURE:
<221> NAME/KEY: misc_feature
<222> LOCATION: (27)
<223> OTHER INFORMATION: 2',3'deoxycytidine

<400> SEQUENCE: 30
cagttcagca caagtacatc tgtaacn                                    27

<210> SEQ ID NO 31
<211> LENGTH: 55
<212> TYPE: DNA
<213> ORGANISM: Artificial Sequence
<220> FEATURE:
<223> OTHER INFORMATION: Synthetic polynucleotide sequence

<400> SEQUENCE: 31
ttttacttca tctgcaactg tacatctgtc tagctcatca cgtcactgaa tgcat      55

<210> SEQ ID NO 32
<211> LENGTH: 55
<212> TYPE: DNA
<213> ORGANISM: Artificial Sequence
<220> FEATURE:
<223> OTHER INFORMATION: Synthetic polynucleotide sequence

<400> SEQUENCE: 32
tttacttcat ctgcaacaca tgatctcaga tgctcatcac gtcactgaat gcatc      55

<210> SEQ ID NO 33
<211> LENGTH: 53
<212> TYPE: DNA
<213> ORGANISM: Artificial Sequence
<220> FEATURE:
<223> OTHER INFORMATION: Synthetic polynucleotide sequence

<400> SEQUENCE: 33
ttacttcatc tgcaacatct gtcacttgat cactctgagt cactgaatgc atc        53
```